US007842324B2

(12) United States Patent
Tachdjian et al.

(10) Patent No.: US 7,842,324 B2
(45) Date of Patent: Nov. 30, 2010

(54) BIS-AROMATIC AMIDES AND THEIR USES AS SWEET FLAVOR MODIFIERS, TASTANTS, AND TASTE ENHANCERS

(75) Inventors: Catherine Tachdjian, San Diego, CA (US); Andrew P. Patron, San Marcos, CA (US); Farid Bakir, San Diego, CA (US); Claudia Averbuj, San Diego, CA (US); Chad Priest, Encinitas, CA (US); Sara L. Adamski-Werner, San Diego, CA (US); Qing Chen, San Diego, CA (US); Vincent Darmohusodo, San Diego, CA (US); Marketa Lebl-Rinnova, San Diego, CA (US); Rachel D. A. Kimmich, Carlsbad, CA (US); Xiao-Qing Tang, San Diego, CA (US); Rhondi Shigemura, Encinitas, CA (US)

(73) Assignee: Senomyx, Inc., La Jolla, CA (US)

( * ) Notice: Subject to any disclaimer, the term of this patent is extended or adjusted under 35 U.S.C. 154(b) by 1114 days.

(21) Appl. No.: 11/455,314

(22) Filed: Jun. 15, 2006

(65) Prior Publication Data

US 2007/0003680 A1    Jan. 4, 2007

Related U.S. Application Data

(60) Provisional application No. 60/691,342, filed on Jun. 15, 2005.

(51) Int. Cl.
*A23L 1/236* (2006.01)
(52) U.S. Cl. .................... 426/548; 514/43; 514/79
(58) Field of Classification Search .............. 424/78.14; 426/548
See application file for complete search history.

(56) References Cited

U.S. PATENT DOCUMENTS

| 3,294,544 | A | 12/1966 | Stanko et al. |
|---|---|---|---|
| 3,503,962 | A | 3/1970 | Beregi et al. |
| 3,535,335 | A | 10/1970 | Beregi et al. |
| 3,625,949 | A | 12/1971 | Schorre et al. |
| 4,034,109 | A | 7/1977 | Rowsell et al. |
| 4,091,018 | A | 5/1978 | Asato |
| 4,136,163 | A | 1/1979 | Watson et al. |
| 4,150,052 | A | 4/1979 | Watson et al. |
| 4,177,279 | A | 12/1979 | Archibald et al. |
| 4,332,724 | A | 6/1982 | Bentley et al. |
| 4,535,084 | A | 8/1985 | Lombardino et al. |
| 4,645,678 | A | 2/1987 | Nofre et al. |
| 4,810,715 | A | 3/1989 | Schickaneder et al. |
| 4,997,667 | A | 3/1991 | Nofre et al. |
| 5,877,218 | A | 3/1999 | Herzig et al. |
| 5,877,221 | A | 3/1999 | Cohen et al. |
| 5,880,159 | A | 3/1999 | Herzig et al. |
| 5,914,349 | A | 6/1999 | Cohen et al. |
| 5,994,408 | A | 11/1999 | Cohen et al. |
| 6,271,263 | B1 | 8/2001 | Sklarz et al. |
| 6,383,778 | B1 | 5/2002 | Zuker et al. |
| 6,417,370 | B1 | 7/2002 | Lieb et al. |
| 6,429,207 | B1 | 8/2002 | Van Wagenen et al. |
| 6,451,843 | B1 | 9/2002 | Lieb et al. |
| 6,462,148 | B1 | 10/2002 | Suzuki et al. |
| 6,528,685 | B2 | 3/2003 | Cohen et al. |
| 6,617,351 | B1 | 9/2003 | Arnold et al. |
| 6,818,747 | B2 | 11/2004 | Yao et al. |
| 2002/0128433 | A1 | 9/2002 | Yao et al. |
| 2002/0132273 | A1 | 9/2002 | Stryer et al. |
| 2002/0143151 | A1 | 10/2002 | Yao et al. |
| 2002/0160424 | A1 | 10/2002 | Adler et al. |
| 2003/0008344 | A1 | 1/2003 | Adler et al. |
| 2003/0054448 | A1 | 3/2003 | Adler et al. |
| 2003/0089885 | A1 | 5/2003 | Rogers et al. |
| 2003/0139470 | A1 | 7/2003 | Ley et al. |
| 2003/0170608 | A1 | 9/2003 | Pronin et al. |
| 2003/0207337 | A1 | 11/2003 | Han et al. |
| 2003/0220479 | A1 | 11/2003 | Li et al. |
| 2003/0228633 | A1 | 12/2003 | Zoller et al. |
| 2003/0232407 | A1 | 12/2003 | Zoller et al. |
| 2004/0072254 | A1 | 4/2004 | Callamaras et al. |
| 2004/0132075 | A1 | 7/2004 | Elliot et al. |
| 2004/0132134 | A1 | 7/2004 | Adler et al. |
| 2004/0171042 | A1 | 9/2004 | Adler et al. |
| 2004/0175792 | A1 | 9/2004 | Zoller et al. |
| 2004/0175793 | A1 | 9/2004 | Zoller et al. |
| 2004/0185469 | A1 | 9/2004 | Zoller et al. |
| 2004/0191805 | A1 | 9/2004 | Adler et al. |

(Continued)

FOREIGN PATENT DOCUMENTS

EP      0 055 689 A1    7/1982

(Continued)

OTHER PUBLICATIONS

Biagi et al., "N⁶-Cycloalkyl-2-phenyl-3-deaza-8-azaadenines: a new class of $A_1$ adenosine receptor ligands. A comparison with the corresponding adenines and 8-azaadenines," *European. Journal of Medicinal Chemistry*, 38:983-990 (2003).

(Continued)

*Primary Examiner*—Michael G Hartley
*Assistant Examiner*—Jagadishwar R Samala
(74) *Attorney, Agent, or Firm*—Cooley LLP

(57) ABSTRACT

The inventions disclosed herein relate to man-made bi-aromatic amide compounds that, when contacted with comestible food or drinks or pharmaceutical compositions at concentrations preferably on the order of about 100 ppm or lower, serve as sweet taste modifiers, sweet flavoring agents, or sweet flavor enhancers, for use in foods, beverages, and other comestible products, or orally administered medicinal products or compositions, optionally in the presence of or in mixtures with conventional flavoring agents such as known natural saccharide sweeteners and previously known artificial sweeteners.

68 Claims, No Drawings

U.S. PATENT DOCUMENTS

| | | |
|---|---|---|
| 2004/0191862 A1 | 9/2004 | Zoller et al. |
| 2004/0209286 A1 | 10/2004 | Adler et al. |
| 2004/0229239 A1 | 11/2004 | Adler et al. |
| 2005/0032158 A1 | 2/2005 | Adler et al. |
| 2005/0069944 A1 | 3/2005 | Adler |
| 2005/0084506 A1 | 4/2005 | Tachdjian et al. |
| 2005/0084932 A1 | 4/2005 | Zoller et al. |
| 2006/0045953 A1 | 3/2006 | Tachdjian et al. |

FOREIGN PATENT DOCUMENTS

| | | |
|---|---|---|
| EP | 0 413 162 A2 | 2/1991 |
| EP | 0 656 350 A1 | 6/1995 |
| EP | 0 854 134 A1 | 7/1998 |
| EP | 0 976 744 A1 | 2/2000 |
| EP | 1 142 490 A1 | 10/2001 |
| EP | 1 205 116 A1 | 5/2002 |
| EP | 1 500 650 A1 | 1/2005 |
| GB | 1 457 671 | 12/1976 |
| GB | 1 489 359 | 10/1977 |
| GB | 1 502 680 | 3/1978 |
| JP | 50064235 | 5/1975 |
| JP | 4008264 | 1/1992 |
| JP | 2000 169438 A | 6/2000 |
| JP | 2000175650 | 6/2000 |
| WO | WO 95/18617 | 7/1995 |
| WO | WO 96/21640 | 7/1996 |
| WO | WO 98/32733 | 7/1998 |
| WO | WO 99/07235 | 2/1999 |
| WO | WO 99/26927 | 6/1999 |
| WO | WO 00/06156 | 2/2000 |
| WO | WO 00/63166 | 10/2000 |
| WO | WO 01/35768 A1 | 5/2001 |
| WO | WO 01/77292 A2 | 10/2001 |
| WO | WO 01/77676 A1 | 10/2001 |
| WO | WO 01/79204 A1 | 10/2001 |
| WO | WO 02/06254 A1 | 1/2002 |
| WO | WO 02/36622 A2 | 5/2002 |
| WO | WO 02/064139 A1 | 8/2002 |
| WO | WO 02/064631 A2 | 8/2002 |
| WO | WO 03/001876 A2 | 1/2003 |
| WO | WO 03/013517 A1 | 2/2003 |
| WO | WO 03/037332 A1 | 5/2003 |
| WO | WO 03/070713 A1 | 8/2003 |
| WO | WO 2004/000355 A1 | 12/2003 |
| WO | WO 2004/011617 A2 | 2/2004 |
| WO | WO 2004/026840 A1 | 4/2004 |
| WO | WO 2004/080976 A1 | 9/2004 |
| WO | WO 2004/081018 A1 | 9/2004 |
| WO | WO 2004/089470 A2 | 10/2004 |
| WO | WO 2004/092182 A1 | 10/2004 |
| WO | WO 2004/113304 A1 | 12/2004 |
| WO | WO 2005/015158 A2 | 2/2005 |
| WO | WO 2005/041684 | 5/2005 |
| WO | WO 2006/084184 A2 | 8/2006 |

OTHER PUBLICATIONS

Clark et al., "Synthesis and Analgesic Activity of 1,3-Dihydro-3-(Substituted Phenyl)Imidazo[4,5-b]Pyridin-2-Ones and 3-(Substituted Phenyl)-1,2,3-Triazolo[4,5-b]Pyridines," *Journal of Medicinal Chemistry*, 21(9):965-978 (1978).

Evangelista et al., "Sintesi Ed Attività Antiulcera Di Alcuni Nuovi Composti a Struttura Ariltiometil-Piridinica," *Farmaco, Edizione Scientifica, Societa Chimica Italiana*, Pavia, IT, 43(11):901-908 (Nov. 1988) (English abstract included, reference may disclose arguably material compounds).

Huang et al., "2-{2-[3-(Pyridin-3-yloxy)phenyl]-2H-tetrazol-5-yl}pyridine: a highly potent, orally active, metabotropic glutamate subtype 5 (mGlu5) receptor antagonist" *Bioorganic & Medicinal Chemistry Letters*, 14(22):5473-5476 (2004).

Jasiczk et al., "Structure-Activity Relationship of Sweet Molecules: Phenylurea Derivatives," *Polish J. Chem.*, 74:1259-1273 (2000).

Pernak et al, "Activity of new quaternary ammonium compounds on strains of bacteria and fungi. Part 5: Synthesis of 3-Methyl-N-Alkylthiomethylpyridine-,1-Methyl-3-N-Alkylthiomethylimidazole- and 1-Ethyl-3-N-Alkylthiolimid Azoline Chlorides," *Pharmazie, Die, Govi Verlag, Eschborn, DE*, 38(11):752-754 (1983) (English abstract included, reference may disclose arguably material compounds).

Thate, "The Relationship Between Constitution and Taste Among Some Derivatives of Urea," *Recueil Des Travaux Chimiques Des Pays-Bas et de La Belgique*, 48:116-120 (1929).

Crosignani et al., "Polymer-Supported Mukaiyama Reagent: A Useful Coupling Reagent for the Synthesis of Esters and Amides," *Organic Letters*, 6(24):4579-4582 (2004).

Linton et al., "Acyl Dipeptides as Reversible Caspase Inhibitors. Part 1: Initial Lead Optimization," *Bioorganic & Medicinal Chemistry Letters*, 12:2969-2971 (2002).

Turnbull et al., "Disposition and Metabolism of 4-Methyl-2-(4-phenylbenzyl)-2-oxazoline-4-methanol in the Rat and Dog," *Journal of Medicinal Chemistry*, 17(1):45-48 (1974).

Adler et al., "A Novel Family of Mammalian Taste Receptors," *Cell*, 100(6):693-702 (2000).

Ager et al., "Commercial, Synthetic Nonnutritive Sweeteners," *Angew. Chem. Int. Ed.*, 37:1802-1817 (1998).

Ahn et al., "A General Diastereoselective Synthesis of Spiroacetals Related to Those in Ionophores via the Reaction of Lacones with Cerium(III) γ-Cerioalkoxide. MAD Reverses the Diastereoselectivity of the Addition of Methylmetallics to a β-Keto Ether[1,2]," *J. Org. Chem.*, 59:3142-3150 (1994).

Ashby et al., "Definitive Relationships Among Chemical Stucture, Carcinogenicity and Mutagenicity for 301 Chemicals by the U.S. NTP," *Mutation Research*, 257:229-306 (1991).

Ashby et al., "Chemical Structure, Salmonella Mutagenicity and Extent of Carcinogenicity as Indicators of Genotoxic Carcinogenesis Among 222 Chemicals Tested in Rodents by the U.S. NCI/NTP," *Mutation Research*, 204:17-115 (1988).

Beckett et al., "Substituted Oxindoles-I. The Preparation and Spectral Characteristics of Some Simple Oxindole Derivatives," *Tetrahedron*, 24:6093-6109 (1968).

Berge et al., "Pharmaceutical Salts," *J. Pharm. Sci.*, 66:1-19 (1977).

Bors et al., "Antioxidant Mechanisms of Polyphenolic Caffeic Acid Oligomers, Constituents of *Salvia officinalis*," Bio. Res., 37:301-311 (2004).

Chandrashekar et al., "T2Rs Function as Bitter Taste Receptors," *Cell*, 100:703-711 (2000).

Cramer et al., "Estimation of Toxic Hazard—A Decision Tree Approach," *Food and Cosmetics Toxicology*, 16:255-276 (1978).

Date et al., "Reactions of Lithiated *ortho*-Toluamides and Related Compounds with Vinysilanes: Synthesis of 1-Tetralones and 1-Naphtols," S. *Chem. Pharm. Bull.*, 38(4):902-906 (1990).

Duan et al., "Discovery of γ-Lactam Hydroxamic Acids as Selective Inhibitors of Tumor Necrosis Factor α Converting Enzyme: Design, Synthesis, and Structure-Activity Relationships," *Journal of Medicinal Chemistry*, 45(23):4954-4957 (2002).

Firooznia et al., "Enantioselective Synthesis of 4-Substituted Phenylalanines By Cross-Coupling Reactions," *Tetrahedron Letters*, 40:213-216 (1999).

Gawley et al., "(R,R)-1,3-Dibenzylisoindoline: A New C2-Symmetric Secondary Amine, by Stereoselective and Regioselective α,d-Dialkylation of Isoindoline, and an Improved Procedure for the Preparation of Isoindoline," *J. Org. Chem.*, 53:5381-5383 (1988).

Higuchi et al, "4-Alkyl-and 3,4-Dialky1-1,2,3,4-Tetrahydro-8-Pyridono[5,6-g]Quinolines: Potent, Nosteroidal Androgen Receptor Agonists," *Bioorganic & Medicinal Chemistry Letters*, 9:1335-1340 (1999).

Humphrey et al., "A Novel Synthesis of 3-Bromo,1,2,4-oxadiazoles," *Journal of Heterocyclic Chemistry*, 26:23-24 (1989).

Ishiyama et al., "Palladium(0)-Catalyzed Cross-Coupling Reaction of Alkoxydiboron with Haloarenes: A Direct Procedure for Arylboronic Esters," *J. Org. Chem.*, 60:7508-7510 (1995).

Kinghorn et al., "Noncariogenic Intense Natural Sweeteners," *Med. Res. Rev.*, 18(5):347-360 (1998).

Kinoshita et al., "Chalcogeno Morita-Baylis-Hillman Reaction of 2-(Methylchalcogeno)phenyl Vinyl Ketones with Aldehyds, Ketones, and α-Dicarbonyl Compunds," *Eur. J. Org. Chem.*, 4852-4861 (2003).

Knölker et al., "A Novel Method for the Synthesis of Isocyanates Under Mild Conditions," *Angew. Chem. Int. Ed. Engl.*, 34(22):2497-2500 (1995).

Kolb et al., "Catalytic Asymmetric Dihydroxylation," *Chem. Rev.*, 94:2483-2547 (1994).

Li et al., "Human Receptors for Sweet and Umami Taste," *PNAS*, 99(7):4692-4696 (2002).

Liu et al., "Palladium-Catalyzed Arylation of Trimethylsilyl Enolates of Esters and Imides. High Functional Group Tolerance and Stereoselective Synthesis of α-Aryl Carboxylic Acid Derivatives," *Journal of American Chemical Society*, 126:5182-5191 (2004).

Marcus, "Culinary Applications of Flavor Enhancement in Product Development," Slide Presentation Annual Meeting of Institute of Food Technology, Las Vegas, Nevada, Jul. 12-16, 2004.

Matsunami et al., "A Family of Candidate Taste Receptors in Human and Mouse," *Nature*, 404:601-604 (2000).

McMurray, "Isoxazole Annelation Reaction: 1-Methyl-4,4a,5,6,7,8-Hexahydronaphthalen-2(3H)-One," *Org. Syn. Coll.*, vol. 6, p. 781; vol. 53, p. 70.

Miyaura et al., "Palladium-Catalyzed Cross-Coupling Reactions of Organoboron Compounds," *Chemical Review*, 95:2457-2483 (1995).

Montmayeur, et al., "A Candidate Taste Receptor Gene Near a Sweet Taste Locus," *Nature Neuroscience*, 4(5):492-498 (2001).

Morini et al., "From Small Sweeteners to Sweet Proteins: Anatomy of the Binding Sites of the Human T1R2_T1R3 Receptor," *J. Med. Chem.*, 48(17):5520-5529 (Aug. 2005).

Munro et al., "A Procedure for the Safety Evaluation of Flavouring Substances," *Food and Chemical Toxicology*, 37:207-232 (1999).

Musser et al., "Synthesis and Antiallergic Activities of 1,3-Oxazolo[4,5-h]quinolines," *J. Med. Chem.*, 28:1255-1259 (1985).

Nelson et al., "Mammalian Sweet Taste Receptors," *Cell*, 106: 381-390 (2001).

Noyes et al., "Phthalimide," *Organic Syntheses*, Coll. vol. 1, p. 457; vol. 2, p. 75.

Ohmoto et al., "Development of Orally Active Nonpeptidic Inhibitors of Human Neutrophil Elastase," *Journal of Medicinal Chemistry*, 44(8):1268-1285 (2001).

Oshiro et al., "Novel Cerebroprotective Agents with Central Nervous System Stimulating Activity. 1. Synthesis and Pharmacolory of 1-Amino 7-hydroxyindan Derivatives," *J. Med. Chem.*, 34:2004-2013 (1991).

Patonay et al., "Chemo- and Diastereoselectivity in the Dimethyldioxirane Oxidation of 2,3-Dihydro-4H-1-benzothiopyran-4-ones and 4H-1-Benzothiopyran-4-ones. Unusual Reactivity of 4H-1-Benzothiopyran-4-one 1-Oxides[1]," *J. Org. Chem.* 66:2275-2280 (2001).

Roholff et al., "Bromoonitrile Oxide [3+2] Cycloadditions in Water," *Tetrahedron Letters*, 33(22):3113-3116 (1992).

Sarges et al., "5,8-Disubstituted 1-Aminotetralins. A Class of Compounds with a Novel Profile of Central Nervous System Activity," *Journal of Medicinal Chemistry*, 16(9):1003-1011 (1973).

Skupinska et al., "Concise Preparation of Amino-5,6,7,8-tetrahydroquinoline and Amino-5,6,7,8-tetrahydroisoquinolines via Catalytic Hydrogenation of Acetamidoquinolines and Acetamidoisoquinolines," *J. Org. Chem.*, 67:7890-7893 (2002).

Skupinska et al., "Enzymatic Resolution of Bicyclic 1-Heteroarylamines Using *Candida antarcticai* Lipase B," *J. Org. Chem.*, 68(9):3546-3551 (2003).

Smith et al., "GRAS Flavoring Substances 21," *Food Technology*, 57(5):46-59 (2003).

Stalker et al., "Asymmetric Synthesis of Two New Conformationally Constrained Lysine Derivatives," *Tetrahedron*, 58:4837-4849 (2002).

Suzuki, "New Synthetic Transformations via Organoboron Compounds," *Pure & Applied Chem.*, 66(2):213-222 (1994).

Wang et al., "Rapid and Efficient Synthesis of 1,2,4-oxadiazoles Utilizing Polymer-Supported Reagents under Microwave Heating," *Organic Letters*, 7(5):925-928 (2005).

Watanabe et al., "Synthesis of Sterically Hindered Biaryls via the Palladium-Catalyzed Cross-Coupling Reaction of Arylboronic Acids or Their Esters With Haloarenes," *Synlett.*, 207-210 (1992).

BIS-AROMATIC AMIDES AND THEIR USES AS SWEET FLAVOR MODIFIERS, TASTANTS, AND TASTE ENHANCERS

RELATED APPLICATIONS

This application claims the priority of U.S. provisional patent application Ser. No. 60/691,342 filed on Jun. 15, 2005, the entire disclosure of which is hereby incorporated herein by this reference, for all purposes.

FIELD OF THE INVENTION

The present invention relates to the discovery of flavor or taste modifiers, such as a flavoring agents and flavor or taste enhancers, more particularly, sweet taste modifiers, sweet flavoring agents, and sweet flavor enhancers, for foods, beverages, and other comestible or orally administered medicinal products or compositions.

BACKGROUND OF THE INVENTION

For centuries, various natural and unnatural compositions and/or compounds have been added to comestible (edible) foods, beverages, and/or orally administered medicinal compositions to improve their taste. Although it has long been known that there are only a few basic types of "tastes," the biological and biochemical basis of taste perception was poorly understood, and most taste improving or taste modifying agents have been discovered largely by simple trial and error processes.

There has been significant recent progress in identifying useful derivatives of natural flavoring agents, such as for example sweeteners that are derivatives of natural saccharide sweeteners, such as for example erythritol, isomalt, lactitol, mannitol, sorbitol, xylitol. There has also bee recent progress in identifying natural terpenoids, flavonoids, or proteins as potential sweeteners. See, for example, a recent article entitled "Noncariogenic Intense Natural Sweeteners" by Kinghorn et al. (*Med Res Rev* (1998)18(5):347-360), which discussed recently discovered natural materials that are much more intensely sweet than common natural sweeteners such as sucrose, fructose, glucose, and the like. Similarly, there has been recent progress in identifying and commercializing new artificial sweeteners, such as aspartame, saccharin, acesulfame-K, cyclamate, Sucralose, and alitame, etc., see an article by Ager et al. (*Angew Chem Int Ed* (1998) 37:1802-1817). The entire disclosures of the references identified above are hereby incorporated herein by reference, for the purpose of describing at least in part the knowledge of those of ordinary skill in the art regarding known sweetening agents.

Nevertheless, there remains in the art a need for new and improved flavoring agents and/or sweeteners. Discovery of new "High Intensity" sweeteners (i.e., many times sweeter than sucrose) would be of considerable value, especially if the new compounds induce the perception of sweetness when used at extremely low concentrations. Similarly any compounds that, when used at very low concentrations significantly multiply (enhance) the sweetness of known natural or artificial sweeteners, so that less of the known caloric sweeteners would be required, while maintaining or amplifying the perceived taste of the natural sweeteners, could be of very high utility and value in view of the rapidly increasing incidence of undesirable human weight gain and/or associated diseases such as diabetes, atherosclerosis, etc.

In recent years substantial progress has been made in biotechnology in general and in better understanding the underlying biological and biochemical phenomena of taste perception. For example, taste receptor proteins have been recently identified in mammals that are involved in taste perception. Particularly, two different families of G protein coupled receptors believed to be involved in taste perception, T2Rs and T1Rs, have been identified. (See, e.g., Nelson et al., *Cell* (2001) 106(3):381-390; Adler et al., *Cell* (2000) 100(6):693-702; Chandrashekar et al., *Cell* (2000) 100:703-711; Matsunami et al., *Number* (2000) 404:601-604; Li et. al., *Proc Natl Acad Sci USA* (2002) 99:4962-4966; Montmayeur et al., *Nature Neuroscience* (2001) 4(S):492-498; U.S. Pat. No. 6,462,148; and PCT publications WO 02/06254, WO 00/63166 art, WO 02/064631, and WO 03/001876, and U.S. Patent Publication US 2003-0232407 A1). The entire disclosures of the articles, patent applications, and issued patents cited immediately above are hereby incorporated herein by reference, for all purposes, including their disclosures of the identities and structures of T2Rs and T1Rs mammalian taste receptor proteins and methods for artificially expressing those receptors in cell lines and using the resulting cell lines for screening compounds as potential "savory" or "sweet" flavoring agents.

Whereas the T2R family includes over 25 genes that are involved in bitter taste perception, the T1R family only includes three members, T1R1, T1R2 and T1R3. (See Li et al., *Proc Natl Acad Sci USA* (2002) 99:4962-4966.) Recently, it was disclosed in WO 02/064631 and/or WO 03/001876 that certain T1R members, when co-expressed in suitable mammalian cell lines, assemble to form functional taste receptors. It was found that co-expression of T1R2 and T1R3 in a suitable host cell results in a functional T1R2/T1R3 "sweet" taste receptor that responds to different taste stimuli including naturally occurring and artificial sweeteners. (See Li et al., *Proc Natl Acad Sci USA* (2002) 99:4962-4966.) The references cited above also disclosed assays and/or high throughput screens that measure T1R1/T1R3 or T1R2/T1R3 receptor activity by fluorometric imaging in the presence of the target compounds.

It was recently reported in U.S. Patent Publication No. US 2005/0084506 A1, and in PCT Publication No. WO 2005041684, that various amide compounds can, at very low concentrations of a few micromolar or less, serve as savory and/or sweet flavoring agents, and/or savory and/or sweet flavor enhancers. The entire texts of US 2005/0084506 A1 and WO 2005041684 are hereby incorporated herein by reference, for all purposes, including the purpose of their descriptions of particular genera and subgenera of amide compounds with activity as sweet flavoring agents and/or sweet flavor enhancers.

Disclosed herein are a new class of bis-aromatic amide compounds, which because of their particular structures, serve at unexpectedly low concentrations as unexpectedly superior and/or high intensity sweet flavorant or sweet enhancing compounds in comestible compositions. These compounds are particularly valuable when used as high intensity sweeteners in combination with other known but less potent sweeteners, such as for example saccharide sweeteners, so as to allow for the formulation of comestible compositions comprising lower levels of the previously known sweeteners.

SUMMARY OF THE INVENTION

The inventions disclosed and/or claimed herein have many aspects, many of which relate to methods of making or using comestible compositions containing certain non-naturally occurring compounds having the generic structure shown below in Formula (I), or one or more comestibly acceptable salts thereof:

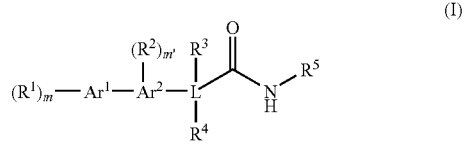

wherein $Ar^1$, $Ar^2$, L, $R^1$, $R^2$, $R^3$, $R^4$, $R^5$, m and m', some of which are optional, can be and are independently further defined in various ways, as is further detailed below in the detailed description of the invention. It is however required that for all the compounds of Formula (I), L is either a carbon atom or a nitrogen atom, the $Ar^1$ and $Ar^2$ groups are independently selected from aromatic ring groups, i.e. aryl or heteroaryl ring groups, and that $R^5$ is an organic group.

In some aspects of the compounds of Formula (I):
  i) $Ar^1$ and $Ar^2$ are independently selected from monocyclic aryl, fused bicyclic aryl, monocyclic heteroaryl, or fused bicyclic heteroaryl rings;
  ii) m is selected from the integers 0, 1, 2, 3, 4, or 5;
  iii) m' is selected from the integers 0, 1, 2, 3, or 4;
  iv) each $R^1$ and $R^2$ is independently selected from the group consisting of an OH, $NH_2$, $NO_2$, SH, $SO_3H$, $PO_3H$, halogen, and a $C_1$-$C_6$ organic radical;
  v) L is a carbon or nitrogen atom;
  vi) $R^3$ is hydrogen, oxygen, hydroxy, halogen, or a $C_1$-$C_6$ organic radical;
  vii) $R^4$ is absent, or hydrogen, oxygen, hydroxy, halogen, or a $C_1$-$C_6$ organic radical;
  viii) $R^5$ is a $C_1$-$C_{14}$ organic radical comprising a normal or branched alkyl or cycloalkyl, wherein the normal or branched alkyl or cycloalkyl optionally comprises one to four substituents independently selected from OH, $NH_2$, $NO_2$, SH, $SO_3H$, $PO_3H$, halogen, and a $C_1$-$C_6$ organic radical;
  or a comestibly acceptable salt thereof.

In many embodiments of the compounds of Formula (I), L is a carbon atom. For example, in many aspects of the inventions disclosed herein relate to an amide compound having the structure:

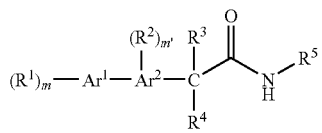

wherein
  i) $Ar^1$ and $Ar^2$ are independently selected from a phenyl, or monocyclic heteroaryl rings;
  ii) m and m' are independently selected from the integers 0, 1, or 2;
  iii) each $R^1$ and $R^2$ is independently selected from the group consisting of OH, $NH_2$, $NO_2$, SH, $SO_3H$, $PO_3H$, halogen, and a $C_1$-$C_4$ organic radical;
  iv) $R^3$ and $R^4$ are independently selected from hydrogen and a $C_1$-$C_4$ alkyl,
  v) $R^5$ is a $C_3$-$C_{10}$ branched alkyl optionally comprising one, two, or three substituents independently selected from OH, $NH_2$, a halogen, and a $C_1$-$C_6$ organic radical;
  or a comestibly acceptable salt thereof.

Alternatively, in some related aspects of the compounds of Formula (I):
  i) $Ar^1$ and $Ar^2$ are independently selected from monocyclic aryl, fused bicyclic aryl, monocyclic heteroaryl, or fused bicyclic heteroaryl rings;
  ii) m is selected from the integers 0, 1, 2, 3, 4, or 5;
  iii) m' is selected from the integers 0, 1, 2, 3, or 4;
  iv) each $R^1$ and $R^2$ is independently selected from the group consisting of an OH, $NH_2$, $NO_2$, SH, $SO_3H$, $PO_3H$, halogen, and a $C_1$-$C_6$ organic radical;
  v) L is a carbon atom;
  vi) $R^3$ is hydrogen, oxygen, hydroxy, halogen, or a $C_1$-$C_6$ organic radical;
  vii) $R^4$ is hydrogen, oxygen, hydroxy, halogen, or a $C_1$-$C_6$ organic radical; and
  viii) $R^5$ is a $C_1$-$C_{14}$ organic radical comprising a normal or branched alkyl or cycloalkyl, wherein the normal or branched alkyl or cycloalkyl optionally comprises one to four substituents independently selected from OH, $NH_2$, $NO_2$, SH, $SO_3H$, $PO_3H$, halogen, and a $C_1$-$C_6$ organic radical;

In yet other aspects of the amide compounds of Formula (I):
  a) $Ar^1$ and $Ar^2$ are independently selected phenyl or 5 or 6 membered monocyclic heteroaryl rings,
  b) each $R^1$ and $R^2$ is independently selected from the group consisting of hydroxy, fluoro, chloro, $NH_2$, $NHCH_3$, $N(CH_3)_2$, CN, $OC(O)CH_3$, $SCH_3$, $S(O)CH_3$, $S(O)_2CH_3$, $S(O)_2NHCH_3$, $SC_2H_5$, methyl, ethyl, propyl, isopropyl, vinyl, allyl, CN, $CH_2OH$, $CH_2OCH_3$, $CH_2OCH_2CH_3$, C(O)H, $C(O)CH_3$, methoxy, ethoxy, and isopropoxy groups,
  c) $R^3$ and $R^4$ are methyl, and
  d) $R^5$ is a $C_3$-$C_{10}$ branched alkyl.

Many of the amide compounds of Formula (I) disclosed herein are novel compounds that have not been previously reported in the prior art. Many of the "amide" compounds of Formula (I) and its subgenera are shown below to bind to and/or activate T1R2/T1R3 sweet receptors in-vitro, at unexpectedly low concentrations on the order of micromolar or lower. The amide compounds of Formula (I) are also believed to similarly interact with sweet flavor receptors of animals or humans in vivo as has been confirmed in some cases by actual human taste tests of some of compounds of Formula (I), as described herein.

Accordingly, most or all of the subgenuses and species of the "amide" compounds of Formula (I) further described hereinbelow can, at useful and often surprisingly low concentrations, preferably on the order of a few micromolar or less or a few ppm or less, be used in comestible compositions as sweet flavoring agents or sweet flavoring agent enhancers, so as to induce or enhance the sweet flavor of the comestible compositions.

Accordingly, in some embodiments, the invention relates to methods for modulating the sweet taste of a comestible or medicinal product comprising:
  a) providing at least one comestible or medicinal product, or at least one precursor thereof, and
  b) combining the at least one comestible or medicinal product or at least one precursor thereof with at least a sweet flavor modulating amount of at least one non-naturally occurring amide compound, or a comestibly acceptable salt thereof, so as to form a modified comestible or medicinal product;

wherein the amide compound is within the scope of any of the compounds of Formula (I) as disclosed or shown below, or any of its various genera or subgenera of compounds or species compounds, or their comestibly acceptable salts, as are further described below:

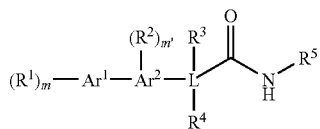

(I)

The invention also relates to the comestible or medicinal products produced by the methods and/or processes mentioned above, and to comestible or medicinal products or compositions, or one or more of their precursors, that contain the amide compounds of Formula (I), even if those products or compositions are not made by the processes recited herein.

In many embodiments, one or more of the amide compounds of Formula (I) further identified, described, and/or claimed herein, or one or more comestibly acceptable salts thereof, can be used singly, or in mixtures or in combination with other known sweet compounds or known sweeteners, or used as flavor enhancers in comestible food, beverage and medicinal compositions, for human or animal consumption.

In some embodiments, the invention relates to novel compounds, flavoring agents, flavor enhancers, flavor modifying compounds, and/or compositions containing the compounds of Formula (I), and its various subgenuses and species compounds.

In some embodiments, the invention relates to comestible or medicinal compositions suitable for human or animal consumption, or precursors thereof, containing at least one compound of Formula (I), or a comestibly or pharmaceutically acceptable salt thereof. These compositions will preferably include comestible products such as foods or beverages, medicinal products or compositions intended for oral administration, and oral hygiene products, and additives which when added to these products modulate the flavor or taste thereof, particularly by enhancing (increasing) the sweet taste thereof.

The present invention also relates to novel genuses and species of amide compounds within the scope of the compounds of Formula (I) and derivatives, flavoring agents, comestible or medicinal products or compositions, including sweet flavoring agents and flavor enhancers containing the same.

The foregoing summary discussion merely summarizes certain aspects of the inventions and is not intended, nor should it be construed, as limiting the invention in any way.

DETAILED DESCRIPTION OF THE INVENTION

The present invention can be understood more readily by reference to the following detailed description of various embodiments of the invention and the Examples included therein and to the chemical drawings and Tables and their previous and following description. Before the present compounds, compositions, and/or methods are disclosed and described, it is to be understood that unless otherwise specifically indicated by the claims, the invention is not limited to specific foods or food preparation methods, specific comestibles or pharmaceutical carriers or formulations, or to particular modes of formulating the compounds of the invention into comestible or medicinal products or compositions intended for oral administration, because as one of ordinary skill in relevant arts is well aware, such things can of course, vary. It is also to be understood that the terminology used herein is for the purpose of describing particular embodiments only and is not intended to be limiting.

Definitions

As used herein, the term "medicinal product" includes both solids and liquid compositions which are ingestible non-toxic materials which have medicinal value or comprise medicinally active agents such as cough syrups, cough drops, aspirin and chewable medicinal tablets.

An oral hygiene product includes solids and liquids such as toothpaste or mouthwash.

A "comestibly, biologically or medicinally acceptable carrier or excipient" is a solid or liquid medium and/or composition that is used to prepare a desired dosage form of the inventive compound, in order to administer the inventive compound in a dispersed/diluted form, so that the biological effectiveness of the inventive compound is maximized. A comestibly, biologically or medicinally acceptable carrier includes many common food ingredients, such as water at neutral, acidic, or basic pH, fruit or vegetable juices, vinegar, marinades, beer, wine, natural water/fat emulsions such as milk or condensed milk, sugars such as sucrose, fructose, glucose, and the like, sugar alcohols such as erythritol, isomalt, lactitol, mannitol, sorbitol, xylitol, and the like, edible oils and shortenings, fatty acids, low molecular weight oligomers of propylene glycol, glyceryl esters of fatty acids, dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids, surface active agents, isotonic agents, thickening or emulsifying agents, preservatives, solid binders, lubricants, and the like, or a mixture of any of the above.

A "flavor" herein refers to the perception of taste and/or smell in a subject, which include sweet, sour, salty, bitter, umami, and others. The subject may be a human or an animal.

A "flavoring agent" herein refers to a compound or a biologically acceptable salt thereof that induces a flavor or taste in an animal or a human.

A "flavor modifier" herein refers to a compound or biologically acceptable salt thereof that modulates, including enhancing, potentiating, inducing, decreasing and/or blocking, the tastes and/or smell of a natural or synthetic flavoring agent in an animal or a human.

"Sweet flavoring agent," or "sweet compound" herein refers to any compound or biologically acceptable salt thereof that elicits a perception of detectable sweet flavor in a human subject, e.g., sucrose, fructose, glucose, and other known natural saccharide-based sweeteners, or known artificial sweeteners such as saccharine, cyclamate, aspartame, Sucralose, and the like as is further discussed herein. While not wishing to be bound by theory, sweet flavoring agents are believed to be agonists of T1R2/T1R3 sweet taste receptor proteins in vitro and in vivo. Many of the amide compounds described herein are sweet flavoring agents, whose sweet taste is perceptible by a human.

A "sweet flavor enhancer" herein refers to a compound or biologically acceptable salt thereof that enhances, potentiates, or multiplies the sweet taste of another natural or synthetic flavoring agent in a comestible composition. For example, a sweet flavor enhancer can increase or multiply the sweet flavor of a comestible composition, when used in combination with another sweet flavoring agent (e.g., a sweetener, such as sucrose, fructose, glucose, saccharine, aspartame, Sucralose, etc.). While the sweet flavor enhancer may also have a sweet flavor at some concentrations when used in the absence of other sweeteners, sweet flavor enhancement occurs when the sweet flavor enhancer is used in combination with another sweet favoring agent with the result that the resulting sweetness perceived in a subject is greater than the additive effects attributable to the sweet flavor enhancer's own sweet flavor (if any), plus the sweetness attributable to presence of the other sweet flavoring agent. While not wishing to be bound by theory, in at least some cases sweet flavor enhancement may occur if the sweet flavor enhancer (such as one of the amide compounds of Formula (I)) functions as an allosteric modifier of the activity of T1R2/T1R3 sweet taste receptor proteins in vitro or in vivo.

A "sweet flavor modifier" herein refers to a compound or biologically acceptable salt thereof that modulates, including enhancing or potentiating, inducing, and blocking, the sweet taste of a natural or synthetic sweet flavoring agents, e.g., sucrose, fructose, glucose, and other known natural saccharide-based sweeteners, or known artificial sweeteners such as saccharine, cyclamate, aspartame, and the like, in an animal or a human.

A "sweet receptor activating compound" herein refers to a compound that activates a sweet receptor, such as a T1R2/T1R3 receptor.

A "sweet receptor modulating compound" herein refers to a compound that modulates (activates, enhances, or blocks) a sweet receptor.

A "sweet flavor modulating amount" herein refers to an amount of a compound of Formula (I) that is sufficient to alter (either increase or decrease) sweet taste in a comestible or medicinal product or composition, or a precursor thereof, sufficiently to be perceived by a human subject. A fairly broad range of a sweet flavor modulating amount can be from about 0.001 ppm to 100 ppm, or a narrow range from about 0.1 ppm to about 10 ppm. Alternative ranges of sweet flavor modulating amounts can be from about 0.01 ppm to about 30 ppm, from about 0.05 ppm to about 15 ppm, from about 0.1 ppm to about 5 ppm, or from about 0.1 ppm to about 3 ppm.

A "sweet flavoring agent amount" herein refers to an amount of a compound (including the compounds of Formula (I), as well as known sweeteners) that is sufficient to induce a sweet taste in a comestible or medicinal product or composition, or a precursor thereof, as perceived by a human subject. A fairly broad range of a sweet flavoring agent amount for the compounds of Formula (I) can be from about 0.001 ppm to 100 ppm, or a narrow range from about 0.1 ppm to about 10 ppm. Alternative ranges of sweet flavoring agent amounts can be from about 0.01 ppm to about 30 ppm, from about 0.05 ppm to about 15 ppm, from about 0.1 ppm to about 5 ppm, or from about 0.1 ppm to about 3 ppm.

A "sweet flavor enhancing amount" herein refers to an amount of a compound of Formula (I) that is sufficient to enhance, potentiate, or multiply the sweet taste of one or more natural or synthetic flavoring agents, or mixtures thereof (e.g., sucrose, fructose, glucose, and other known natural saccharide-based sweeteners, or known artificial sweeteners such as saccharine, cyclamate, aspartame, Sucralose, and the like as is further discussed herein) in a comestible or medicinal product or composition. A fairly broad range of a sweet flavor enhancing amount can be from about 0.001 ppm to 100 ppm, or a narrow range from about 0.1 ppm to about 10 ppm. Alternative ranges of sweet flavor enhancing amounts can be from about 0.01 ppm to about 30 ppm, from about 0.05 ppm to about 15 ppm, from about 0.1 ppm to about 5 ppm, or from about 0.1 ppm to about 3 ppm.

A "sweet receptor modulating amount" herein refers to an amount of a compound that is sufficient to modulate (activate, enhance, or block) a sweet receptor. A preferable range of a sweet receptor modulating amount is 1 pM to 100 mM and most preferably 1 nM to 100 μM and most preferably 1 nM to 30 μM.

A "T1R2/T1R3 receptor modulating or activating amount" is an amount of compound that is sufficient to modulate or activate a T1R2/T1R3 receptor. These amounts are preferably the same as the sweet receptor modulating amounts.

A "sweet receptor" is a taste receptor that can be modulated by a sweet compound. Preferably a sweet receptor is a G protein coupled receptor, and more preferably the sweet receptor is a T1R2/T1R3 receptor.

Many compounds of Formula (I) can modulate a sweet receptor and preferably are agonists of the T1R2/T1R3 receptor. An agonist of this receptor has the effect of activating the G protein signaling cascade. In many cases, this agonist effect of the compound on the receptor also produces a perceived sweet flavor in a taste test. It is desirable, therefore, that such inventive compounds serve as a replacement for sucrose, fructose, glucose, and other known natural saccharide-based sweeteners, or known artificial sweeteners such as saccharine, cyclamate, aspartame, and the like, or mixtures thereof as is further discussed herein.

A "synergistic effect" relates to the increased sweet flavor of a combination of sweet compounds or receptor activating compounds, in comparison to the sum of the taste effects or flavor associated effects associated with each individual compound. In the case of sweet enhancer compounds, a synergistic effect on the effectiveness of a sweetener may be indicated for a compound of Formula (I) having an $EC_{50}$ ratio (defined hereinbelow) of 2.0 or more, or preferably 5.0 or more, or 10.0 or more, or 15.0 or more. A synergistic effect can be confirmed by human taste tests, as described elsewhere herein.

As used herein, "Degrees Brix" or "brix" (symbol ° Bx) refers to a measurement of the mass ratio of dissolved sucrose to water in a liquid. It is measured with a saccharimeter that measures specific gravity of a liquid, or more easily with a refractometer. A 25 ° Bx solution has 25 grams of sucrose sugar per 100 grams of liquid. Or, to put it another way, there are 25 grams of sucrose sugar and 75 grams of water in the 100 grams of solution.

When the compounds described here include one or more chiral centers, the stereochemistry of such chiral centers can independently be in the R or S configuration, or a mixture of the two. The chiral centers can be further designated as R or S or R,S or d,D, l,L or d,l, D,L. Correspondingly, the amide compounds of the invention, if they can be present in optically active form, can actually be present in the form of a racemic mixture of enantiomers, or in the form of either of the separate enantiomers in substantially isolated and purified form, or as a mixture comprising any relative proportions of the enantiomers.

Regarding the compounds described herein, the suffix "ene" added to any of the described terms means that the substituent is connected to two other parts in the compound. For example, "alkylene" is $(CH_2)_n$; "alkenylene" is such a moiety that contains a double bond; and "alkynylene" is such a moiety that contains a triple bond.

As used herein, "hydrocarbon residue" refers to a chemical sub-group or radical within a larger chemical compound which contains only carbon and hydrogen atoms. The hydrocarbon residue may be aliphatic or aromatic, straight-chain, cyclic, branched, saturated or unsaturated. In many embodiments the hydrocarbon residues are of limited dimensional size and molecular weight, and may comprise 1 to 18 carbon atoms, 1 to 16 carbon atoms, 1 to 12 carbon atoms, 1 to 10 carbon atoms, 1 to 8 carbon atoms, 1 to 6 carbon atoms, or 1 to 4 carbon atoms.

The hydrocarbon residue, when described as "substituted," contains or is substituted with one or more independently selected heteroatoms such as O, S, N, P, or the halogens (fluorine, chlorine, bromine, and iodine), or one or more substituent groups containing heteroatoms (OH, $NH_2$, $NO_2$, $SO_3H$, and the like) over and above the carbon and hydrogen atoms of the substituent residue. Substituted hydrocarbon residues can also contain carbonyl groups, amino groups, hydroxyl groups and the like, or contain heteroatoms inserted into the "backbone" of the hydrocarbon residue.

As used herein, "inorganic" group or residue refers to a neutral, cationic, or anionic radical substituents on the organic molecules disclosed or claimed herein that have from one to 16 atoms that do not include carbon, but do contain other heteroatoms from the periodic table that preferably include one or more atoms independently selected from the group consisting of H, O, N, S, one or more halogens, or alkali metal or alkaline earth metal ions. Examples of inorganic radicals include, but are not limited to, H, $Li^+$, $Na^+$, $K^+$, $Zn^{++}$, $Mg^{++}$, $Ca^{++}$, halogens, which include fluorine, chlorine, bromine, and iodine, OH, SH, $SO_3H$, $SO_3^-$, $PO_3H$, $PO_3^-$, NO, $NO_2$, $NH_2$, and the like.

As used herein, the term "alkyl," "alkenyl," and "alkynyl" include straight- and branched-chain and cyclic monovalent substituents that respectively are saturated, unsaturated with at least one double bond, and unsaturated with at least one triple bond.

"Alkyl" refers to a hydrocarbon group that can be conceptually formed from an alkane by removing hydrogen from the structure of a non-cyclic hydrocarbon compound having straight or branched carbon chains and replacing the hydrogen atom with another atom or organic or inorganic substitutent group. In some embodiments of the invention, the alkyl groups are "$C_1$ to $C_6$ alkyl" such as methyl, ethyl, propyl, isopropyl, n-butyl, iso-butyl, sec-butyl, tert-butyl, amyl, tert-amyl, hexyl, and the like. Many embodiments of the invention comprise "$C_1$ to $C_4$ alkyl" groups (alternatively termed "lower alkyl" groups) that include methyl, ethyl, propyl, isopropyl n-butyl, iso-butyl, sec-butyl, and t-butyl groups. Some of the preferred alkyl groups of the invention have three or more carbon atoms preferably 3 to 16 carbon atoms, 4 to 14 carbon atoms, or 6 to 12 carbon atoms.

The term "alkenyl" denotes a hydrocarbon group or residue that comprises at least one carbon-carbon double bond. In some embodiments, alkenyl groups are "$C_2$ to $C_7$ alkenyls" which are exemplified by vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains. In other embodiments, alkenyls are limited to two to four carbon atoms.

The term "alkynyl" denotes a hydrocarbon residue that comprises at least one carbon-carbon triple bond. Preferred alkynyl groups are "$C_2$ to $C_7$ alkynyl" such as ethynyl, propynyl, 2-butynyl, 2-pentynyl, 3-pentynyl, 2-hexynyl, 3-hexynyl, 4-hexynyl, 2-heptynyl, 3-heptynyl, 4-heptynyl, 5-heptynyl as well as di- and tri-ynes of straight and branched chains including ene-ynes.

The terms "substituted alkyl," "substituted alkenyl," "substituted alkynyl," and "substituted alkylene" denote that the alkyl, alkenyl, alkynyl and alkylene groups or radicals as described above have had one or more hydrogen atoms substituted by one or more, and preferably one or two organic or inorganic substituent groups or radicals, that can include halogen, hydroxy, $C_1$ to $C_7$ alkoxy, alkoxy-alkyl, nitrile, amide, and substituted amide, oxo, $C_3$ to $C_7$ cycloalkyl, naphthyl, amino, (monosubstituted)amino, (disubstituted)amino, guanidino, heterocycle, substituted heterocycle, imidazolyl, indolyl, pyrrolidinyl, $C_1$ to $C_7$ acyl, $C_1$ to $C_7$ acyloxy, nitro, carboxy, carbamoyl, carboxamide, N—($C_1$ to $C_6$ alkyl)carboxamide, N,N-di($C_1$ to $C_6$ alkyl)carboxamide, cyano, $C_1$ to $C_4$ alkylsulfonamide, thiol, $C_1$ to $C_4$ alkylthio or $C_1$ to $C_4$ alkylsulfonyl groups. The substituted alkyl groups may be substituted once or more, and preferably once or twice, with the same or with different substituents. In many embodiments of the invention a preferred group of substituent groups include hydroxy, fluoro, chloro, $NH_2$, $NO_2$, $NHCH_3$, $N(CH_3)_2$, $CO_2CH_3$, SH, $SC_2H_5$, $S(O)CH_3$, $S(O)_2CH_3$, $SCH_3$, $SO_3H$, $PO_3H$, methyl, ethyl, isopropyl, vinyl, trifluoromethyl, methoxy, ethoxy, isopropoxy, and trifluoromethoxy groups. In many embodiments of the invention that comprise the above lists of substituent groups an even more preferred group of substituent groups include hydroxy, $SC_2H_5$, $SCH_3$, methyl, ethyl, isopropyl, trifluromethyl, methoxy, ethoxy, and trifluoromethoxy groups.

Examples of the above substituted alkyl groups include the 2-oxo-prop-1-yl, 3-oxo-but-1-yl, cyanomethyl, nitromethyl, chloromethyl, trifluoromethyl, hydroxymethyl, tetrahydropyranyloxymethyl, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chloromethyl, trifluoromethyl, 6-hydroxyhexyl, 2,4-dichloro(n-butyl), 2-aminopropyl, 1-chloroethyl, 2-chloroethyl, 1-bromoethyl, 2-chloroethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 2-aminoethyl, 1-aminoethyl, N-benzoyl-2-aminoethyl, N-acetyl-2-aminoethyl, N-benzoyl-1-aminoethyl, N-acetyl-1-aminoethyl, and the like.

Examples of substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl, and the like. The geometrical isomerism is not critical and all geometrical isomers for a given substituted double bond can be included.

Examples of substituted alkynyl groups include phenylacetylen-1-yl, 1-phenyl-2-propyn-1-yl and the like.

Haloalkyls are substituted alkyl groups or residues wherein one or more hydrogens of the corresponding alkyl group have been replaced with a halogen atom (fluorine, chlorine, bromine, and iodine). Preferred haloalkyls can have one to four carbon atoms. Examples of preferred haloalkyl groups include trifluoromethyl and pentafluoroethyl groups.

Haloalkoxy groups alkoxy groups or residues wherein one or more hydrogens from the R group of the alkoxy group are a halogen atom (fluorine, chlorine, bromine, and iodine). Preferred haloalkoxy groups can have one to four carbon atoms. Examples of preferred haloalkoxy groups include trifluoromethyoxy and pentafluoroethoxy groups.

The term "oxo" denotes a carbon atom bonded to two additional carbon atoms substituted with an oxygen atom doubly bonded to the carbon atom, thereby forming a ketone radical or residue.

"Alkoxy" or "alkoxyl" refers to an —OR radical or group, wherein R is an alkyl radical. In some embodiments the alkoxy groups can be $C_1$ to $C_8$, and in other embodiments can be $C_1$ to $C_4$ alkoxy groups, wherein R is a lower alkyl, such as a methoxy, ethoxy, n-propoxy, isopropoxy, n-butoxy, t-butoxy, and like alkoxy groups. The term "substituted alkoxy" means that the R group is a substituted alkyl group or residue. Examples of substituted alkoxy groups include trifluoromethoxy, hydroxymethyl, hydroxyethyl, hydroxypropyl, and alkoxyalkyl groups such as methoxymethyl, methoxyethyl, polyoxoethylene, polyoxopropylene, and similar groups.

"Alkoxyalkyl" refers to an —R—O—R' group or radical, wherein R and R' are alkyl groups. In some embodiments the alkoxyalkyl groups can be $C_1$ to $C_8$ and in other embodiments can be $C_1$ to $C_4$. In many embodiments both R and R' are a lower alkyl, such as a methoxy, ethoxy, n-propoxy, isopropoxy, n-butoxy, t-butoxy and like alkoxy groups. Examples of alkoxyalkyl groups include methoxymethyl, ethoxyethyl, methoxypropyl, and methoxybutyl and similar groups.

"Hydroxyalkyl" refers to an —R—OH group or radical, wherein R is an alkyl group. In some embodiments the hydoxyalkyl groups can be $C_1$ to $C_8$ and in other embodiments can be $C_1$ to $C_4$. In many embodiments R is a lower alkyl. Examples of alkoxyalkyl groups include hydroxymethyl, 1-hydroxyethyl, 2-hydroxyethyl 3-hydroxypropyl, and similar groups.

"Acyloxy" refers to an $RCO_2$— ester group where R is an alkyl, cycloalkyl, aryl, heteroaryl, substituted alkyl, substituted cycloalkyl, substituted aryl, or substituted heteroaryl group or radical wherein the R radical comprises one to seven or one to four carbon atoms. In many embodiments, R is an alkyl radical, and such acyloxy radicals are exemplified by formyloxy, acetoxy, propionyloxy, butyryloxy, pivaloyloxy, pentanoyloxy, hexanoyloxy, heptanoyloxy, and the like. In other embodiments the R groups are $C_1$-$C_4$ alkyls.

As used herein, "acyl" encompasses the definitions of alkyl, alkenyl, alkynyl and the related hetero-forms which are coupled to an additional organic residue through a carbonyl group to form a ketone radical or group. Preferred acyl groups are "$C_1$ to $C_7$ acyl" such as formyl, acetyl, propionyl, butyryl, pentanoyl, pivaloyl, hexanoyl, heptanoyl, benzoyl, and the like. More preferred acyl groups are acetyl and benzoyl.

The term "substituted acyl" denotes an acyl group wherein the R group substituted by one or more, and preferably one or two, halogen, hydroxy, oxo, alkyl, cycloalkyl, naphthyl, amino, (monosubstituted)amino, (disubstituted)amino, guanidino, heterocyclic ring, substituted heterocyclic ring, imidazolyl, indolyl, pyrrolidinyl, $C_1$ to $C_7$ alkoxy, alkoxyalkyl, $C_1$ to $C_7$ acyl, $C_1$ to $C_7$ acyloxy, nitro, $C_1$ to $C_6$ alkyl ester, carboxy, alkoxycarbonyl, carbamoyl, carboxamide, N—($C_1$ to $C_6$ alkyl)carboxamide, N,N-di($C_1$ to $C_6$ alkyl)carboxamide, cyano, $C_1$ to $C_4$ alkylsulfonamide, thiol, $C_1$ to $C_4$ alkylthio or $C_1$ to $C_4$ alkylsulfonyl groups. The substituted acyl groups may be substituted once or more, and preferably once or twice, with the same or with different substituents.

Examples of $C_1$ to $C_7$ substituted acyl groups include 4-phenylbutyroyl, 3-phenylbutyroyl, 3 phenylpropanoyl, 2-cyclohexanylacetyl, cyclohexanecarbonyl, 2-furanoyl and 3 dimethylaminobenzoyl.

Cycloalkyl residues or groups are structurally related to cyclic monocylic or bicyclic hydrocarbon compounds wherein one or more hydrogen atoms have been replaced with an organic or inorganic substituent group. The cycloalkyls of the current inventions comprise 3 to 12, or more preferably 3 to 8, or more preferably 4 to 6 ring carbon atoms. Examples of such cycloalkyl residues include cyclopropyl, cyclobutyl, cyclopentyl, cyclohexyl, cycloheptyl, cyclooctyl rings, and saturated bicyclic or fused polycyclic cycloalkanes such as decalin groups, polycyclic norbornyl or adamantly groups, and the like.

Preferred cycloalkyl groups include "$C_3$ to $C_7$ cycloalkyl" such as cyclopropyl, cyclobutyl, cyclopentyl, cyclohexyl, or cycloheptyl rings. Similarly, the term "$C_5$ to $C_7$ cycloalkyl" includes cyclopentyl, cyclohexyl, and cycloheptyl rings.

"Substituted cycloalkyl" denote a cycloalkyl rings as defined above substituted by 1 to 4, or preferably 1 or 2, substituents independently selected from a halogen, hydroxy, $C_1$ to $C_4$ alkylthio, $C_1$ to $C_4$ alkylsulfoxide, $C_1$ to $C_4$ alkylsulfonyl, $C_1$ to $C_4$ substituted alkylthio, $C_1$ to $C_4$ substituted alkylsulfoxide, $C_1$ to $C_4$ substituted alkylsulfonyl, $C_1$ to $C_4$ alkyl, $C_1$ to $C_4$ alkoxy, $C_1$ to $C_6$ substituted alkyl, $C_1$ to $C_4$ alkoxy-alkyl, oxo (monosubstituted)amino, (disubstituted) amino, trifluoromethyl, carboxy, phenyl, substituted phenyl, phenylthio, phenylsulfoxide, phenylsulfonyl, or amino. In many embodiments of substituted cycloalkyl groups the substituted cycloalkyl group will have 1, 2, 3, or 4 substituent groups independently selected from hydroxy, fluoro, chloro, $NH_2$, $NHCH_3$, $N(CH_3)_2$, $CO_2CH_3$, $SC_2H_5$, $SCH_3$, $S(O)CH_3$, $S(O)_2CH_3$, methyl, ethyl, isopropyl, vinyl, trifluoromethyl, methoxy, ethoxy, isopropoxy, and trifluoromethoxy groups.

The term "cycloalkylene" means a cycloalkyl, as defined above, where the cycloalkyl radical is bonded at two positions connecting together two separate additional groups. Similarly, the term "substituted cycloalkylene" means a cycloalkylene where the cycloalkyl radical is bonded at two positions connecting together two separate additional groups and further bearing at least one additional substituent.

The term "cycloalkenyl" indicates preferably a 1,2, or 3-cyclopentenyl ring, a 1,2,3 or 4-cyclohexenyl ring or a 1,2,3,4 or 5-cycloheptenyl ring, while the term "substituted cycloalkenyl" denotes the above cycloalkenyl rings substituted with a substituent, preferably by a $C_1$ to $C_6$ alkyl, halogen, hydroxy, $C_1$ to $C_7$ alkoxy, alkoxy-alkyl, trifluoromethyl, carboxy, alkoxycarbonyl oxo, (monosubstituted)amino, (disubstituted)amino, phenyl, substituted phenyl, amino, or protected amino.

The term "cycloalkenylene" is a cycloalkenyl ring, as defined above, where the cycloalkenyl radical is bonded at two positions connecting together two separate additional groups. Similarly, the term "substituted cycloalkenylene" means a cycloalkenylene further substituted preferably by halogen, hydroxy, $C_1$ to $C_4$ alkylthio, $C_1$ to $C_4$ alkylsulfoxide, $C_1$ to $C_4$ alkylsulfonyl, $C_1$ to $C_4$ substituted alkylthio, $C_1$ to $C_4$ substituted alkylsulfoxide, $C_1$ to $C_4$ substituted alkylsulfonyl, $C_1$ to $C_6$ alkyl, $C_1$ to $C_7$ alkoxy, $C_1$ to $C_6$ substituted alkyl, $C_1$ to $C_7$ alkoxy-alkyl, oxo, (monosubstituted)amino, (disubstituted)amino, trifluoromethyl, carboxy, alkoxycarbonyl, phenyl, substituted phenyl, phenylthio, phenylsulfoxide, phenylsulfonyl, amino, or substituted amino group.

The term "heterocycle" or "heterocyclic ring" denotes optionally substituted 3 to 8-membered rings having one or more carbon atoms connected in a ring that also comprise 1 to 5 ring heteroatoms, such as oxygen, sulfur, and/or nitrogen inserted into the ring. These heterocyclic rings can be saturated, unsaturated or partially unsaturated, but are preferably saturated. An "amino-substituted heterocyclic ring" means any one of the above-described heterocyclic rings is substituted with at least one amino group. Preferred unsaturated heterocyclic rings include furanyl, thiofuranyl, pyrrolyl, pyridyl, pyrimidyl, pyrazinyl, benzoxazole, benzthiazole, quinolinlyl, triazolyl, and like heteroaromatic rings. Preferred saturated heterocyclic rings include piperidyl, aziridinyl, piperidinyl, piperazinyl, tetrahydrofurano, tetrahydropyrrolyl, and tetrahydrothiophenyl rings.

The term "substituted heterocycle" or "substituted heterocyclic ring" means the above-described heterocyclic ring is substituted with, for example, one or more, and preferably one or two, substituents which are the same or different which substituents preferably can be halogen, hydroxy, thio, alkylthio, cyano, nitro, $C_1$ to $C_4$ alkyl, $C_1$ to $C_4$ alkoxy, $C_1$ to $C_4$ substituted alkoxy, alkoxy-alkyl, $C_1$ to $C_4$ acyl, $C_1$ to $C_4$ acyloxy, carboxy, alkoxycarbonyl, carboxymethyl, hydroxymethyl, alkoxy-alkyl amino, monosubstituted)amino, (disubstituted)amino carboxamide, N—($C_1$ to $C_6$ alkyl) carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino groups, or substituted with a fused ring, such as benzo-ring. In many embodiments of substituted heterocyclic groups the substituted cycloalkyl group will have 1, 2, 3, or 4 substituent groups independently selected from hydroxy, fluoro, chloro, $NH_2$, $NHCH_3$, $NO_2$, CN, amide, mono or disubstituted amide, $SO_3H$, $PO_3H$, $N(CH_3)_2$, $CO_2CH_3$, $SC_2H_5$, $SCH_3$, $S(O)CH_3$, $S(O)_2CH_3$, methyl, ethyl, isopropyl, vinyl, trifluoromethyl, methoxy, ethoxy, isopropoxy, and trifluoromethoxy groups.

An "aryl" groups refers to a monocyclic, linked bicyclic, or fused bicyclic radical or group comprising at least one six membered aromatic "benzene" ring. Aryl groups preferably comprise between 6 and 12 ring carbon atoms and are exemplified by phenyl, biphenyl, naphthyl indanyl, and tetrahydronapthyl groups. Aryl groups can be optionally substituted with various organic and/or inorganic substituent groups, wherein the substituted aryl group in combination with all its substituents comprises between 6 and 18, or preferably 6 and 16 total carbon atoms. Preferred optional substituent groups include 1, 2, 3, or 4 substituent groups independently selected from hydroxy, fluoro, chloro, $NH_2$, $NHCH_3$, $NO_2$, $SO_3H$, $PO_3H$, $N(CH_3)_2$, $CO_2CH_3$, $SC_2H_5$, $SCH_3$, methyl, ethyl, isopropyl, vinyl, trifluoromethyl, methoxy, ethoxy, isopropoxy, and trifluoromethoxy groups.

The term "heteroaryl" means a heterocyclic aryl derivative that preferably contains a five-membered or six-membered conjugated and aromatic ring system having from 1 to 4 heteroatoms independently selected from oxygen, sulfur, and/or nitrogen, inserted into the unsaturated and conjugated heterocyclic ring. Heteroaryl groups include monocyclic heteroaromatic, linked bicyclic heteroaromatic, or fused bicyclic heteroaromatic moieties. Examples of heteroaryls include pyridinyl, pyrimidinyl, and pyrazinyl, pyridazinyl, pyrrolyl, furanyl, thiofuranyl, oxazoloyl, isoxazolyl, phthalimido, thiazolyl, quinolinyl, isoquinolinyl, indolyl, triazolyl, or a furan or thiofuran directly bonded to a phenyl, pyridyl, or pyrrolyl ring and like unsaturated and conjugated heteroaromatic rings. Any monocyclic, linked bicyclic, or fused bicyclic heteroaryl ring system that has the characteristics of aromaticity in terms of electron distribution throughout the ring system is included in this definition. Typically, the heteroaromatic ring systems contain 3 to 12 ring carbon atoms and 1 to 5 ring heteroatoms independently selected from oxygen, nitrogen, and sulfur atoms.

The term "substituted heteroaryl" means the above-described heteroaryl is substituted with, for example, one or more, and preferably one or two, substituents which are the same or different which substituents preferably can be halogen, hydroxy, protected hydroxy, thio, alkylthio, cyano, nitro, $C_1$ to $C_6$ alkyl, $C_1$ to $C_7$ substituted alkyl, $C_1$ to $C_7$ alkoxy, $C_1$ to $C_7$ substituted alkoxy, alkoxy-alkyl, $C_1$ to $C_7$ acyl, $C_1$ to $C_7$ substituted acyl, $C_1$ to $C_7$ acyloxy, carboxy, alkoxycarbonyl, carboxymethyl, hydroxymethyl, amino, (monosubstituted) amino, (disubstituted)amino, carboxamide, N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino or N-(phenylsulfonyl)amino groups. In many embodiments of substituted heteroaryl groups, the substituted cycloalkyl group will have 1, 2, 3, or 4 substituent groups independently selected from hydroxy, fluoro, chloro, $NH_2$, $NHCH_3$, $N(CH_3)_2$, $NO_2$, $SO_3H$, $PO_3H$, $CO_2CH_3$, $SC_2H_5$, $SCH_3$, methyl, ethyl, isopropyl, vinyl, trifluoromethyl, methoxy, ethoxy, isopropoxy, and trifluoromethoxy groups.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1 to 6 carbon atoms. These carbon chains may also include a carbonyl group, thus making them able to provide substituents as an acyl moiety. Preferably, arylalkyl or heteroarylalkyl is an alkyl group substituted at any position by an aryl group, substituted aryl, heteroaryl or substituted heteroaryl. Preferred groups also include benzyl, 2-phenylethyl, 3-phenyl-propyl, 4-phenyl-n-butyl, 3-phenyl-n-amyl, 3-phenyl-2-butyl, 2-pyridinylmethyl, 2-(2-pyridinyl)ethyl, and the like.

The term "substituted arylalkyl" denotes an arylalkyl group substituted on the alkyl portion with one or more, and preferably one or two, groups preferably chosen from halogen, hydroxy, oxo, amino, (monosubstituted)amino, (disubstituted)amino, guanidino, heterocyclic ring, substituted heterocyclic ring, $C_1$ to $C_6$ alkyl, $C_1$ to $C_6$ substituted alkyl, $C_1$ to $C_7$ alkoxy, $C_1$ to $C_7$ substituted alkoxy, alkoxy-alkyl, $C_1$ to $C_7$ acyl, $C_1$ to $C_7$ substituted acyl, $C_1$ to $C_7$ acyloxy, nitro, carboxy, alkoxycarbonyl, carbamoyl, carboxamide, N—($C_1$ to $C_6$ alkyl)carboxamide, N,N—($C_1$ to $C_6$ dialkyl)carboxamide, cyano, N—($C_1$ to $C_6$ alkylsulfonyl)amino, thiol, $C_1$ to $C_4$ alkylthio, $C_1$ to $C_4$ alkylsulfonyl groups; and/or the phenyl group may be substituted with one or more, and preferably one or two, substituents preferably chosen from halogen, hydroxy, protected hydroxy, thio, alkylthio, cyano, nitro, $C_1$ to $C_6$ alkyl, $C_1$ to $C_6$ substituted alkyl, $C_1$ to $C_7$ alkoxy, $C_1$ to $C_7$ substituted alkoxy, alkoxy-alkyl, $C_1$ to $C_7$ acyl, $C_1$ to $C_7$ substituted acyl, $C_1$ to $C_7$ acyloxy, carboxy, alkoxycarbonyl, carboxymethyl, hydroxymethyl, amino, (monosubstituted) amino, (disubstituted)amino, carboxamide, N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino, cyclic $C_2$ to $C_7$ alkylene or a phenyl group, substituted or unsubstituted, for a resulting biphenyl group. The substituted alkyl or phenyl groups may be substituted with one or more, and preferably one or two, substituents which can be the same or different.

Examples of the term "substituted arylalkyl" include groups such as 2-phenyl-1-chloroethyl, 2-(4-methoxyphenyl)ethyl, 4-(2,6-dihydroxyphenyl)-n-hexyl, 2-(5-cyano-3-methoxyphenyl)-n-pentyl, 3-(2,6-dimethylphenyl)propyl, 4-chloro-3-aminobenzyl, 6-(4-methoxyphenyl)-3-carboxy-n-hexyl, 5-(4-aminomethylphenyl)-3-(aminomethyl)-n-pentyl, 5-phenyl-3-oxo-n-pent-1-yl and the like.

The term "arylalkylene" specifies an arylalkyl, as defined above, where the arylalkyl radical is bonded at two positions connecting together two separate additional groups. The definition includes groups of the formula: -phenyl-alkyl- and alkyl-phenyl-alkyl-. Substitutions on the phenyl ring can be 1,2, 1,3, or 1,4. The term "substituted arylalkylene" is an arylalkylene as defined above that is further substituted preferably by halogen, hydroxy, protected hydroxy, $C_1$ to $C_4$ alkylthio, $C_1$ to $C_4$ alkylsulfoxide, $C_1$ to $C_4$ alkylsulfonyl, $C_1$ to $C_4$ substituted alkylthio, $C_1$ to $C_4$ substituted alkylsulfoxide, $C_1$ to $C_4$ substituted alkylsulfonyl, $C_1$ to $C_6$ alkyl, $C_1$ to $C_7$ alkoxy, $C_1$ to $C_6$ substituted alkyl, $C_1$ to $C_7$ alkoxy-alkyl, oxo, (monosubstituted)amino, (disubstituted)amino, trifluoromethyl, carboxy, alkoxycarbonyl, phenyl, substituted phenyl, phenylthio, phenylsulfoxide, phenylsulfonyl, amino, or protected amino group on the phenyl ring or on the alkyl group.

The term "substituted phenyl" specifies a phenyl group substituted with one or more, and preferably one or two, moieties preferably chosen from the groups consisting of halogen, hydroxy, protected hydroxy, thio, alkylthio, cyano, nitro, $C_1$ to $C_6$ alkyl, $C_1$ to $C_6$ substituted alkyl, $C_1$ to $C_7$ alkoxy, $C_1$ to $C_7$ substituted alkoxy, alkoxy-alkyl, $C_1$ to $C_7$ acyl, $C_1$ to $C_7$ substituted acyl, $C_1$ to $C_7$ acyloxy, carboxy, alkoxycarbonyl, carboxymethyl, hydroxymethyl, amino, (monosubstituted)amino, (disubstituted)amino, carboxamide, N—($C_1$ to $C_6$ alkyl)carboxamide, N,N-di($C_1$ to $C_6$ alkyl) carboxamide, trifluoromethyl, N—(($C_1$ to $C_6$ alkyl)sulfonyl) amino, N-(phenylsulfonyl)amino or phenyl, wherein the phenyl is substituted or unsubstituted, such that, for example, a biphenyl results. In many embodiments of substituted phenyl groups, the substituted cycloalkyl group will have 1, 2, 3, or 4 substituent groups independently selected from hydroxy, fluoro, chloro, $NH_2$, $NO_2$, $NHCH_3$, $N(CH_3)_2$, $CO_2CH_3$, SH, $SC_2H_5$, $SO_3H$, $SCH_3$, $PO_3H$, methyl, ethyl, isopropyl, vinyl, trifluoromethyl, methoxy, ethoxy, isopropoxy, and trifluoromethoxy groups.

The term "phenoxy" denotes a phenyl bonded to an oxygen atom. The term "substituted phenoxy" specifies a phenoxy group substituted with one or more, and preferably one or two, moieties chosen from the group consisting of halogen, hydroxy, protected hydroxy, thio, alkylthio, cyano, nitro, $C_1$ to $C_6$ alkyl, $C_1$ to $C_7$ alkoxy, $C_1$ to $C_7$ substituted alkoxy, alkoxy-alkyl, $C_1$ to $C_7$ acyl, $C_1$ to $C_7$ acyloxy, carboxy, alkoxycarbonyl, carboxymethyl, hydroxymethyl, amino, (monosubstituted)amino, (disubstituted)amino, carboxamide, N—($C_1$ to $C_6$ alkyl)carboxamide, N,N-di($C_1$ to $C_6$ alkyl) carboxamide, trifluoromethyl, N—(($C_1$ to $C_6$ alkyl)sulfonyl) amino, and N-phenylsulfonyl)amino.

The term "substituted phenylalkoxy" denotes a phenylalkoxy group wherein the alkyl portion is substituted with one or more, and preferably one or two, groups selected from halogen, hydroxy, protected hydroxy, oxo, amino, (monosubstituted)amino, (disubstituted)amino, guanidino, heterocyclic ring, substituted heterocyclic ring, $C_1$ to $C_7$ alkoxy, alkoxy-alkyl, $C_1$ to $C_7$ acyl, $C_1$ to $C_7$ acyloxy, nitro, carboxy, alkoxycarbonyl, carbamoyl, carboxamide, N—($C_1$ to $C_6$ alkyl)carboxamide, N,N—($C_1$ to $C_6$ dialkyl)carboxamide, cyano, N—($C_1$ to $C_6$ alkylsulfonyl)amino, thiol, $C_1$ to $C_4$ alkylthio, $C_1$ to $C_4$ alkylsulfonyl groups; and/or the phenyl group can be substituted with one or more, and preferably one or two, substituents chosen from halogen, hydroxy, protected hydroxy, thio, alkylthio, cyano, nitro, $C_1$ to $C_6$ alkyl, $C_1$ to $C_7$ alkoxy, alkoxy-alkyl, $C_1$ to $C_7$ acyl, $C_1$ to $C_7$ acyloxy, carboxy, alkoxycarbonyl carboxymethyl, hydroxymethyl, amino, (monosubstituted)amino, (disubstituted)amino, carboxamide, N—($C_1$ to $C_6$ alkyl) carboxamide, N,N-di($C_1$ to $C_6$ alkyl) carboxamide, trifluoromethyl, N—(($C_1$ to $C_6$ alkyl)sulfonyl) amino, N-(phenylsulfonyl)amino, or a phenyl group, substituted or unsubstituted for a resulting biphenyl group. The substituted alkyl or phenyl groups may be substituted with one or more, and preferably one or two, substituents that can be the same or different.

The term "substituted naphthyl" specifies a naphthyl group substituted with one or more, and preferably one or two, moieties either on the same ring or on different rings chosen from the group consisting of halogen, hydroxy, protected hydroxy, thio, alkylthio, cyano, nitro, $C_1$ to $C_6$ alkyl, $C_1$ to $C_7$ alkoxy, alkoxy-alkyl, $C_1$ to $C_7$ acyl, $C_1$ to $C_7$ acyloxy, carboxy, alkoxycarbonyl, carboxymethyl, hydroxymethyl, amino, (monosubstituted)amino, (disubstituted)amino, carboxamide, N—($C_1$ to $C_6$ alkyl)carboxamide, N,N-di($C_1$ to $C_6$ alkyl) carboxamide, trifluoromethyl, N—(($C_1$ to $C_6$ alkyl)sulfonyl) amino, or N-(phenylsulfonyl)amino.

The terms "halo" and "halogen" refer to the fluoro, chloro, bromo or iodo atoms. There can be one or more halogen, which are the same or different. Preferred halogens are chloro and fluoro.

The term "(monosubstituted)amino" refers to an amino (NHR) group wherein the R group is chosen from the group consisting of phenyl, $C_6$-$C_{10}$ substituted phenyl, $C_1$ to $C_6$ alkyl, $C_1$ to $C_6$ substituted alkyl, $C_1$ to $C_7$ acyl, $C_1$ to $C_7$ substituted acyl, $C_2$ to $C_7$ alkenyl, $C_2$ to $C_7$ substituted alkenyl, $C_2$ to $C_7$ alkynyl, $C_2$ to $C_7$ substituted alkynyl, $C_7$ to $C_{12}$ phenylalkyl, $C_7$ to $C_{12}$ substituted phenylalkyl, and heterocyclic ring. The (monosubstituted)amino can additionally have an amino-protecting group as encompassed by the term "protected (monosubstituted)amino."

The term "(disubstituted)amino" refers to an amino group ($NR_2$) with two substituents independently chosen from the group consisting of phenyl, $C_6$-$C_{10}$ substituted phenyl, $C_1$ to $C_6$ alkyl, $C_1$ to $C_6$ substituted alkyl, $C_1$ to $C_7$ acyl, $C_2$ to $C_7$ alkenyl, $C_2$ to $C_7$ alkynyl, $C_7$ to $C_{12}$ phenylalkyl, and $C_7$ to $C_{12}$ substituted phenylalkyl. The two substituents can be the same or different.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom. In addition, the term "protected carboxamide" means there is an amino-protecting group on the carboxamide nitrogen. Similarly, the term "protected N—($C_1$ to $C_6$ alkyl)carboxamide" means there is an amino-protecting group on the carboxamide nitrogen.

The term "alkylthio" refers to —SR groups wherein R is an optionally substituted $C_1$-$C_7$ or $C_1$-$C_4$ organic group, preferably an alkyl, cycloalkyl, aryl, or heterocyclic group, such as methylthio, ethylthio, n-propylthio, isopropylthio, n-butylthio, t-butylthio, and like groups.

The term "alkylsulfoxide" indicates —S(O)R groups wherein R is an optionally substituted $C_1$-$C_7$ or $C_1$-$C_4$ organic group, preferably an alkyl, cycloalkyl, aryl, or heterocyclic group, such as methylthio, ethylthio, n-propylthio, isopropylthio, n-butylthio, t-butylthio and like groups, such as methylsulfoxide, ethylsulfoxide, n-propylsulfoxide, isopropylsulfoxide, n-butylsulfoxide, sec-butylsulfoxide, and the like.

The term "alkylsulfonyl" indicates —$S(O)_2$R groups wherein R is an optionally substituted $C_1$-$C_7$ or $C_1$-$C_4$ organic group, which include for example groups such as methylsulfonyl, ethylsulfonyl, n-propylsulfonyl, isopropylsulfonyl, n-butylsulfonyl, t-butylsulfonyl, and the like.

The terms "phenylthio," "phenylsulfoxide," and "phenylsulfonyl" specify a sulfoxide (—S(O)—R), or sulfone (—$SO_2$R) wherein the R group is a phenyl group. The terms "substituted phenylthio," "substituted phenylsulfoxide," and "substituted phenylsulfonyl" means that the phenyl of these groups can be substituted as described above in relation to "substituted phenyl."

The term "alkoxycarbonyl" means an "alkoxy" group attached to a carbonyl group, (—C(O)—OR, wherein R is an alkyl group, preferably a $C_1$-$C_4$ alkyl group. The term "substituted alkoxycarbonyl" denotes a substituted alkoxy bonded to the carbonyl group, which alkoxy may be substituted as described above in relation to substituted alkyl.

The term "phenylene" means a phenyl group where the phenyl radical is bonded at two positions connecting together two separate additional groups. Examples of "phenylene" include 1,2-phenylene, 1,3-phenylene, and 1,4-phenylene.

The term "substituted alkylene" means an alkyl group where the alkyl radical is bonded at two positions connecting together two separate additional groups and further bearing an additional substituent. Examples of "substituted alkylene" includes aminomethylene, 1-(amino)-1,2-ethyl, 2-(amino)-1,2-ethyl, 1-(acetamido)-1,2-ethyl, 2-(acetamido)-1,2-ethyl, 2-hydroxy-1,1-ethyl, and 1-(amino)-1,3-propyl.

The term "substituted phenylene" means a phenyl group where the phenyl radical is bonded at two positions connecting together two separate additional groups, wherein the phenyl is substituted as described above in relation to "substituted phenyl."

The terms "cyclic alkylene," "substituted cyclic alkylene," "cyclic heteroalkylene," and "substituted cyclic heteroalkylene," defines such a cyclic group or radical bonded ("fused") to a phenyl radical, resulting in a fused bicyclic ring group or radical. The non-fused members of the cyclic alkylene or heteroalkylene ring may contain one or two double bonds, or often are saturated. Furthermore, the non-fused members of the cyclic alkylene or heteroalkylene ring can have one or two methylene or methine groups replaced by one or two oxygen, nitrogen, or sulfur atoms, or NH, NR, S(O) or $SO_2$ groups, where R is a lower alkyl group.

The cyclic alkylene or heteroalkylene group may be substituted once or twice by the same or different substituents preferably selected from the group consisting of the following moieties: hydroxy, protected hydroxy, carboxy, protected carboxy, oxo, protected oxo, $C_1$ to $C_4$ acyloxy, formyl, $C_1$ to $C_7$ acyl, $C_1$ to $C_6$ alkyl, $C_1$ to $C_7$ alkoxy, $C_1$ to $C_4$ alkylthio, $C_1$ to $C_4$ alkylsulfoxide, $C_1$ to $C_4$ alkylsulfonyl, halo, amino, protected amino, (monosubstituted)amino, protected (monosubstituted)amino, (disubstituted)amino, hydroxymethyl, and a protected hydroxymethyl. The cyclic alkylene or heteroalkylene group fused onto the benzene radical can contain two to ten ring members, but it preferably contains three to six members. Examples of saturated cyclic alkylene groups are 2,3-dihydro-indanyl and a tetralin ring systems. When the cyclic groups are unsaturated, examples include a naphthyl ring or indolyl group or radical. Examples of fused cyclic groups which each contain one nitrogen atom and one or more double bond, preferably one or two double bonds, are when the benzene radical is fused to a pyridyl, pyranyl, pyrrolyl, pyridinyl, dihydropyrolyl, or dihydropyridinyl groups or radicals. Examples of fused cyclic groups that each contain one oxygen atom and one or two double bonds are illustrated by a benzene radical ring fused to a furanyl, pyranyl, dihydrofuranyl, or dihydropyranyl ring. Examples of fused cyclic groups which each have one sulfur atom and contain one or two double bonds are when the benzene radical is fused to a thienyl, thiopyranyl, dihydrothienyl, or dihydrothiopyranyl ring. Examples of cyclic groups which contain two heteroatoms selected from sulfur and nitrogen and one or two double bonds are when the benzene radical ring is fused to a thiazolyl, isothiazolyl, dihydrothiazolyl, or dihydroisothiazolyl ring. Examples of cyclic groups which contain two heteroatoms selected from oxygen and nitrogen and one or two double bonds are when the benzene ring is fused to an oxazolyl, isoxazolyl, dihydrooxazolyl or dihydroisoxazolyl ring. Examples of cyclic groups which contain two nitrogen heteroatoms and one or two double bonds occur when the benzene ring is fused to a pyrazolyl, imidazolyl, dihydropyrazolyl or dihydroimidazolyl ring or pyrazinyl.

The term "carbamoyl" refers to a carbamate group or radical, which often derived from the reaction of an organic isocyanate compound $R_1$—NCO with an alcohol $R_2$—OH, to yield a carbamate compound having the structure $R_1$—NH—C(O)—$OR_2$ wherein the nature of the $R_1$ and $R_2$ radicals are further defined by the circumstances.

One or more of the compounds of the invention may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as nitrogen containing heterocycles or amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to positively charged counter-ions for the carboxylate anion of a carboxylate salt. Inorganic positively charged counter-ions include but are not limited to the alkali and alkaline earth metals, (such as lithium, sodium, potassium, calcium, magnesium, etc.) and other divalent and trivalent metallic cations such as barium, aluminum and the like, and ammonium $(NH_4)^+$ cations. Organic cations include ammonium cations derived from acid treatment or alkylation of primary, secondary, or tertiary amines such as trimethylamine and cyclohexylamine. Examples of organic cations include dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., *J. Pharm. Sci.* (1977) 66:1-19, which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when $R^5$ is substituted with a (quaternary ammonium)methyl group. A preferred cation for the carboxylate anion is the sodium cation.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), L- or D-naphthalanine, ornithine ("Orn"), homoarginine (homoArg) and others well known in the peptide art, such as those described in M. Bodanzsky, "Principles of Peptide Synthesis," 1st and 2nd Revised Ed., Springer-Verlag, New York, N.Y., 1984 and 1993, and Stewart and Young, "Solid Phase Peptide Synthesis," 2nd Ed., Pierce Chemical Co., Rockford, Ill., 1984, both of which are incorporated herein by reference. Amino acids and amino acid analogs can be purchased commercially (Sigma Chemical Co.; Advanced Chemtech) or synthesized using methods known in the art.

"Amino acid side chain" refers to any side chain from the above-described "amino acids."

"Substituted" herein refers to a substituted moiety, such as a hydrocarbon, e.g., substituted alkyl or benzyl wherein at least one element or radical, e.g., hydrogen, is replaced by another, e.g., a halogen, as in chlorobenzyl.

A residue of a chemical species, as used in the specification and concluding claims, refers to a structural fragment or a moiety that is the resulting product of the chemical species in a particular reaction scheme or subsequent formulation or chemical product, regardless of whether the structural fragment or moiety is actually obtained from the chemical species. Thus, an ethylene glycol residue in a polyester refers to one or more —$OCH_2CH_2O$— repeat units in the polyester, regardless of whether ethylene glycol is used to prepare the polyester.

The term "organic residue" or "organic group" defines a carbon containing residue or group, i.e., a residue comprising at least one carbon atom. Organic residues can contain various heteroatoms, or be bonded to another molecule through a heteroatom, including oxygen, nitrogen, sulfur, phosphorus, or the like. Examples of organic residues include but are not limited to alkyl or substituted alkyls, alkoxy or substituted alkoxy, hydroxyalkyls and alkoxyalkyls, mono or di-substituted amino, amide groups, CN, $CO_2H$, CHO, $COR^6$, $CO_2R^6$, $SR^6$, $S(O)R^6$, $S(O)_2R^6$, alkenyl, cycloalkyl, cycloalkenyl, aryl, and heteroaryl, wherein $R^6$ is an alkyl. More specific examples of species of organic groups or residues include but are not limited to, $NHCH_3$, $N(CH_3)_2$, $CO_2CH_3$, $SC_2H_5$, $SCH_3$, $S(O)CH_3$, $S(O)_2CH_3$, methyl, ethyl, isopropyl, vinyl, trifluoromethyl, methoxy, ethoxy, isopropoxy, trifluoromethoxy, $CH_2OCH_3$, $CH_2OH$, $CH_2NH_2$, $CH_2NHCH_3$, or $CH_2N(CH_3)_2$ groups or residues. Organic resides can comprise 1 to 18 carbon atoms, 1 to 15 carbon atoms, 1 to 12 carbon atoms, 1 to 8 carbon atoms, 1 to 6 carbon atoms, or 1 to 4 carbon atoms.

By the term "effective amount" of a compound as provided herein is meant a sufficient amount of one or more compounds in a composition that is sufficient to provide the desired regulation of a desired biological function, such as gene expression, protein function, or more particularly the induction of sweet taste perception in an animal or a human. As will be pointed out below, the exact amount required will vary from subject to subject, depending on the species, age, general condition of the subject, specific identity and formulation of the comestible composition, etc. Thus, it is not possible to specify an exact "effective amount." However, an appropriate effective amount can be determined by one of ordinary skill in the art using only routine experimentation.

It must be noted that, as used in the specification and the appended claims, the singular forms "a," "an," and "the" include plural referents unless the context clearly dictates otherwise. Thus, for example, reference to "an aromatic compound" includes mixtures of aromatic compounds.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyls where there is substitution.

Further, unless stated to the contrary, a formula with chemical bonds shown only as solid lines and not as wedges or dashed lines contemplates each possible isomer, e.g., each enantiomer and diastereomer, and a mixture of isomers, such as racemic or scalemic mixtures.

The Amide Compounds of the Invention

The compounds of the invention are all organic (carbon containing) compounds that have at least one "amide" group therein and have the following general structure, which will be hereinafter referred to as the amide compounds having Formula (I):

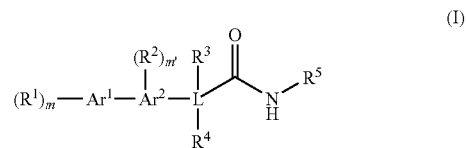

(I)

Also, disclosed are comestibly acceptable salts of compounds of Formula (I).

The amide compounds of Formula (I) do not include amide compounds that are known to naturally occur in biological systems or foods, such as for example naturally occuring amino acids, peptides, proteins, nucleotides, nucleosides, nucleic acids, polysaccharide, certain amino sugars and/or amino polysaccharides, glycopeptides or glycoproteins, or the like. Neither does the present invention relate to compounds that are synthetic close structural analogs of amino acids, peptides, proteins, nucleotides, nucleosides, nucleic acids, certain amino sugars and/or amino polysaccharides, glycopeptides or glycoproteins, or the like, such as for example the peptide analog sweeteners such as aspartame and neotame, or saccharide analog sweeteners such as Sucralose. The amide compounds of Formula (I) of the invention are man-made and artificial synthetic amide compounds that typically do not comprise peptide or saccharide residues.

For the various embodiments of the compounds of Formula (I), the $Ar^1$, $Ar^2$, L, $R^1$, $R^2$, $R^3$, $R^4$, and $R^5$ groups can be and are independently further defined and/or limited in various ways, as will now be further detailed hereinbelow, so as to define and/or include a substantial number of structurally related subgenera and/or species of the compounds of Formula (I), and hence the various inventions disclosed herein are related because of their relationship to the compounds of Formula (I).

It is hereby specifically contemplated that any of the subgenuses and/or species of compounds of Formula (I) described herein can, either in their specified form or as one or more comestibly acceptable salts, be combined in an effective amount with one or more comestible or medicinal products or precursors thereof by the processes and/or methods described elsewhere herein, or by any such other processes as would be apparent to those of ordinary skill in preparing comestible or medicinal products or precursor thereof, to form one or more sweet flavor modified comestible or medicinal products, or one or more precursors or sweetener concentrate compositions thereof.

As one of ordinary skill in the art can discern, the compounds of Formula (I) comprise a —C(O)NH— group, which is well known to those of ordinary skill in the art as an "amide" group. Moreover, the compounds of Formula (I) as disclosed and claimed herein typically comprise a common and linked core of molecular/structural features that at least include an $R^5$ group which is bonded to the nitrogen atom of the "amide" group, which amide group is additionally linked from its carbonyl carbon atom to the L, $Ar^1$, and $Ar^2$ groups, as illustrated above. The $R^1$, $R^2$, $R^3$, and $R^4$ groups can be hydrogen, or optional substituent groups as disclose hereinbelow. Without wishing to be bound by any scientific theory, it is believed that this core of structural features (the amide, $R^5$, and L groups, and the $Ar^1$ and $Ar^2$ aryl or heteroaryl groups) together form a "scaffold" of suitable size, shape, and polarity so as to promote binding of the compounds as a whole to the relevant biological receptors such as sweet taste T1R2/T1R3 receptors. The $R^1$, $R^2$, $R^3$, and $R^4$ groups, and optional substituents on $R^5$, on the periphery of the common core can also be of suitable size, shape, and polarity to allow binding to the relevant biological receptors, and/or optimize other parameters such as solubility, but can in some embodiments be optional, i.e., present or absent, and can comprise substituent groups having substantial chemical and structural diversity. The $R^1$, $R^2$, $R^3$, and $R^4$ groups can be selected for suitable combinations of size, polarity, and/or molecular weight to promote binding to the relevant biological receptors, such as for example, being limited to selected ranges of carbon atoms per substituent. The overall molecular weight and/or number of carbon atoms of the compounds of Formula (I) can also be selelected or limited as is further discussed below.

In some embodiments of the compounds of Formula (I), $Ar^1$ and $Ar^2$ are independently selected from monocyclic, aryl, fused bicyclic aryl, monocyclic heteroaryl or fused bicyclic heteroaryl rings; m is selected from the integers 0, 1, 2, 3, 4, or 5; m' is selected from the integers 0, 1, 2, 3, or 4; each $R^1$ and $R^2$ is independently selected from the group consisting of OH, $NH_2$, SH, $SO_3H$, $PO_3H$, halogen, and a $C_1$-$C_6$ organic radical; L is a carbon or nitrogen atom; $R^3$ is hydrogen, oxygen, hydroxy, halogen, or a $C_1$-$C_6$ organic radical; $R^4$ is absent, or hydrogen, oxygen, hydroxy, halogen, or a $C_1$-$C_6$ organic radical; $R^5$ a $C_1$-$C_{14}$ organic radical comprising a normal or branched alkyl or cycloalkyl, wherein the normal or branched alkyl or cycloalkyl optionally comprises one to four substituents independently selected from OH, $NH_2$, $NO_2$, SH, $SO_3H$, $PO_3H$, halogen, and a $C_1$-$C_6$ or $C_3$-$C_{10}$ organic radical, such as an optionally substituted $C_3$-$C_{10}$ alkyl or cycloalkyl radical.

In some other embodiments, alternative, and/or additional and optional limitations on the chemical and physical characteristics of the $Ar^1$, $Ar^2$, L, $R^1$, $R^2$, $R^3$, $R^4$, and $R^5$ groups are further described below.

Ar Groups

In some embodiments of the compounds of Formula (I), $Ar^1$ and $Ar^2$ are independently selected from monocyclic aryl, fused bicyclic aryl, monocyclic heteroaryl, and fused bicyclic heteroaryl groups. In some embodiments, $Ar^1$ and $Ar^2$ are independently selected from a monocyclic aryl rings (such as phenyl), and monocyclic heteroaryl rings having five or six ring atoms.

The monocyclic aryl groups include at least phenyl rings, and can be substituted (m or m' are not zero) or unsubstituted (m or m' are zero). The fused bicyclic aryl groups include at least napthyl rings, tetrahydronapthyl, and indanyl rings, and can be substituted (m or m' are not zero) or unsubstituted (m or m' are zero). The monocyclic heteroaryl groups can include heteroaromatic rings with either five or six ring atoms, wherein at least one ring atom is carbon and at least one ring heteroatom is selected from nitrogen, oxygen, and sulfur. Such monocyclic heteroaryls include but are not limited to pyridinyl, pyrimidinyl, pyrazinyl, pyrazolyl, pyrrolyl, furanyl, thiofuranyl, oxazoloyl, isoxazolyl, oxadiazolyl, triazolyl, tetrazolyl, and like heteroaromatic ring groups. The monocyclic heteroaryl groups and can be substituted (m or m' are not zero) or unsubstituted (m or m' are zero). The fused bicyclic heteroaromatic groups comprise two fused rings wherein at least one ring is aromatic, such an aryl ring or heteroaryl ring, and at least one of the two fused rings has at least one ring heteroatom selected from nitrogen, oxygen, and sulfur. Example of fused bicyclic heteroaromatic groups include quinolinyl, isoquinolinyl, indolyl, benzofuran, dihydrobenzofuran, benzothiofuran, dihydrobenzothiofuran, phthalimido, thiazolyl, and like fused ring groups. The fused bicyclic heteroaryl groups and can be substituted (m or m' are not zero) or unsubstituted (m or m' are zero).

To further illustrate the inventions disclosed herein, in some embodiments, the invention relates to compounds where $Ar^1$ is a monocyclic aryl group such as a phenyl group, and $Ar^2$ is selected from a monocyclic aryl such as a phenyl group, a fused bicyclic aryl such as a napthyl group, a monocyclic heteroaryl group such as a pyridyl group, or a fused bicyclic heteroaryl group such as a quinolinyl group. In other embodiments, $Ar^1$ can be a fused bicyclic aryl group such as a napthyl or indanyl group, and $Ar^2$ is selected from a monocyclic aryl, fused bicyclic aryl, monocyclic heteroaryl, or fused bicyclic heteroaryl group. In yet other examples, $Ar^1$ can be a monocyclic heteroaryl group such a pyridyl, pyrimidyl, furanyl, or thiofuranyl group, and $Ar^2$ is a monocyclic aryl such as a phenyl, fused bicyclic aryl such as napthyl group, a monocyclic heteroaryl group, or fused bicyclic heteroaryl group. In yet additional examples, $Ar^1$ can be a fused bicyclic heteroaryl group such as a quinolinyl or benzofuranyl group, and $Ar^2$ is a monocyclic aryl, fused bicyclic aryl, monocyclic heteroaryl, or fused bicyclic heteroaryl group.

Alternatively, in some embodiments, $Ar^2$ can be a monocyclic aryl group such as a phenyl group, and $Ar^1$ is selected a monocyclic aryl, fused bicyclic aryl, monocyclic heteroaryl, or fused bicyclic heteroaryl ring. In yet another example, $Ar^2$ can be a fused bicyclic aryl group such as a napthyl or tetrahydronapthyl group, and $Ar^1$ is a monocyclic aryl, fused bicyclic aryl, monocyclic heteroaryl, or fused bicyclic heteroaryl ring. In yet another example, $Ar^2$ can be a monocyclic heteroaryl group such as a pyridyl group, and $Ar^1$ is a monocyclic aryl, fused bicyclic aryl, monocyclic heteroaryl, or fused bicyclic heteroaryl ring. In still another example, $Ar^2$ can be a fused bicyclic heteroaryl group such a quinolinyl or benzofuran group, and $Ar^1$ is a monocyclic aryl, fused bicyclic aryl, monocyclic heteroaryl, or fused bicyclic heteroaryl ring.

In one particular aspect of the invention, the $Ar^1$ and $Ar^2$ groups can be independently selected from the group consisting of phenyl, napthyl, indole, pyridyl, pyrimidyl, furan, thiofuran, benzofuran, triazolyl, and benzothiofuran groups, or alternatively, $Ar^1$ and $Ar^2$ groups can be independently selected from a phenyl, pyridyl, pyrimidyl, pyrizinyl, pyrrolyl, pyrazolyl, furanyl, thiofuranyl, or triazolyl ring.

In some aspects of the compounds of the invention, $Ar^1$ can be a phenyl ring. In many related aspects, $Ar^2$ can be a phenyl ring. In aspects, $Ar^1$ and $Ar^2$ are both phenyl rings. In many aspects of the compounds of Formula (I), $Ar^2$ is a phenyl ring, and $Ar^1$ is a five or six membered monocyclic heteroaryl ring, such as for example a pyridyl, pyrimidyl, pyrazinyl, furanyl, thiofuranyl, pyrrolyl, imidazolyle, thiazolyly, oxazolyl, or like five or six-membered heteroaryl rings.

In some embodiments, the Ar¹ and Ar² groups of Formula (I) comprise an aryl ring, i.e., they each contain somewhere within their ring structures at least one six-membered aromatic phenyl ring. The aryls can include benzene and napthalene rings, which may not, but in many embodiments are, further substituted with at least 1, 2, 3, 4, or 5 independentely selected R¹ or R² substituent groups, which can be any of the alternatives recited below.

Ar¹

The Ar¹ ring radical, which is bonded to the Ar² ring radical, can be a monocyclic aryl, fused bicyclic aryl, monocyclic heteroaryl, or fused bicyclic heteroaryl group, which can be substituted (m is not zero) or unsubstituted (m is zero). In many embodiments, the Ar¹ ring radical plus all of its R¹ substituents comprise from 3 to 18 carbon atoms, or from 4 to 12 carbon atoms, or from 5 to 10 carbon atoms.

In some aspects of the compounds of Formula (I), Ar¹ can be a monocyclic aryl ring such as a 2-, 3-, or 4-mono-substituted phenyl, 2,4-, 2,3-, 2,5, 2,6, 3,5-, or 3,6-disubstituted phenyl, 3-alkyl-4-substituted phenyl, a tri-, tetra-, or penta-substituted phenyl, wherein the substituent groups (i.e., R¹) can be defined as recited elsewhere herein. In some embodiments, the R¹ substituents of the Ar¹ ring can be independently selected from any of the groups described hereinbelow, including for example inorganic substituents such as hydrogen, OH, $NH_2$, $NO_2$, SH, $SO_3H$, $PO_3H$, or halogens (e.g., fluoro and chloro), the R¹ substituents of the Ar¹ ring can be independently selected from various $C_1$-$C_6$ or $C_1$-$C_4$ organic radicals as described hereinbelow, includeing for example $NHCH_3$, $N(CH_3)_2$, $CO_2CH_3$, $SC_2H_5$, $SCH_3$, $S(O)CH_3$, $S(O)_2CH_3$, $S(O)_2NHCH_3$, methyl, ethyl, isopropyl, vinyl, trifluoromethyl, methoxy, ethoxy, isopropoxy, and trifluoromethoxy, In some aspects, two adjacent substituents on Ar¹ may together form a heterocyclic ring fused to Ar1, such as for example a methylenedioxy or ethylenedioxy ring fused to two adjacent carbons on the aromatic Ar¹ ring. In other aspects, two adjacent positions on the Ar¹ ring can be substituted so that the two substituents together form a five to seven membered saturated carbocyclic or heterocyclic ring that may optionally comprise one or two ring heteroatoms selected from oxygen, nitrogen, or sulfur ring atoms.

In some other embodiments, Ar¹ can be a monocyclic heteroaryl such as a pyridyl ring. Further examples of monocyclic heteroaryl rings for Ar¹ are pyrimidyl, pyrizinyl, or pyridazinyl rings having the following formulas:

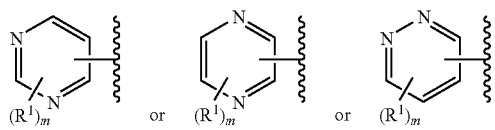

wherein m is selected from the integer 0, 1, 2, or 3.

Additional examples of monocyclic heteroaryl groups for Ar¹ include, but are not limited to, five membered heteroaryl rings having one of the following formulae:

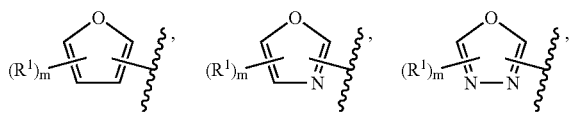

-continued

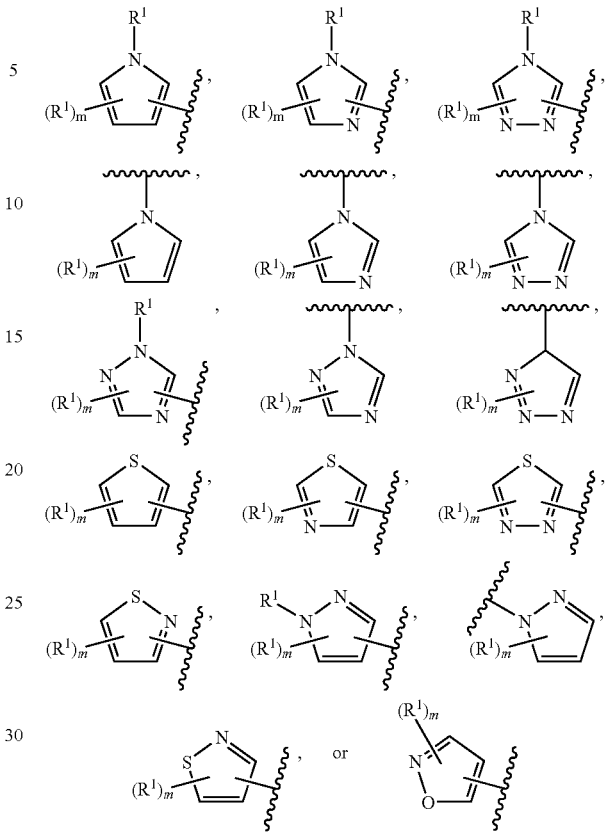

wherein m is 0, 1, 2, or 3. In such compounds of Formula (I), each R¹ can be as defined elsewhere herein. In some preferred embodiments of the monocyclic heteroaryl amide compounds Ar¹ is a furan, thiofuran, or oxazole ring, which may be either substituted or unsubstituted.

In some aspects of the invention, two adjacent substituents for Ar¹ can together form a five to eight membered bicyclic carbocyclic or heterocyclic ring fused to Ar¹, such as for example a methylenedioxy ring. In some examples, the Ar¹ group of the compounds of Formula (I) can have the following fused bicyclic heterocyclic structures:

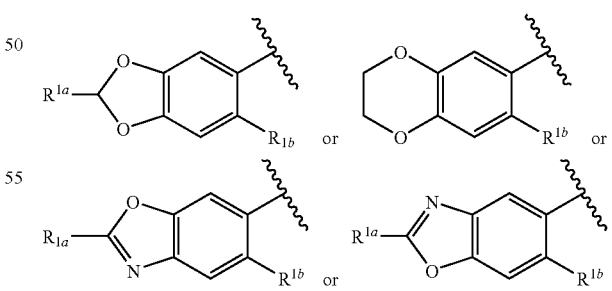

wherein $R^{1a}$ and $R^{1b}$ are independently chosen from any of the R¹ substituents defined elsewhere herein.

In additional embodiments of the compounds of Formula (I), Ar¹ is a substituted heteroaryl ring comprising 5 to 12 carbon atoms, with optional R¹ substituent groups as described further elsewhere herein.

Ar²

The Ar² ring radical, is bonded to the Ar¹ ring and the L atom, and can be a monocyclic aryl, fused bicyclic aryl, monocyclic heteroaryl, and fused bicyclic heteroaryl ring, which can be substituted (m' is not zero) or unsubstituted (m' is zero). In many embodiments, Ar² is a monocyclic aryl ring, such as a phenyl ring, or any of a variety of five-membered or six-membered heteroaryl rings, as is further described below.

In many embodiments, the Ar² ring radical plus all of its R² substituents comprise from 3 to 18 carbon atoms, or from 4 to 12 carbon atoms, or from 5 to 10 carbon atoms.

In some embodiments of the compounds of Formula (I), Ar² can be a monocyclic aryl ring such as a 2-, 3-, or 4-mono-substituted phenyl, 2,4-, 2,3-, 2,5, 2,6, 3,5-, or 3,6-disubstituted phenyl, 3-alkyl-4-substituted phenyl, a tri- or tetra-substituted phenyl wherein the substituent groups (i.e., R²) can be independently selected from the various alternatives described elsewhere herein, such as for example inorganic substitents such as hydrogen, OH, $NH_2$, $NO_2$, SH, $SO_3H$, $PO_3H$, halogens (e.g., fluoro and chloro), or $C_1$-$C_6$ or $C_1$-$C_4$ organic radicals as recited below. In some aspects of the invention, two adjacent substituents for Ar² can together form a five to eight membered carbocyclic or heterocyclic ring fused to Ar², such as for example a methylenedioxy ring. In some aspects of the invention, two adjacent substituents for Ar¹ can together form a five to eight membered bicyclic carbocyclic or heterocyclic ring fused to Ar¹, such as for example a methylenedioxy ring.

In other embodiments, Ar² can be a monocyclic heteroaryl group such as a pyridyl ring. Some specific examples of other monocyclic heteroaryl rings for Ar² have the following formulae:

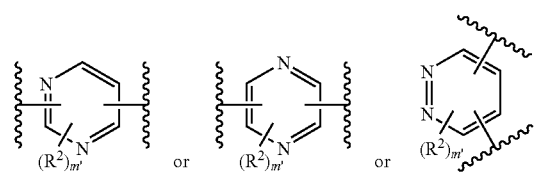

wherein m' is selected from the integers 0, 1, or 2. Additional examples of monocyclic heteroaryl rings for Ar², include, but are not limited to five-membered heteroaryl rings having at least one ring carbon atom and at least one ring heteroatom selected from oxygen, sulfur, and nitrogen, examples of such heteroaryls having the following exemplary formulae:

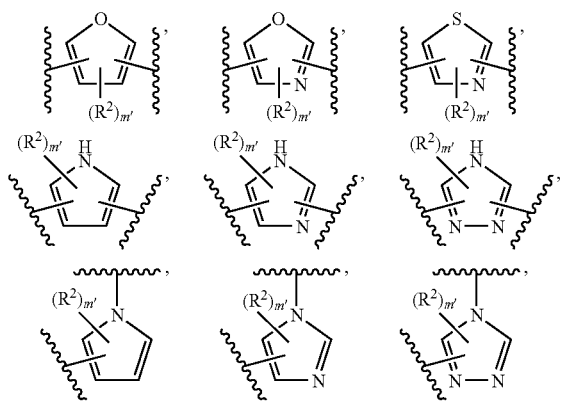

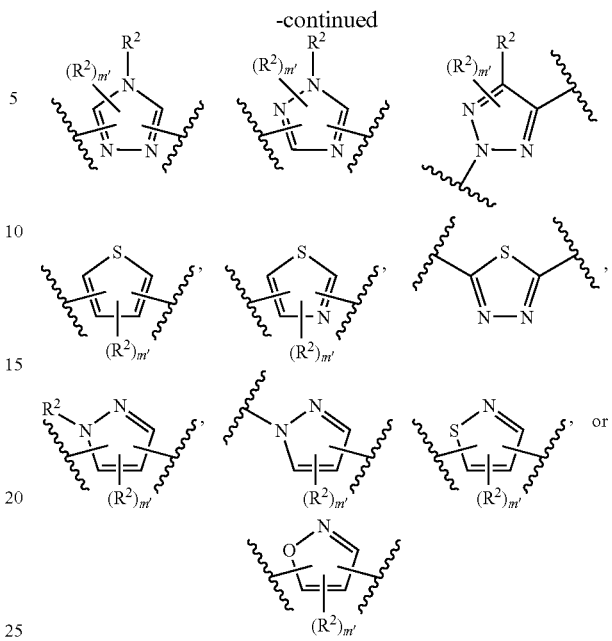

wherein m' is 0, 1, or 2. In such compounds of Formula (I), each R² can be as defined elsewhere herein.

In additional embodiments of the compounds of Formula (I), Ar² can be a substituted heteroaryl ring comprising 5 to 12 carbon atoms and wherein the optional substituent groups (R²) are independently selected from any of the alternatives listed elsewhere hereinbelow.

R¹ and R²

In the compounds of Formula (I), the groups Ar¹ and/or Ar² can be substituted with various substituents disclosed herein. Specifically, Ar¹ can have 0, 1, 2, 3, 4, or 5 substituents, denoted in Formula (I) as R¹ (i.e., $(R^1)_m$, where m is selected from the integers 0, 1, 2, 3, 4, or 5). Ar² can have 0, 1, 2, 3, or 4 substituents, denoted in Formula (I) as R² (i.e., $(R^2)_m$, where m' is selected from the integers 0, 1, 2, 3, or 4. In some specific examples, m and m' are independently selected from the integers 0, 1, or 2. In other examples, m and m' are independently 0 or 1. It will be understood by those of ordinary skill in the art that if m or m' are zero, any carbon atom in a ring that could be substituted an R¹ or an R² substituent is assumed to carry a hydrogen substituent.

In many embodiments of the compounds of Formula (I), the substituents R¹ and R² can be independently selected from the group consisting of an inorganic radical such as OH, $NH_2$, SH, $NO_2$, $SO_3OH$, $PO_3H$, halogen, and $C_1$-$C_6$ organic radical, or $C_1$-$C_4$ organic radicals. The organic radicals R¹ and R² for can be independently selected from, for example, alkyl, alkoxy, alkoxy-alkyl, hydroxyalkyl, $NHR^6$, $NR^6R^{6'}$, CN, $CO_2H$, $CO_2R^6$, C(O)H, $C(O)R^6$, $C(O)NHR^6$, $C(O)NR^6$, $R^{6'}$, $OC(O)R^6$, $NHC(O)R^6$, $SR^6$, $S(O)R^6$, $S(O)_2R^6$, $S(O)NHR^6$, alkenyl, cycloalkyl, cycloalkenyl, heterocycle, aryl, and heteroaryl, where $R^6$ and $R^{6'}$ can be a $C_1$-$C_6$ or $C_1$-$C_4$ alkyl, or methyl. The organic radicals R¹ and R² radical can also be independently selected from alkyl, haloalkyl, haloalkoxy, alkoxyl, alkoxy-alkyl, hydroxy-alkyl, aryl, heteroaryl, CN, C(O)H, $CO_2H$, $NHR^6$, $NR^6_2$, $CO_2R^6$, $COR^6$, $C(O)R^6$, $SR^6$, $S(O)R^6$, $S(O)_2R^6$, $S(O)_2NHR^6$, and $C(O)NHR^6$, wherein $R^6$ is $C_1$-$C_4$ alkyl.

In some aspects of the compounds of Formula (I), each R¹ and R² can be independently selected from the group consisting of hydroxy, fluoro, chloro, $NH_2$, $NO_2$, $NHCH_3$, $N(CH_3)_2$, CN, $OC(O)CH_3$, $SCH_3$, $S(O)CH_3$, $S(O)_2CH_3$, $S(O)_2NHCH_3$, $SC_2H_5$, methyl, ethyl, propyl, isopropyl, vinyl, allyl, $CH_2OH$, $CH_2OCH_3$, $CH_2OCH_2CH_3$, C(O)H, $C(O)CH_3$, trifluoromethyl, methoxy, ethoxy, isopropoxy, trifluoromethoxy, cyclopentyl, cyclhexyl, phenyl, pyridyl, pyrimidyl, pyrrolyl, furanyl, and thiofuranyl groups. In related aspects of the compounds of Formula (I), each $R^1$ and $R^2$ can be independently selected from the group consisting of hydroxy, fluoro, chloro, $NH_2$, $NO_2$, $NHCH_3$, $N(CH_3)_2$, $COOCH_3$, $SCH_3$, $SC_2H_5$, methyl, ethyl, propyl, isopropyl, vinyl, allyl, $S(O)CH_3$, $S(O)_2CH_3$, $S(O)_2NHCH_3$, CN, $CH_2OH$, C(O)H, $C(O)CH_3$, trifluoromethyl, methoxy, ethoxy, isopropoxy, trifluoromethoxy groups.

In additional related aspects of the compounds of Formula (I), each $R^1$ and/or each $R^2$ can be independently selected from alkyl, alkoxy, alkoxy-alkyl, hydroxyalkyl, OH, CN, $CO_2H$, $CO_2R^6$, CHO, $COR^6$, $CONHR^6$, $SR^6$, $S(O)R^6$, $S(O)_2R^6$, $S(O)NHR^6$, halogen, alkenyl, cycloalkyl, cycloalkenyl, heterocycle, aryl, and heteroaryl, where $R^6$ is $C_1-C_6$ alkyl. In some related but alternative embodiments of the compounds of Formulas (I), each $R^1$ and/or each R can be independently selected from the group consisting of OH, $NH_2$, SH, $NO_2$, $SO_3H$, $PO_3H$, halogen, $C_1-C_4$ alkyl, $C_1-C_4$ haloalkyl, $C_1-C_4$ haloalkoxy, $C_1-C_4$ alkoxyl, $C_1-C_4$ alkoxy-alkyl, $C_1-C_4$ hydroxy-alkyl, $NHR^6$, $NR^6_2$, CN, $CO_2H$, $CO_2R^6$, CHO, $COR^6$, SH, $SR^6$, $S(O)R^6$, $S(O)_2R^6$, or $S(O)_2NHR$ wherein $R^6$ is $C_1-C_4$ alkyl. In many aspects of the compounds of Formulas (I), each $R^1$ and/or each $R^2$ can be independently selected from the group consisting of hydroxy, fluoro, chloro, $NH_2$, $NO_2$, $SO_3H$, $PO_3H$, CN, $NHCH_3$, $N(CH_3)_2$, $OC(O)CH_3$, $SCH_3$, $S(O)CH_3$, $S(O)_2CH_3$, $S(O)NHCH_3$, $SC_2H_5$, methyl, ethyl, isopropyl, n-propyl, n-butyl, 1-methyl-propyl, isobutyl, t-butyl, vinyl, trifluoromethyl, methoxy, ethoxy, isopropoxy, and trifluoromethoxy groups.

L Group

In other embodiments of the compounds of Formula (I), L can be a carbon or nitrogen atom. In many embodiments of the invention, L is a carbon atom.

$R^3$ and $R^4$

In some embodiments of the compounds of Formula (I), $R^3$ can be hydrogen, oxygen, hydroxy, amino, halogen, or a $C_1-C_6$ organic radical. In some specific examples, $R^3$ can be a hydrogen, a $C_1-C_4$ alkyl, $C_1-C_4$ alkoxy, $C_1-C_4$ hydroxyalkyl, $C_1-C_4$ alkoxyalkyl, $C_1-C_4$ monoalkylamino, or $C_1-C_4$ dialkylamino. In many aspects, $R^3$ can be a methyl.

In related embodiments of the compounds of Formula (I), $R^4$ can be absent (for example, when L is a nitrogen atom), or be a hydrogen, oxygen, hydroxy, amino, halogen, or a $C_1-C_6$ organic radical. In some specific examples, $R^4$ can be a hydrogen, a $C_1-C_4$ alkyl, $C_1-C_4$ alkoxy, $C_1-C_4$ hydroxyalkyl, $C_1-C_4$ alkoxyalkyl, $C_1-C_4$ monoalkylamino, or $C_1-C_4$ dialkylamino. In many aspects, $R^4$ can be methyl.

In other related aspects, $R^3$ and $R^4$ together can form a cyclopropyl, cyclobutyl, cyclopentyl, or cyclohexyl ring. Also, $R^3$ and $R^4$ can together form an ethylenedioxy or a trimethylenedioxy ring. Independently, $R^3$ and $R^4$ can also be selected from $C_1-C_4$ alkyls. In many aspects, $R^3$ and $R^4$ are both methyl.

Still further examples of combinations of $R^3$ and $R^4$ include where one of $R^3$ and $R^4$ is a $C_1-C_4$ alkyl (methyl, ethyl, n-propyl, i-propyl, n-buytl, i-butyl, or t-butyl) and the other of $R^3$ and $R^4$ is hydrogen. Also included are where one of $R^3$ and $R^4$ is methyl and the other of $R^3$ and $R^4$ is hydrogen. In another example, $R^3$ and $R^4$ together can be an oxygen atom and L can be a carbon atom, thus forming a pyruvate derivative.

In some embodiments of the compounds of Formula (I), $R^4$ can be absent, for example, when L is a nitrogen atom. In these examples, $R^3$ can be any of the $R^3$ disclosed herein. For example, $R^3$ can be a $C_1-C_4$ alkyl and $R^4$ can be absent. In another example, $R^3$ can be a methyl and $R^4$ can be absent.

In some preferred embodiments of the compounds of Formula (I), L is a carbon atom and both $R^3$ and $R^4$ are methyl groups.

$R^5$

In many embodiments of the compounds of Formula (I), the substituent $R^5$ can be a $C_1-C_{14}$ organic radical, a $C_1-C_{10}$ organic radical, a $C_3-C_{10}$ organic radical, or a $C_1-C_6$ organic radical.

The organic radicals can comprise monocyclic aryl, fused bicyclic aryl, monocyclic heteroaryl, or fused bicyclic heteroaryl rings, which may be optionally substituted with 1, 2, 3, 4, or 5 substituent groups independently selected from the group consisting of OH, $NH_2$, SH, $NO_2$, $SO_3H$, $PO_3H$, halogen, $C_1-C_4$ alkyl, $C_1-C_4$ haloalkyl, $C_1-C_4$ haloalkoxy, $C_1-C_4$ alkoxyl, $C_1-C_4$ alkoxy-alkyl, $C_1-C_4$ hydroxy-alkyl, $NHR^6$, $NR^6_2$, CN, $CO_2H$, $CO_2R^6$, CHO, $COR^6$, SH, $SR^6$, $S(O)R^6$, $S(O)_2NHR^6$, or $S(O)_2R^6$, wherein $R^6$ is $C_1-C_4$ alkyl. In some embodiments, the substituent groups are independently selected from the group consisting of hydroxy, fluoro, chloro, $NH_2$, $NO_2$, $SO_3H$, $PO_3H$, $NHCH_3$, $N(CH_3)_2$, $COOCH_3$, $SCH_3$, $S(O)CH_3$, $S(O)NHCH_3$, $S(O)_2CH_3$, $SC_2H_5$, methyl, ethyl, isopropyl, n-propyl, n-butyl, 1-methyl-propyl, isobutyl, t-butyl, vinyl, trifluoromethyl, methoxy, ethoxy, isopropoxy, and trifluoromethoxy groups.

The organic radicals can also comprise a normal or branched alkyl or cycloalkyl, wherein the normal or branched alkyl or cycloalkyl can optionally comprise one to four substituents independently selected from OH, $NH_2$, $NO_2$, SH, $SO_3H$, $PO_3H$, halogen, and a $C_1-C_6$ organic radical. In some specific examples, $R^5$ can be $C_1-C_6$ branched alkyl or cycloalkyl. In other examples, $R^5$ can be a $C_1-C_{10}$ normal or branched alkyl or cycloalkyl, substituted with 1, 2, or 3 substituents independently selected from the group consisting of hydroxy, fluoro, chloro, $NH_2$, $NO_2$, $NHCH_3$, $N(CH_3)_2$, $COOCH_3$, $SCH_3$, $S(O)CH_3$, $S(O)_2CH_3$, $S(O)_2NHCH_3$, $SC_2H_5$, methyl, ethyl, propyl, isopropyl, vinyl, trifluoromethyl, methoxy, ethoxy, isopropoxy, and trifluoromethoxy groups.

In other embodiments of the amide compounds of Formula (I), $R^5$ can be a "benzylic" radical having the structure:

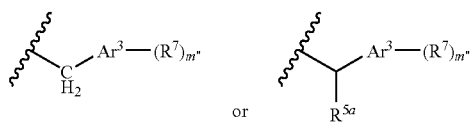

wherein $Ar^3$ is an aromatic or heteroaromatic ring such as phenyl, pyridyl, furanyl, thiofuranyl, pyrrolyl, or similar aromatic ring systems, m" is 0, 1, 2, or 3, and each $R^7$ is independently selected from hydroxy, fluoro, chloro, $NH_2$, $NO_2$, $NHCH_3$, $N(CH_3)_2$, $CO_2CH_3$, $CONH_2$, $SC_2H_5$, $SCH_3$, $S(O)CH_3$, $S(O)_2CH_3$, $S(O)_2NHCH_3$, $SO_3H$, $PO_3H$, methyl, ethyl, isopropyl, vinyl, trifluoromethyl, methoxy, ethoxy, isopropoxy, and trifluoromethoxy, and each $R^{5a}$ substituent group can be independently selected from the group consisting of an alkyl, alkoxy-alkyl, alkenyl, cycloalkenyl, cycloalkyl, $-R^8OH$, $-R^8OR^5$, $-R^8CN$, $-R^8CO_2H$, $-R^8CO_2R^5$, $-R^8COR^5$, $-R^8SR^5$, and $-R^8SO_2R^5$ group, where $R^8$ is a $C_1-C_6$ organic radical.

In still other embodiments of the compounds of Formula (I), $R^5$ can be a $C_3$-$C_{10}$ branched alkyl. These $C_3$-$C_{10}$ branched alkyls have been found to be highly effective $R^5$ groups for producing sweet amide compounds of Formula (I). In some embodiments, $R^5$ can be a $C_4$-$C_8$ branched alkyl. Examples of such branched alkyls include the following structures:

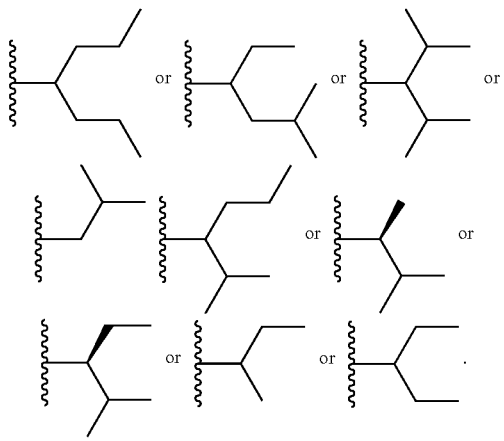

In further embodiments the branched alkyls may optionally contain, inserted into what would have been an alkyl chain, one or two heteroatoms such as nitrogen, oxygen, or sulfur atoms to form amines, ethers, and/or thioethers, sulfoxides, or sulfones respectively, or one, two, or three heteroatomic substituents bonded to the alkyl chains independently selected from a hydroxy, fluoro, chloro, bromo, $NH_2$, $NO_2$, $NHCH_3$, $N(CH_3)_2$, $CO_2CH_3$, $SCH_3$, $SC_2H_5$, $SO_3H$, $PO_3H$, trifluoromethyl, methoxy, ethoxy, isopropoxy, and trifluoromethoxy groups.

In further embodiments of the compounds of Formula (I), $R^5$ can be an α-substituted carboxylic acid or α-substituted carboxylic acid lower alkyl ester. For example, $R^5$ can be an α-substituted carboxylic acid lower alkyl (especially methyl) ester. In some such embodiments, the α-substituted carboxylic acid or α-substituted carboxylic acid ester residue corresponds to that of a naturally occurring and optically active α-amino acid or an ester thereof, or its opposite enantiomer.

In many embodiments of the compounds of Formula (I), $R^5$ can be a 5 or 6 membered aryl or heteroaryl ring, optionally substituted with 1, 2, 3 or 4 substituent groups selected from the group consisting of hydroxyl, $NH_2$, SH, halogen, or a $C_1$-$C_4$ organic radical. In related embodiments, the substituents for the aryl or heteroaryl ring are selected from alkyl, alkoxy, alkoxy-alkyl, OH, CN, $CO_2H$, CHO, $COR^6$, $CO_2R^6$, $SR^6$, halogen, alkenyl, cycloalkyl, cycloalkenyl, aryl, and heteroaryl, wherein and $R^6$ is $C_1$-$C_6$ alkyl. Preferably the aryl or heteroaryl ring is substituted with 1, 2, 3 or 4 substituent groups selected from the group consisting of hydroxy, fluoro, chloro, $NH_2$, $NO_2$, $NHCH_3$, $N(CH_3)_2$, $CO_2CH_3$, $SCH_3$, $S(O)CH_3$, $S(O)_2CH_3$, $S(O)_2NHCH_3$, $SC_2H_5$, $SO_3H$, $PO_3H$, methyl, ethyl, isopropyl, vinyl, trifluoromethyl, methoxy, ethoxy, isopropoxy, and trifluoromethoxy groups.

In some embodiments of the compounds of Formula (I), $R^5$ can be a phenyl, pyridyl, furanyl, thiofuranyl, or pyrrolyl ring optionally substituted with one or two substituents independently selected from hydroxy, fluoro, chloro, $NH_2$, $NO_2$, $NHCH_3$, $N(CH_3)_2$, $CO_2CH_3$, $SCH_3$, $S(O)CH_3$, $S(O)_2CH_3$, $S(O)_2NHCH_3$, $SC_2H_5$, $SO_3H$, $PO_3H$, methyl, ethyl, isopropyl, vinyl, trifluoromethyl, methoxy, ethoxy, isopropoxy, and trifluoromethoxy.

In many embodiments of the compounds of Formula (I), $R^5$ can be a cycloalkyl, cycloalkenyl, or saturated heterocyclic ring having 3 to 10 ring carbon atoms, optionally substituted with 1, 2, or 3 substituents independently selected from the group consisting of $NH_2$, $NO_2$, $SO_3H$, $PO_3H$, $NHCH_3$, $N(CH_3)_2$, $CO_2CH_3$, $SC_2H_5$, $SCH_3$, $S(O)CH_3$, $S(O)_2CH_3$, $S(O)_2NHCH_3$, $C_1$-$C_4$ alkyl, $C_1$-$C_4$ haloalkyl, $C_1$-$C_4$ alkoxy, $C_1$-$C_4$ haloalkoxy, hydroxy, and halogen. In some further embodiments, $R^5$ can be a cyclopentyl, cyclohexyl, cycloheptyl, cyclooctyl ring, or piperidyl ring optionally substituted with 1, 2, or 3 substituents independently selected from the group consisting of hydroxy, fluoro, chloro, $NH_2$, $NO_2$, $SO_3H$, $PO_3H$, $NHCH_3$, $N(CH_3)_2$, $CO_2CH_3$, $SC_2H_5$, $SCH_3$, methyl, ethyl, isopropyl, vinyl, trifluoromethyl, methoxy, ethoxy, isopropoxy, and trifluoromethoxy.

In some other embodiments, $R^5$ can be a cyclohexyl ring, optionally substituted with 1, 2, or 3 substitutent groups selected from $NH_2$, $NO_2$, $SO_3H$, $PO_3H$, $NHCH_3$, $N(CH_3)_2$, $CO_2CH_3$, $SC_2H_5$, $SCH_3$, $C_1$-$C_4$ alkyl, $C_1$-$C_4$ haloalkyl, $C_1$-$C_4$ alkoxy, $C_1$-$C_4$ haloalkoxy, hydroxy, and halogen groups. For example, in some such embodiments, $R^5$ can have one of the following structures:

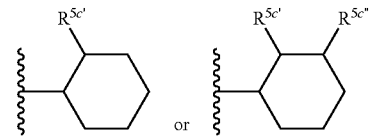

wherein $R^{5c'}$ and $R^{5c''}$ are independently selected from hydroxy, fluoro, chloro, bromo, $NH_2$, $NO_2$, $SO_3H$, $PO_3H$, $NHCH_3$, $N(CH_3)_2$, $COOCH_3$, $SCH_3$, $SC_2H_5$, methyl, ethyl, isopropyl, vinyl, trifluoromethyl, methoxy, ethoxy, isopropoxy, and trifluoromethoxy groups, or preferably methyl groups. Examples of such methyl substituted cyclohexyl rings have the formula:

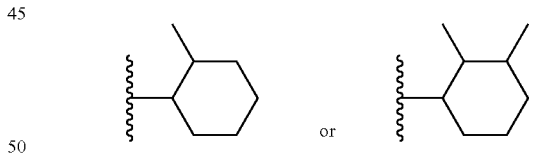

In many embodiments of the compounds of Formula (I), especially compounds having enhancer activity for other sweeteners, $R^5$ can be a cyclopentyl or cyclohexyl ring having a phenyl ring fused thereto, i.e., a 1-(1,2,3,4)tetrahydronapthalene ring radical or an 2,3-dihydro-1H-indene ring radical having the structures:

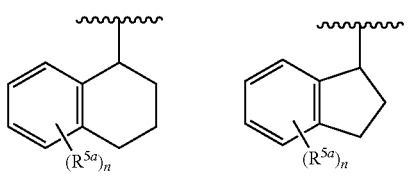

wherein n is 0, 1, 2, or 3, and each $R^{5a}$ can be bonded to either the aromatic or non-aromatic ring. In other embodiments, each $R^{5a}$ can be bonded to the aromatic ring as is shown below:

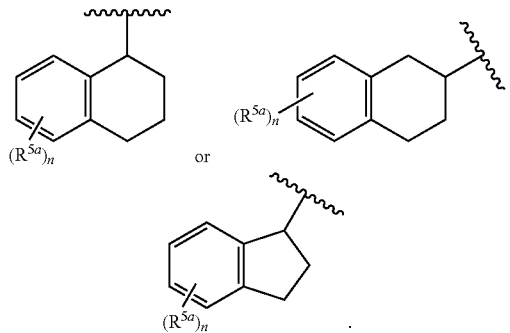

In the tetrahydronapthalenyl and indanyl embodiments shown above, each $R^{5a}$ can be independently selected from the group consisting of hydroxyl, $NH_2$, SH, halogen, or a $C_1$-$C_4$ organic radical. In alternative but related embodiments, each $R^{5a}$ can be independently selected from the group consisting of hydroxyl, $NH_2$, SH, halogen, $C_1$-$C_4$ alkyl, $C_1$-$C_4$ haloalkyl, $C_1$-$C_4$ haloalkoxy, $C_1$-$C_4$ alkoxy, $C_1$-$C_4$ alkoxy-alkyl, $C_1$-$C_4$ hydroxy-alkyl, OH, $NH_2$, $NHR^6$, $NR^6_2$, CN, $CO_2H$, $CO_2R^6$, CHO, $COR^6$, SH, $SR^6$, $S(O)R^6$, $S(O)_2R^6$, $S(O)_2NHR^6$, and halogen, wherein $R^6$ is $C_1$-$C_4$ alkyl. In some embodiments, each $R^{5a}$ can be independently selected from the group consisting of hydroxy, fluoro, chloro, $NH_2$, $NHCH_3$, $N(CH_3)_2$, $CO_2CH_3$, $SCH_3$, $SC_2H_5$, $NO_2$, $SO_3H$, $PO_3H$, methyl, ethyl, isopropyl, vinyl, trifluoromethyl, methoxy, ethoxy, isopropoxy, and trifluoromethoxy.

In some embodiments $R^5$ can be a 1-(1,2,3,4)tetrahydronapthalene ring with certain preferred substitution patterns. In particular, in some embodiments of the compounds of Formula (I) $R^5$ can be a cyclohexyl ring having one of the formulas:

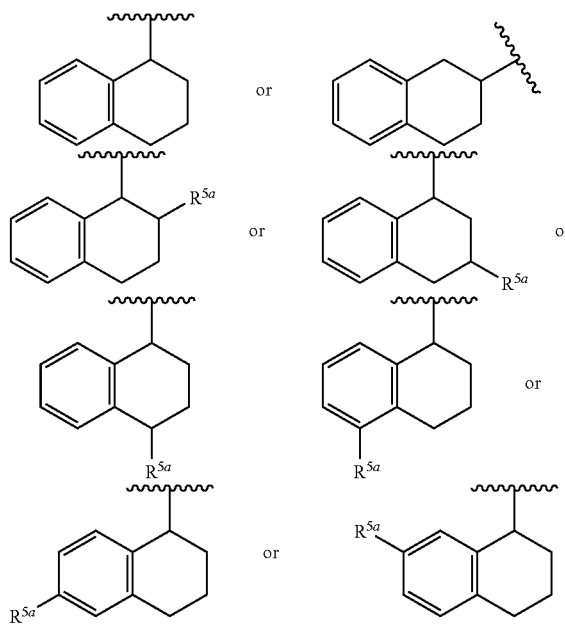

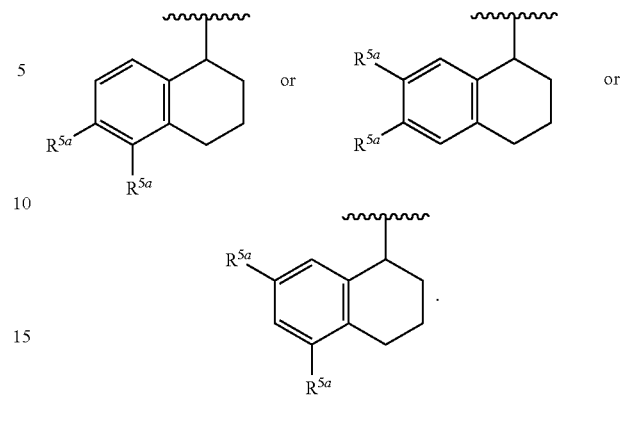

wherein each $R^{5a}$ can be independently selected from the groups described above. Similarly, in some preferred embodiments, $R^5$ can include one of the structures:

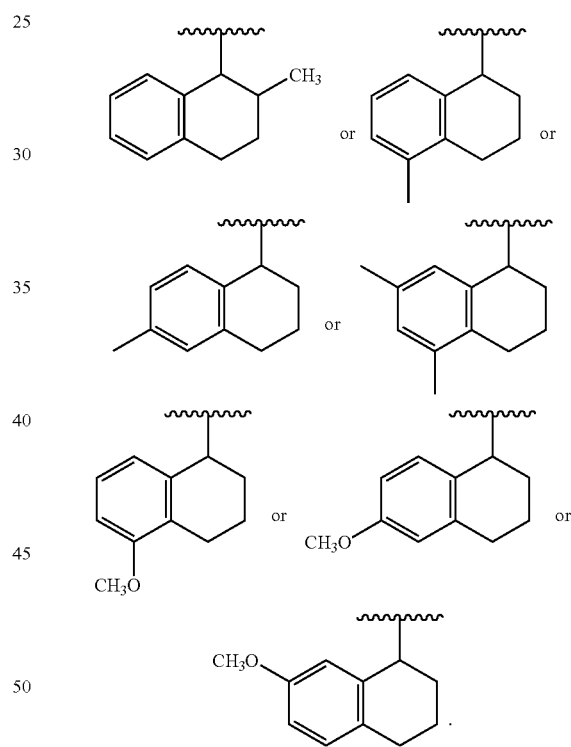

In some embodiments $R^5$ can be an unsubstituted 1-(1,2,3,4)tetrahydronapthalene ring in racemic or optically active form, as shown below:

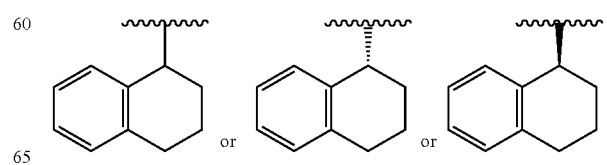

Similarly in the indanyl series $R^5$ can have the structures:

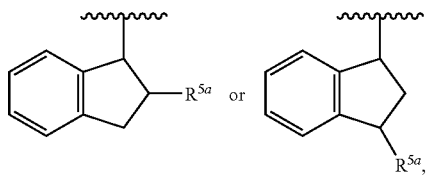

or the $R^{5a}$ substituents can bound to the aromatic ring as show below:

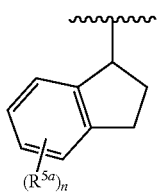

or in more specific embodiments, $R^5$ can have one of the exemplary structures show below:

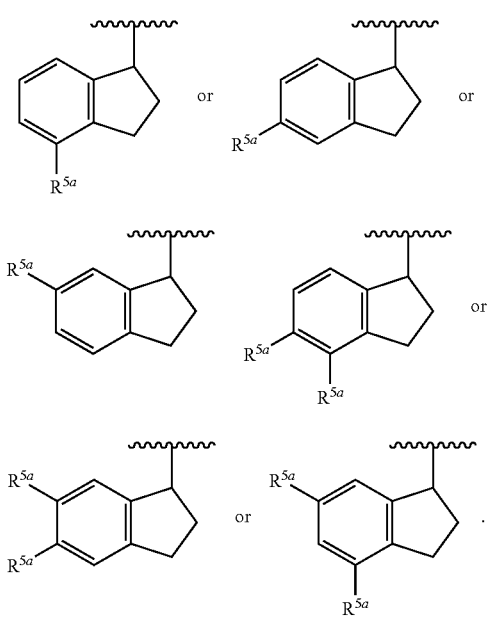

In some embodiments of the amide compounds of the invention, the tetrahydronapthalene and indane ring systems of the $R^5$ groups described above can be modified to comprise one or more heteroatoms or heteroatomic groups into the bicyclic ring systems, to form new heterocyclic and bicyclic analogs of the tetrahydronapthalene and indane ring systems, so as to form new $R^5$ groups. For example, it is possible to substitute a nitrogen atom for one of the aromatic rings of a tetrahydronapthalenyl group to form new tetrahydroquinolinyl or tetrahydroisoquinolinyl radicals having the structures shown below:

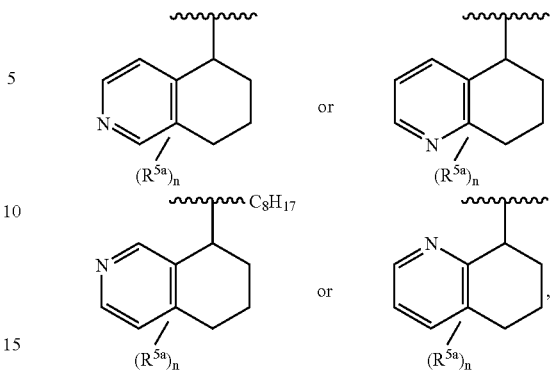

wherein the $R^{5a}$ groups can be bonded to either the aromatic or non-aromatic rings, and can be defined in any of the ways described above in connection with the tetrahydronapthalenyl groups. It will be apparent to those of ordinary skill in the art that at least one additional nitrogen atom could be similarly inserted to form additional and isomeric heteroaryl groups, such as the following exemplary $R^5$ groups:

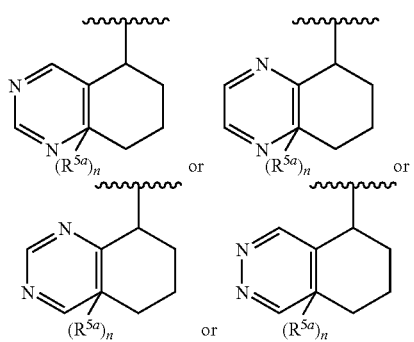

The indanyl $R^5$ groups described above can be similarly modified with one or more nitrogen atoms to form additional bicyclic heteroaryl $R^5$ groups, such as for example the following structures:

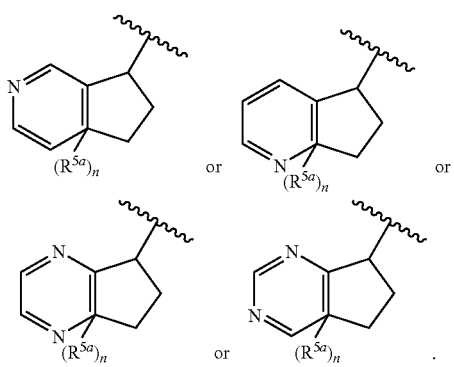

Additionally, one or more heteroatoms or substituted heteratomic groups can be inserted into the cyclopentyl or cyclohexyl groups of the tetrahydronapthalenyl or indanyl groups described above to form additional fused bicyclic heteroaryls, which include but are not limited to the exemplary structures listed below:

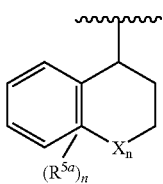

wherein n is 0, 1, 2, or 3, each $R^{5a}$ can be defined in any of the ways described above, and $X_h$ is O, S, SO, $SO_2$, NH, or $NR_h$; wherein $R_h$ is a $C_1$-$C_4$ organic radical. Examples of such $R^5$ groups are listed below:

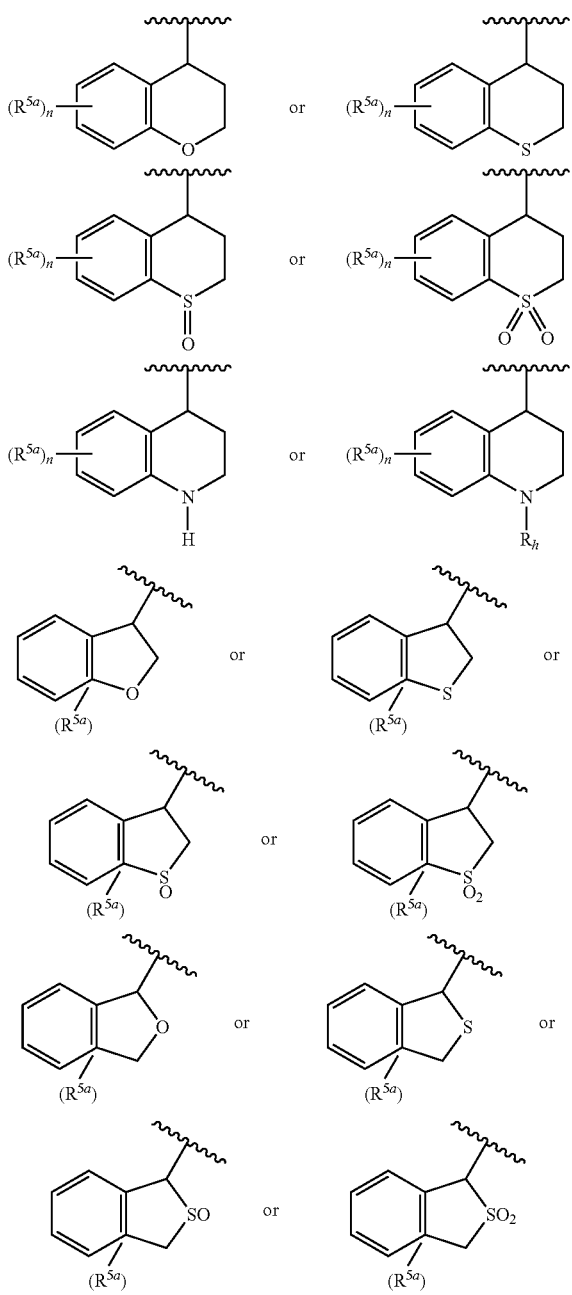

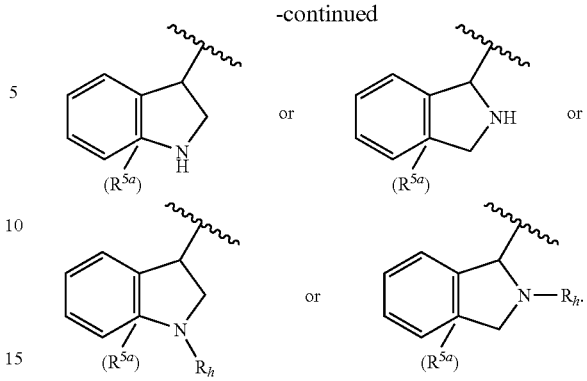

It will also be understood by those of ordinary skill in the art that optical and/or diastereomeric isomerism can occur on the unsaturated five and six membered rings of the $R^5$ groups described above, and in many other of the $R^1$, $R^2$, $R^3$, and $R^4$ groups disclosed herein, and that the differing optical isomers (enantiomers) and/or diastereomers can have differing biological activities with respect to the relevant sweet and savory taste receptors. Prediction of which diastereomer or enantiomer of a particular $R^5$ group is most likely to be biologically effective can be difficult, and the finding that one particular isomer is more effective for one ring system may not necessarily mean that an analogous isomer of a differently substituted group will be similarly effective.

In still other embodiments of compounds of Formula (I), $R^5$ can be a cyclic alkyl group for example, a cycloproryl, cyclobutyl, cyclopentyl, or cyclohexyl, including substituted derivatives thereof.

Also, $R^5$ can be alkylalkoxyl groups, such as those shown below:

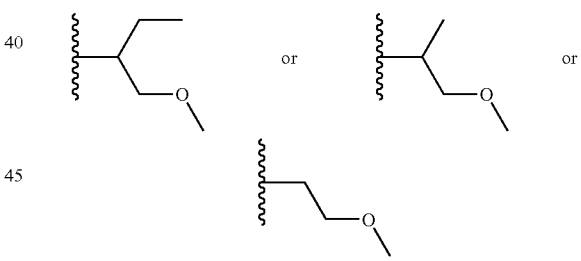

Organic Radicals

In addition to the above described general physical and chemical characteristics and/or limitations, which can be shared by the various subgenuses of the sweet compounds of Formula (I), the compounds of Formula (I) can also share more specifically definable chemical structural features or chemical groups or residues, as is further described below.

For example, in some embodiments, $R^1$, $R^2$, $R^3$, $R^4$, and $R^5$ can be independently selected from $C_1$-$C_6$ organic radicals. In one aspect, a $C_1$-$C_6$ organic radical can be selected from the group consisting of an arylalkenyl, heteroarylalkenyl, arylalkyl, heteroarylalkyl, alkyl, alkoxy-alkyl, alkenyl, cycloalkyl, cycloalkenyl, heterocycle, aryl and heteroaryl groups, and optionally substituted derivatives thereof comprising 1, 2, 3 or 4 carbonyl, amino groups, hydroxyl, or chlorine, or fluorine groups. A preferred set of optional substituent groups can be substituents independently selected from the group consisting of hydroxy, fluoro, chloro, $NH_2$, $NO_2$, $NHCH_3$, $N(CH_3)_2$, $CO_2CH_3$, $SC_2H_5$, $SCH_3$, $S(O)CH_3$, $S(O)_2CH_3$, $S(O)_2NHCH_3$, $SO_3H$, $PO_3H$, methyl, ethyl, isopropyl, vinyl, trifluoromethyl, methoxy, ethoxy, isopropoxy, and trifluoromethoxy substituent groups. In other examples, the organic radicals can be $C_1$-$C_4$ organic radicals. In still other examples, the $C_1$-$C_6$ organic radicals can independently be selected from the group consisting of alkyl, haloalkyl, haloalkoxy, alkoxyl, alkoxy-alkyl, hydroxy-alkyl, aryl, heteroaryl, CN, $C(O)H$, $CO_2H$, $NHR^6$, $NR^6_2$, $COR^6$, $C(O)R^6$, $SR^6$, $S(O)R^6$, $S(O)_2R^6$, $S(O)_2NHR^6$, and $C(O)NHR^6$, wherein $R^6$ is $C_1$-$C_4$ alkyl.

The compounds of Formula (I) are relatively "small molecules" as compared to many biological molecules, and can often have a variety of limitations on their overall absolute physical size, molecular weight, and physical characteristics, so that they can be at least somewhat soluble in aqueous media, and are of appropriate size to effectively bind to the heterodimeric T1R2/T1R3 taste receptors.

As an example of the physical and chemical properties and/or physical/chemical limitations on the sweet amides of Formula (I), in most embodiments of the compounds of Formula (I), the molecular weight of the compounds of Formula (I) should be less than about 800 grams per mole, or in further related embodiments less than or equal to about 700 grams per mole, 600 grams per mole, 500 grams per mole, 450 grams per mole, 400 grams per mole, 350 grams per mole, or 300 grams per mole.

Similarly, the compounds of Formula (I) can have preferred ranges of molecular weight, such as for example from about 175 to about 500 grams per mole, from about 200 to about 450 grams per mole, from about 225 to about 400 grams per mole, from about 250 to about 350 grams per mole.

As discussed above, the amide compounds employed in the inventions described herein can have any combination of the structural features and groups discussed hereinabove.

The subgenera of aromatic or heteroaromatic amide compounds of Formula (I) described immediately above contain many excellent agonists of T1R2/T1R3 sweet taste receptors, at very low concentrations of the amide compound on the order of micromolar concentrations or less, and can significantly supplement enhance the effectiveness of a variety of known sweeteners, especially saccharide based sweeteners, so as to allow the formulation of comestible products with reduced concentrations of saccharide based sweeteners.

Accordingly, many of the aromatic or heteroaromatic amide compounds of Formula (I) can be utilized as sweet flavoring agents or sweet flavor enhancers when contacted with a wide variety of comestible products and/or compositions, or their precursors, to produce taste modified comestible or medicinal compositions, as is described elsewhere herein.

The amide compounds of the invention can be present in the form of enantiomers when the $R^3$ and $R^4$ groups are different, or when any of the "R" groups comprise an optically active carbon atom. When the specification, claims, and/or drawings of this document indicate that a compound is present in optically active form, as is implied by the discussion and drawings immediately above, it is to be understood that the indicated compounds of Formula (I) are present in at least a small enantiomeric excess (i.e. more than about 50% of the molecules have the indicated optical configuration). Further embodiments preferably comprise an enantiomeric excess of the indicated isomer of at least 75%, or 90%, or 95%, or 98%, or 99%, or 99.5%. Depending on the difference in the biological activities, the cost of production, and/or any differences in toxicity between the two enantiomers, for a given compound it may be advantageous to produce and sell for human consumption a racemic mixture of the enantiomers, or a small or large enantiomeric excess one of the enantiomers of a given compound.

One preferred subgenus of the compounds of Formula (I) are compounds of subgenus Formula (II) wherein the various groups are defined as follows:

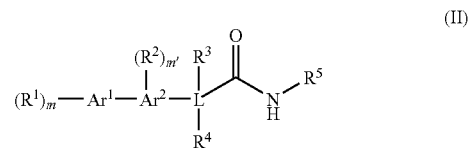

(II)

wherein
i) $Ar^1$ and $Ar^2$ are independently selected from monocyclic aryl or fused bicyclic aryl monocyclic heteroaryl or fused bicyclic heteroaryl rings;
ii) m is selected from the integers 0, 1, 2, 3, 4, or 5;
iii) m' is selected from the integers 0, 1, 2, 3, or 4;
iv) each $R^1$ and $R^2$ is independently selected from the group consisting of an OH, $NH_2$, $NO_2$, SH, $SO_3H$, $PO_3H$, halogen, and a $C_1$-$C_6$ organic radical;
v) L is a carbon or nitrogen atom;
vi) $R^3$ is hydrogen, oxygen, hydroxy, halogen, or a $C_1$-$C_6$ organic radical;
vii) $R^4$ is absent, or hydrogen, oxygen, hydroxy, halogen, or a $C_1$-$C_6$ organic radical;
viii) $R^5$ is a $C_1$-$C_{14}$ organic radical comprising a normal or branched alkyl or cycloalkyl, wherein the normal or branched alkyl or cycloalkyl optionally comprises one to four substituents independently selected from OH, $NH_2$, $NO_2$, SH, $SO_3H$, $PO_3H$, halogen, and a $C_1$-$C_6$ organic radical;

or a comestibly acceptable salt thereof.

Another preferred subgenus of the compounds of Formula (I) are compounds wherein L is a carbon atom, i.e. the amide compound has subgenus Formula (III):

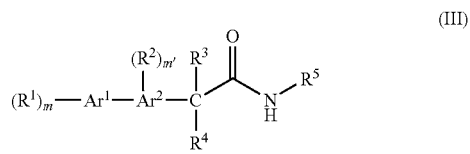

(III)

wherein
i) $Ar^1$ and $Ar^2$ are independently selected from phenyl, napthyl, indolyl, pyridyl, pyrimidyl, pyrazinyl, pyrrolyl, pyrrazolyl, furanyl, thiofuranyl, oxazolyl, isoxazolyl, oxadiazolyl, quinolinyl, benzofuranyl, triazolyl, tetrazolyl, and benzothiofuranyl groups;
ii) m is selected from the integers 0, 1, 2, or 3;
iii) m' is selected from the integers 0, 1, or 2;
iv) each $R^1$ and $R^2$ is independently selected from the group consisting of a hydroxy, fluoro, chloro, $NH_2$, $NO_2$, $NHCH_3$, $N(CH_3)_2$, $COOCH_3$, $SCH_3$, $SC_2H_5$, methyl, ethyl, propyl, isopropyl, vinyl, allyl, $S(O)CH_3$, $S(O)_2CH_3$, $S(O)_2NHCH_3$, CN, $CH_2OH$, C(O)H, C(O)$CH_3$, trifluoromethyl, methoxy, ethoxy, isopropoxy, and trifluoromethoxy radical;
v) $R^3$ is a $C_1$-$C_4$ alkyl;
vi) $R^4$ is hydrogen, or a $C_1$-$C_4$ alkyl;

vii) $R^5$ is a $C_1$-$C_{10}$ normal or branched alkyl or cycloalkyl, wherein the normal or branched alkyl or cycloalkyl optionally comprises one to or two substituents independently selected from hydroxy, fluoro, chloro, $NH_2$, $NO_2$, $NHCH_3$, $N(CH_3)_2$, $COOCH_3$, $SCH_3$, $SC_2H_5$, methyl, ethyl, propyl, isopropyl, vinyl, allyl, $S(O)CH_3$, $S(O)_2CH_3$, CN, $CH_2OH$, $C(O)H$, $C(O)CH_3$, trifluoromethyl, methoxy, ethoxy, isopropoxy, and trifluoromethoxy radical;

or one or more comestibly acceptable salts thereof.

In yet additional aspects, the amide compounds of the invention can have the structure:

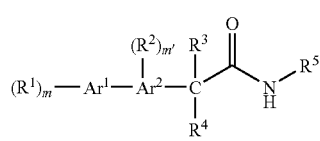

(IV)

wherein
i) $Ar^1$ and $Ar^2$ are independently selected from a phenyl, or monocyclic heteroaryl rings;
ii) m and m' are independently selected from the integers 0, 1, or 2;
iii) each $R^1$ and $R^2$ is independently selected from the group consisting of OH, $NH_2$, $NO_2$, SH, $SO_3H$, $PO_3H$, halogen, and a $C_1$-$C_4$ organic radical;
iv) $R^3$ and $R^4$ are independently selected from hydrogen and a $C_1$-$C_4$ alkyl,
v) $R^5$ is a $C_3$-$C_{10}$ branched alkyl optionally comprising one, two, or three substituents independently selected from OH, $NH_2$, a halogen, and a $C_1$-$C_6$ organic radical;

or a comestibly acceptable salt thereof.

Comestibly or Pharmaceutically Acceptable Compounds

Many of the amide compounds of Formula (I) or its various enumerated subgenuses comprise acidic or basic groups, so that depending on the acidic or basic character ("pH") of the comestible or medicinal compositions in which they are formulated, they may be present as salts, which are preferably comestibly acceptable (i.e., designated as generally recognized as safe, or GRAS) or pharmaceutically acceptable salts (many of which have been recognized by the Federal Food and Drug Administration).

The amide compounds of Formula (I) having acidic groups, such as carboxylic acids, will tend (at near neutral physiological pH) to be present in solution in the form of anionic carboxylates such as acetates, lactates, fumarates, succinates, salts of fatty acids, etc., and therefore will in preferred embodiments have an associate comestibly and/or pharmaceutically acceptable cation, many of which are known to those of ordinary skill in the art. Such comestibly and/or pharmaceutically acceptable cations include alkali metal cations (lithium, sodium, and potassium cations), alkaline earth metal cations (magnesium, calcium, and the like), or ammonium $(NH_4)^+$ or organically substituted ammonium cations such as $(R—NH_3)^+$, $(NH_2R_2)^+$, $(NHR_3)^+$, or $(NR_4)^+$ cations, wherein the ammonium "R" groups can be independently selected and can be a variety or organic groups, including C1-C18 alkyls, hydroxyalkyls, or alkoxyalkyl groups.

The amide compounds of Formula (I) having basic substituent groups, such as amino or nitrogen containing heterocyclic groups, will tend (at near neutral physiological pH, or at the acidic pH common in many foods) to be present in solution in the form of cationic ammonium groups, and therefore will in preferred embodiments have an associate comestibly and/or pharmaceutically acceptable anion, many of which are known to those of ordinary skill in the art. Such comestibly and/or pharmaceutically acceptable anionic groups include the anionic form of a variety of carboxylic acids (acetates, citrates, tartrates, anionic salts of fatty acids, etc.), halides (especially fluorides or chlorides), nitrates, and the like.

The amide compounds of Formula (I) and its various subgenuses should preferably be comestibly acceptable, i.e., deemed suitable for consumption in food or drink, and should also be pharmaceutically acceptable. A well known method of demonstrating that a flavorant compound is comestibly acceptable is to have the compound tested and/or evaluated by an Expert Panel of the Flavor and Extract Manufacturers Association and declared as to be "Generally Recognized As Safe" ("GRAS"). The FEMA/GRAS evaluation process for flavorant compounds is complex but well known to those of ordinary skill in the food product preparation arts, as is discussed by Smith et al. in an article entitled "GRAS Flavoring Substances 21," Food Technology, 57(5), pp. 46-59, May 2003, the entire contents of which are hereby incorporated herein by reference.

When being evaluated in the FEMA/GRAS process, a new flavorant compound is typically tested for any adverse toxic effects on laboratory rats when fed to such rats for at least about 90 days at a concentration 100-fold, or 1000-fold, or even higher concentrations than the proposed maximum allowable concentration of the compound in a particular category of food products being considered for approval. For example, such testing of the amide compounds of the invention might involve combining the amide compound with rat chow and feeding it to laboratory rats such as Crl:CD(SD)IGS BR rats, at a concentration of about 100 milligrams/Kilogram body weight/day for 90 days, and then sacrificing and evaluating the rats by various medical testing procedures to show that the amide compound of Formula (I) causes no adverse toxic effects on the rats.

The Compounds of the Invention as Sweet Tastants and/or Sweet Taste Enhancers

The amide compounds of Formula (I) and its various compound sub-genuses and species, as described above are intended to be sweet taste flavorant compounds or flavor modifiers for comestible or medicinal products. As is apparent from the teachings and Examples herein, many compounds of Formula (I) are agonists of an hT1R2/hT1R3 sweet receptor, at concentrations on the order of from about 0.001 to about 100 micromolar, or higher. Accordingly many or all of the amide compounds of Formula (I) can have utility as sweet flavorants or flavor enhancers, in their own right. In many favored aspects of the invention, inclusion of such concentrations of the amide compounds of the present inventions in a comestible composition can permit a significant reduction in the amount of known caloric or carbohydrate sweeteners, especially sucrose, fructose, glucose, and sugar alcohols that are necessary to obtain the desired degree of sweetness in comestible compositions.

Nevertheless, it is desirable to minimize the concentration of the compounds of the invention, so as to minimize cost, any possible "off-tastes," and any unknown or undesirable side effects of the use of the compounds of Formula (I) at high concentration levels. Accordingly, it is desirable to test the compounds of Formula (I) for their effectiveness as taste receptor agonists at lower concentration levels, so as to identify the best and most effective amide compounds within the genus of compounds described by Formula (I), and so that lower limits of concentrations for the practical use of each compound can be identified. As was disclosed in WO 03/001876, and U.S. Patent publication US 2003-0232407 A1, which are incorporated by reference herein in their entireties, and as described hereinbelow, laboratory procedures now exist for measuring the agonist activities of compounds for an hT1R2/hT1R3 sweet receptors. Such measurement methods typically measure an "$EC_{50}$", i.e., the concentration at which the compound causes 50% activation of the relevant receptor, i.e. such $EC_{50}$ measurements can be a measure of the agonist activity of the amide compounds with respect to hT1R2/hT1R3 sweet receptors.

Preferably, the amide compounds of Formula (I) are sweet flavor modifiers or sweet flavor enhancers have an $EC_{50}$ for the hT1R2/hT1R3 receptor of less than about 100 μM, or less than about 10 micromolar. Ideally, such amide compounds have an $EC_{50}$ for the hT1R2/hT1R3 receptor of less than about 5 μM, 3 μM, 2 μM, 1 μM, or 0.5 μM.

The amide compounds of Formula (I) can in some cases modulate the binding of a known sweetener such as for example sucrose, fructose, glucose, erythritol, isomalt, lactitol, mannitol, sorbitol, xylitol, maltodextrin, or the like, a known natural terpenoid, flavonoid, or protein sweetener, aspartame, saccharin, acesulfame-K, cyclamate, Sucralose, alitame or erythritol to an hT1R2/hT1R3 receptor.

The above identified assays are useful in identifying the most potent of the amide compounds of Formula (I) for sweet taste modifier or enhancer properties, and the results of such assays correlate reasonably well with actual sweet taste perception in animals and humans, but ultimately the results of the assays can be confirmed, at least for the most potent of the compounds of Formula (I), by human taste testing. Such human taste testing experiments can be well quantified and controlled by tasting the candidate compounds in aqueous solutions, as compared to control aqueous solution, or alternatively by tasting the amides of the inventions in actual food compositions. Examples of human taste test experiments in the form of both aqueous solutions that can be a model for sweet beverage compositions, and actual examples of comestible compositions such as ice cream, sweetener coated breakfast cereals, and actual beverage compositions can be found hereinbelow.

Preferred sweet taste modifiers of Formula (I) can be identified when a modified comestible or medicinal product has a sweeter taste than a control comestible or medicinal product that does not comprise the amide compound, as judged by the majority of a panel of at least eight human taste testers.

Preferred sweet taste enhancers of Formula (I) can be identified when a water solution comprising a sweet tasting amount of a known sweetener selected from the group consisting of sucrose, fructose, glucose, erythritol, isomalt, lactitol, mannitol, sorbitol, xylitol, maltodextrin, a known natural terpenoid, flavonoid, or protein sweetener, aspartame, saccharin, acesulfame-K, cyclamate, Sucralose, and alitame, or a mixture thereof, and a sweet flavor modifying amount of the amide compound (preferably about 30, 10, 5, 2, 1, or less than 1 ppm) has a sweeter taste than a control water solution comprising the sweet tasting amount of the known sweetener, as judged by the majority of a panel of at least eight human taste testers. In such taste test experiments, sucrose would preferably be present at a concentration of about 6 grams/100 milliliters, or a 50:50 mixture of glucose and fructose would preferably be present at a concentration of about 6 grams/100 milliliters, or aspartame would preferably be present at a concentration of about 1.6 mM, acesulfame-K would preferably be present at a concentration of about 1.5 mM, cyclamate would preferably be present at a concentration of about 10 mM, Sucralose would preferably be present at a concentration of about 0.4 mM, or alitame would preferably be present at a concentration of about 0.2 mM.

Nevertheless the agonist activity for the compounds of the invention is not however the only factor to be considered when selecting one or more amide compounds disclosed herein for formulating a particular comestible composition. For example, the solubility of the amide compound in water or other common precursors of comestible compositions, such as milk, sweetener concentrates containing sweeteners such as sucrose or fructose, such as corn syrup, edible oils, etc, should also be considered. The compounds of the invention are typically soluble to the extent of at least about 1 ppm in water, but many of the amide compounds have desirably increased solubility in common organic liquid precursors of comestible compositions, and can be soluble to the extent of at least about 5, 10, 20, 50, 100, or 1000 ppm in water, or other common precursors of sweet comestible compositions, such as for example sweet syrups such as corn syrup, milk, edible oils, etc. or mixtures thereof.

Using the Compounds of Formula (I) to Prepare Comestible Compositions

Many of the amide compounds of Formula (I) and/or its various subgenuses of amide compounds are potent T1R2/T1R3 receptor agonists at concentrations as low as 0.001 micromolar. In some such embodiments, the amide compounds of Formula (I) can have at surprisingly low sweet flavoring agent amounts, a sweet flavor when tasted in isolation, which is independent of the presence of other sweeteners, and therefore can be employed at very low concentrations as stand alone sweeteners in a comestible or medicinal composition, or a precursor thereof.

In many embodiments of the invention, the amide compounds disclosed herein can be used at very low concentrations on the order of a few parts per million, in combination with one or more known sweeteners, natural or artificial, so as to reduce the concentration of the known sweetener required to prepare a comestible composition having the desired degree of sweetness. The reduction of the concentrations of the natural saccharide sweeteners is particularly desirable, because of the reduction of caloric intake and/or tooth decay associated with the reduction of the use of such sweeteners.

Commonly used known or artificial sweeteners for use in such combinations of sweeteners include but are not limited to the common saccharide sweeteners sucrose, fructose, glucose, and sweetener compositions comprising those natural sugars, such as corn syrup or other syrups or sweetener concentrates derived from natural fruit and vegetable sources, or semi-synthetic "sugar alcohol" sweeteners such as erythritol, isomalt, lactitol, mannitol, sorbitol, xylitol, maltodextrin, and the like, or well known artificial sweeteners such as aspartame, saccharin, acesulfame-K, cyclamate, Sucralose, and alitame; or any mixture thereof. Such use of a few parts per million of the amide compounds of the invention in combination with known saccharide sweeteners can be particularly beneficial in that it can allows for a reduction of the concentration of the saccharide sweeteners (and their associated calories) by 30-50%, while maintaining the basic taste of the saccharide sweeteners, and allowing for continuation of some of the other functions of the saccharide sweeteners in maintaining desirable physical properties (such as melting point, "bulking," and "browning") of the comestible product.

Some of the amide compounds of Formula (I), while having imperceptibly little or perhaps no sweet flavor when tasted in isolation at relevant concentrations can surprisingly be employed at very low sweet flavor enhancing amounts in order to significantly enhance, (i.e., potentiate or multiply) the sweetness of one or more other sweet flavor agents in a comestible or medicinal composition, or a precursor thereof, such as sucrose, fructose, glucose, and other like and well known natural saccharide-based sweeteners, or known artificial sweeteners such as saccharine, cyclamate, aspartame, and the like. The inventions described herein also relate in many embodiments to the flavor-modified comestible or medicinal products that contain sweet flavor enhancing amounts of one or more of the amide compounds disclosed herein.

In other words, some of the amide compounds of Formula (I) are not perceived by human beings as being sweet tastants in isolation from other sweeteners, but can perceptibly enhance, potentiate, modulate or induce the perception in humans of the sweet taste of other natural, semi-synthetic, or synthetic sweet flavoring agents, such as for example sucrose, fructose, glucose, erythritol, isomalt, lactitol, mannitol, sorbitol, xylitol, certain known natural terpenoids, flavonoids, or protein sweeteners, aspartame, saccharin, acesulfame-K, cyclamate, Sucralose, and alitame, and the like, or mixtures thereof. In some preferred embodiments, the amide compounds of the invention enhance the sweet taste of certain naturally occurring sweeteners that comprise one or more of sucrose, fructose, and glucose, or mixtures thereof.

Flavors, flavor modifiers, flavoring agents, flavor enhancers, sweet flavoring agents and/or flavor enhancers, the compounds of Formula (I) and its various subgenuses and species of compounds have application in foods, beverages, and medicinal compositions wherein sweet compounds are conventionally utilized. These compositions include compositions for human and animal consumption. This includes foods for consumption by agricultural animals, pets and zoo animals.

Those of ordinary skill in the art of preparing and selling comestible compositions (i.e., edible foods or beverages, or precursors or flavor modifiers thereof) are well aware of a large variety of classes, subclasses and species of the comestible compositions, and utilize well-known and recognized terms of art to refer to those comestible compositions while endeavoring to prepare and sell various of those compositions. Such a list of terms of art is enumerated below, and it is specifically contemplated hereby that the various subgenuses and species of the compounds of Formula (I) could be used to modify or enhance the sweet flavors of the following list comestible compositions, either singly or in all reasonable combinations or mixtures thereof:

One or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other rte cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, uht soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads.

Preferably, the compounds of Formula (I) can be used to modify or enhance the sweet flavor of one or more of the following subgenuses of comestible compositions: confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads, or a mixture thereof. In some favored aspects of the inventions described herein, one or more of the amide compounds disclosed herein can be added to ice creams, breakfast cereals, sweet beverages or solid or liquid concentrate compositions for preparing beverages, ideally so as to enable the reduction in concentration of previously known saccharide sweeteners, or artificial sweeteners.

In general an ingestible composition will be produced that contains a sufficient amount of at least one compound within the scope of Formula (I) or its various subgenuses described hereinabove to produce a composition having the desired flavor or taste characteristics such as "sweet" taste characteristics.

Typically at least a sweet flavor modulating amount, a sweet flavoring agent amount, or a sweet flavor enhancing amount of one or more of the compounds of Formula (I) will be added to the comestible or medicinal product, optionally in the presence of known sweeteners, so that the sweet flavor modified comestible or medicinal product has an increased sweet taste as compared to the comestible or medicinal product prepared without the amide compound, as judged by human beings or animals in general, or in the case of formulations testing, as judged by a majority of a panel of at least eight human taste testers, via procedures described elsewhere herein.

The concentration of sweet flavoring agent needed to modulate or improve the flavor of the comestible or medicinal product or composition will of course depend on many variables, including the specific type of comestible composition and its various other ingredients, especially the presence of other known sweet flavoring agents and the concentrations thereof, the natural genetic variability and individual preferences and health conditions of various human beings tasting the compositions, and the subjective effect of the particular compound on on the taste of such sweet compounds. As noted, a significant application of the compounds of Formula (I) is for modulating (inducing, enhancing or inhibiting) the sweet taste or other taste properties of other natural or synthetic sweet tastants, and comestible compositions made therefrom. A broad but also low range of concentrations of the amide compounds of Formula (I) would typically be required, i.e., from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

Examples of foods and beverages wherein compounds according to the invention may be incorporated included by way of example the Wet Soup Category, the Dehydrated and Culinary Food Category, the Beverage Category, the Frozen Food Category, the Snack Food Category, and seasonings or seasoning blends.

"Wet Soup Category" means wet/liquid soups regardless of concentration or container, including frozen Soups. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

"Dehydrated and Culinary Food Category" means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

"Beverage Category" means beverages, beverage mixes and concentrates, including but not limited to, alcoholic and non-alcoholic, ready to drink beverages, liquid concentrate formulations for preparing beverages such as sodas, and dry powdered beverage precursor mixes.

Other examples of foods and beverages wherein compounds according to the invention may be incorporated included by way of example carbonated and non-carbonated beverages, e.g., sodas, fruit or vegetable juices, alcoholic and non-alcoholic beverages, confectionary products, e.g., cakes, cookies, pies, candies, chewing gums, gelatins, ice creams, sorbets, puddings, jams, jellies, salad dressings, and other condiments, cereal, and other breakfast foods, canned fruits and fruit sauces and the like. The amide compounds of Formula (I) can also be of value for producing reduced sugar or reduced calorie formulations of sweet coatings, frostings, or glazes for comestible productes comprising a mixture of the at least one amide compound of Formula (1) in an amount from about 0.1 to about 10 ppm, and one or more other sweeteners independently selected from sucrose, fructose, glucose, erythritol, isomalt, lactitol, mannitol, sorbitol, xylitol, aspartame, neotame, saccharin, acesulfame-K, cyclamate, Sucralose, and alitame, or a mixture thereof.

Additionally, the subject compounds can be used in flavor preparations to be added to foods and beverages. In preferred instances the composition will comprise another flavor or taste modifier such as a sweet tastant.

Methods for Modifying the Taste of Comestible or Medicinal Compositions

In many embodiments, the inventions relate to methods for modulating (e.g., increasing) the sweet taste of a comestible or medicinal product comprising:

a) providing at least one comestible or medicinal product, or at least one precursor thereof, and b) combining the at least one comestible or medicinal product or at least one precursor thereof with at least a sweet flavor modulating amount of at least one bi-aromatic amide compound, or a comestibly acceptable salt thereof, so as to form a modified comestible or medicinal product;

wherein the amide compound has the structure:

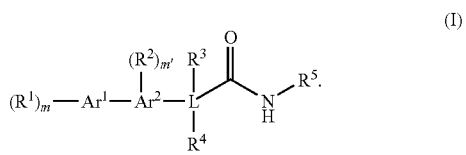

Examples of such methods include but are not limited to the methods embodied below.

As disclosed herein, the amide compound is the amide of Formula (I), or any of its various subgenuses or species compounds described herein, wherein $Ar^1$, $Ar^2$, $R^1$, $R^2$, $R^3R^4$, $R^5$, and L, can be defined in the many ways also described hereinabove. For example, in some aspects of the methods of the invention, $Ar^1$ and $Ar^2$ can be independently selected from monocyclic or fused bicyclic aryl and monocyclic or fused bicyclic heteroaryl rings; m is selected from the integers 0, 1, 2, 3, 4, or 5; m' is selected from the integers 0, 1, 2, 3, or 4; each $R^1$ and $R^2$ is independently selected from the group consisting of an OH, $NH_2$, $NO_2$, SH, $SO_3H$, $PO_3H$, halogen, and a $C_1$-$C_6$ organic radical; L is a carbon or nitrogen atom; $R^3$ is hydrogen, oxygen, hydroxy, halogen, or a $C_1$-$C_6$ organic radical; $R^4$ is absent, or hydrogen, oxygen, hydroxy, halogen, or a $C_1$-$C_6$ organic radical; $R^5$ is a $C_1$-$C_{14}$ organic radical comprising a normal or branched alkyl or cycloalkyl, wherein the normal or branched alkyl or cycloalkyl optionally comprises one to four substituents independently selected from OH, $NH_2$, $NO_2$, SH, $SO_3H$, $PO_3H$, halogen, and a $C_1$-$C_6$ organic radical; or a comestibly acceptable salt thereof.

In additional embodiments, the invention relates to methods for enhancing the sweet taste of a comestible or medicinal product comprising:
a) providing at least one comestible or medicinal product, or at least one precursor thereof, and
b) combining the at least one comestible or medicinal product or at least one precursor thereof with at least about 0.001 ppm of at least one bi-aromatic amide compound of Formula (I), or a comestibly acceptable salt thereof, so as to form a modified comestible or medicinal product, and
wherein the modified comestible or medicinal product optionally comprises one or more known sweeteners or a mixture thereof.

Preferably, the known sweeteners are selected from sucrose, fructose, glucose, erythritol, isomalt, lactitol, mannitol, sorbitol, xylitol, a known natural terpenoid, flavonoid, or protein sweetener, aspartame, saccharin, acesulfame-K, cyclamate, Sucralose, alitame, and a mixture thereof. Even more preferably, the known sweeteners are selected from sucrose, fructose, glucose, and a mixture thereof.

The invention also relates to the modified comestible or medicinal products produced by the processes disclosed above.

The invention also relates to similar processes for producing comestible or medicinal products well known to those of ordinary skill in the art. The amide compounds of Formula (I) and its various subgenuses can be combined with or applied to the comestible or medicinal products or precursor thereof in any of innumerable ways known to cooks, food preparers the world over, or producers of comestible or medicinal products.

Nevertheless, the amide compounds disclosed herein are typically far higher intensity sweeteners than previously known sweeteners, even previously known sweeteners such as aspartame, neotame, acesulfame K, and the like. Only a few ppm, or less of the amide compounds of the invention are typically needed to impart the desired sweet tast in a comestible composition, and concentrations substantially higher than 10-20 ppm on either an overall basis or in a localized area of the comestible compositions can impart an undesirable level of sweetness, or perhaps even off-tastes.

Accordingly, it can therefore be desirable that the amide compounds of the invention are highly dispersed and/or dissolved in one or more suitable precursors for the comestible compostions that can also serve as diluents for the amide compounds of the inventions, to prepare "sweetener concentrate compositions" comprising from about 10 to about 100,000 ppm of one or more of the amide compounds. In such sweetener concentrate compostions, the amide compounds are typically well and homogeneously dispersed in the the one or more suitable precursors for the comestible compositions, then the sweetener concentrate compositions are used to prepare the final comestible compositions, in which the amide compounds are typically also well and homogeneously dispersed. As a result of this high degree of dispersion, the amide compounds used efficiently and not present in the final comestible compositions in either bulk or local concentrations that are much higher than necessary in order to saturate the available sweet taste receptors. Such high dispersion and/ or dilution of the amide compounds described herein is also desirable so as to avoid any off-tastes or other side-effects that can sometimes result if the amide compounds of the invention are present at concentrations that are higher than necessary.

For example, the amide compounds of Formula (I) could be dissolved in water or sugary aqueous solution, to form a sweetener concentrate composition, then the liquid sweetener concentrate composition used to disperse the amide into the comestible compositions. Water does not always constitute the optimum dilluent, especially for storage or stability purposes. Alternatively, the amide compounds of Formula (I) can be dissolved in or highly dispersed with one or more of many comestibly acceptable precursors, or mixtures thereof, such as liquids, solids, or other comestibly acceptable carriers, to form a sweetener concentrate concentration with particularly suitable properties. In such sweetener concentrate compositions, the amide compounds can be well dissolved dispersed, or emulsified in the carrier, and often can be more easily handled in bulk food processing operations than the pure amide compound itself. Such solutions, dispersions or emulsions can be generated by various mixing, grinding, milling, and/or homogenization procecesses well known to those of ordinary skill in the art. In such sweetener concentrate compositions, the amide compound can be typically present at significantly higher concentration than is desired in the ultimate comestible composition, for example from about 10 to about 100,000 ppm, or from about 20 to about 10,000 ppm, or from about 100 to about 1000 ppm, or from about 10 to about 1000 ppm of one or more of the amide compounds.

Examples of the many suitable precursor liquids, solids, or other comestibly acceptable carriers suitable for the practice of the inventions disclosed herein include water at neutral, acidic, or basic pH, fruit or vegetable juices, vinegar, marinades, beer, wine, natural water/fat emulsions such as milk or condensed milk, edible oils and shortenings comprising fatty acid esters of glycerol, fatty acids or esters thereof, certain low molecular weight oligomers of propylene glycol, glyceryl esters of fatty acids, and dispersions or emulsions of such hydrophobic substances in aqueous media. Suitable liquid carriers or diluents can also include comestibly acceptable solvents such as ethanol, propylene glycol, certain low molecular weight oligomers of propylene glycol and their ethyl ethers or acetates. Solid commestibly acceptable precursors, carriers, or diluents can include salts such as sodium chloride, vegetable flours and powders; flavor concentrates and extracts, spices, seasonings, saccharide sugars such as sucrose, fructose, glucose/dextrin, lactose and the like, or polysaccharides such as starch, modified starches, dextrins, maltodextrins, celluloses and modified celluloses, and the like, or emulsifying and stabilizing polysaccharides such as pectins, alginates, chitosan and chitosan derivatives, gum Arabic, carrageenans, locust bean gum, guar gum, and the like, common anti-oxidants or stabilizers or bulking agents, or mixtures of the precursors of the comestible composition, as exemplified above.

The compounds of the invention typically have sufficient solubility in water and/or polar organic substances, and mixtures thereof, for formulation at the desired concentration ranges by simply dissolving them in the appropriate liquids. Concentrate compositions comprising solid but water soluble substances such as sugars or polysaccharides, and the amide compounds described herein can be prepared by dissolving or dispersing the amide compound and soluble carrier in water or polar solvents, then drying the resulting liquid, via well know processes such as spray drying.

The solubility of the amide compounds of the invention may however be limited in less polar or apolar liquid carriers, such as oils or fats. In such embodiments it can be desirable to prepare a very fine dispersion or emulsion of the solid amide compound in the carrier, by grinding, milling, or homogenizing a physical mixture of the amide compound and the liquid carrier. The amide compounds can therefore in some cases be formulated as sweetner concentrate compositions comprising dispersions of solid microparticles the amide compound in the precursor substances. For example, some of the amide compounds of the invention can have limited solubility in non-polar substances such as edible fats or oils, and therefore can be formulated as sweetener concentrate compositions by milling or grinding the solid amide compound to microparticle size and mixing with the edible fat or or oil, or by homogenizing a dispersion of the solid amide compound and the edible fat or oil, or a commestibly acceptable analog thereof, such as the Neobee™ triglyceride ester based oils sold by Stephan Corporation of Northfield Ill., U.S.A.

It is also possible to prepare solids coated, frosted, or glazed with the well dispersed compounds of the invention by dissolving the amide compound in water or a polar solvent, then spraying the solid carrier or composition onto the solid comestible carrier or substrate, as exemplified below in connection with frosted cereals.

By means of the methods described above, many well known and valuable comestible compositions that currently contain sugar and/or equivalent saccharide sweeteners can be reformulated to comprise a few ppm of one or more of the amide compounds described herein, with a concomitant ability to reduce the concentration of the sugar and/or equivalent saccharide sweeteners by as much as 30 to 50%, with a corresponding drop in the caloric content of the comestible compositions.

For example, carbohydrate and/or saccharide sweeteners have long been used to sweeten and modify the melting point, texture, and palatability of ice cream formulations. Examples of carbohydrate sweeteners that are typically used in ice cream formulation include, but are not limited to, sugar, corn syrups, corn syrup solids, maltodextrin, and mixtures thereof. While such sweeteners add sweetness and calories, they also affect the texture and freezing and melting points of the frozen ice cream. Disclosed herein are examples of methods for reducing the amount of carbohydrate and/or saccharide sweeteners by using the compounds disclosed herein. By means of such methods and the ice cream formlations that result, the concentration of carbohydrate sweeteners required to achieve the desired sweetness can be reduced, along with calories. Moreover, the texture, freezing, and melting points of the resulting ice cream formulation can be adjusted in view of the lower sweeteners levels, by use of other known stabilizers, diluents, or more healthful natural incredients, to achieve a high quality ice cream product with reduced calories, as is well known to those of skill in the art, in view of the reduced sweetener ice creams already on the market.

The sweet enhancers disclosed herein can also be used with reduced calorie ice cream formulations that utilize artificial sweeteners (Sucralose, aspartame, acesulfame K, etc.) and/or sugar alcohol sweeteners (xylitol, sorbitol, erythritol, etc.). There are potential cost benefits that are associated with the use of the compounds of the invention to allow the reduction of these types of sweeteners, and there can also be some textural improvements as well as decreased gastrointestinal side effects associated with the usage of sugar alcohol sweeteners.

The amide compounds disclosed herein can be used at any desired concentration, and are effective sweeteners at concentrations of from about 0.01 to about 20 ppm, but are often optimally effective in ice cream formulation at levels of from about 0.1 to about 6.0 ppm. When properly formulated, the concentrations of sugar and carbohydrate type sweeteners can be effectively reduced by up to 50% while maintaining the desired degree of sweet flavor of the ice cream. Artificial sweeteners and sugar alcohols can also be effectively and optimally reduced up to 50% by using the disclosed sweet enhancers at levels of from about 0.1 to about 8 ppm.

Carbohydrate sweeteners have also long been used to coat processed cereals such as snacks and frosted breakfast cereals, to provide sweetness and texture. Typical sugar contents range from about 20 to 60% in known finished cereals, and the high sugar content of the cereal gives the cereals a "frosted" white appearance. The use of the amide compounds described herein in such cereal coatings allows for the reduction of sweetener levels and/or calories of the frosted cereals, and can also improve the appearance and/or marketability of the cereal. Similar approaches can be taken to form reduced sugar formulations of a wide variety of sweet coatings, frostings for baked goods, glazes, or sauces for other comestible products.

Carbohydrate sweeteners (typically sucrose, fructose, glucose/dextrose, dried corn syrup, etc.) have also long been used to formulate both liquid and dry beverage concentrate compositions, to provide for sweet taste and/or desirable mouthfeel. The use of a combination of disclosed amide compounds and significantly lower levels of existing sweeteners in liquid or solid beverage concentrate compositions allows the reduction unwanted calories in the final beverages, while maintaining similar taste, sweet flavor profile, and mouthfeel of the beverage. By use of the amide compounds of the invention at optimum 0.5 to 2.0 ppm concentrations, concentrations of the existing sweeteners can be reduced up to 50%, while achieving similar sweetness levels of the full sugar product. The sweet enhancers can also be used with reduced calorie and or sugar-free liquid beverages, dry beverage base formulations, or liquid concentrate formulations that utilize artificial sweeteners (Sucralose, aspartame, ace K, etc.) and or sugar alcohol sweeteners (xylitol, sorbitol, erythritol, etc.). There are potential cost benefits that are associated with the reduction of carbohydrate sweeteners, artificial sweeteners and sugar alcohol sweeteners. Qualitatively similar results and/or improvements can be made in many other comestible composition formulations by use of one or more of the amide compounds described herein.

Carbohydrate sweeteners (HFSC, corn syrups, sucrose/sugar, fructose, glucose/dextrose, dried corn syrup, etc.) are also used to sweeten soda flavor concentrate syrups, which are typically mixed with carbonated water in a 1:5 ratio to prepare the fountain soda drinks commonly sold in fast food restaurants and convenience stores. The most commonly used sweetener in soda syrup formulations is HFCS 55 (corn syrup comprising about 55% fructose). The use of HFCS in fountain syrups and carbonated beverages (soda) has been criticized for contributing to the rise in both child and adult obesity, but its usage can be lowered by the use of the amide compounds described herein. The amide compounds can also be used in reduced calorie and or sugar-free soda syrup base formulations that utilize artificial sweeteners (Sucralose, aspartame, ace K, etc.). There are potential cost benefits that are associated with the reduction of carbohydrate sweeteners and artificial sweeteners.

Making the Amide Compounds of Formula (I)

It will be apparent to the skilled artisan that methods for preparing precursors and functionality related to the compounds claimed herein are generally described in the literature. The skilled artisan given the literature and this disclosure is well equipped to prepare any of the necessary starting materials and/or claimed compounds. In some of the Examples cited below starting materials were not readily available, and therefore were synthesized, and the synthesis of the starting materials is therefore exemplified.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification, saponification, nitrations, hydrogenations, reductive amination and the like. These manipulations are discussed in standard texts such as March's *Advanced Organic Chemistry* (3d Edition, 1985, Wiley-Interscience, New York), Feiser and Feiser's *Reagents for Organic Synthesis*, Carey and Sundberg, *Advanced Organic Chemistry* and the like, the entire disclosures of which are hereby incorporated by reference in their entirety for their teachings regarding methods for synthesizing organic compounds.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts, *Protecting Groups in Organic Synthesis*, 3$^{rd}$ Ed., John Wiley & Sons (1999).

The following abbreviations have the indicated meanings:

| | |
|---|---|
| $CH_3CN$ = acetonitrile | HCl = hydrochloric acid |
| $CHCl_3$ = chloroform | $H_2SO_4$ = sulfuric acid |
| DIC = N,N'-diisopropylcarbodiimide | HOBt = 1-hydroxybenzotriazole |
| DIPEA = diisopropylethylamine | MeOH = methyl alcohol |
| DMAP = 4-(dimethylamino)-pyridine | $MgSO_4$ = magnesium sulfate |
| DMF = N,N-dimethylformamide | $NaHCO_3$ = sodium bicarbonate |
| EDC = 1-(3-dimethylaminopropyl)-3-ethylcarbodiimide hydrochloride | NaOH = sodium hydroxide |
| Fmoc = N-(9-fluorenylmethoxycarbonyl | $Na_2SO_4$ = sodium sulfate |
| DCM = dichloromethane | Ph = phenyl |
| DME = 1,2-dimethoxyethane | |
| ESIMS = electron spray mass spectrometry | r.t. = room temperature |
| $Et_3N$ = triethylamine | SPOS = solid phase organic synthesis |
| EtOAc = ethyl acetate | THF = tetrahydrofuran |
| EtOH = ethyl alcohol | TLC = thin layer chromatography |
| Alkyl group abbreviations | |
| Me = methyl | i-Bu = isobutyl |
| Et = ethyl | t-Bu = tertiary butyl |
| n-Pr = normal propyl | s-Bu = secondary butyl |
| i-Pr = isopropyl | n-Pen = normal pentyl |
| n-Bu = normal butyl | i-Pen = isopentyl |

The following example schemes are provided for the guidance of the reader, and represent preferred methods for making the compounds of Formula (I). These methods are not limiting, and it will be apparent that other routes may be employed to prepare these compounds. Such methods specifically include solid phase based chemistries, including combinatorial chemistry. The skilled artisan is thoroughly equipped to prepare the necessary and/or claimed compounds by those methods given the literature and this disclosure.

The starting materials used in preparing the compounds Formula (I) and their synthetic precursors, especially the substituted or unsubstituted aryls and heteroaryls, organic carboxylic acids and benzoic acids, isocyanates, and the various amines, anilines, alcohols, amino acids, etc., are often known compounds, or can be readily made by known methods of the literature, or are commercially available from various sources well known to those of ordinary skill in the art, such as for example, Sigma-Aldrich Corporation of St. Louis, Mo. USA, and their subsidiaries Fluka and Riedel-de Haen, at their various other worldwide offices, and other well know suppliers such as Fisher Scientific, TCI America of Philadelphia Pa., ChemDiv of San Diego, Calif., Chembridge of San Diego, Calif., Asinex of Moscow, Russia, SPECS/BIOSPECS of the Netherlands, Maybridge of Cornwall, England, Acros, TimTec of Russia, Comgenex of South San Francisco, Calif., and ASDI Biosciences of Newark, Delaware.

Well known organic reactions useful in the synthesis of the compounds of Formula (I) include halogenations, esterifications and de-esterifications, the reduction of carbonyl compounds to their corresponding alcohols, the condensation of carboxylic acids with amines to form amides, oxidations, alkylations, acylations, aromatic substitutions, both electrophilic and nucleophilic, etherifications, esterification, saponification, nitrations, hydrogenations, reductive amination, palladium catalyzed coupling reactions, and the like. These and many more well known to those of ordinary skill are discussed in standard texts such as March's Advanced Organic Chemistry (3d Edition, 1985, Wiley-Interscience, New York), Feiser and Feiser's Reagents for Organic Synthesis, Carey and Sundberg, Advanced Organic Chemistry and the like, the entire disclosures of which are hereby incorporated by reference in their entireties for their teachings regarding synthetic reactions and methods for synthesizing organic compounds.

A representative synthetic pathway for producing the compounds of Formula (I) wherein L is carbon are shown in Scheme 1:

Scheme 1

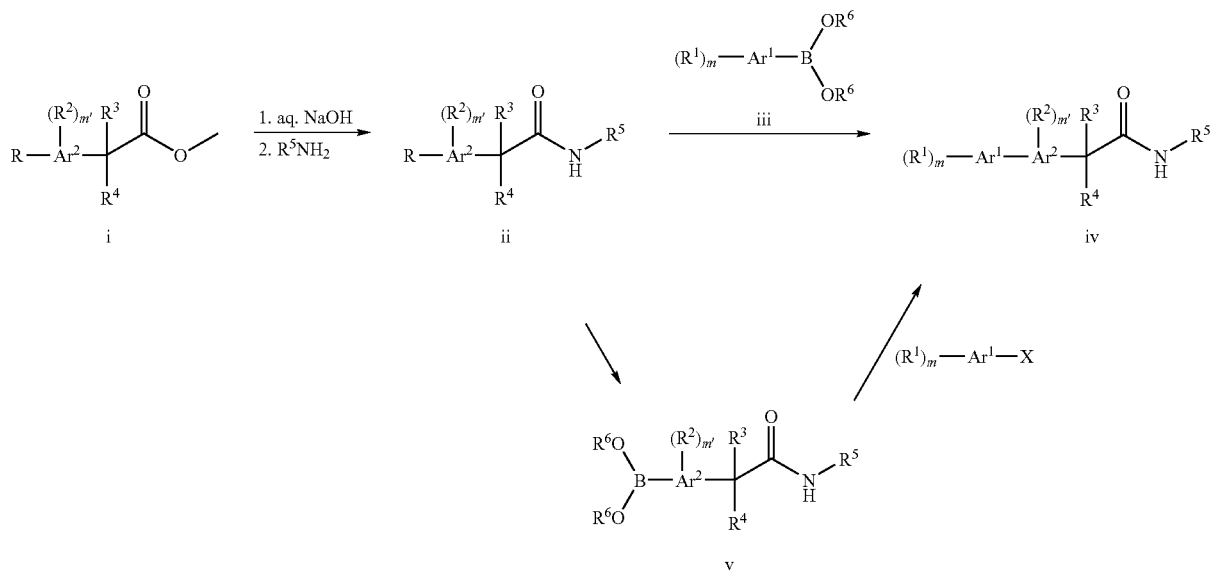

The methods of Scheme 1 begin with monoaromatic carboxylic acid esters of structure i, whose synthesis will be further described below. The monoaromatic carboxylic acid esters are hydrolyzed, typically under basic conditions, to give the parent carboxylic acids, which are condensed with primary amine precursors of the $R^5$ group ($R^5NH_2$) in presence of a variety of well known dehydrating/coupling reagents, such as 1-ethyl-3-(3-dimethylaminopropyl)-carbodiimide hydrochloride, to yield the amide compound of structure ii. The amide compound of structure ii is then coupled with a precursor of the $Ar^1$ group, by one of the known variations of palladium catalyzed "Suzuki" coupling of boronic acids iii or v (see Suzuki, *Pure & Applied Chem.*, (1994) 66:213-222, Miyaura and Suzuki, *Chem. Rev.* (1995) 95:2457-2483, Watanabe et al., *Synlett.* (1992) 207-210). In such Suzuki coupling reactions, precursors such as (ii) and (iii) may be employed wherein $R^6$ is either alkyl or hydrogen, and R is a halide (such as, iodo, bromo, or chloro) or triflate. Alternatively, the aryl borate v can be prepared by lithiation of a precursor aryl halide (e.g., iodo, bromo) ii, followed by treatment with a boric acid triester or can be prepared by palladium-catalyzed cross coupling reaction of a precursor aryl halide (e.g., iodo, bromo, or chloro) or a triflate ii with pinacol borane. Coupling reactions to produce biaryls such as iv may be conducted using either aryl boronic acids or aryl boronic esters, including cyclic esters in which two of the $R^6$ groups together with the boron atom from a pinacol borate ester (formation of pinacol borane esters: Ishyama et al., *J. Org. Chem.* (1995)60:7508-7510; coupling pinacol borane esters: Firooznia et al., *Tetrahedron Lett.* (1999) 40:213-216).

Scheme 1a

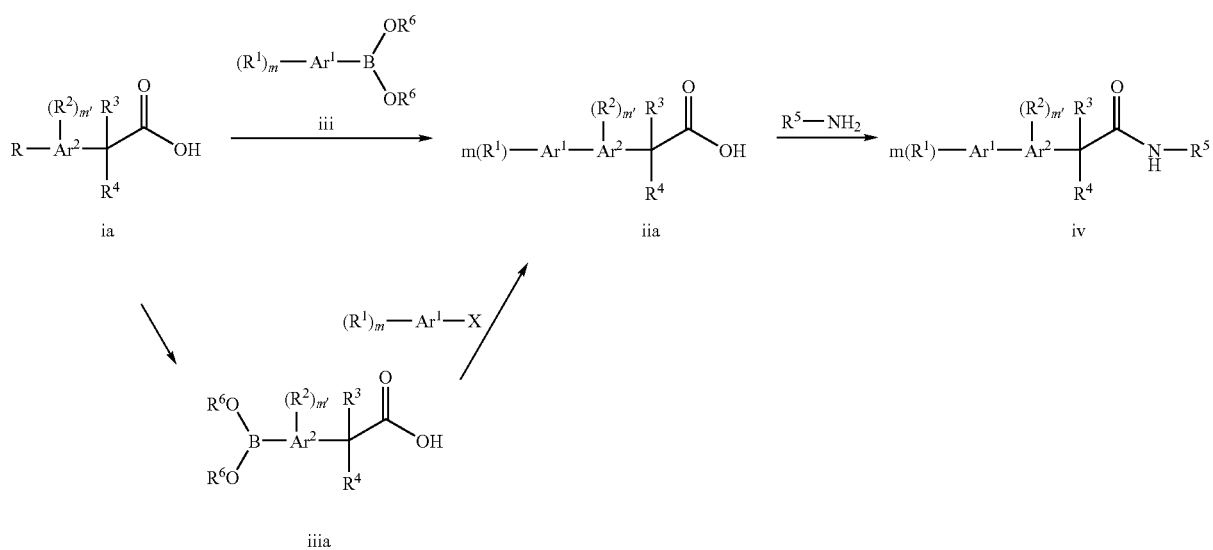

Alternatively, according to the Scheme 1a, the synthesis of compounds of Formula (I) can start with monoaromatic carboxylic acid or ester precursors ia wherein R is a halogen or triflate, that can be directly coupled under "Suzuki coupling" conditions with boronic acids iii to give the biaryl acid iia. Alternatively iia can be prepared from the aryl borate iiia which can be prepared by lithiation of a precursor aryl halide (e.g., iodo, bromo) ia, followed by treatment with a boric acid triester or can be prepared by palladium-catalyzed cross coupling reaction of a precursor aryl halide (e.g., iodo, bromo, or chloro) or a triflate ia with pinacol borane followed by Suzuki coupling with a precursor of the $Ar^1$ group $[(R^1)m-Ar^1—X]$ wherein X is either alkyl, halogen or triflate. The biaryl acids iiia can be then condensed with primary amine precursors of $R^5$ group ($R^5NH_2$) typically in presence of a carbodiimide type of reagent to yield the amide-biaryl compounds of structure iv.

Scheme 2 discloses a method that can be used to prepare urea compounds of Formula (I) wherein L is a nitrogen atom:

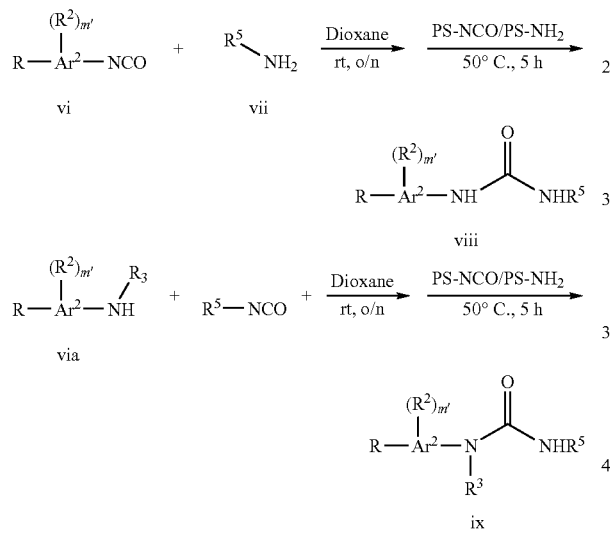

The synthesis of compounds of Formula (I) wherein L is nitrogen can begin with readily available aryl isocyanates (vi). Aryl isocyanates can also be prepared by the phosphogenation of aryl amines by treatment with phosgene. In another method that avoids the use of phosgene, aryl isocyanates (vi) can be prepared by treating an aryl amine with a dialkyldicarbonate (e.g., di-tert-butyldicarbonate (i.e., (Boc)$_2$O) in the presence of a base (see e.g., *Angew. Chem. Int. Ed. Engl.* (1995) 34:2497, which is incorporated by reference herein for its teachings of aryl isocyanate preparations). In yet another route to aryl isocyanates (vi), an aryl carboxylic acid or aryl acid chloride, upon treatment with diphenyphosphoryl azide or sodium azide, respectively, can undergo the Curtius rearrangement to provide the aryl isocyanate (vi). Alternatively, to synthesize a starting material via that will produce a final compound of Formula (I) having a non-hydrogen $R^3$ substitutent, the N-substituted aromatic precursor compound XV can be condensed with an isocyanate precursor of the R5 group vi.

With the desired aryl isocyanate starting material (vi) in hand, it can be treated with amine (vii) in dioxane, followed by treatment with methylisocyanate polystyrene and polystyrene amine, two polymer supported reagents, to yield the desired urea starting materials. The result is precursor (viii) (where $R^3$ is hydrogen and $R^4$ is absent), which can be functionalized with aryl substituent $Ar^1—(R^1)_m$, as shown above in Scheme 1.

Various methods for synthesizing precursors of starting materials such as compound i are illustrated in Scheme 3. A representative synthetic method for synthesizing precursors i can start using bromination of readily available substituted tolyl compounds of structure x, followed by substitution by cyanide providing the nitrile intermediate xi. Hydrolysis of the nitrile under either basic or acidic conditions followed by esterification can provide various phenyl acetic acid esters xii, that can be alkylated on their activated methylene groups by treatment with a base (such as NaH, lithium diisopropyl amide (LDA), or $K_2CO_3$) then alkyl halides (e.g., iodo, chloro, bromo), providing depending on reaction stoichiometry and reaction conditions, either monoalkylated xiii or dialkylated precursors i, where $R^3$ is the same as $R^4$. Subsequent alkylation of precursor (xii) can give compound i, where $R^3$ is not the same as $R^4$. These reactions were described for example by Beckett et al. *Tetrahedron* (1968) 24:6093-6109, by Duan et al. *J. Med. Chem.* (2002) 45:4954-4957, and by Ohmoto et al. *J. Med. Chem.* (2001) 44:1268-1285.

In other aspects, a new $R^4$ substituent bonded through an oxygen, nitrogen, or sulfur atom can be introduced onto compound xiii by bromination at the activated methylene group, followed by substitution of the bromide by nucleophiles such as alkoxides, organic amines, thiols, and the like.

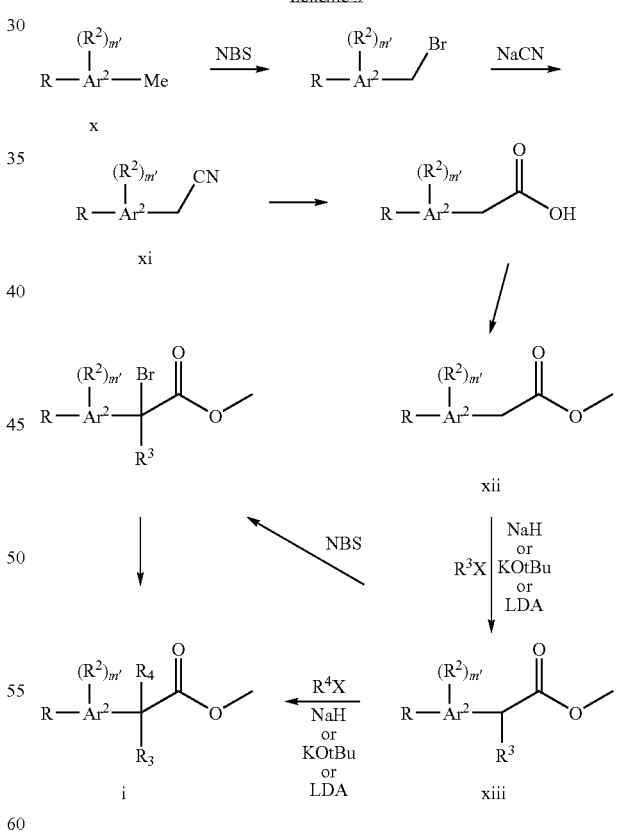

Specifically, methods for the synthesis of acetic acid methyl ester starting materials having 5-membered heteroaromatic $Ar^1$ rings, represented by general formula ii, are described in Scheme 4. N-Alkylation of xiv with NaH/BrCH$_2$CO$_2$Me can give carboxy methyl substituted heterocycles compounds xv. Similar α-C-alkylations or α-C-functionalization as described above gave the key precursors ic.

Scheme 4

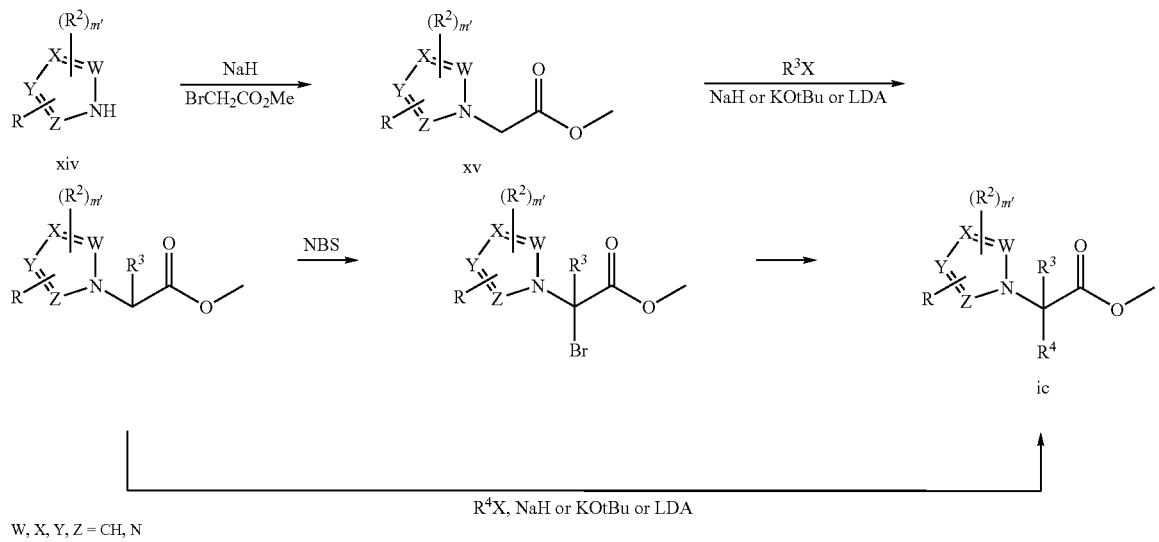

W, X, Y, Z = CH, N

An alternative route for the convenient synthesis of methyl phenylacetic acid esters i is described in Scheme 5, which employs a Palladium-catalyzed coupling of silylketene acetals with aryl halides developed by Hartwig, J. F. et al (Liu, X. and Hartwig, J. F. *J. Am. Chem. Soc.* 2004, 126, 5182).

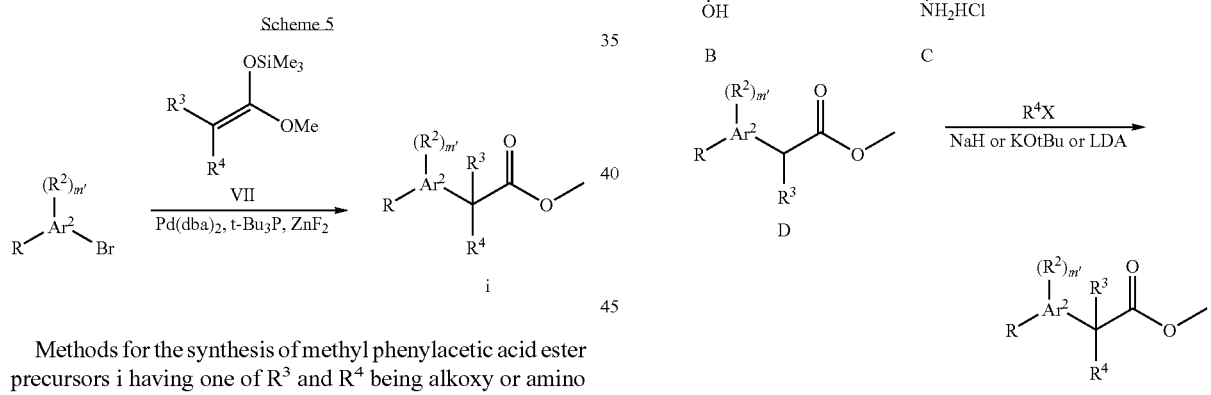

Methods for the synthesis of methyl phenylacetic acid ester precursors i having one of $R^3$ and $R^4$ being alkoxy or amino substitutions is described in Scheme 6. α-Hydroxyphenylacetic acid derivatives B can be obtained by reaction of the corresponding benzaldehyde derivatives A with $Me_3SiCN$, followed by hydrolysis with HCl, and subsequent esterification. O-Alkylation, followed by α-C-alkylation provided the precursors i. The α-amino-phenylacetic acid derivatives C can be similarly obtained via the Strecker synthesis, followed by esterification. The subsequent N-alkylation or N-protection, followed by α-C-alkylation, provided the precursors i.

Scheme 6

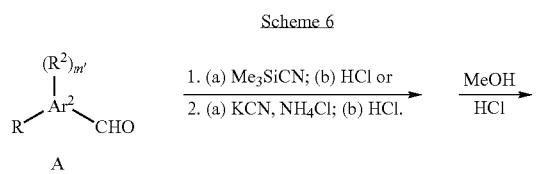

Methods for the synthesis of phenyl acetic acid methyl ester precursors i with more functionalized $R^3$ and $R^4$ substitutions are described in Scheme 7. α-C-Alkylation or Aldol reaction of methyl phenylacetic acid esters E gave the corresponding α-C-mono-substituted methyl phenylacetic acid esters F. The subsequent base catalyzed condensation with esters or aldehydes provides the more functionalized phenylacetic acid methyl ester precursors i. Condensation of methyl phenylacetic acid esters E with formaldehyde in the presence of $K_2CO_3$ gave α-phenyl methyl acrylate intermediates G. Asymmetric dihydroxylation, followed by selective alkylation of the resultant two hydroxyls (see Kolb, H. C., Chem Rev. 1994, vol 94, 2483-2547) can provide a variety of the phenylacetic acid methyl ester precursors wherein $R^3$ and $R^4$ are different.

Scheme 7
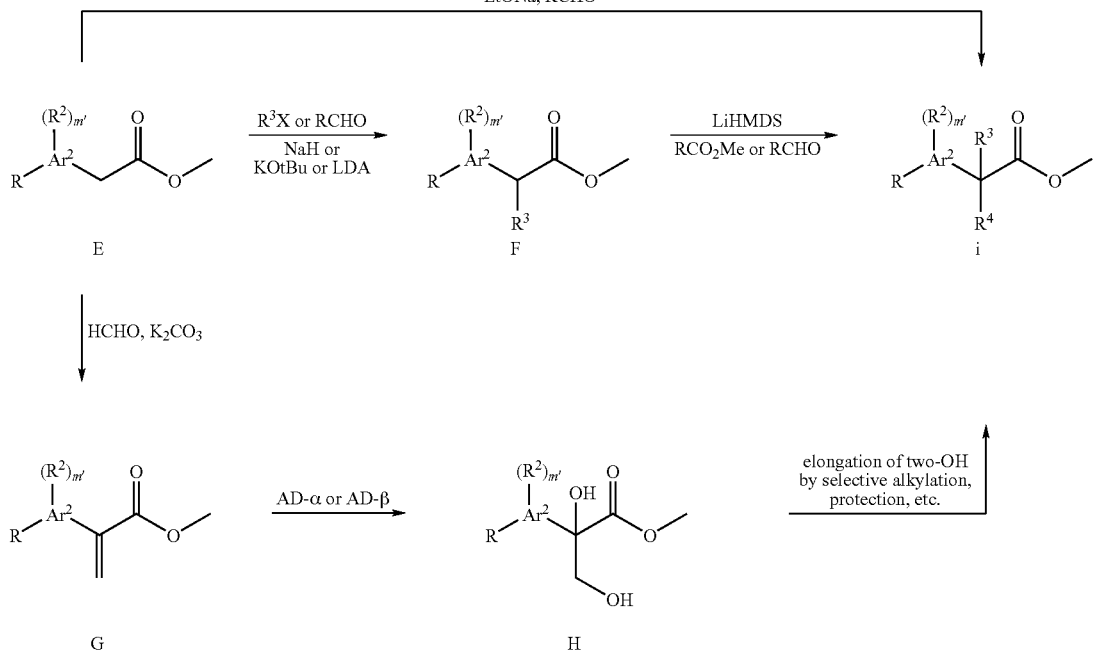
Disclosed below are methods for synthesizing compounds wherein $Ar^1$ is an oxadiazole heterocycle:
Scheme 8
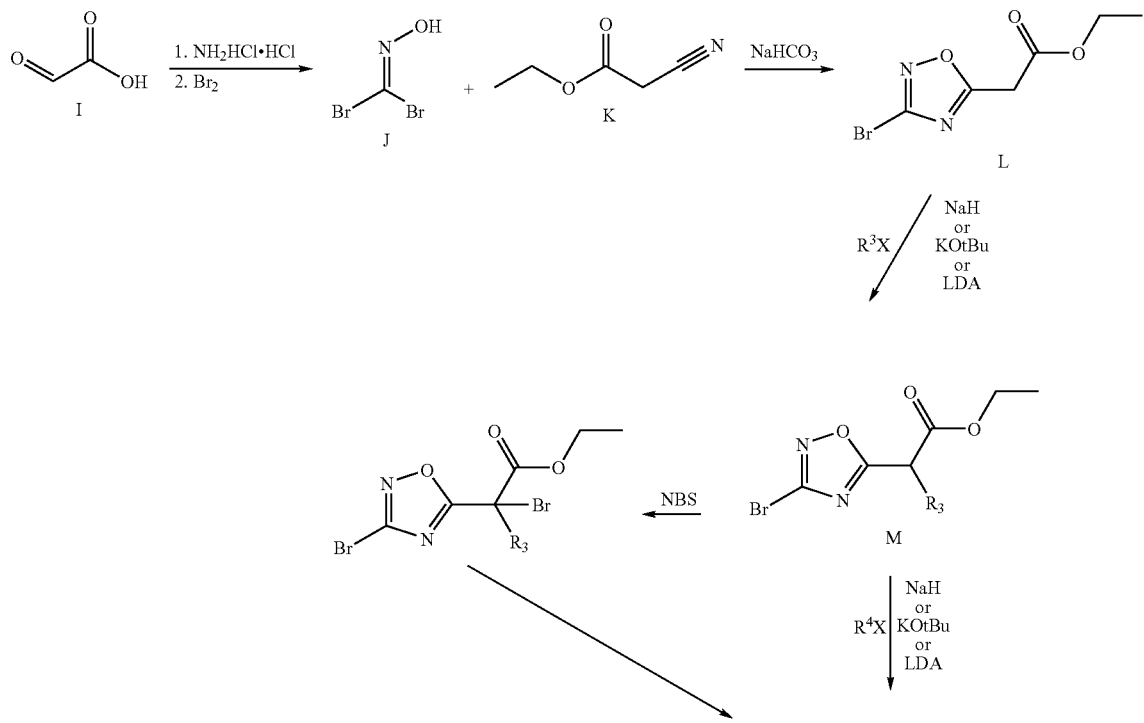

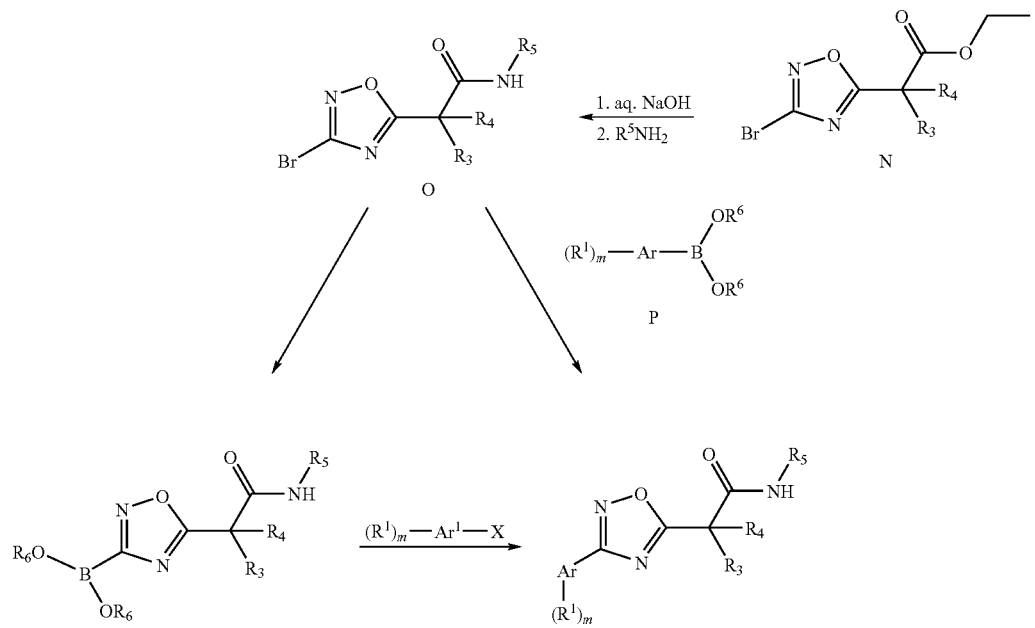

The methods of Scheme 8 begin with formation of dibromoformaldoxime I from glyoxylic acid J, as described by Rohloff et al. *Tetrahedron Lett.* (1992) 33:3113-3116. Cyclization with ethyl cyanoacetate K under basic conditions provides the 3-brominated-1,2,4-oxadiazole intermediate L (see Humphrey, et al. *J. Heterocyclic Chem.* (1989) 26:23-24), which can be further functionalized by treatment with a strong base (such as NaH, lithium diisopropyl amide (LDA), KOtBu) and alkyl halides (e.g., iodo, chloro, bromo) providing either monoalkylated M or dialkylated precursors N, where $R^3$ is the same as $R^4$. Sequential alkylation of precursor (M) can give compounds N, where $R^3$ is not the same as $R^4$. These reactions were described for example by Beckett et al. *Tetrahedron* (1968) 24:6093-6109, by Duan et al. *J. Med. Chem.* (2002) 45:4954-4957, and by Ohmoto et al. *J. Med. Chem.* (2001) 44:1268-1285.

The monoaromatic carboxylic acid esters N are hydrolyzed, typically under basic conditions, to give the parent carboxylic acid, which is condensed with primary amine precursors of the $R^5$ group ($R^5NH_2$) in the presence of a dehydrating/coupling reagent such as 1-ethyl-3-(3-dimethylaminopropyl)-carbodiimide hydrochloride, to yield the amide compound of structure O. The amide compound of structure O is then coupled with a precursor of the Ar group, by palladium catalyzed "Suzuki" coupling of boronic acids P (see Suzuki, *Pure & Applied Chem.*, (1994) 66:213-222, Miyaura and Suzuki, *Chem. Rev.* (1995) 95:2457-2483, Watanabe et al., *Synlett.* (1992) 207-210). In this Suzuki coupling reaction, precursors such as P may be employed wherein $R^6$ is either alkyl or hydrogen.

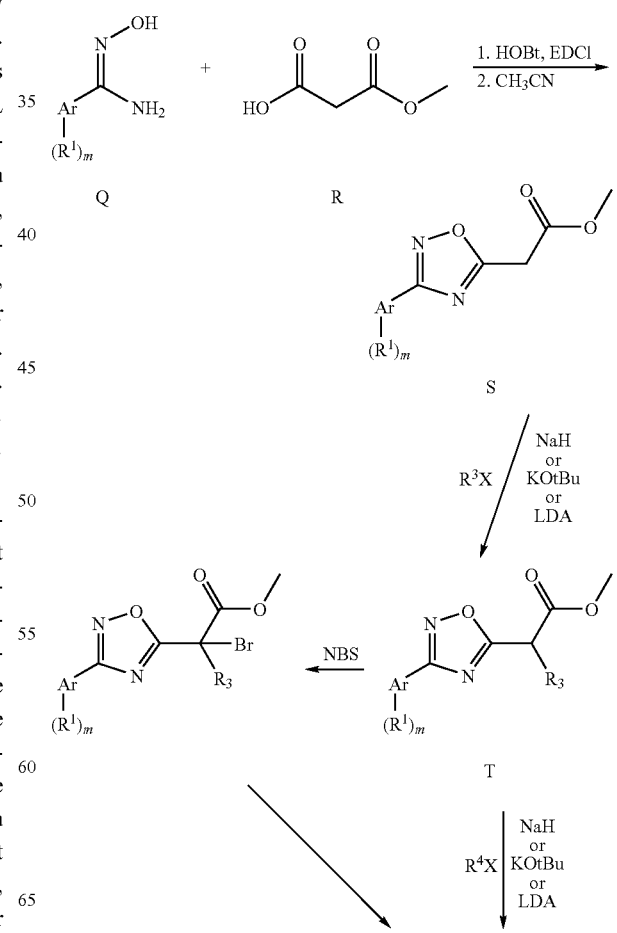

Scheme 9

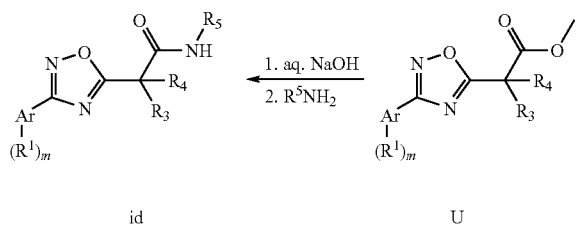

Alternatively, 1,2,4-oxadiazole-containing biaryl amides of Formula id may be synthesized as described in Scheme 9 from aryl hydroxybenzimidamides Q by cyclization with 3-methoxy-3-oxopropanoic acid R in two steps to provide the biaryl esters of structure S (see Wang et al. *Org. Lett.* (2005) 7:925-928). Further modification of the cyclized intermediate to form the substituted structures T and U, followed by saponification and amide formation.

Scheme 10 provides for synthesis of other compounds of Formula (I) wherein $Ar^1$ is an isoxazole heterocycle. The methods of Scheme 10 begin with reduction of the bisaromatic isoxazole aldehyde of structure V with sodium borohydride, followed by mesylation and substitution with the cyano group to give compound W. Functionalization alpha to the cyano substituent can be carried out base catalyzed alkylations as described in Scheme 10, to provide intermediates X and Y. Subsequent hydrolysis of the nitrile functionality under acidic conditions, and condensation with an amine of formula $R^5NH_2$ using coupling reagents (1-ethyl-3-(3-dimethylaminopropyl)-carbodiimide hydrochloride and 1-hydroxybenzotriazole) provide the biaryl isoxazole amides Z.

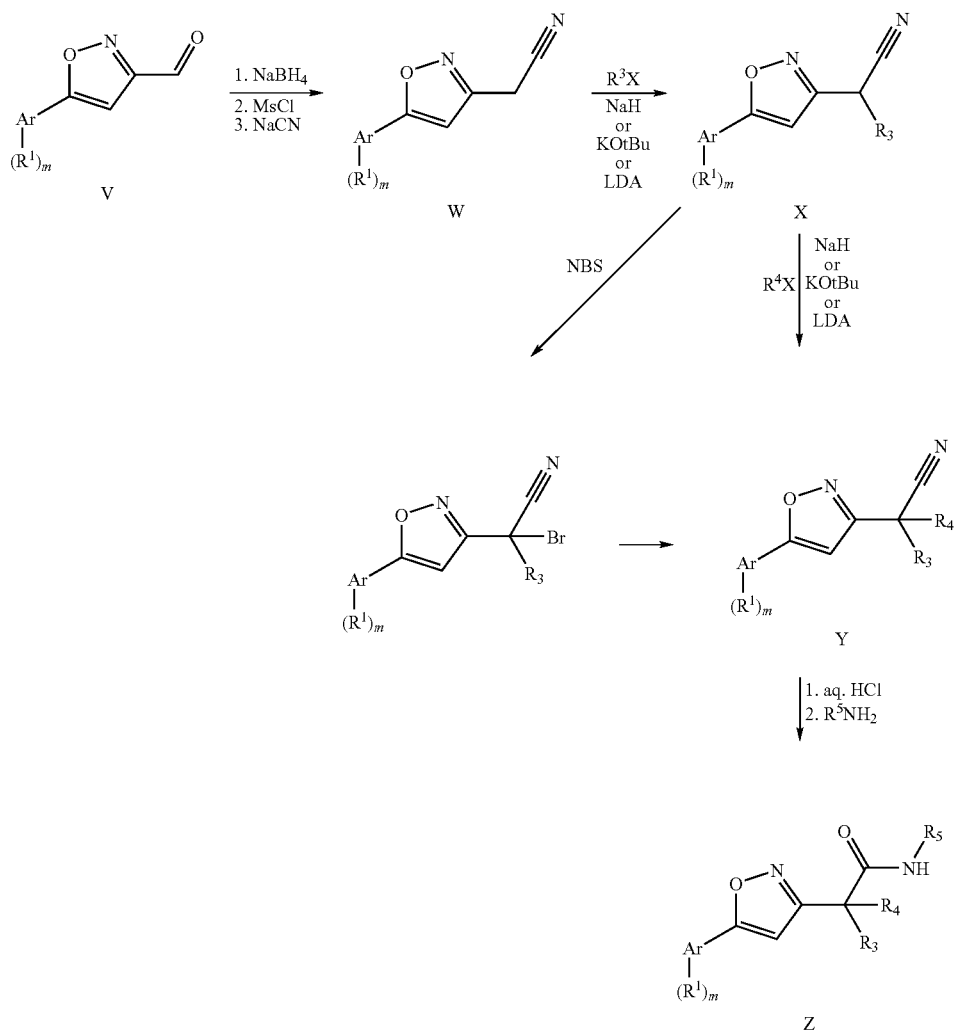

The references mentioned above in connection with the synthesis of the compounds of Formula (I) are hereby incorporated herein by reference in their entireties, for their teachings of generic synthetic reaction methodologies.

Measuring the Biological Activity of the Compounds of Formula (I)

Cell based technologies and assays, such as those disclosed in WO 02/064631, and WO 03/001876, and U.S. Patent Publication US 2003-0232407 A1 were used both to initially screen amide compounds for agonist or antagonist activity for T1R2/T1R3 "sweet" taste receptors that had been expressed in appropriate cell lines. Once initial "hits" corresponding to interesting levels of agonist activity of compounds of Formula (I) had been obtained in assays using such cell lines, the same assays and also certain cell and/or receptor-based assays for the ability to enhance the sweet taste of known sweeteners such as sucrose, fructose, and the like were used to provide data to guide an iterative process of synthesizing and testing structural variants of the amide compounds of Formula (I), in combination with occasional human taste testing of high interest compounds, so as to design, test, and identify species and genera of compounds with increased and optimized levels of desirable biological activities.

Some aspects of the inventions relate to the quantification of the degree of activity of specific compounds and classes of the amide compounds of Formula (I) that are agonists of, or modulate (increase or decrease) the activity of the T1R2/T1R3 sweet taste receptors, alone or in combination with another compound that activates hT1R2/hT1R3, e.g., sucrose or fructose. Particularly, in many embodiments the invention relates to the amides of Formula (I) that are agonists for, or modulate the activity of hT1R2/hT1R3 (human sweet receptor) in vitro and/or in vivo.

In another aspect, the invention relates to compounds that modulate the human perception of sweet taste, alone or in combination with another compound or flavorant, when added to a comestible or medicinal product or composition.

Prior to conducting "swish and spit" taste testing by human volunteers, compounds of Formula (I) that met desired activity criteria in the receptor-based screening assays, as well as suitable purity, solubility and other physical properties requirements, undergo a preliminary safety assessment. The preliminary safety assessment involves a preliminary toxicity review from the literature and a structure search and a substructure search, as well as searches on potential break-down products or metabolites. This safety assessment process is intended to identify structural alerts (described by Ashby and Tennant in "Chemical Structure, Salmonella Mutagenicity and Extent of Carcinogenicity as Indicators of Genotoxic Carcinogenesis Among 222 chemicals Tested in Rodents by the U.S. NCI/NTP," *Mutation Research,* 204:17-115 (1988), "Definitive Relationships Among Chemical Structure, Carcinogenicity and Mutagenicity for 301 Chemicals Tested by the U.S. NTP," *Mutation Research,* 257:229-306 (1991), and by Cramer, Ford, and Hall, "Estimation of toxic hazard—A decision tree approach," *Food and Cosmetic Toxicology* 16, 255-276 (1978)) using the principles outlined by Munro et al. ("A Procedure for the Safety Evaluation of Flavouring Substances." *Food and Chemical Toxicology,* 37:207-232 (1999)). Searches include chemical structures and reactions, associated chemical and physical properties, scientific literature, and detailed pharmacological, toxicological, and ecological data. A committee reviews a summary of relevant information, and if approved, compounds of Formula (I) whose chemical structure permits no strong initial presumption of safety (Class III) were tasted at or below the human exposure threshold of 90 microgram/day describe by Munro et al.

As a result of the iterative process of making and assaying the activity of compounds of Formula (I), and selected human taste tests, it has been unexpectedly discovered that at the amide compounds of Formula (I) are agonists of hT1R2/hT1R3 (human sweet receptor) in vitro and/or in vivo at concentrations significantly below the millimolar level, and often are agonists at concentrations of a few micromolar or less. Moreover it has been discovered that many of the amide compounds of Formula (I) can, at concentrations significantly below the millimolar level, and often are agonists at concentrations of a few micromolar or less modulate the human perception of sweet taste, alone or in combination with another compound or flavorant compound or composition, when added to a comestible or medicinal product or composition, or a precursor thereof.

In Vitro hT1R2/hT1R3-HEK293 Taste Receptor Activation Assay

An HEK293 cell line derivative (Chandrashekar et al., *Cell* (2000) 100:703-711) that stably expresses Gα15 and hT1R2/hT1R3 (Li et al., *Proc Natl Acad Sci USA* (2002) 99:4692-4696), see also PCT Publication No. WO 03/001876 A2) was used to identify compounds with sweet taste enhancing properties.

Compounds covered in this document were initially selected based on their activity on the hT1R2/hT1R3-HEK293-Gα15 cell line (Li et al. vide supra). Activity was determined using an automated fluorometric imaging assay on a FLIPR instrument (Fluorometric Intensity Plate Reader, Molecular Devices, Sunnyvale, Calif.) (designated FLIPR assay). Cells from one clone (designated S-9 cells) were seeded into 384-well plates (at approximately 50,000 cells per well) in a medium containing DMEM Low Glucose (Invitrogen, Carlsbad, Calif.), 10% dialyzed fetal bovine serum (Invitrogen, Carlsbad, Calif.), 100 Units/ml Penicillin G, and 100 µg/ml Streptomycin (Invitrogen, Carlsbad, Calif.) (Li et al. vide supra) see also PCT Publication No. WO 03/001876 A2). S-9 cells were grown for 24 hours at 37° C. S-9 cells were then loaded with the calcium dye Fluo-3AM (Molecular Probes, Eugene, Oreg.), 4 µM in a phosphate buffered saline (D-PBS) (Invitrogen, Carlsbad, Calif.), for 1 hour at room temperature. After replacement with 25 µl D-PBS, stimulation was performed in the FLIPR instrument and at room temperature by the addition of 25 µl D-PBS supplemented with different stimuli at concentrations corresponding to twice the desired final level. Receptor activity was quantified by determining the maximal fluorescence increases (using a 480 nm excitation and 535 nm emission) after normalization to basal fluorescence intensity measured before stimulation.

For dose-responses analysis, stimuli were presented in duplicates at 10 different concentrations ranging from 60 nM to 30 µM. Activities were normalized to the response obtained with 400 mM D-fructose, a concentration that elicits maximum receptor response. $EC_{50}$s were determined using a non-linear regression algorithm (using a Senomyx, Inc. software), where the Hill slope, bottom asymptotes and top asymptotes were allow to vary. Identical results were obtained when analyzing the dose-response data using commercially available software for non-linear regression analysis such as GraphPad PRISM (San Diego, Calif.).

In order to determine the dependency of hT1R2/hT1R3 for the cell response to different stimuli, selected compounds were subjected to a similar analysis on HEK293-Gα15 cells (not expressing the human sweet receptor). The HEK293-

Gα15 cells do not show any functional response in the FLIPR assay to D-fructose or any other known sweeteners. Similarly, compounds covered in this document do not induce any functional response when using HEK293-Gα15 cells in the FLIPR assay.

Sweet Flavor and Sweet Flavor Enhancement Measurement Using Human Panelists Difference from Reference Human Taste Test Procedures To determine how the intensity of a test sample of an experimental compound differs from that of a reference sample in terms of sweetness, the following assay can be used. This type of study can use a larger number of evaluations in order to obtain statistically significant data, so the test can be repeated with the same or additional panelists.

Generally, a group of preferably 10 or more panelists taste pairs of solutions where one sample is the "Reference" (which typically does not include an experimental compound and is an approved substance or Generally Recognized As Safe (GRAS) substance, i.e., a sweetener) and one sample is the "Test" (which may or may not include an experimental compound). Subjects rate the difference in intensity of the test sample compared to the reference sample for the key attribute on a scale of −5 (much less sweet than the reference) to +5 (much sweeter than the reference). A score of 0 indicates the test sample is equally as sweet as the reference.

Ten or more subjects can be used for the Difference from Reference tests. Preferably subjects have been previously familiarized with the key attribute taste and are trained to use the −5 to +5 scale. It can also be helpful to have subjects refrain from eating or drinking (except water) for at least 1 hour prior to the test. Subjects can eat a cracker and rinse with water four times to clean the mouth.

Test solutions can include the experimental compound in water, the experimental compound plus a key tastant (e.g., 4% sucrose, 6% sucrose, 6% fructose, 6% fructose/glucose, or 7% fructose/glucose, at pH 7.1 or 2.8), and a range of key tastant only solutions as references.

Samples of the key tastant without the experimental compound can be used to determine if the panel is rating accurately; i.e., the reference is tested against itself (blind) to determine how accurate the panel is rating on a given test day. The solutions can be dispensed in 10 ml volumes into 1 oz. sample cups and served to the subjects at room temperature. The subjects are instructed to thoroughly "swish" a sample of the aqueous liquid containing the compounds to be tested around in their mouths, then "spit" out the bulk of the aqueous solution, so as to minimize the amount of compound actually ingested, and to minimize cross-contamination with subsequent test samples.

Typically, subjects first taste the reference sample then immediately taste the test sample and rate the difference in intensity of the key attribute on the Difference from Reference scale (−5 to +5). All samples are usually expectorated. Subjects may retaste the samples but can only use the volume of sample given. Subjects should rinse at least twice with water between pairs of samples. Eating a cracker between sample pairs may be required depending on the samples tasted.

The scores for each test are averaged across subjects and standard error is calculated. Panel accuracy can be determined using the score from the blind reference test. ANOVA and multiple comparison tests (such as Tukey's Honestly Significant Difference test) can be used to determine differences among pairs, provided the reference sample is the same among all tests. If the identical test pair is tested in another session, a student's t-test (paired, two-tailed; alpha=0.05) can be used to determine if there is any difference in the ratings between sessions.

A number of different reference sweeteners can be used for the measurement of sweet taste enhancement. A 6% fructose/glucose mixture can be approximately equal in sweet taste perception as 6% sucrose, which is within the range where panelists are sensitive to small changes in sweet taste perception. After initial studies in, for example, 6% fructose/glucose at pH 7.1, studies can shift to evaluating the performance of the compound in a product prototype more similar to a cola beverage, i.e., higher concentrations of sweetener and lower pH.

EXAMPLES

The following examples are given to illustrate a variety of exemplary embodiments of the invention and are not intended to be limiting in any manner.

For the purpose of this document, the compounds individually disclosed in the following Examples 1-57 and corresponding Table A comprising compound examples s A1-A93 can be referred to in shorthand by the number of the Example. For example, as shown immediately bellow, Example 1 discloses a synthesis of a particular compound 2-(4-(furan-3-yl)phenyl)-N-isobutyl-2-methylpropanamide, and the results of experimental assays of its biological effectiveness, which compound is and can be referred to herein in shorthand form as Compound 1. Similarly, the first compound illustrated in Table A can be referred to elsewhere herein as Compound A1.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the sensitivity and resolution of analyses, product purity, and yield obtained from the described process. Only reasonable and routine experimentation will be required to optimize such process conditions.

Example 1

2-(4-(Furan-3-yl)phenyl)-N-isobutyl-2-methylpropanamide

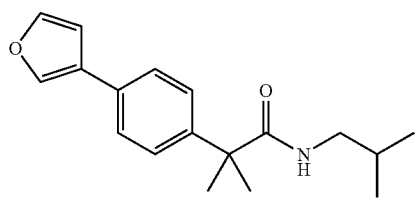

2-(4-Bromophenyl)-N-isobutyl-2-methylpropanamide (Example 1a) (850 mg, 2,85 mmol) was dissolved in 30 ml of toluene, 6 ml of EtOH and 4.5 ml of water followed by 1.38 g (10 mmol) of K$_2$CO$_3$ and 560 mg (5 mmol) of 3-furanboronic acid. The suspension was degassed using argon stream and sonication (30 min). Then 1.16 g (1 mmol) of tetrakis(triphenylphosphine)palladium was added under argon and the mixture was stirred at 80° C. overnight. The solution was dried down on vacuum, diluted with EtOAc and extracted with water. The organic phase was dried over MgSO$_4$ and evaporated on vacuum providing a crude product that was further purified using RP HPLC yielding 300 mg (41%) of the title compound as a white solid. $^1$H NMR (400 MHz, dDMSO): δ 0.74-0.75 (d 6H), 1.45 (s, 6H), 1.67-1.70 (m,1H), 2.83-2.86 (dd, 2H), 6.94-6.95 (dd, 1H), 7.30-7.32 (m, 3H), 7.54-7.57 (m, 2H), 7.72-7.73 (t, 1H), 8.15-8.16 (t, 1H). MS (M+H, 286).

Example 1a 2-(4-Bromophenyl)-N-isobutyl-2-methylpropanamide: Methyl 2-(4-bromophenyl)-2-methylpropanoate (1.29 ml, 5 mmol) was added to 30 ml of 1M aq. NaOH and the mixture was stirred at 60° C. overnight. The solution was acidified with 6M aq. HCl (pH 2) and extracted with EtOAc. The organic extract was washed with brine, dried over MgSO$_4$ and concentrated on vacuum. The crude 2-(4-bromophenyl)-2-methylpropanoic acid was coupled without further purification with 2-methylpropan-1-amine (0.5 ml, 5 mmol) in presence of EDC (1.1 g, 5.5 mmol) and HOBt (675 mg, 5 mmol) in 8 ml of DMF at rt overnight. The mixture was dried down on vacuum and extracted with EtOAc and washed with saturated NaHCO$_3$, 10% citric acid and brine. Organic extracts were dried over MgSO$_4$ and concentrated on vacuum to give 2-(4-bromophenyl)-N-isobutyl-2-methylpropanamide as a white solid (1.4 g, 94%). (M+H, 298).

The compound had an EC$_{50}$ for activation of a hT1R2/hT1R3 sweet receptor expressed in HEK293 cell line of 0.34 μM.

Example 2

N-Isobutyl-2-methyl-2-(4-(4-methylthiophen-3-yl)phenyl)propanamide

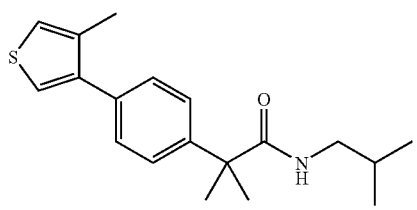

Prepared in a similar manner to Example 1 from 2-(4-Bromophenyl)-N-isobutyl-2-methylpropanamide (Example 1a) and 4-methylthiophen-3-ylboronic acid. Yield: 67%. $^1$H NMR (400 MHz, dDMSO): δ 0.73-0.79 (d, 6H), 1.48 (s, 6H), 1.67-1.74 (m, 1H), 2.23 (s, 3H), 2.84-2.87 (m, 2H), 7.26-7.27 (m, 1H), 7.34-7.40 (m, 5H), 7.43-7.44 (d, 1H). MS(M+H, 316).

The compound had an EC$_{50}$ for activation of a hT1R2/hT1R3 sweet receptor expressed in HEK293 cell line of 0.85 μM.

Example 3

2-(2-fluorobiphenyl-4-yl)-N-isobutylpropanamide

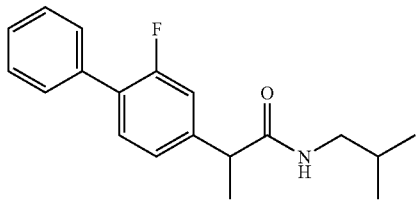

To a solution of 2-(2-fluorobiphenyl-4-yl)propanoic acid (Aldrich) (172.3 mg), HOBt (133.2 mg, 1.4 eq) and triethylamine (196.5 mL, 2 eq) in dichoromethane (7 mL) was added at room temparature EDC (270.4 mg, 2.0 eq). The reaction was stired at room temperature for 30 minutes and 2-methylpropan-1-amine (0.1 mL, 1.5 eq) was added. The solution was stirred overnight then diluted with dichlorometahne and washed successively with aqueous NaHCO$_3$, water, aqoueous HCL (1N), water, dried over MGSO$_4$, filtered and evaporated. Chromatogarphy on silica gel (eluent:ethyl acetate/hexane 1:1) afforded 170 mg of 2-(2-fluorobiphenyl-4-yl)-N-isobutylpropanamide. Yield: 80%. $^1$H NMR (500 MHz, CDCl$_3$): δ 0.83-0.79 (d, 6H), 1.55-1.56 (d, 3H), 1.69-1.74 (m, 1H), 3.04-3.07 (m, 2H), 3.56-3.58 (m, 1H), 5.4 (s br, 1H), 7.11-7.16 (m, 2H), 7.37-7.46 (m, 4H), 7.53-7.55 (m, 2H).

The compound had an EC$_{50}$ for activation of a hT1R2/hT1R3 sweet receptor expressed in HEK293 cell line of 2.8 μM.

Example 4

2-(2-fluorobiphenyl-4-yl)-N-(furan-2-ylmethyl)propanamide

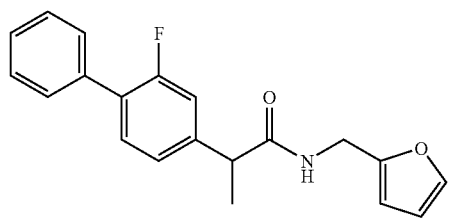

Prepared in a similar manner to Example 3 from 2-(2-fluorobiphenyl-4-yl)propanoic acid and furan-2-ylmethanamine. Yield: 75%. $^1$H NMR (500 MHz, CDCl$_3$): δ 1.55-1.56 (d, 3H), 3.56-3.58 (m, 1H), 4.35-4.40 (dd, 1H, J$_1$=5.3 Hz, J$_2$=15.5 Hz), 4.45-4.49 (dd, 1H, J$_1$=5.7 Hz, J$_2$=15.6 Hz), 5.72 (s br, 1H), 6.16 (d, 1H, J=2.7 Hz), 6.39 (m, 1H), 7.10-7.15 (m, 2H), 7.25-7.45 (m, 5H), 7.54 (m, 2H).

The compound had an $EC_{50}$ for activation of a hT1R2/hT1R3 sweet receptor expressed in HEK293 cell line of 4.55 μM.

Example 5

2-(2-fluorobiphenyl-4-yl)-N-(2-methoxyethyl)propanamide

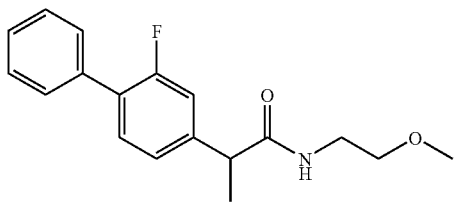

Prepared in a similar manner to Example 3 from 2-(2-fluorobiphenyl-4-yl)propanoic acid and 2-methoxyethanamine. Yield: 50%. $^1$H NMR (500 MHz, CDCl$_3$): δ 1.54-1.56 (d, 3H), 3.30 (s, 3H), 3.38-3.45 (m, 4H), 3.55 (q, 1H), 5.58 (s br, 1H), 7.11-7.16 (m, 2H), 7.36-7.45 (m, 5H), 7.54 (m, 2H).

The compound had an $EC_{50}$ for activation of a hT1R2/hT1R3 sweet receptor expressed in HEK293 cell line of 6.5 μM.

Example 6

2-(2-fluorobiphenyl-4-yl)-N-(1-methoxybutan-2-yl)-2-methylpropanamide

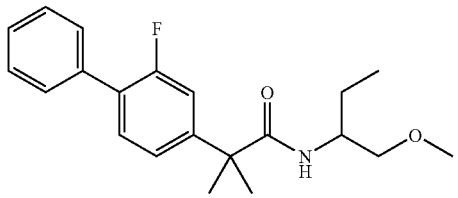

Prepared in a similar manner to Example 3 from 2-(2-fluorobiphenyl-4-yl)propanoic acid and 1-methoxybutan-2-amine. Yield: 67%. $^1$H NMR (500 MHz, CDCl$_3$): δ 0.83 (t, 3H), 1.40 (m, 1H), 1.51 (m, 1H), 1.55 (s, 3H), 1.58 (s, 3H), 3.25 (s, 3H), 3.26 (dd, 1H), 3.35 (dd, 1H), 3.95 (m, 1H), 5.38 (d br, 1H), 7.15-7.22 (m, 2H), 7.37-7.54 (m, 4H), 7.54 (m, 2H). m.p. 81-82° C.

The compound had an $EC_{50}$ for activation of a hT1R2/hT1R3 sweet receptor expressed in HEK293 cell line of 3.81 μM.

Example 7

N-isobutyl-2-methyl-2-(4-(thiophen-3-yl)phenyl)propanamide

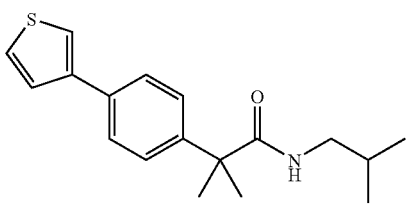

Prepared in a similar manner to Example 1 from 2-(4-Bromophenyl)-N-isobutyl-2-methylpropanamide (Example 1a) and thiophen-3-ylboronic acid. MS (M+H, 302).

The compound had an $EC_{50}$ for activation of a hT1R2/hT1R3 sweet receptor expressed in HEK293 cell line of 1.24 μM.

Example 8

N-isobutyl-2-methyl-2-(3'-nitrobiphenyl-4-yl)propanamide

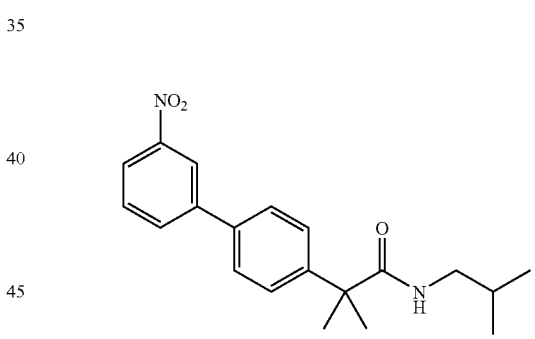

2-(4-Bromophenyl)-N-isobutyl-2-methylpropanamide (Example 1a) (100 mg, 0.33 mmol) was weigh out in a microwave vial and dissolved in 3 ml of DME, 2 ml of EtOH and 1.5 ml of water followed by addition of Na$_2$CO$_3$ (70 mg, 0.66 mmol) and 3-nitrophenylboronic acid (67 mg, 0.4 mmol). Pd(PPh$_3$)$_4$ (8 mg, 6.6 μmol) was then added and the tube was immediately sealed. The reaction mixture was heated in a Smith Synthesizer at 150° C. for 5 min. The solution was filtered and the compound purified by preparative HPLC to yield 75 mg (67%) of the title compound as a white solid. $^1$H NMR (400 MHz, CDCl$_3$): δ 0.8 (d, 6H), 1.65 (s, 6H), 1.67-1.70 (m,1H), 3 (dd, 2H), 5.2 (broad, 1H), 7.5 (d, 2H), 7.6 (d, 3H), 7.9 (d, 1H), 8.2 (dd, 1H), 8.4 (d, 1H). MS (M+H, 341).

The compound had an $EC_{50}$ for activation of a hT1R2/hT1R3 sweet receptor expressed in HEK293 cell line of 0.4 μM.

Example 9

2-(3'-cyanobiphenyl-4-yl)-N-isobutyl-2-methylpropanamide

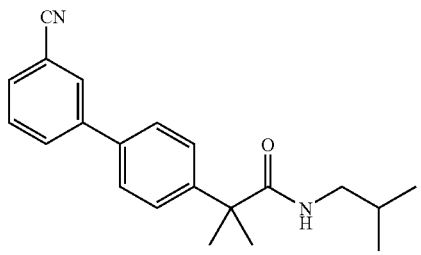

Prepared in a similar manner to example 8 from 2-(4-Bromophenyl)-N-isobutyl-2-methylpropanamide (Example 1a) and 3-cyanophenylboronic acid. Yield: 63%. $^1$H NMR (400 MHz, CDCl$_3$): δ 0.8 (d, 6H), 1.65 (s, 6H), 1.67-1.70 (m,1H), 3 (dd, 2H), 5.2 (broad, 1H), 7.45 (d, 2H), 7.55 (d, 3H), 7.65 (d, 1H), 8.2 (dd, 1H), 8.4 (d, 1H). MS (M+H, 321).

The compound had an EC$_{50}$ for activation of a hT1R2/hT1R3 sweet receptor expressed in HEK293 cell line of 0.2 µM.

Example 10

Methyl 4'-(1-(isobutylamino)-2-methyl-1-oxopropan-2-yl)biphenyl-3-carboxylate

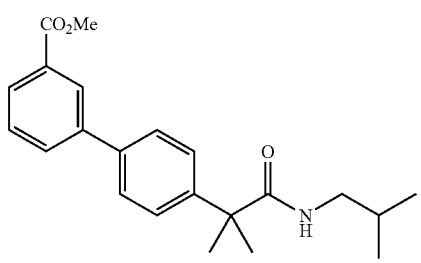

Prepared in a similar manner to Example 8 from 2-(4-Bromophenyl)-N-isobutyl-2-methylpropanamide (Example 1a) and 3-(methoxycarbonyl)phenylboronic acid. Yield: 65%. $^1$H NMR (400 MHz, CDCl$_3$): δ 0.8 (d, 6H), 1.65 (s, 6H), 1.67-1.70 (m, 1H), 3 (t, 2H), 3.9 (s, 1H), 5.2 (broad, 1H), 7.4-7.56 (m, 3H), 7.6 (d, 2H), 7.8 (d, 1H), 8.1 (dd, 1H), 8.3 (d, 1H). MS (M+H, 354).

The compound had an EC$_{50}$ for activation of a hT1R2/hT1R3 sweet receptor expressed in HEK293 cell line of 0.9 µM.

Example 11

2-(3'-hydroxybiphenyl-4-yl)-N-isobutyl-2-methylpropanamide

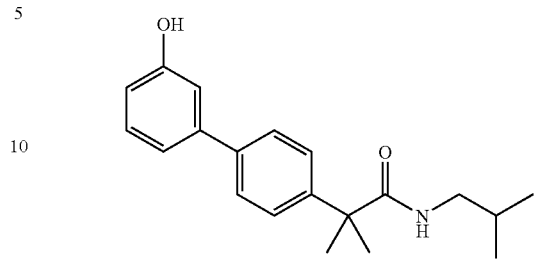

Prepared in a similar manner to example 8 from 2-(4-Bromophenyl)-N-isobutyl-2-methylpropanamide (Example 1a) and 3-hydroxyphenylboronic acid. Yield: 70%. MS (M+H, 312).

The compound had an EC$_{50}$ for activation of a hT1R2/hT1R3 sweet receptor expressed in HEK293 cell line of 1.9 µM.

Example 12

N-isobutyl-2-methyl-2-(2'-methylbiphenyl-4-yl)propanamide

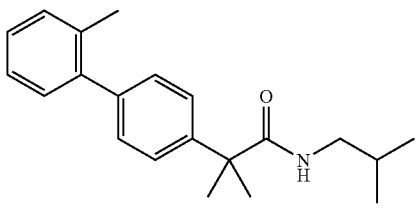

Prepared in a similar manner to Example 8 from 2-(4-Bromophenyl)-N-isobutyl-2-methylpropanamide (Example 1a) and o-tolylboronic acid. Yield: 80%. $^1$H NMR (400 MHz, CDCl$_3$): δ 0.8 (d, 6H), 1.65 (s, 6H), 1.67-1.70 (m,1H), 2.3 (s, 3H), 3 (t, 2H), 5.2 (broad, 1H), 7.2-7.25 (m, 4H), 7.3 (d, 2H), 7.4 (d, 2H). MS (M+H, 310).

The compound had an EC$_{50}$ for activation of a hT1R2/hT1R3 sweet receptor expressed in HEK293 cell line of 1.9 µM.

Example 13

2-(2'-aminobiphenyl-4-yl)-N-isobutyl-2-methylpropanamide

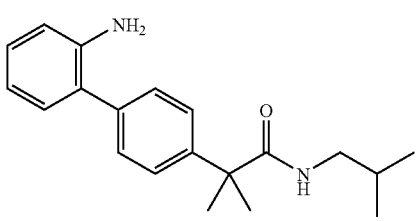

Prepared in a similar manner to example 8 from 2-(4-Bromophenyl)-N-isobutyl-2-methylpropanamide (Example 1a) and 2-aminophenylboronic acid. Yield: 65%. $^1$H NMR (400 MHz, CDCl$_3$): δ 0.8 (d, 6H), 1.65 (s, 6H), 1.67-1.70 (m,1H), 3 (t, 2H), 6.65-6.75 (m, 1H), 6.9 (m, 1H), 7.0 (m, 1H), 7.2 (m, 1H), 7.4 (d, 2H), 7.55 (d, 2H). MS (M+H, 311).

Example 14

2-(2'-cyanobiphenyl-4-yl)-N-isobutyl-2-methylpropanamide

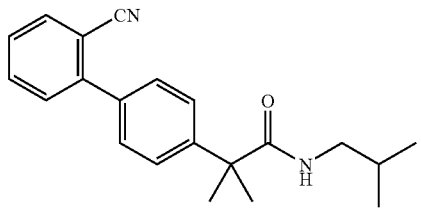

Prepared in a similar manner to Example 8 from 2-(4-Bromophenyl)-N-isobutyl-2-methylpropanamide (Example 1a) and 2-cyanophenylboronic acid. Yield: 60%. $^1$H NMR (400 MHz, CDCl$_3$): δ 0.8 (d, 6H), 1.65 (s, 6H), 1.67-1.70 (m,1H), 3 (t, 2H), 7.4-7.55. (m, 3H), 7.6 (d, 2H), 7.65 (td, 2H), 7.8 (d, 1H). MS (M+H, 321).

The compound had an EC$_{50}$ for activation of a hT1R2/hT1R3 sweet receptor expressed in HEK293 cell line of 1.9 μM.

Example 15

N-isobutyl-2-methyl-2-(3'-methylbiphenyl-4-yl)propanamide

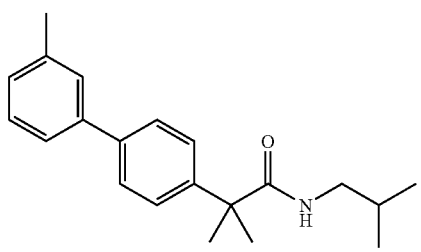

Prepared in a similar manner to Example 8 from 2-(4-Bromophenyl)-N-isobutyl-2-methylpropanamide (Example 1a) and m-tolylboronic acid. Yield: 60%. $^1$H NMR (400 MHz, CDCl$_3$): δ 0.8 (d, 6H), 1.65 (s, 6H), 1.67-1.70 (m,1H), 2.3 (s, 3H), 3(t, 2H), 7.18 (d, 1H), 7.34 (t, 1H), 7.42 (m, 4H), 7.6 (dd, 2H). MS (M+H, 310).

The compound had an EC$_{50}$ for activation of a hT1R2/hT1R3 sweet receptor expressed in HEK293 cell line of 3 μM.

Example 16

Ethyl 4'-(1-(isobutylamino)-2-methyl-1-oxopropan-2-yl)biphenyl-3-carboxylate

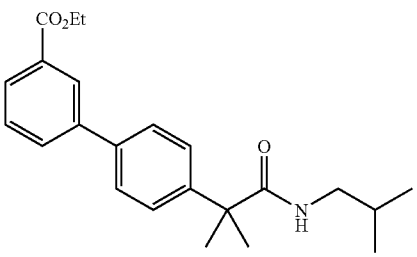

Prepared in a similar manner to Example 8 from 2-(4-Bromophenyl)-N-isobutyl-2-methylpropanamide (Example 1a) and 3-(ethoxycarbonyl)phenylboronic acid. Yield: 65%. $^1$H NMR (400 MHz, CDCl$_3$): δ 0.8 (d, 6H), 1.4 (t, 3H), 1.65 (s, 6H), 1.67-1.70 (m,1H), 3 (t, 2H), 4.4 (t, 2H), 7.48 (d, 2H), 7.54 (d, 1H), 7.64 (d, 2H), 7.8 (d, 1H), 8.04 (d, 1H), 8.3 (t, 1H). MS (M+H, 368).

The compound had an EC$_{50}$ for activation of a hT1R2/hT1R3 sweet receptor expressed in HEK293 cell line of 2.6 μM.

Example 17

2-(3'-((dimethylamino)carbonyl)biphenyl-4-yl)-N-isobutyl-2-methylpropanamide

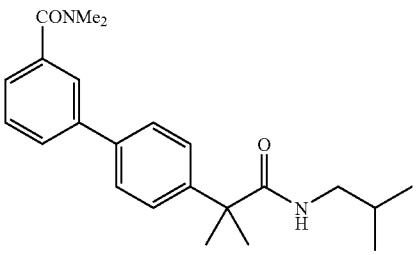

Prepared in a similar manner to Example 8 from 2-(4-Bromophenyl)-N-isobutyl-2-methylpropanamide (Example 1a) and 3-((dimethylaminooxy)carbonyl)phenylboronic acid. Yield: 60%. $^1$H NMR (400 MHz, CDCl$_3$): δ 0.8 (d, 6H), 1.65 (s, 6H), 1.67-1.70 (m, 1H), 3 (m, 5H), 3.15 (s, 3H), 7.38 (d, 1H), 7.54 (d, 1H), 7.46 (m, 3H), 7.6 (m, 4H). MS (M+H, 383).

The compound had an EC$_{50}$ for activation of a hT1R2/hT1R3 sweet receptor expressed in HEK293 cell line of 2.7 μM.

Example 18

N-isobutyl-2-(3'-isopropoxybiphenyl-4-yl)-2-methyl-propanamide

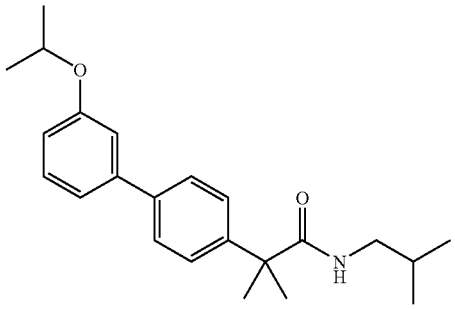

Prepared in a similar manner to Example 8 from 2-(4-Bromophenyl)-N-isobutyl-2-methylpropanamide (Example 1a) and 3-isopropoxyphenylboronic acid. Yield: 60%. $^1$H NMR (400 MHz, CDCl$_3$): δ 0.8 (d, 6H), 1.35 (d, 6H), 1.65 (s, 6H), 1.67-1.70 (m,1H), 3 (m, 2H), 4.6 (m, 1H), 6.9 (dd, 1H), 7.1 (t, 1H), 7.15 (d, 1H), 7.35 (t, 1H), 7.45 (d, 2H), 7.6 (d, 2H). MS (M+H, 354).

The compound had an EC$_{50}$ for activation of a hT1R2/hT1R3 sweet receptor expressed in HEK293 cell line of 4.2 μM.

Example 19

N-isobutyl-2-(3'-methoxybiphenyl-4-yl)-2-methyl-propanamide

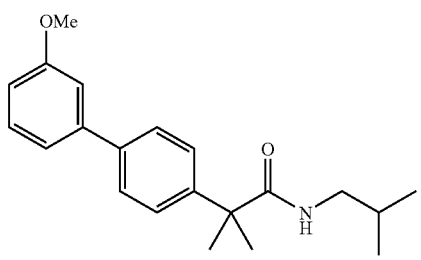

Prepared in a similar manner to example 8 from 2-(4-Bromophenyl)-N-isobutyl-2-methylpropanamide (Example 1a) and 3-methoxyphenylboronic acid. Yield: 60%. $^1$H NMR (400 MHz, CDCl$_3$): δ 0.8 (d, 6H), 1.65 (s, 6H), 1.67-1.70 (m,1H), 3 (t, 2H), 3.85 (s, 3H), 6.9 (dd, 1H), 7.1 (s, 1H), 7.2 (d, 1H), 7.4 (t, 1H), 7.45 (d, 2H), 7.6 (d, 2H). MS (M+H, 326).

The compound had an EC$_{50}$ for activation of a hT1R2/hT1R3 sweet receptor expressed in HEK293 cell line of 4.3 μM.

Example 20

2-(4-(6-cyanopyrazin-2-yl)phenyl)-N-isobutyl-2-methylpropanamide

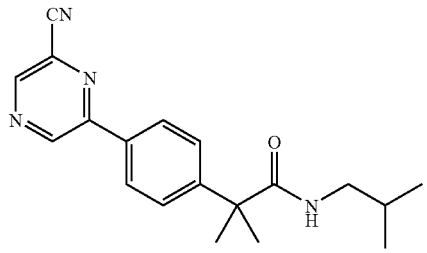

2-(4-(6-Cyanopyrazin-2-yl)phenyl)-2-methylpropanoic acid (example 20a) (267 mg, 1 mmol) was placed in microwavable tube and dissolved in acetonitrile (3 mL) and DMF (0.2 mL). Then HOBt (153 mg, 1 mmol) and EDC (211 mg, 1.1 mmol) were added followed by isobutyl amine (0.1 mL, 1 mmol) and the tube was sealed and irradiated in a microwave at 150° C. for 5 min. The solvents were removed under reduced pressure and the mixture was purified using preparative RP HPLC (water/acetonitrile). The product was co-evaporated with EtOH to give 2-(4-(6-cyanopyrazin-2-yl)phenyl)-2-methylpropanoic acid as a white solid (166 mg, 62%). $^1$H NMR (400 MHz, dMSO): δ 0.74-0.75 (d, 6H), 1.49 (s, 6H), 1.69 (m, 1H), 2.83-2.87 (t, 2H), 7.42-7.51 (d, 2H), 8.12-8.14 (d, 2H), 9.16 (s, 1H), 9.56 (s, 1H); M+H(323.2).

Example 20a 2-(4-(6-Cyanopyrazin-2-yl)phenyl)-2-methylpropanoic acid: 6-Chloropyrazine-2-carbonitrile (example 20b) (890 mg, 6.4 mmol) was dissolved in DME (24 mL) and water (6 mL) followed by 2-methyl-2-(4-(4,4,5,5-tetramethyl-1,3,2-dioxaborolan-2-yl)phenyl)propanoic acid (example 20d) (1.86 g, 6.4 mmol) and K$_2$CO$_3$ (1.76 g, 12.7 mmol). The mixture was degassed using an argon stream, Pd(PPh$_3$)$_4$ (369 mg, 0.32 mmol) was added and the mixture was heated (80° C.) overnight. The solvents were removed under reduced pressure and a residue was suspended in 1M aq. NaOH (10 mL) and washed with EtOAc. The aqueous phase was then acidified to pH 4-5 using 6N aq. HCl and extracted with EtOAc (3×60 mL). The organic extracts were combined, washed with water and brine, dried over MgSO$_4$, filtered and evaporated. The residue was purified on silica gel (5% MeOH in DCM) to give 1.2 g (70%) of the pure intermediate 2-(4-(6-cyanopyrazin-2-yl)phenyl)-2-methylpropanoic acid. $^1$H NMR (400 MHz, dMSO): δ 1.50 (s, 6H), 1.69 (m, 1H), 7.54-7.56 (d, 2H), 8.13-8.15 (d, 2H), 9.17 (s, 1H), 9.56 (s, 1H), 12.50 (s, 1H).

Example 20b

6-Chloropyrazine-2-carbonitrile: Pyrazine-2-carboxamide-4-N-oxide (example 20c) (2 g, 14.4 mmol) was suspended in dry DMF (20 mL) and cooled to 0° C., then POCl$_3$ (6 mL) was added. The mixture was stirred at room temperature for 24 h and then poured in water/ice (100 mL). The product was extracted with EtOAc (3×100 ml). The extracts were combined, washed with water and brine, dried over MgSO$_4$, filtered and evaporated under reduced pressure to give 890 mg of 6-chloropyrazine-2-carbonitrile as brown oil.

$^1$H NMR (400 MHz, dMSO): δ 9.16 (s, 1H), 9.26 (s, 1H); $^{13}$C NMR (400 MHz, dMSO): δ 115.62, 129.02, 147.75, 149.09, 149.67.

Example 20c pyrazine-2-carboxamide-4-N-oxide: A mixture of pyrazine-2-carboxamide (10 g, 81 mmol) in 43 mL of glacial acetic acid and 38 mL of 30% $H_2O_2$ was heated at 55° C. for 30 h. The mixture was cooled to rt and filtered. The solid was washed with n-butanol and dried in vacuo to yield 6.18 g (54%) of pyrazine-2-carboxamide-4-N-oxide. $^1$H NMR (400 MHz, dMSO): δ 8.02 (bs, 1H), 8.31 (bs, 1H), 8.48-8.50 (dd, 1H), 8.54 (b, 1H), 8.57-8.58 (d, 1H).

Example 20d 2-methyl-2-(4-(4,4,5,5-tetramethyl-1,3,2-dioxaborolan-2-yl)phenyl)propanoic acid: A solution of 2-(4-bromophenyl)-2-methylpropanoic acid (160 g, 0.66 mol), AcOK (196 g, 1 mol) and bis(pinacolato)diboron.

(168.8 g, 0.66 mol) in dry DMF (1.6 L) was degassed at room temperature. Pd(dppf)Cl2 (24 g, 32 mmol) was added under $N_2$ atmosphere. The reaction was stirred at 60° C. overnight. The solution was diluted with EtOAc (2 L) and filtrated through a celite pie. The filtrate was washed with water (1 L×2) and brine (1 L×2), dried over $MgSO_4$, filtered, and concentrated in vacuo. The residue was recrystallized in EtOAc to give 2-methyl-2-(4-(4,4,5,5-tetramethyl-1,3,2-dioxaborolan-2-yl)phenyl)propanoic acid (110 g, yield 57.8%). $^1$H NMR (dMSO): δ 12.35 (s,1H), 7.61 (d, J=6.8 Hz, 2H), 7.322 (d, J=7.2 Hz,2H), 1.43 (s, 6H), 1.25 (s, 12H).

The compound had an $EC_{50}$ for activation of a hT1R2/hT1R3 sweet receptor expressed in HEK293 cell line of 0.02 μM.

Example 21

2-(4-(5-cyanopyridin-3-yl)phenyl)-2-methyl-N-(pentan-3-yl)propanamide

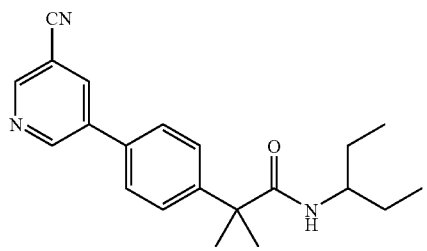

Prepared in a similar manner to Example 3 from 2-(4-(5-cyanopyridin-3-yl)phenyl)-2-methylpropanoic acid (example 21a) and 3-pentanamine. Yield 55%. $^1$H NMR (400 MHz, DMSO): δ 0.69-0.73 (t, 6H), 1.27 (m, 2H), 1.36 (m, 2H), 1.47 (s, 6H), 3.56 (m, 1H), 6.90-6.93 (d, 1H), 7.43-7.45 (d, 2H), 7.77-7.79 (d, 2H), 8.63-8.64 (t, 1H), 8.96-8.98 (d, 1H), 9.17-9.18 (d, 1H). MS (M+H, 336).

Example 21a 2-(4-(5-cyanopyridin-3-yl)phenyl)-2-methylpropanoic acid: 5-bromonicotinonitrile (8.8 g, 48.08 mmol), 2-(4-boronophenyl)-2-methylpropanoic acid (example 21b) (11.50 g, 52.89 mmol) and $K_2CO_3$ (13.3 g, 96.16 mmol were dissolved in a mixture of DME (120 mL) and water (30 mL). The mixture was degassed for 30 minutes and Pd(PPh$_3$)$_4$ (2.7 g, 2.40 mmol) was added. The reaction mixture was heated to reflux for 16 hr then cooled to room temperature, and evaporated under reduced pressure. The residue was diluted with aq. 0.5 N NaOH (100 mL) and stirred for about 30 min., and then the mixture was extracted with ether (30 mL×3) The aqueous layer was cooled to 0° C., acidified with 2 N HCl, and then extracted with EtOAc. The combined organic layers were washed successively with water and brine, dried over $MgSO_4$, filtered and evaporated. The residue was triturated with hexane, filtered and dried to give 9.4 g of 2-(4-(5-cyanopyridin-3-yl)phenyl)-2-methylpropanoic acid as a white solid in 73% yield.

$^1$H NMR (400 MHz, DMSO): δ 1.49 (s, 6H), 7.46-7.48 (d, 2H), 7.76-7.78 (d, 2H), 8.63 (s, 1H), 8.98 (s, 1H), 9.17 (s, 1H), 12.43 (s, 1H). MS (M+H, 267).

Example 21b 2-(4-boronophenyl)-2-methylpropanoic acid: To a solution of 2-(4-bromophenyl)-2-methylpropanoic acid (15 g, 61.7 mmol) in anhydrous THF (150 mL) was added at −78° C. under argon a 2.5 M solution of n-butyllithium in hexane (37 ml, 92.6 mmol) dropwise, followed by triisopropyl borate (43 ml, 185.1 mmol). After the addition, the reaction mixture was stirred at −50° C. for 2 hrs and allowed to warm up to room temperature and stirred over night. The reaction mixture was quenched with 1 N HCl then extracted with EtOAc and washed successively with water and brine, dried over MgSO4, filtered and evaporated to give 13 g of product as a white solid in 99% yield. $^1$H NMR (400 MHz, DMSO): δ 1.41 (s, 6H), 7.25-7.27 (d, 2H), 7.29-7.47 (dd, 1H), 7.68-7.70 (d, 1H), 12.31 (s, 1H).

The compound had an $EC_{50}$ for activation of a hT1R2/hT1R3 sweet receptor expressed in HEK293 cell line of 0.07 μM.

Example 22

(R)-N-sec-butyl-2-(4-(5-cyanopyridin-3-yl)phenyl)-2-methylpropanamide

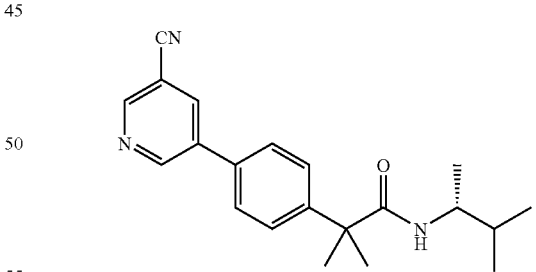

Prepared in a similar manner to Example 3 from 2-(4-(5-cyanopyridin-3-yl)phenyl)-2-methylpropanoic acid (example 21a) and (R)-3-Methyl-2-butylamine. Yield 48%. $^1$H NMR (400 MHz, DMSO): δ 0.71-0.73 (d, 3H), 0.74-0.76(d, 3H), 0.91-0.93 (d, 3H), 1.46 (s, 3H), 1.47 (s, 3H), 1.59 (m, 1H), 3.58 (m, 1H), 6.98-7.01 (d, 1H), 7.42-7.44 (d, 2H), 7.77-7.79 (d, 2H), 8.64 (s, 1H), 8.98 (s, 1H), 9.17 (s, 1H). MS (M+H, 336).

The compound had an $EC_{50}$ for activation of a hT1R2/hT1R3 sweet receptor expressed in HEK293 cell line of 0.14 μM.

Example 23

2-(4-(5-cyanopyridin-3-yl)phenyl)-N-isobutyl-2-methylpropanamide

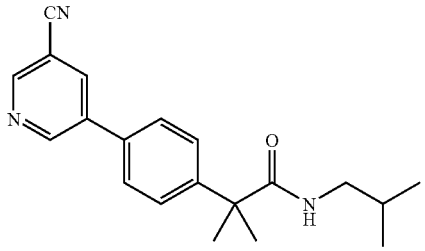

N-isobutyl-2-methyl-2-(4-(4,4,5,5-tetramethyl-1,3,2-dioxaborolan-2-yl)phenyl)propanamide (example 23a) (14.86 g, 43.03 mmol), 5-bromonicotinonitrile (7.50 g, 40.98 mmol) and potassium carbonate (11.33 g, 81.96 mmol) were mixed in toluene (75 mL), ethanol (15 mL) and water (11.25 mL). The mixture was degassed for 30 minutes and Pd(PPh$_3$)$_4$ (950 mg, 0.82 mmol) was added. The reaction mixture was heated to reflux for 16 hr and cooled to room temperature then diluted with EtOAc/water, washed successively with water and brine, dried over MgSO$_4$, filtered and evaporated. The residue was chromatographed on silica gel (eluant 40% EtOAc in hexane) twice, then recrystallized from EtOAC/hexane and co-evaporated with ethanol to give 11.6 g of the product as a white solid in 88% yield. $^1$H NMR (400 MHz, DMSO-d$_6$): δ 0.75 (d, 6H)), 1.48 (s, 6H), 1.70 (m, 1H), 2.85 (t, 2H), 7.45 (m, 3H), 7.8 (d, 2H), 8.65 (t, 1H), 9 (d, 1H), 9.2 (d, 1H). MS(M+H, 322).

Example 23a

N-isobutyl-2-methyl-2-(4-(4,4,5,5-tetramethyl-1,3,2-dioxaborolan-2-yl)phenyl)propanamide: 2-methyl-2-(4-(4,4,5,5-tetramethyl-1,3,2-dioxaborolan-2-yl)phenyl)propanoic acid (example 20d) (10 g, 34.46 mmol), EDC (7.26 g, 37.91 mmol) and HOBt (5.12 g, 37.91 mmol) were mixed in DCM (350 mL) and stirred for 5 minutes then 2-methylpropan-1-amine (3.6 mL, 36.19 mmol) was added. The reaction mixture was stirred at room temperature overnight then diluted with dichloromethane and washed successively with aq. HCl (0.5N), water, aq. NaHCO$_3$, water and brine, dried over MgSO$_4$, filtered and evaporated. The residue was crystallized from EtOAc/hexane to give 11.8 g of product as a white solid in 99% yield. $^1$H NMR (400 MHz, CDCl$_3$): δ 0.76-0.78 (d, 6H), 1.35(s, 12H), 1.57 (s, 6H), 1.62 (m, 1H), 2.97 (t, 2H), 5.15 (br-s, 1H), 7.38-7.40 (d, 2H), 7.79-7.81 (d, 2H). MS (M+H, 346).

The compound had an EC$_{50}$ for activation of a hT1R2/hT1R3 sweet receptor expressed in HEK293 cell line of 0.15 μM.

Example 24 tert-butyl 1-(biphenyl-4-yl)-2-(isobutylamino)-2-oxoethylcarbamate

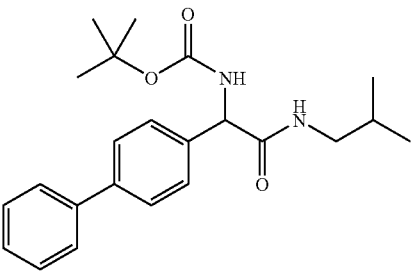

Prepared in a similar manner to Example 20 from 2-(biphenyl-4-yl)-2-(tert-butoxycarbonylamino)acetic acid and isobutyl amine. Yield: 55%. $^1$H NMR (400 MHz, dMSO): δ 0.76-0.78 (d, 6H), 1.38 (s, 9H), 1.63-1.66 (m, 1H), 2.84-2.92 (m, 2H), 5.30-5.22 (d, 1H), 7.25-7.27 (d, 1H), 7.35-7.37 (m, 1H), 7.43-7.51 (m, 4H), 7.61-7.66 (m, 4H), 8.14-8.17 (t, 1H); MS+H (383).

The compound had an EC$_{50}$ for activation of a hT1R2/hT1R3 sweet receptor expressed in HEK293 cell line of 7.54 μM.

Example 25

2-methyl-N-(2-methylbutyl)-2-(4-(pyrimidin-5-yl)phenyl)propanamide

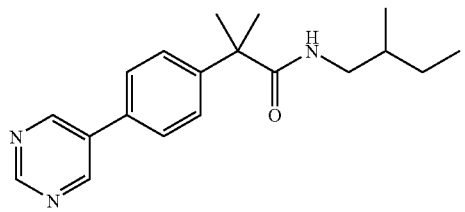

Prepared in a similar manner to Example 20 from 2-methyl-2-(4-(pyrimidin-5-yl)phenyl)propanoic acid (example 25a) and 2-methylbutan-1-amine. Yield: 58%. $^1$H NMR (400 MHz, dMSO): δ 0.72-0.74 (d, 3H), 0.79-0.84 (m, 3H) 0.97-1.00 (m, 1H), 1.24-1.27 (m, 1H), 1.47 (m, 1H), 1.48 (s, 6H), 2.81-2.87 (m, 1H), 2.93-2.98 (m, 1H), 7.37-7.39 (t, 1H), 7.44-7.47 (d, 2H), 7.76-7.79 (d, 2H), 9.13 (s, 1H), 9.18 (s, 1H); MS+H (312.1).

Example 25a

2-Methyl-2-(4-(pyrimidin-5-yl)phenyl)propanoic acid: 2-(4-Bromophenyl)-2-methylpropanoic acid (5.71 g, 23.5 mmol) was dissolved in DME (140 mL) and water (35 mL) and pyrimidin-5-ylboronic acid (2.92 g, 23.5 mmol) and potassium carbonate (11.4 g, 82.2 mmol) were added to the solution. The mixture was degassed using an argon stream, and Pd(PPh$_3$)$_4$ (1.35 g, 1.17 mmol) was added. The mixture was heated (80° C.) under argon overnight then cooled to room temperature. The solution was diluted with 1M NaOH (20 mL) and washed with EtOAc. The aqueous phase was acidified with 6N aq. HCl to pH 4-5 and extracted with EtOAc (3×). The combined extract was successively washed with water and brine, dried over MgSO$_4$, filtered and evaporated to yield 4.2 g (74%) of the crude 2-Methyl-2-(4-(pyrimidin-5-yl)phenyl)propanoic acid (MS+H, 243) that was used in the next step without further purification.

The compound had an EC$_{50}$ for activation of a hT1R2/hT1R3 sweet receptor expressed in HEK293 cell line of 0.23 µM.

Example 26

2-(4-(5-(ethoxymethyl)pyridin-3-yl)phenyl)-N-isobutyl-2-methylpropanamide

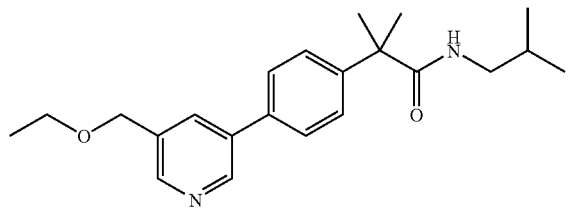

Prepared in a similar manner to Example 3 from 2-(4-(5-(ethoxymethyl)pyridin-3-yl)phenyl)-2-methylpropanoic acid (example 26a) and isobutylamine. Yield: 80%. $^1$H NMR (400 MHz, dMSO): δ 0.72 (s, 3H); 0.74 (s, 3H); 1.15 (t, 3H, J=6.8); 1.46 (s, 6H); 1.68 (m, 1H); 2.83 (t, 2H, J=5.6); 3.51 (q, 2H, J=7.2); 4.54 (s, 2H); 7.4 (t, 1H); 7.41 (d, 2H, J=6.4); 7.66 (d, 2H, J=6.8); 7.95 (t, 1H, J=2.4); 8.49 (d, 1H, J=1.6); 8.78 (d, 1H, J=2.8). MS (M+H, 355).

Example 26a 2-(4-(5-(ethoxymethyl)pyridin-3-yl)phenyl)-2-methylpropanoic acid: Prepared in a similar manner as example 21a starting from 3-Bromo-5-(ethoxymethyl)pyridine (example 26b) and 2-(4-boronophenyl)-2-methylpropanoic acid (example 21b). Yield: 90%. MS (M+H, 300).

Example 26b

3-Bromo-5-(ethoxymethyl)pyridine: To a mixture of powdered KOH (5.96 g, 106.4 mmol) in anhydrous DMSO (20 mL) was added under argon a solution of (5-bromopyridin-3-yl)methanol (example 26c) (5 g, 26.6 mmol) in anhydrous DMSO (20 mL), followed by EtI (2.6 mL, 31.9 mmol). The reaction mixture was stirred at room temperature for 1 hour then diluted with water and extracted with EtOAc. The organic phase was washed with water and brine, dried over MgSO$_4$, filtered and evaporated to give 5.6 g of 3-bromo-5-(ethoxymethyl)pyridine as a dark brown oil in 97% yield. $^1$H NMR (400 MHz, CDCl$_3$): 1.27 (t, 3H), 3.57-3.59 (q, 2H), 4.50 (s, 2H,), 8.48 (s, 1H), 8.60 (s, 1H).

Example 26c (5-bromopyridin-3-yl)methanol: A suspension of 5-bromo-nicotinic acid methyl ester (example 26d) (10 g, 46.29 mmol) in anhydrous EtOH (100 ml) was cooled to 0° C. and NaBH$_4$ (4.03 g, 106.47 mmol) was added in portions within 15 min. After stirred at 0° C. for 1 hour the ice bath was removed and stirring was continued at room temperature for 3 hours, then the reaction mixture was heated to reflux overnight. The solvent was evaporated and acetone (50 mL) was added and the solution stirred for 30 minutes then the acetone was evaporated. Saturated aqueous K$_2$CO$_3$ (50 mL) was added and the mixture was reflux for 1 hour then diluted with water (100 mL) and extracted with DCM. The organic phase was dried over MgSO$_4$, filtered and evaporated. The residue was chromatographed on silica gel (5% MeOH in DCM) to give 4.78 g of pure (5-bromopyridin-3-yl)methanol as a light yellow oil. Yield 55%. 1H NMR (400 MHz, CDCl$_3$): 2.60 (t, 1H); 4.73-4.74 (d, 2H), 7.90 (s, 1H,), 8.47 (s, 1H), 8.57 (s, 1H).

Example 26d

5-Bromo-nicotinic acid methyl ester

To a suspension of 5-bromonicotinic acid (20 g, 99.0 mmol) in anhydrous MeOH (100 mL), was carefully added conc. H$_2$SO$_4$ (12 mL) via a syringe. After the addition the reaction mixture was heated to reflux overnight, then cooled to room temperature and concentrated on rotary evaporator. Ice-water (200 mL) was added and a white solid crashed out. The solid was collected by filtration, dissolved in EtOAc (300 mL), washed with aq. NaHCO$_3$, water and brine, dried over MgSO$_4$, filtered and evaporated to give 18 g of 5-Bromo-nicotinic acid methyl ester as a white powder. Yield 84%. 1H NMR (400 MHz, DMSO): 3.88 (s, 3H); 0.74 (s, 3H), 8.43 (s, 1H,), 8.96 (s, 1H), 9.02 (s, 1H). MS (M+H, 217).

The compound had an EC$_{50}$ for activation of a hT1R2/hT1R3 sweet receptor expressed in HEK293 cell line of 0.26 µM.

Example 27

N-isobutyl-2-(2-methoxy-3'-(methoxymethyl)biphenyl-4-yl)-2-methylpropanamide

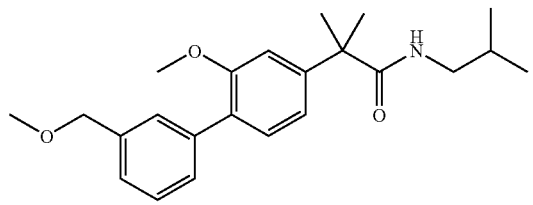

To a solution of 2-(2-methoxy-5'-(methoxymethyl)biphenyl-4-yl)-2-methylpropanoic acid (example 27a) (315 mg, 1 mmol) in DCM (10 mL) and DMF (1 mL) were added HOBt (135 mg, 1 mmol) and isobutyl amine (98 µL, 1 mmol) followed by EDC (197 mg, 1 mmol). The mixture was stirred at room temperature overnight and concentrated under reduced pressure. The residue was dissolved in EtOAc, washed with water and brine, dried over MgSO$_4$, filtered and evaporated. The residue was purified by preparative RP HPLC (water-acetonitrile) to give a colorless oil that was further evaporated from EtOH (3×) and dried to yield 150 mg (41%) of the product. $^1$H NMR (400 MHz, dMSO): δ 0.76-0.77 (t, 3H), 1.49 (s, 6H), 1.10-1.72 (m, 1H), 2.85-2.88 (t, 2H), 3.30 (s, 3H), 3.74 (s, 3H), 4.44 (s, 2H), 6.96-6.98 (m, 2H), 7.22-7.26 (m, 2H), 7.36-7.38 (m, 4H); MS+H (370.2).

Example 27a 2-(2-Methoxy-5'-(methoxymethyl)biphenyl-4-yl)-2-methylpropanoic acid Ethyl 2-(2-methoxy-5'-(methoxymethyl)biphenyl-4-yl)-2-methylpropanoate (example 27b) (986 mg, 2.88 mmol) was suspended in EtOH (10 mL) and 1M aq. NaOH (15 mL) and stirred at 100° C. for 3 h. EtOH was removed under reduced pressure and the residue was diluted with water (10 mL) and acidified with 6N aq. HCl to pH 2-3. The product was extracted with EtOAc, washed with water and brine, dried over MgSO$_4$, filtered and evaporated to give 900 mg (99%) of 2-(2-Methoxy-5'-(methoxymethyl)biphenyl-4-yl)-2-methylpropanoic acid. $^1$H NMR(400 MHz, DMSO): δ 1.48 (s, 6H), 3.29 (s, 3H), 4.45 (s, 2H), 7.40-7.61 (m, 8H), 12.44 (s, 1H).

Example 27b

Ethyl 2-(2-methoxy-5'-(methoxymethyl)biphenyl-4-yl)-2-methylpropanoate

Ethyl 2-(2-methoxy-5'-(methoxymethyl)biphenyl-4-yl) acetate (example 27c) (1.38 g, 4.39 mmol) was dissolved in dry THF (10 mL) and transferred under argon into a suspension of NaH (518 mg, 13.2 mmol) in dry THF (40 mL). The suspension was stirred under argon for 30 min and MeI (686 µL, 10 98 mmol) was added drop-wise and the mixture was stirred at room temperature overnight then quenched with water (15 mL) and extracted with EtOAc. The organic phase was successively washed with water and brine, dried over MgSO$_4$, filtered and evaporated to give 986 mg (66%) of Ethyl 2-(2-methoxy-5'-(methoxymethyl)biphenyl-4-yl)-2-methylpropanoate. $^1$H NMR(400 MHz, dMSO): δ 1.11-1.15 (t, 3H), 1.51 (s, 6H), 3.28 (s, 3H), 3.73 (s, 3H), 4.01-4.09 (q, 2H), 4.41 (s, 2H), 6.94 (d, 2H), 7.21-7.22 (m, 2H), 7.34-7.36 (m 3H).

Example 27c

Ethyl 2-(2-methoxy-5'-(methoxymethyl)biphenyl-4-yl)acetate

To a solution of Ethyl 2-(3-methoxy-4-(trifluoromethylsulfonyloxy)phenyl)acetate (example 27d) (2 g, 5.8 mmol) in DME (36 mL) and water (9 mL) was added potassium carbonate (1.61 g, 11.6 mmol) and 3-(methoxymethyl)phenylboronic acid (962 mg, 5.8 mmol) and the mixture was degassed using argon stream for 30 minutes. Pd[PPh$_3$]$_4$ (330 mg, 0.29 mmol) was added and the mixture was heated at 80° C. under argon overnight. The solvents were removed under reduced pressure and the residue extracted with EtOAc, washed with water and brine, dried over MgSO$_4$, filtered and evaporated. The residue was purified on silica gel (20% EtOH/hexanes) to yield 1.38 g (76%) of ethyl 2-(2-methoxy-5'-(methoxymethyl)biphenyl-4-yl)acetate. $^1$H NMR(400 MHz, dMSO): δ 1.16-1.20 (t, 3H), 3.27 (s, 3H), 3.68 (s, 2H), 3.72 (s, 3H), 4.06-4.11 (q, 2H) 4.41 (s, 2H) 6.89 (d, 1H), 7.00 (s, 1H) 7.19-7.24 (m, 2H), 7.34-7.36 (m, 3H).

Example 27d

Ethyl 2-(3-methoxy-4-(trifluoromethylsulfonyloxy)phenyl)acetate

Ethyl hommovanilate (4 g, 19 mmol) was dissolved in DCM (40 mL) and dry pyridine (3 mL, 38 mmol) was added. The mixture was cooled to 0° C. and triflic anhydride (3.78 mL, 22.8 mmol) was added drop-wise. The mixture was stirred at room temperature overnight, diluted with DCM and washed successively with water, sat. NaHCO$_3$, water and brine, dried over MgSO$_4$, filtered and evaporated to give 6.4 g (98%) of ethyl 2-(3-methoxy-4-(trifluoromethylsulfonyloxy) phenyl)acetate.

The compound had an EC$_{50}$ for activation of a hT1R2/hT1R3 sweet receptor expressed in HEK293 cell line of 0.26 µM.

Example 28

2-(4-(1H-pyrrol-1-yl)phenyl)-N-isobutyl-2-methylpropanamide

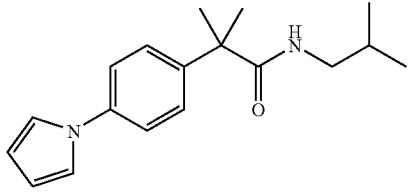

To a solution of 2-(4-bromophenyl)-N-isobutyl-2-methylpropanamide (example 1a) (100 mg, 0.33 mmol) in DMF (5 mL) was added 1-H-pyrrole (0.66 mmol, 44 mg), K$_2$CO$_3$ (2.4 eq., 115 mg) and catalytic CuI (3 mg). The reaction tube was sealed, and heated in a microwave at 195° C. for 3 hours. The solution was extracted with ethyl acetate and washed with cold water. The product was purified twice by reverse phase HPLC (10 to 95% acetonitrile/water). The compound was re-dissolved in ethanol and evaporated to dryness. $^1$H NMR (400 MHz, DMSO-d$_6$): δ 0.75 (d, 6H)), 1.48 (s, 6H), 1.70 (m, 1H), 2.85 (t, 2H), 6.1 (d, 2H), 7.3 (m, 5H), 7.5 (d,2H). MS: M+H=285.

The compound had an EC$_{50}$ for activation of a hT1R2/hT1R3 sweet receptor expressed in HEK293 cell line of 0.35 µM.

Example 29

N-isobutyl-2-(4-(6-(methoxymethyl)pyrazin-2-yl)phenyl)-2-methylpropanamide

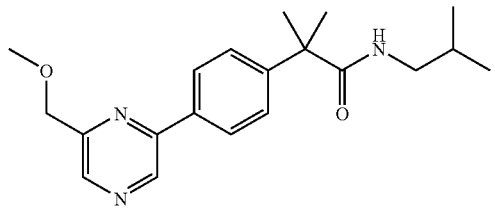

2-(4-(6-(Hydroxymethyl)pyrazin-2-yl)phenyl)-N-isobutyl-2-methylpropanamide (example 29a) (37 mg, 0113 mmol) in DMSO (1 mL) was added under argon to a solution of KOH (9.5 mg, 0.169 mmol) in DMSO (1 mL) and the mixture was stirred for 5 min then cooled to 0° C. MeI (7.7 μL, 0.124 mmol) in DMSO (1 mL) was added dropwise and the mixture was stirred at room temperature for 20 min. The reaction was quenched with water (100 μL) and the product was purified by RP HPLC (water-acetonitrile) to give 19 mg (50%) of the product. $^1$H NMR (400 MHz, dMSO): δ 0.73-0.75 (d, 6H), 1.49 (s, 6H), 1.68-1.71 (m, 1H), 2.83-2.86 (m, 2H), 3.37 (s, 3H), 4.63 (s, 2H), 7.37 (t, 1H), 7.45-7.48 (d, 2H), 8.07-8.09 (d, 2H), 8.60 (s, 1H), 9.16 (s, 1H); MS+H (342).

Example 29a 2-(4-(6-(Hydroxymethyl)pyrazin-2-yl)phenyl)-N-isobutyl-2-methylpropanamide Prepared in a similar manner to Example 26c starting from ethyl 6-(4-(1-(isobutylamino)-2-methyl-1-oxopropan-2-yl)phenyl)pyrazine-2-carboxylate (example 29b). Yield: 32%. MS+H(328).

Example 29b ethyl 6-(4-(1-(isobutylamino)-2-methyl-1-oxopropan-2-yl)phenyl)pyrazine-2-carboxylate 2-(4-(6-Cyanopyrazin-2-yl)phenyl)-N-isobutyl-2-methylpropanamide (example 20) (110 mg, 0.34 mmol) was dissolved in 1.5M HCl in EtOH (3 mL) and heated at 80° C. for 12 h. The mixture was concentrated in vacuo and purified on silica gel (50% EtOAc-hexanes) to yield 122 mg (97%). MS+H (371).

The compound had an $EC_{50}$ for activation of a hT1R2/hT1R3 sweet receptor expressed in HEK293 cell line of 0.26 μM.

Example 30

N-isobutyl-2-(3'-(methoxymethyl)biphenyl-4-yl)-2-methylpropanamide

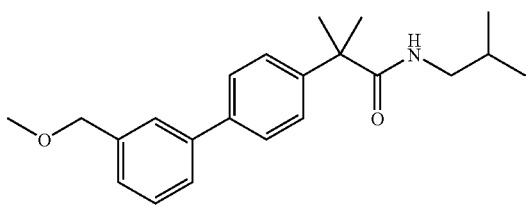

Prepared in a similar manner to Example 1 from 2-(4-bromophenyl)-N-isobutyl-2-methylpropanamide (example 1a) and 3-(methoxymethyl)phenylboronic acid. Yield: 91%. $^1$H NMR (400 MHz, DMSO): δ 0.72-0.74 (d, 6H), 1.46 (s, 6H), 1.68 (m, 1H), 2.83 (t, 2H), 3.29 (s, 3H), 4.45 (s, 2H), 7.27-7.29 (d, 1H), 7.33 (t, 1H), 7.36-7.38 (d, 2H), 7.41 (t, 1H), 7.53-7.55 (d, 2H), 7.58-7.60 (d, 2H). MS (M+H, 340).

The compound had an $EC_{50}$ for activation of a hT1R2/hT1R3 sweet receptor expressed in HEK293 cell line of 0.61 μM.

Example 31

N-isobutyl-2-methyl-2-(1-phenyl-1H-pyrazol-4-yl)propanamide

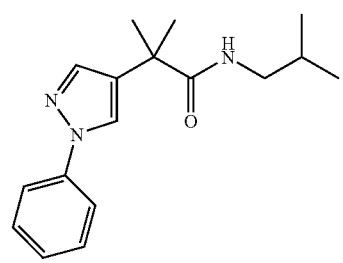

Prepared in a similar manner to Example 21a from 2-(4-bromo-1H-pyrazol-1-yl)-N-isobutyl-2-methylpropanamide (example 31a) and phenylbronic acid. Yield: 89%. $^1$H NMR (400 MHz, CDCl$_3$): δ 0.81 (d, 3H, J=6.8 Hz), 1.64-1.69 (m, 1H), 1.90 (s, 6H), 3.00 (t, 2H, J=6.8 Hz), 6.29 (br, 1H), 7.26 (d, 1H, J=7.6 Hz), 7.38 (t, 2H, J=7.6 Hz), 7.50 (d, 2H, J=7.6 Hz), 7.86 (s, 1H), 7.92 (s, 1H). MS(MH$^+$) 286.

Example 31a 2-(4-Bromo-1H-pyrazol-1-yl)-N-isobutyl-2-methylpropanamide

Prepared in a similar manner to Example 3 from 2-(4-bromo-1H-pyrazol-1-yl)-2-methylpropanoic acid and isobutylamine. Yield: 95%. $^1$H NMR (400 MHz, CDCl$_3$): δ 0.81 (d, 3H, J=6.8 Hz), 1.63-1.67 (m, 1H), 1.84 (s, 6H), 2.99 (t, 2H, J=6.8 Hz), 6.19 (br, 1H), 7.61 (s, 1H), 7.64 (s, 1H). MS(MH$^+$) 288, 290.

The compound had an $EC_{50}$ for activation of a hT1R2/hT1R3 sweet receptor expressed in HEK293 cell line of 14.88 μM.

Example 32

N-isobutyl-2-(4-(5-(methoxymethyl)pyridin-3-yl)phenyl)-2-methylpropanamide

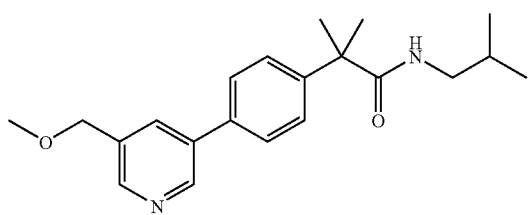

Prepared in a similar manner to example 3 from 2-(4-(5-(methoxymethyl)pyridine-3-yl)phenyl)-2-methylpropanoic acid (example 32a) and isobutylamine. Yield 73%. $^1$H NMR (400 MHz, DMSO): δ 0.72-0.74 (d, 6H), 1.46 (s, 6H), 1.68 (m, 1H), 2.83 (t, 2H), 3.32 (s, 3H), 4.5 (s, 2H), 7.36 (t, 1H), 7.39-7.42 (d, 2H), 7.66-7.68 (d, 2H), 7.95 (t, 1H), 8.48-8.49 (d,1H), 8.78-8.79 (d, 1H). MS (M+H, 341).

Example 32a 2-(4-(5-(methoxymethyl)pyridine-3-yl)phenyl)-2-methylpropanoic acid 3-bromo-5-(methoxymethyl)pyridine (example 32b) (4.8 g, 23.56 mmol), 2-(4-boronophenyl)-2-methylpropanoic acid (example 21b) (5.4 g, 25.92 mmol) and $K_2CO_3$ (6.5 g, 47.12 mmol) were mixed in DME (60 mL) and 15 ml of water (15 mL). The mixture was degassed for 30 minutes and $Pd(PPh_3)_4$ (0.55 g, 0.47 mmol) was added. The reaction mixture was heated to reflux for 16 hr then cooled to room temperature, and evaporated under reduced pressure. The residue was diluted with aqueous NaOH (0.5 N, 60 mL) and stirred for 30 min., and the solution extracted with ether (20 mL×3). The aqueous phase was cooled to 0° C., acidified with 2 N HCl to PH=5~6, then extracted with EtOAc. The organic phase was washed successively with water and brine, dried over $MgSO_4$, filtered and evaporated. The residue was triturated with hexane, filtered and evaporated to give 5.9 g of 2-(4-(5-(methoxymethyl)pyridine-3-yl)phenyl)-2-methylpropanoic acid as a light brown solid in 88% yield. $^1H$ NMR (400 MHz, $CDCl_3$): δ 1.66 (s, 6H), 3.44 (s, 3H), 4.54 (s, 2H), 7.54-7.56 (d, 4H), 7.92 (s, 1H), 8.56 (s, 1H), 8.76 (s, 1H). MS (M+H, 286).

Example 32b 3-bromo-5-(methoxymethyl)pyridine

Prepared in a similar manner to Example 26a starting from (5-bromopyridin-3-yl)methanol (example 26d) and iodoethane. Yield: 89%. $^1H$ NMR (400 MHz, $CDCl_3$): δ 3.43 (s, 3H), 4.46 (s, 2H), 7.85 (s, 1H), 8.47 (s, 1H), 8.61 (s, 1H).

The compound had an $EC_{50}$ for activation of a hT1R2/hT1R3 sweet receptor expressed in HEK293 cell line of 0.91 μM.

Example 33

N-isobutyl-2-methyl-2-(3-phenylisoxazol-5-yl)propanamide

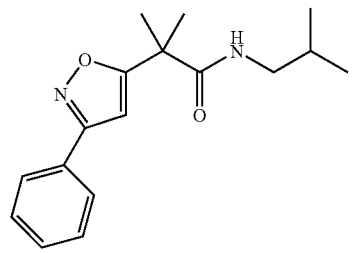

Prepared in a similar manner to Example 68 from 2-methyl-2-(5-phenylisoxazol-3-yl)propanoic acid (example 33a) and isobutylamine. Yield: 24%. $^1H$ NMR (500 MHz, DMSO-$d_6$): δ 0.78-0.79 (d, 6H, J=6.7 Hz), 1.53 (s, 6H), 1.68-1.78 (sept, 1H, J=6.7 Hz), 2.86-2.89 (t, 2H, J=6.7 Hz), 7.00 (s, 1H), 7.48-7.57 (m, 4H), 7.84-7.87 (m, 2H). MS(M+H, 287).

Example 33a 2-methyl-2-(5-phenylisoxazol-3-yl)propanoic acid

To a solution of 2-methyl-2-(5-phenylisoxazol-3-yl)propanenitrile (example 33b) (45.9 mg, 0.22 mmol) in dioxane (3 mL), was added a 1N HCl solution (2.2 mL, 2.2 mmol). The reaction was stirred at reflux for 24 h, diluted with $H_2O$ (10 mL) and extracted with EtOAc (3×). The organic layers were combined and washed with brine, dried over $MgSO_4$ and concentrated to yield a yellow syrup, carried onto the next step without further purification.

Example 33b 2-methyl-2-(5-phenylisoxazol-3-yl)propanenitrile

To a solution of 2-(5-phenylisoxazol-3-yl)acetonitrile (example 33c) (209 mg, 1.13 mmol) in anhydrous THF (5 mL), was added a solution of NaH (60% in mineral oil, 136 mg, 3.40 mmol) in anhydrous THF (8 mL) under Ar. The reaction was stirred at room temperature for 30 min, at which time methyl iodide (150 μL, 2.71 mmol) was added dropwise. The reaction was stirred at room temperature for 3 h under Ar, quenched with 1 drop of $H_2O$ and diluted with EtOAc. The mixture was washed with $H_2O$ (1×), saturated $NaHCO_3$ (2×), 10% citric acid solution (1×) and brine. The organic layers were dried over $MgSO_4$, filtered, concentrated and purified by flash-chromatography, (0-50% EtOAc in Hexane) to yield a yellow solid (88.1 mg, 37%). $^1H$ NMR (DMSO-$d_6$, 400 MHz): 1.77 (s, 6H), 7.35 (s, 1H), 7.55-7.59 (m, 3H), 7.87-7.89 (m, 2H).

Example 33c 2-(5-phenylisoxazol-3-yl)acetonitrile

To a solution of (5-phenylisoxazol-3-yl)methyl methanesulfonate (example 33d) (261 mg, 1.03 mmol) in anhydrous DMSO (8 mL) was added NaCN (252 mg, 5.15 mmol). The reaction mixture was heated at 80° C. under $N_2$ for 15 hours, then diluted with EtOAc and washed with $H_2O$ (5×). The combined organic layers were dried over $MgSO_4$, filtered and concentrated to yield a yellow solid (209 mg, 40%). $^1H$ NMR (DMSO-$d_6$, 400 MHz): 4.30 (s, 2H), 7.12 (s, 1H), 7.55-7.57 (m, 3H), 7.89-7.92 (m, 2H).

Example 33d (5-phenylisoxazol-3-yl)methyl methanesulfonate

To a solution of 5-phenylisoxazole-3-carbaldehyde (500 mg, 2.89 mmol) in MeOH (10 mL) at 0° C., was added $NaBH_4$ (327 mg, 8.67 mmol). The reaction was slowly warmed to room temperature, stirred for 15 h and concentrated in vacuo. The solid obtained was dissolved in EtOAc, washed with $H_2O$ (1×) and saturated $NH_4Cl$ (3×). The organic layers were combined, dried over $MgSO_4$, filtered, concentrated and dissolved in anhydrous $CH_2Cl_2$ (8 mL). The mixture was cooled to 0° C., followed by addition of $Et_3N$ (1.02 mL, 7.25 mmol) and methanesulfonyl chloride (337 μL, 4.35 mmol). The reaction was slowly warmed to room temperature and stirred for 15 h. Upon completion, the reaction was quenched with aqueous $NaHCO_3$ (5 mL) and extracted with EtOAc. The combined organic layers were washed with NaHCO$_3$ (2×), dried over MgSO$_4$, filtered, concentrated and carried onto the next step without further purification.

The compound had an EC$_{50}$ for activation of a hT1R2/hT1R3 sweet receptor expressed in HEK293 cell line of 6.75 μM.

Example 34

N-isobutyl-2-methyl-2-(4-(1-methyl-1H-pyrrol-2-yl)phenyl)propanamide

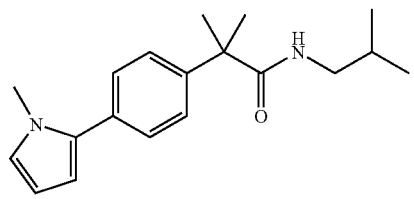

To a solution of N-isobutyl-2-methyl-2-(4-(4,4,5,5-tetramethyl-1,3,2-dioxaborolan-2-yl)phenyl)propanamide (example 23a) (19.04 g, 55.14 mmol), K$_2$CO$_3$ (22.86 g, 165.4 mmol), and N-methyl-2-bromopyrrole (7.50 g, 93.74 mmol) in DME/H$_2$O (4/1, 300 mL) was added Pd(PPh$_3$)$_4$ (3.20 g, 2.76 mmol) at RT under argon and the reaction mixture was stirred at 85° C. overnight. After it was cooled down to room temperature, the reaction mixture was diluted with brine, and extracted with EtOAc (3×). The combined organic layers were washed with brine, and dried over Na$_2$SO$_4$. After evaporation of the solvent under reduced pressure, the residue was purified twice by chromatography on silica gel eluting with EtOAc/Hexanes (1/9) to give the title compound as off-white white solid, which was further purified by recrystallization from hexanes, and dried under vacuum overnight. mp: 59-60° C. $^1$H NMR (400 MHz, DMSO-d$_6$) δ 7.35 (d, J=7.2 Hz, 2H), 7.31 (d, J=7.2 Hz, 2H), 6.79 (m, 1H), 6.09 (m, 1H), 6.01 (m, 1H), 3.60 (s, 3H), 2.82 (t, J=6.4 Hz, 2H), 1.7 (m, 1H), 1.44 (s, 6H), 0.2 (d, J=7.2 Hz, 6H). MS 299 (MH$^+$).

The compound had an EC$_{50}$ for activation of a hT1R2/hT1R3 sweet receptor expressed in HEK293 cell line of 0.96 μM.

Example 35

2-(3-hydroxy-4-(4-methylthiophen-3-yl)phenyl)-N-isobutyl-2-methylpropanamide

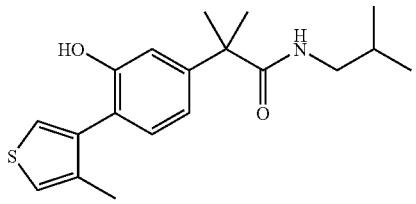

N-isobutyl-2-(3-methoxy-4-(4-methylthiophen-3-yl)phenyl)-2-methylpropanamide (example 35a) (103 mg, 0.3 mmol) was dissolved in dry DCM (5 mL), the mixture was under argon cooled to −78° C. and BBr$_3$ (1.69 mL of 1M solution in DCM) was added drop-wise and the mixture was stirred at room temperature for 72 hrs. The solution was diluted with DCM and treated with 1M aq. HCl. The organic phase was washed with water and brine, dried over MgSO$_4$ filtered and evaporated. The residue was purified on preparative RP HPLC (acetonitrile/water) and on silica gel (EtOAc/hexanes) and the product was co-evaporated with ethanol to give 2-(3-hydroxy-4-(4-methylthiophen-3-yl)phenyl)-N-isobutyl-2-methylpropanamide (69 mg, 70%). $^1$H NMR (400 MHz, dMSO): δ 0.74-0.76 (d, 6H), 1.42 (s, 6H), 1.67-1.74 (m, 1H), 2.09 (s, 3H), 2.83-2.86 (t, 2H), 6.76-6.78 (dd, 1H), 6.87-6.88 (d, 1H), 7.01-7.03 (d, 1H), 7.13-7.14 (m, 1H), 7.21-7.22 (d, 1H), 7.27-7.29 (t, 1H), 9.38-9.39 (b, 1H); MS (332).

Example 35a

N-isobutyl-2-(3-methoxy-4-(4-methylthiophen-3-yl)phenyl)-2-methylpropanamide

To a solution of 2-(3-methoxy-4-(4-methylthiophen-3-yl)phenyl)-2-methylpropanoic acid (example 35b) (630 mg, 2.2 mmol) in DMF (7 mL) were added HOBt (297 mg, 2.2 mmol), EDC (434 mg, 2.2 mmol) and isobutyl amine (214 μL, 2.2 mmol). The mixture was stirred at room temperature overnight and evaporated under reduced pressure. The residue was dissolved in EtOAc and successively washed with water, 10% citric acid, sat. NaHCO$_3$ and water, dried over MgSO$_4$, filtered and evaporated. The residue was chromatographed on silica gel (30% EtOAc-hexanes) to give 190 mg (37%) of N-isobutyl-2-(3-methoxy-4-(4-methylthiophen-3-yl)phenyl)-2-methylpropanamide. $^1$H NMR (400 MHz, dMSO): δ 0.73-0.75 (d, 6H), 1.48 (s, 6H), 1.69-1.72 (m, 1H), 2.00 (s, 3H), 2.49-2.50 (m, 2H), 3.71 (s, 3H), 6.91-6.94 (m, 2H), 7.08-7.10 (d, 1H), 7.18 (s, 1H), 7.24-7.25 (d, 1H), 7.34-7.35 (t, 1H).

Example 35b 2-(3-methoxy-4-(4-methylthiophen-3-yl)phenyl)-2-methylpropanoic acid Prepared in a similar manner to example 27a from ethyl 2-(3-methoxy-4-(4-methylthiophen-3-yl)phenyl)-2-methylpropanoate (example 35c). Yield: 92%. $^1$H NMR (400 MHz dMSO): δ 1.51 (s, 6H), 2.01 (s, 3H), 3.73 (s, 3H), 6.89-6.99 (m, 2H), 7.10-7.12 (d, 1H), 7.16-7.17 (d, 1H), 7.26-7.27 (d, 2H), 12.31 (s, 1H).

Example 35c

Ethyl 2-(3-methoxy-4-(4-methylthiophen-3-yl)phenyl)-2-methylpropanoate

Prepared in a similar manner to example 27b from ethyl 2-(3-methoxy-4-(4-methylthiophen-3-yl)phenyl)acetate (example 35d). Yield: 94%.

Example 35d

Ethyl 2-(3-methoxy-4-(4-methylthiophen-3-yl)phenyl)acetate

Prepared in a similar manner to example 1 from ethyl 2-(3-methoxy-4-(trifluoromethylsulfonyloxy)phenyl)acetate (example 27d) and 4-methylthiophen-3-ylboronic acid. Yield: 72%. $^1$H NMR (400 MHz, dMSO): δ 1.19-1.22 (m, 3H), 2.00 (s, 3H), 3.62 (s, 2H), 3.69-3.73 (m, 3H), 4.08-4.13

(m, 2H), 6.86-6.88 (d, 1H), 6.98-6.99 (d, 1H), 7.08-7.10 (d, 1H), 7.16-7.17 (t, 1H), 7.26-7.27 (d,1H).

The compound had an EC$_{50}$ for activation of a hT1R2/hT1R3 sweet receptor expressed in HEK293 cell line of 1.04 µM.

Example 36

2-(2'-(hydroxymethyl)biphenyl-4-yl)-N-isobutyl-2-methylpropanamide

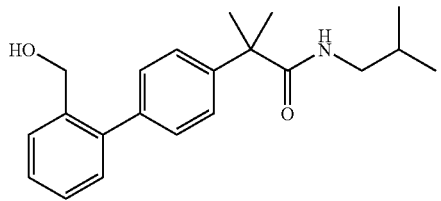

2-(2'-Formylbiphenyl-4-yl)-N-isobutyl-2-methylpropanamide (example 37) (190 mg, 0.59 mmol) was dissolved in anhydrous MeOH (6 mL) and the mixture was cooled to 0° C. A solution of NaBH$_4$ (45 mg, 1.2 mmol) in anhydrous MeOH (4 mL) was then added to the solution. The mixture was stirred for 4 hrs at room temperature and then evaporated. The residue was dissolved in EtOAc and washed successively with water and brine, dried over MgSO$_4$, filtered and evaporated. The residue was successively purified on preparative RP HPLC (acetonitrile/water) and on silica gel (EtOAc/hexanes) and co-evaporated with ethanol to give 119 mg (62%) of white crystals. $^1$H NMR (400 MHz, dMSO): δ 0.72-0.74 (d, 6H), 1.47 (s, 6H), 1.67-1.70 (m, 1H), 2.82-2.86 (t, 2H), 4.37-4.38 (d, 2H), 5.01-5.1 (t, 1H), 7.17 (d, 1H), 7.27-7.36 (m, 7H), 7.53-7.55 (d, 1H); MS+H (326).

The compound had an EC$_{50}$ for activation of a hT1R2/hT1R3 sweet receptor expressed in HEK293 cell line of 1.05 µM.

Example 37

2-(2'-formylbiphenyl-4-yl)-N-isobutyl-2-methylpropanamide

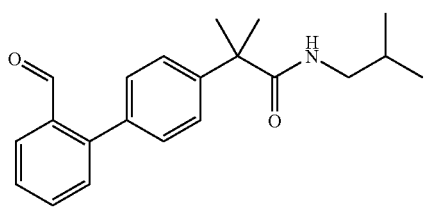

Prepared in a similar manner to Example 1 from 2-(4-bromophenyl)-N-isobutyl-2-methylpropanamide (example 1a) and 2-formylphenylboronic acid. Yield: 59%. $^1$H NMR (400 MHz, dMSO): δ 0.72-0.75 (d, 6H), 1.49 (s, 6H), 1.65-1.72 (m, 1H), 2.80-2.85 (t, 2H), 7.35-7.44 (m, 5H), 7.47-7.50 (d, 1H), 7.55-7.65 (t, 1H), 7.70-7.75 (t, 1H), 7.85-7.90 (d,1H), 9.9 (s, 1H); MS+H (324).

The compound had an EC$_{50}$ for activation of a hT1R2/hT1R3 sweet receptor expressed in HEK293 cell line of 0.81 µM.

Example 38

N-isobutyl-2-methyl-2-(1-phenyl-1H-pyrazol-4-yl)propanamide

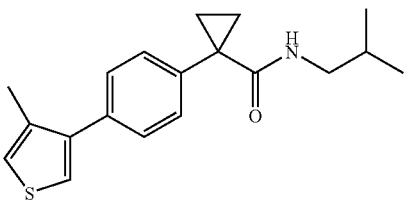

Prepared in a similar manner to Example 1 starting from 4-(1-(isobutylcarbamoyl)cyclopropyl)phenyl trifluoromethanesulfonate (example 38a) and 4-methylthiophen-3-ylboronic acid. Yield: 69%. $^1$H NMR (400 MHz, dMSO): δ 0.73-0.75 (d, 6H), 0.97-1.00 (m, 2H), 1.31-1.33 (m, 2H), 1.64-1.67 (m, 1H), 2.24 (s, 3H), 2.83-2.86 (m, 2H), 6.72-6.75 (t, 1H), 7.27-7.47 (m, 6H); MS+H (411).

Example 38a 4-(1-(isobutylcarbamoyl)cyclopropyl)phenyl trifluoromethanesulfonate Prepared in a similar manner to Example 27d starting from 1-(4-hydroxyphenyl)-N-isobutylcyclopropanecarboxamide (example 38b). Yield: 98%. MS+H (366).

Example 38b 1-(4-hydroxyphenyl)-N-isobutylcyclopropanecarboxamide

Prepared in a similar manner to Example 35 starting from N-isobutyl-1-(4-methoxyphenyl)cyclopropanecarboxamide (example 38c). Yield: 91%. MS+H(234).

Example 38c

N-isobutyl-1-(4-methoxyphenyl)cyclopropanecarboxamide

Prepared in a similar manner to Example 35a starting from 1-(4-methoxyphenyl) cyclopropanecarboxylic acid and isobutyl amine. Yield: 97%. MS+H (248).

The compound had an EC$_{50}$ for activation of a hT1R2/hT1R3 sweet receptor expressed in HEK293 cell line of 3.36 µM.

Example 39

(S)-N-(1-hydroxybutan-2-yl)-2-(3'-(methoxymethyl)biphenyl-4-yl)-2-methylpropanamide

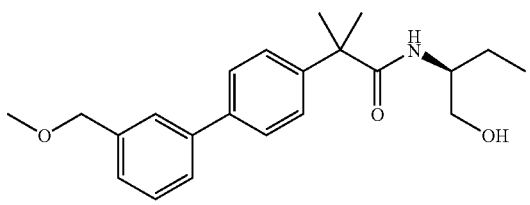

Prepared in a similar manner to Example 27 from 2-(3'-(methoxymethyl)biphenyl-4-yl)-2-methylpropanoic acid (example 39a) and (S)-2-aminobutan-1-ol. Yield: 52%. $^1$H NMR (DMSO-$d_6$, 400 MHz) δ 7.61 (m, 4H), 7.44 (m, 3H), 7.31 (d, 1H, J=7.2 Hz), 6.83 (d, 1H, J=8.5 Hz), 4.57 (t, 1H, J=5.8 Hz), 4.84 (s, 2H), 3.68 (m, 1H), 3.34 (m, 1H), 3.33 (s, 3H), 3.22 (m, 1H), 1.56 (m, 1H), 1.49 (s, 6H), 1.29 (m, 1H), 0.76 (t, 3H, J=7.3 Hz). $^{13}$C NMR (DMSO-$d_6$, 100 MHz) δ 175.5, 145.8, 139.8, 139.2, 137.8, 128.9, 126.5, 126.5, 126.4, 125.6, 125.6, 73.6, 63.0, 57.6, 52.5, 46.1, 27.1, 27.0, 23.5, 10.6. M+H=356, m.p.=73-75° C.

Example 39a 2-(3'-(methoxymethyl)biphenyl-4-yl)-2-methylpropanoic acid: Prepared in a similar manner to Example 1 starting from 3-(methoxymethyl)phenylboronic acid and 2-(4-bromophenyl)-2-methylpropanoic acid. Yield: 82%. $^1$H NMR (400 MHz, DMSO): δ 1.48 (s, 6H), 4.46 (s, 2H), 7.27-7.29 (d, 1H), 7.40-7.44 (m, 3H), 7.54-7.56 (d, 2H), 7.60-7.62 (d, 2H), 12.40 (s, 1H).

The compound had an $EC_{50}$ for activation of a hT1R2/hT1R3 sweet receptor expressed in HEK293 cell line of 1.87 μM.

Example 40

2-(5'-cyano-2,3'-bipyridin-5-yl)-N-isobutyl-2-methylpropanamide

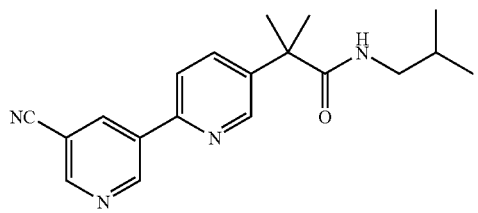

Prepared in a similar manner to Example 23 from 2-(6-bromopyridin-3-yl)-N-isobutyl-2-methylpropanamide (example 40a) and 5-(4,4,5,5-tetramethyl-1,3,2-dioxaborolan-2-yl)nicotinonitrile. Yield: 47%. $^1$H NMR (400 MHz, dMSO): δ 0.72-0.74 (d, 6H), 1.51 (s, 6H), 1.66-1.69 (m, 1H), 2.82-2.86 (m, 2H), 7.62-7.64 (m, 1H), 7.82-7.85 (m, 1H), 8.10-8.12 (d, 1H), 8.65-8.66 (d, 1H), 8.89-8.90 (t,1H), 9.05-9.06 (d, 1H), 9.50-9.51 (d, 1H); MS+H (323).

Example 40a 2-(6-bromopyridin-3-yl)-N-isobutyl-2-methylpropanamide

Prepared in a similar manner to Example 35a from 2-(6-Bromopyridin-3-yl)-2-methylpropanoic acid (example 40b) and isobutyl amine. Yield: 93%. MS+H (300).

Example 40b 2-(6-Bromopyridin-3-yl)-2-methylpropanoic acid

To a solution of LiOH (252 mg, 10.5 mmol) in MeOH (15 mL) and water (5 mL) was added 2-(6-bromopyridin-3-yl)-2-methylpropanenitrile (example 40c) (800 mg, 3.5 mmol) and the reaction mixture was heated at 85° C. for 48 hrs. The methanol was evaporated and aqueous NaOH (1N, 10 mL) was added and the solution was washed with EtOAc, acidified with aq. HCl (6N) to pH~4-5 and extracted with EtOAc. The organic layer was suuccessively washed with water and brine, dried over $MgSO_4$, filtered and evaporated to give 700 mg (96%) of 2-(6-Bromopyridin-3-yl)-2-methylpropanoic acid (MS+H, 243.8).

Example 40c 2-(6-Bromopyridin-3-yl)-2-methylpropanenitrile

Prepared in a similar manner to Example 27b from 2-(6-bromopyridin-3-yl)acetonitrile (example 40d). Yield: 71%. $^1$H NMR (400 MHz, dMSO): δ 1.73 (s, 6H), 7.73-7.75 (d, 1H), 7.91-7.94 (dd, 1H), 8.57-8.59 (d, 1H). MS+H (226).

Example 40d 2-(6-Bromopyridin-3-yl)acetonitrile

A solution of 2-bromo-5-(bromomethyl)pyridine (example 40e) (6 g, 24 mmol) and NaCN (1.42 g, 29 mmol) in absolute EtOH (50 mL) was heated at 80° C. for 8 h. The mixture was then cooled to room temperature then evaporated. The residue was suspended in water and extracted with EtOAc. The organic phase was washed with brine, dried over $MgSO_4$, filtered and evaporated. The residue was purified by chromatography on silica gel (5-30% EtOAc/hexanes) to give 2.89 g (63%) of 2-(6-Bromopyridin-3-yl)acetonitrile. $^1$H NMR (400 MHz, dMSO): δ 4.07 (s, 2H), 7.66-7.68 (d, 1H), 7.72-7.73 (dd, 1H), 8.36-8.37 (d, 1H).

Example 40e

2-Bromo-5-(bromomethyl)pyridine

To a solution of 2-bromo-5-methylpyridine (5 g, 29 mmol) in carbon tetrachloride (50 mL) was added N-bromosuccinimide (7.79 g, 44 mmol). The mixture was heated to 80° C., then dibenzoyl peroxide (53 mg, 0.22 mmol) was added and the mixture was stirred at 80° C. for 4 h then cooled to room temperature, washed with water and brine, dried over $Na_2SO_4$, filtered and evaporated. The residue was chromatographed on silica gel (30% EtOAc/heaxanes) to give 6 g of 2-Bromo-5-(bromomethyl)pyridine (MS+H, 251.8).

The compound had an $EC_{50}$ for activation of a hT1R2/hT1R3 sweet receptor expressed in HEK293 cell line of 2.19 μM.

Example 41

N-isobutyl-2-methyl-2-(3-phenyl-1,2,4-oxadiazol-5-yl)propanamide

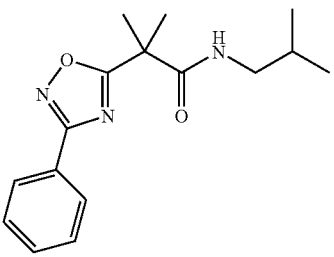

To a solution of 2-methyl-2-(3-phenyl-1,2,4-oxadiazol-5-yl)propanoic acid (example 41a) (307 mg, 1.32 mmol) in $CH_2Cl_2$ (10 mL) were added HOBt (196 mg, 1.45 mmol), EDCI.HCl (278 mg, 1.45 mmol) and isobutylamine (146 μL, 1.45 mmol). The reaction was stirred at room temperature under $N_2$ for 18 h. Upon completion, the reaction was concentrated and purified by flash-chromatography (0-75% EtOAc in Hexane) to yield N-isobutyl-2-methyl-2-(3-phenyl-1,2,4-oxadiazol-5-yl)propanamide (198 mg, 52%) as a white solid. $^1$H NMR (500 MHz, DMSO-$d_6$): δ 0.81-0.83 (d, 6H, J=6.7 Hz), 1.66 (s, 6H), 1.70-1.80 (sept, 1H, J=6.7 Hz), 2.89-2.92 (t, 2H, J=6.4 Hz), 7.56-7.61 (m, 3H), 7.92-7.95 (t, 1H, J=5.6 Hz), 8.01-8.03 (m, 2H). MS(M+H, 288).

Example 41a

2-Methyl-2-(3-phenyl-1,2,4-oxadiazol-5-yl)propanoic acid

To a solution of methyl 2-(3-phenyl-1,2,4-oxadiazol-5-yl)acetate (example 41b) (700 mg, 3.2 mmol) dissolved in THF (10 mL) under Ar, were added a solution of NaH (60% dispersion in mineral oil, 385 mg, 9.6 mmol) dissolved in THF (6 mL) and methyl iodide (480 μL, 7.68 mmol). The reaction was stirred for 16 h at room temperature under Ar. Upon completion, the reaction was quenched with MeOH (15 mL) and $H_2O$ (15 mL). The solution was adjusted to pH 12 with a concentrated NaOH solution, and the resulting mixture was stirred at room temperature for 8 h. Upon completion, the reaction was adjusted to pH 2 with 6N HCl, and extracted with EtOAc (4×). The organic layers were combined and washed with brine, dried over $MgSO_4$, filtered and concentrated to yield 2-methyl-2-(3-phenyl-1,2,4-oxadiazol-5-yl)propanoic acid as a yellow oil (731 mg, 98%). $^1$H NMR (500 MHz, DMSO-$d_6$): δ 1.68 (s, 6H), 7.56-7.62 (m, 3H), 8.01-8.04 (m, 2H), 13.4 (br. s, 1H). MS(M+H, 247).

Example 41b

Methyl 2-(3-phenyl-1,2,4-oxadiazol-5-yl)acetate

A mixture of 2,2-dimethyl-1,3-dioxane-4,6-dione (5.0 g, 34.6 mmol) and MeOH (1.4 mL, 34.6 mmol) was heated at 80° C. for 18 h. The reaction was concentrated, the residue (2.05 g, 17.3 mmol) was dissolved in $CH_3CN$ (10 mL) and added to a solution of HOBt (2.3 g, 17.3 mmol), EDCI.HCl (3.3 g, 17.3 mmol), N,N-diisopropylethylamine (3.01 mL, 17.3 mmol) and N'-hydroxybenzimidamide (2.0 g, 8.5 mmol) in $CH_3CN$ (5 mL). The reaction was stirred at 40° C. for 18 h under $N_2$, and upon completion, diluted with EtOAc and washed with $H_2O$ (2×). The combined organic layers were dried over $Na_2SO_4$, concentrated and purified by flash-chromatography (0-50% EtOAc in Hexane). The resulting residue was dissolved in $CH_3CN$ (10 mL), and heated in a microwave reactor (110° C., 30 min). Upon completion, the solvent was removed in vacuo and the residue was purified by flash-chromatography (0-50% EtOAc in Hexane) to yield methyl 2-(3-phenyl-1,2,4-oxadiazol-5-yl)acetate as a yellow oil (700 mg, 38%). $^1$H NMR (500 MHz, DMSO-$d_6$): δ 3.72 (s, 3H), 4.41 (s, 2H), 7.56-7.62 (m, 3H), 8.01-8.04 (m, 2H). MS(M+H, 219).

The compound had an $EC_{50}$ for activation of a hT1R2/hT1R3 sweet receptor expressed in HEK293 cell line of 6.53 μM.

Example 42

2-(5'-cyano-3,3'-bipyridin-6-yl)-N-isobutyl-2-methylpropanamide

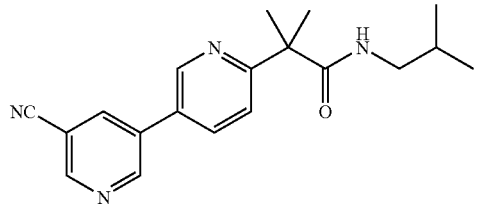

Prepared in a similar manner to Example 23 from 2-(5-bromopyridin-2-yl)-N-isobutyl-2-methylpropanamide (example 42a) and 5-(4,4,5,5-tetramethyl-1,3,2-dioxaborolan-2-yl)nicotinonitrile. Yield 49%. $^1$H NMR (400 MHz, acetonitrile-$d_6$): δ 0.80-0.81 (d, 6H), 1.63 (s, 6H), 1.71-1.77 (m, 1H), 2.97-3.00 (t, 2H), 7.01 (bs, 1H), 7.59-7.62 (d, 1H), 8.18-8.21 (dd, 1H), 8.59-8.60 (t, 1H), 8.99 (d, 1H), 9.20-9.21 (d, 1H); MS+H (323).

Example 42a 2-(5-Bromopyridin-2-yl)-N-isobutyl-2-methylpropanamide

Prepared in a similar manner to example 27 from 2-(5-bromopyridin-2-yl)-2-methylpropanoic acid (example 46b) and isobutyl amine. Yield 32%. MS+H (301).

Example 42b 2-(5-Bromopyridin-2-yl)-2-methylpropanoic acid

Methyl 2-(5-bromopyridin-2-yl)-2-methylpropanoate (514 mg, 2 mmol) was dissolved in dry DCM (10 mL) and cooled to −10° C. $BBr_3$ (20 mL of 1M solution in DCM) was added drop-wise under argon to the solution. The reaction mixture was stirred 30 min at −10° C. and then at room temperature for 72 h and evaporated to give 2-(5-Bromopyridin-2-yl)-2-methylpropanoic acid used in the next step without further purification. MS+H (244, 246).

Example 42c

Methyl 2-(5-bromopyridin-2-yl)-2-methylpropanoate

Prepared in similar manner to Example 27b from methyl 2-(5-bromopyridin-2-yl)acetate (example 46d). Yield 67%. $^1$H NMR (400 MHz, dMSO): δ 1.50 (s, 6H), 3.57 (s, 3H), 7.39-7.41 (d, 1H), 8.01-8.04 (dd, 1H), 8.62-8.63 (d, 1H); MS+H (258, 259).

Example 42d

Methyl 2-(5-bromopyridin-2-yl)acetate 2-(5-Bromopyridin-2-yl)acetic acid hydrochloride (example 42e) (2.34 g, 9.3 mmol) was dissolved in MeOH (18 mL) and conc. H$_2$SO$_4$ (1.5 mL). The mixture was stirred at 80° C. overnight. The solvent was removed under reduced pressure and the mixture was treated with sat. NaHCO$_3$ then extracted with EtOAc, washed with brine, dried over MgSO$_4$, filtered and evaporated to give methyl 2-(5-bromopyridin-2-yl)acetate as a yellow oil (1.97 g, 92%). $^1$H NMR (400 MHz, dMSO): δ 3.60 (s, 3H), 3.83 (s, 2H), 7.34-36 (d, 1H), 7.99-8.02 (dd, 1H), 8.60-8.61 (d, 1H); MS+H (230, 231).

Example 42e

2-(5-Bromopyridin-2-yl)acetic acid hydrochloride 5-(5-Bromopyridin-2(1H)-ylidene)-2,2-dimethyl-1,3-dioxane-4,6-dione (example 42f) (3.55 g, 11.87 mmol) was suspended in conc. HCl (55 mL) and refluxed for 3 h. The solution was concentrated under reduced pressure and a residue was triturated with EtOH to provide white crystals that were filtered off and washed with EtOH (2.34 g, 78%). $^1$H NMR (400 MHz, dMSO): δ 3.81 (s, 2H), 7.44-7.46 (d, 1H), 8.12-8.15 (dd, 1H), 8.70-8.71 (d, 1H), 11.30 (bs, 1H); MS+H (218).

Example 42f

5-(5-Bromopyridin-2(1H)-ylidene)-2,2-dimethyl-1,3-dioxane-4,6-dione

3-Bromopyridine N-oxide (10 g, 57.5 mmol) was slowly added into a solution of 2,2-dimethyl-1,3-dioxane-4,6-dione (Meldrum's acid, 8.28 g, 57.5 mmol) in acetic anhydride (58 mL) at 0° C. The temperature was allowed to come to room temperature overnight. The mixture was filtered and yellow crystals were washed with small amount of acetic anhydride and dried in vacuo. The residue was triturated with warm chloroform and insoluble residue was filtered off. The chloroform soluble fraction was evaporated and the residue triturated with 5% MeOH in DCM. The solid material was filtered off and the soluble fraction was evaporated to give 3.55 g (20%) of 5-(5-Bromopyridin-2(1H)-ylidene)-2,2-dimethyl-1,3-dioxane-4,6-dione. $^1$H NMR (400 MHz, dMSO): δ 1.61 (s, 6H), 1.64 (s, 1H), 8.20-8.23 (dd, 1H), 8.51-8.52 (d, 1H), 8.62-8.65 (d, 1H).

The compound had an EC$_{50}$ for activation of a hT1R2/hT1R3 sweet receptor expressed in HEK293 cell line of 10.64 μM.

Example 43

N-isobutyl-2-methyl-2-(4-(pyrimidin-5-yl)phenyl)propanamide

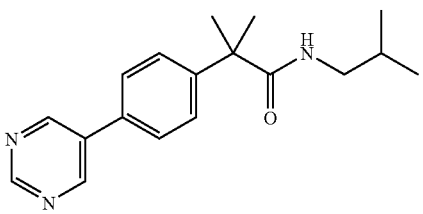

Prepared in a similar manner to Example 1 from 2-(4-bromophenyl)-N-isobutyl-2-methylpropanamide (example 1a) and pyrimidin-5-ylboronic acid. Yeild: 64%. $^1$H NMR (400 MHz, dMSO): δ 0.75-0.77 (d, 6H), 1.49 (s, 6H), 1.69-1.72 (m, 1H), 2.84-2.87 (t, 2H), 7.41 (t, 1H), 7.45-7.47 (d, 3H), 7.77-7.79 (d, 2H), 9.14 (s, 2H), 9.18 (s, 1H); MS+H (297.7).

The compound had an EC$_{50}$ for activation of a hT1R2/hT1R3 sweet receptor expressed in HEK293 cell line of 1.01 μM.

Example 44

(R)-2-methyl-N-(3-methylbutan-2-yl)-2-(4-(pyrimidin-5-yl)phenyl)propanamide

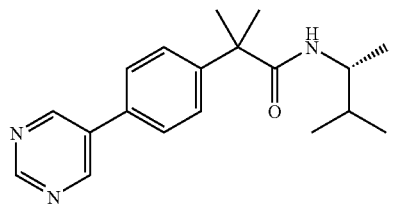

Prepared in a similar manner to Example 20 from 2-methyl-2-(4-(pyrimidin-5-yl)phenyl)propanoic acid (example 25a) and (R)-3-methylbutan-2-amine. Yield 60%. $^1$H NMR (400 MHz, dMSO): δ 0.74-0.79 (m, 6H), 0.94-0.96 (d, 3H), 1.48-1.49 (d, 6H), 1.59-1.64 (m, 1H), 3.59-3.65 (m, 1H), 6.99-7.02 (d, 1H), 7.44-7.45 (d, 2H), 7.77-7.80 (d, 2H), 9.14 (s, 1H), 9.18 (s, 1H); MS+H (312.1).

The compound had an EC$_{50}$ for activation of a hT1R2/hT1R3 sweet receptor expressed in HEK293 cell line of 0.65 μM.

Example 45

2-(4-(6-cyanopyrazin-2-yl)phenyl)-N-(2-methoxypropyl)-2-methylpropanamide

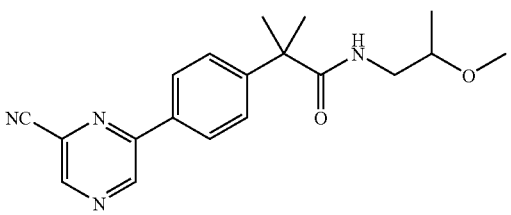

Prepared in a similar manner to Example 20 from 2-(4-(6-Cyanopyrazin-2-yl)phenyl)-2-methylpropanoic acid (example 20a) and 2-methoxypropan-1-amine. Yield 70%. $^1$H NMR (400 MHz, dMSO): δ 0.93-0.94 (d, 3H), 1.48-1.49 (d, 6H), 2.99-3.11 (m, 2H), 3.17 (s, 3H), 3.29-3.30 (m, 1H), 7.41-7.42 (m, 1H), 7.49-7.51 (d, 2H), 8.11-8.14 (d, 2H), 9.15 (s, 1H), 9.55 (s, 1H); MS+H (339).

The compound had an $EC_{50}$ for activation of a hT1R2/hT1R3 sweet receptor expressed in HEK293 cell line of 0.92 μM.

Example 46

2-(4-(5-cyanopyridin-3-yl)phenyl)-N-(2-(furan-2-yl)-2-hydroxyethyl)-2-methylpropanamide

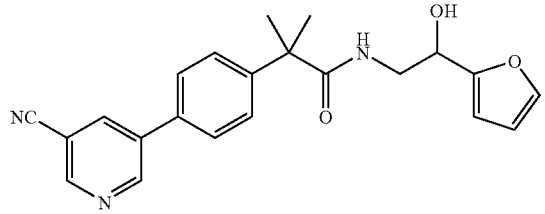

Prepared in a similar manner to Example 3 starting from 2-(4-(5-cyanopyridin-3-yl)phenyl)-2-methylpropanoic acid (example 21a) and 2-amino-1-(furan-2-yl)ethanol. Yield: 75%. $^1$H NMR (400 MHz, DMSO): δ 1.41 (s, 6H), 3.26 (m, 1H), 3.41 (m, 1H), 4.63 (t, 1H), 5.45 (br-s, 1H), 6.21-6.22 (d, 1H), 6.35 (t, 1H), 7.34 (t, 3H), 7.35-7.37 (dd, 2H), 7.54-7.55 (d, 1H), 7.71-7.73 (dd, 2H), 8.61 (t, 1H), 8.97-8.98 (d, 1H), 9.15-9.16 (d, 1H). MS (M+H, 358).

The compound had an $EC_{50}$ for activation of a hT1R2/hT1R3 sweet receptor expressed in HEK293 cell line of 1.19 μM.

Example 47

(R)-N-sec-butyl-2-(4-(6-cyanopyrazin-2-yl)phenyl)-2-methylpropanamide

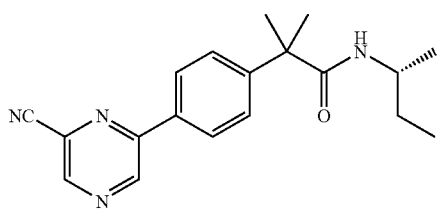

Prepared in a similar manner to Example 20 from 2-(4-(6-Cyanopyrazin-2-yl)phenyl)-2-methylpropanoic acid (example 20a) and (R)-butan-2-amine. Yield 43%.

$^1$H NMR (400 MHz, dMSO): δ 0.70-0.74 (m, 3H), 0.95-0.97 (d, 3H), 1.31-1.35 (m, 2H), 1.47 (s, 6H), 3.70-3.73 (m, 1H), 7.04-7.06 (d, 1H), 7.48-7.50 (dd, 2H), 8.11-8.13 (dd, 2H), 9.14 (s, 1H), 9.55 (s, 1H); MS+H (323).

The compound had an $EC_{50}$ for activation of a hT1R2/hT1R3 sweet receptor expressed in HEK293 cell line of 0.14 μM.

Example 48

2-(4-(6-cyanopyrazin-2-yl)phenyl)-N-(1-(furan-2-yl)ethyl)-2-methylpropanamide

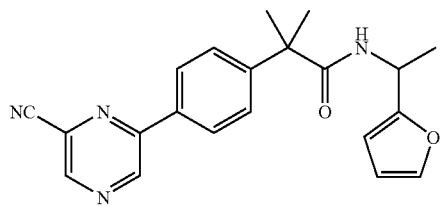

Prepared in a similar manner to Example 20 from 2-(4-(6-Cyanopyrazin-2-yl)phenyl)-2-methylpropanoic acid (example 20a) and 1-(furan-2-yl)ethanamine. Yield 35%. $^1$H NMR (400 MHz, dMSO): δ 1.32-1.33 (d, 3H), 1.49-1.52 (d, 6H), 5.09 (m, 1H), 6.06 (d, 1H), 6.33-6.35 (dd, 1H), 7.49-7.51 (d, 2H), 7.54 (d, 1H), 8.12-8.14 (d, 2H), 9.16 (s, 1H), 9.56 (s, 1H); MS+H (361).

The compound had an $EC_{50}$ for activation of a hT1R2/hT1R3 sweet receptor expressed in HEK293 cell line of 0.19 μM.

Example 49

2-(4-(6-cyanopyrazin-2-yl)phenyl)-N-(furan-2-ylmethyl)-2-methylpropanamide

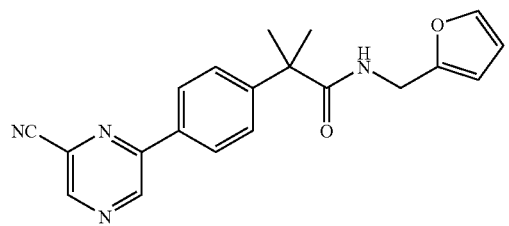

Prepared in a similar manner to Example 20 from 2-(4-(6-Cyanopyrazin-2-yl)phenyl)-2-methylpropanoic acid (example 20a) and furan-2-ylmethanamine. Yield 30%. $^1$H NMR (400 MHz, dMSO): δ 1.51 (s, 6H), 4.23-4.25 (d, 2H), 6.06-6.07 (d, 1H), 6.34-6.35 (t, 1H), 7.48-7.50 (d, 2H), 7.53 (t, 1H), 7.97-8.00 (t, 1H), 9.16 (s, 1H), 9.56 (s, 1H); MS+H (347).

The compound had an $EC_{50}$ for activation of a hT1R2/hT1R3 sweet receptor expressed in HEK293 cell line of 0.47 μM.

Example 50

N-isobutyl-2-methyl-2-(2-methylbiphenyl-4-yl)propanamide

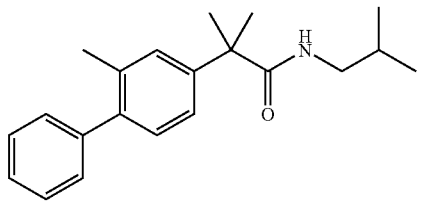

Prepared in a similar manner to Example 1 from 4-(1-(isobutylamino)-2-methyl-1-oxopropan-2-yl)-2-methylphenyl trifluoromethanesulfonate (example 50a) and phenyl boronic acid. Yield: 75%. $^1$H NMR (400 MHz, dMSO): δ 0.76-0.77 (d, 6H), 1.46 (s, 6H), 1.72-1.73 (m, 1H), 2.21 (s, 3H), 2.84-2.87 (m, 2H), 7.13-7.21 (m, 3H), 7.30-7.37 (m, 4H), 7.41-7.45 (m, 2H); MS+H (310).

Example 50a

4-(1-(Isobutylamino)-2-methyl-1-oxopropan-2-yl)-2-methylphenyl trifluoromethanesulfonate Prepared in a similar manner to Example 27d starting from 2-(4-hydroxy-3-methylphenyl)-N-isobutyl-2-methylpropanamide (example 50b). Yield: 94%. MS+H (382)

Example 50b

2-(4-hydroxy-3-methylphenyl)-N-isobutyl-2-methylpropanamide

Prepared in a similar manner to Example 35 starting from N-isobutyl-2-(4-methoxy-3-methylphenyl)-2-methylpropanamide (example 50c). Yield: 60%. MS+H (250).

Example 50c

N-isobutyl-2-(4-methoxy-3-methylphenyl)-2-methylpropanamide

Prepared in a similar manner to Example 35a starting from 2-(4-methoxy-3-methylphenyl)-2-methylpropanoic acid (example 50d) and isobutylamine. Yield: 64%. MS+H (264).

Example 50d

2-(4-methoxy-3-methylphenyl)-2-methylpropanoic acid

Prepared in a similar manner as example 27b starting from methyl 2-(4-methoxy-3-methylphenyl)acetate (example 50e) followed by hydrolysis using 1M NaOH (50 mL) at 60° C. overnight. The mixture was cooled to room temperature and acidified with 6N aq. HCl to pH 2. The product was extracted to EtOAc, washed with water and brine, dried over MgSO$_4$, filtered and evaporated to give 1.82 g (79%) of the product. $^1$H NMR (400 MHz, dMSO): δ 1.44 (s, 6H), 2.14 (s, 3H), 3.76 (s, 3H), 6.86-6.88 (d, 1H), 7.11-7.14 (m, 2H); MS+H (209).

Example 50e

2-(4-methoxy-3-methylphenyl)acetate

Prepared in a similar manner to Example 42d starting from 2-(4-methoxy-3-methylphenyl)acetic acid. Yield 98%.

The compound had an EC$_{50}$ for activation of a hT1R2/hT1R3 sweet receptor expressed in HEK293 cell line of 1.42 μM.

Example 51

(S)-2-(4-(6-cyanopyrazin-2-yl)phenyl)-N-(1-hydroxybutan-2-yl)-2-methylpropanamide

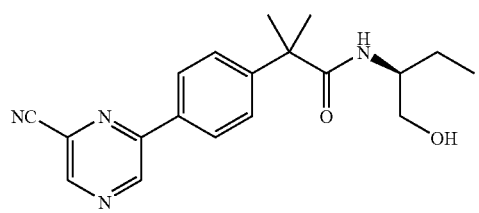

Prepared in a similar manner to Example 20 from 2-(4-(6-Cyanopyrazin-2-yl)phenyl)-2-methylpropanoic acid (example 20a) and 2-aminobutan-1-ol. Yield 37%.

$^1$H NMR (400 MHz, dMSO): δ 0.70-0.74 (t, 3H), 1.02-1.06 (m, 1H), 1.48-1.56 (m, 7H), 3.18-3.22 (m, 1H), 3.28-3.33 (m, 2H), 3.64-3.68 (m, 1H), 4.53-4.56 (m, 1H), 6.86-6.88 (d, 1H), 7.49-7.52 (d, 2H), 8.10-8.13 (d, 2H), 9.14 (s, 1H), 9.55 (s, 1H); MS+H (339).

The compound had an EC$_{50}$ for activation of a hT1R2/hT1R3 sweet receptor expressed in HEK293 cell line of 1.03 μM

Example 52

2-methyl-N-(pentan-3-yl)-2-(4-(pyrimidin-5-yl)phenyl)propanamide

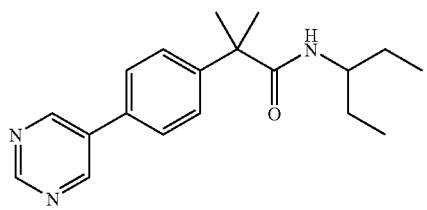

Prepared in a similar manner to Example 20 starting from 2-methyl-2-(4-(pyrimidin-5-yl)phenyl)propanoic acid (example 25a) and pentan-3-amine. Yield: 67%. $^1$H NMR (400 MHz, dMSO): δ 0.71-0.75 (m, 6H), 1.26-1.42 (m, 4H), 1.49 (s, 6H), 3.57-3.59 (m, 1H), 6.91-6.93 (d, 1H), 7.45-7.48 (d, 2H), 7.77-7.79 (d, 2H), 9.14 (s, 2H), 9.17 (s, 1H); MS+H (312).

The compound had an $EC_{50}$ for activation of a hT1R2/hT1R3 sweet receptor expressed in HEK293 cell line of 0.38 μM.

Numerous amide compounds of Formula (I) were also synthesized and experimentally tested for effectiveness as activator of a hT1R2/hT1R3 "sweet" receptor expressed in an HEK293 cell line. The results of that testing are shown below in Table A.

TABLE A

| COMPOUND NO. | COMPOUND | SWEET $EC_{50}$ μM |
|---|---|---|
| A1 | 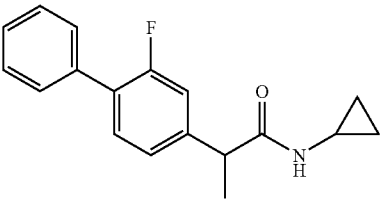 N-cyclopropyl-2-(2-fluorobiphenyl-4-yl)propanamide | 3.52 |
| A2 | 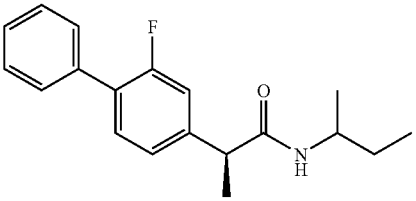 (2S)-N-sec-butyl-2-(2-fluorobiphenyl-4-yl)propanamide | 2.38 |
| A3 | 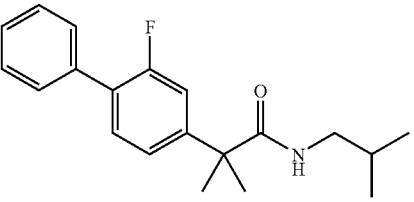 2-(2-fluorobiphenyl-4-yl)-N-isobutyl-2-methylpropanamide | 1.71 |
| A4 | 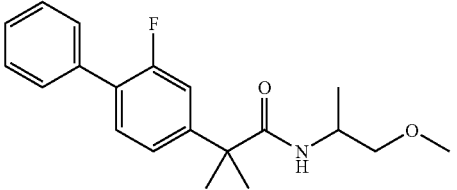 2-(2-fluorobiphenyl-4-yl)-N-(1-methoxypropan-2-yl)-2-methylpropanamide | 3.19 |
| A5 | 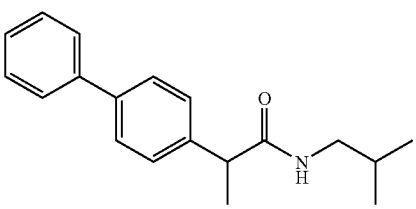 2-(biphenyl-4-yl)-N-isobutylpropanamide | 4.26 |

TABLE A-continued
| COMPOUND NO. | COMPOUND | SWEET EC$_{50}$ μM |
|---|---|---|
| A6 | 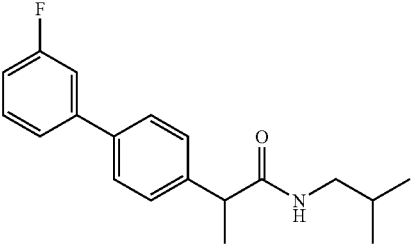<br>2-(3'-fluorobiphenyl-4-yl)-N-isobutylpropanamide | 1.80 |
| A7 | 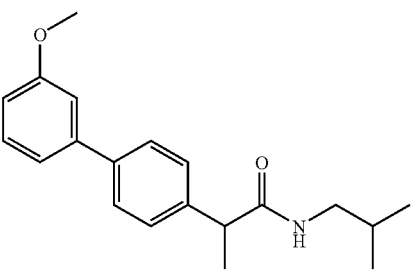<br>N-isobutyl-2-(3'-methoxybiphenyl-4-yl)propanamide | 5.58 |
| A8 | 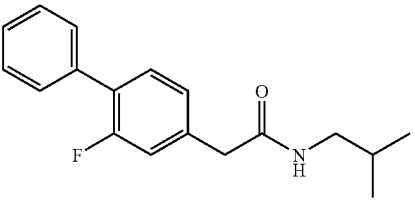<br>2-(2-fluorobiphenyl-4-yl)-N-isobutylacetamide | 7.5 |
| A9 | 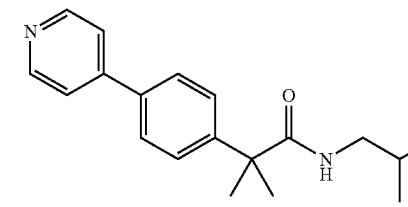<br>N-isobutyl-2-methyl-2-(4-(pyridin-4-yl)phenyl)propanamide | 1.66 |
| A10 | 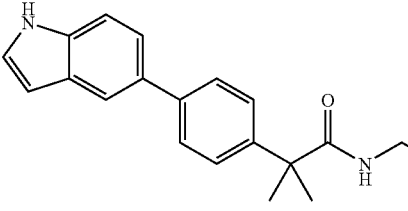<br>2-(4-(1H-indol-5-yl)phenyl)-N-isobutyl-2-methylpropanamide | 3.36 |

TABLE A-continued

| COMPOUND NO. | COMPOUND | SWEET EC$_{50}$ μM |
|---|---|---|
| A11 | 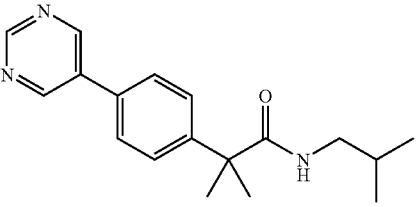<br>N-isobutyl-2-methyl-2-(4-(pyrimidin-5-yl)phenyl)propanamide | 2.13 |
| A12 | 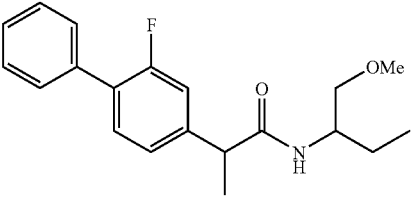<br>N-cyclopropyl-2-(2-fluorobiphenyl-4-yl)propanamide | 4.5 |
| A13 | 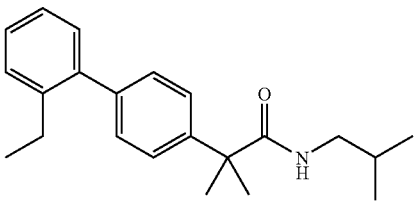<br>2-(2'-ethylbiphenyl-4-yl)-N-isobutyl-2-methylpropanamide | 7.0 |
| A14 | 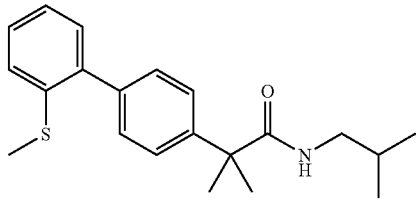<br>N-isobutyl-2-methyl-2-(2'-(methylthio)biphenyl-4-yl)propanamide | 9.0 |
| A15 | 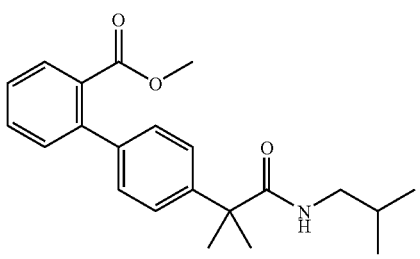<br>Methyl 4'-(1-(isobutylamino)-2-methyl-1-oxopropan-2-yl)biphenyl-2-carboxylate | 4.0 |
| A16 | 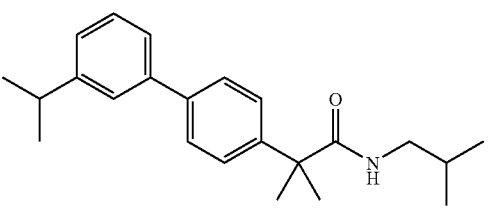<br>N-isobutyl-2-(3'-isopropylbiphenyl-4-yl)-2-methylpropanamide | 6.0 |

TABLE A-continued
| COMPOUND NO. | COMPOUND | SWEET EC$_{50}$ μM |
|---|---|---|
| A17 | 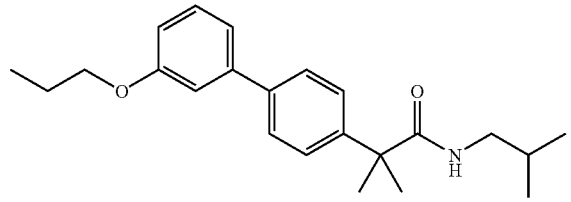<br>N-isobutyl-2-methyl-2-(3'-propoxybiphenyl-4-yl)propanamide | 5.6 |
| A18 | 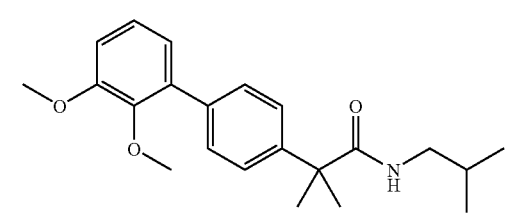<br>2-(2',3'-dimethoxybiphenyl-4-yl)-N-isobutyl-2-methylpropanamide | 6.6 |
| A19 | 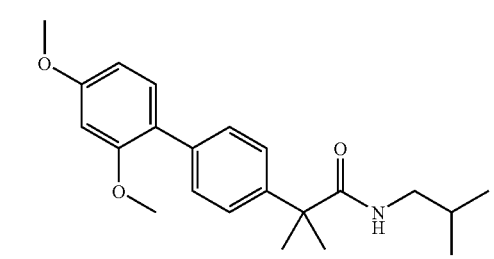<br>2-(2',4'-dimethoxybiphenyl-4-yl)-N-isobutyl-2-methylpropanamide | 7.1 |
| A20 | 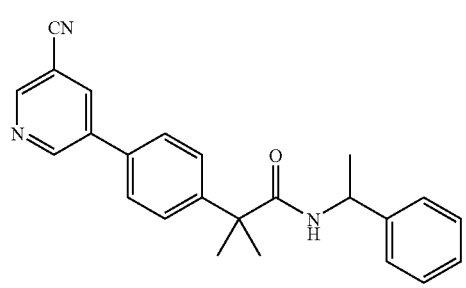<br>2-(4-(5-cyanopyridin-3-yl)phenyl)-2-methyl-N-(1-phenylethyl)propanamide | 0.71 |
| A21 | 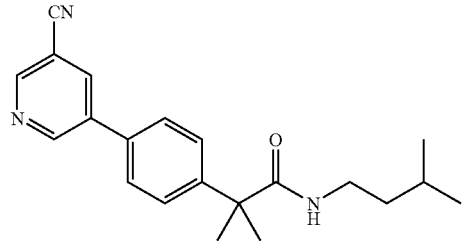<br>2-(4-(5-cyanopyridin-3-yl)phenyl)-N-isopentyl-2-methylpropanamide | 0.94 |

TABLE A-continued

| COMPOUND NO. | COMPOUND | SWEET EC$_{50}$ μM |
|---|---|---|
| A22 | 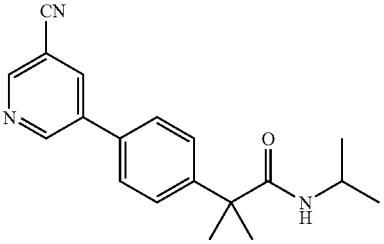<br>2-(4-(5-cyanopyridin-3-yl)phenyl)-N-isopropyl-2-methylpropanamide | 0.94 |
| A23 | 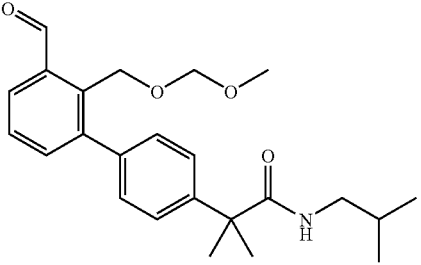<br>2-(3'-formyl-2'-((methoxymethoxy)methyl)biphenyl-4-yl)-N-isobutyl-2-methylpropanamide | 1.10 |
| A24 | 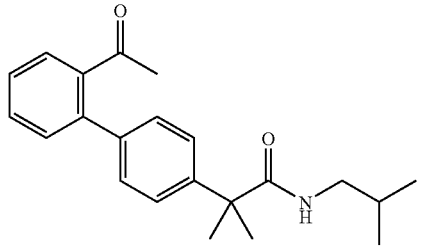<br>2-(2'-acetylbiphenyl-4-yl)-N-isobutyl-2-methylpropanamide | 1.17 |
| A25 | 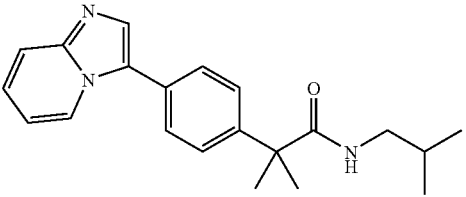<br>2-(4-(imidazo[1,2-a]pyridin-3-yl)phenyl)-N-isobutyl-2-methylpropanamide | 1.23 |
| A26 | 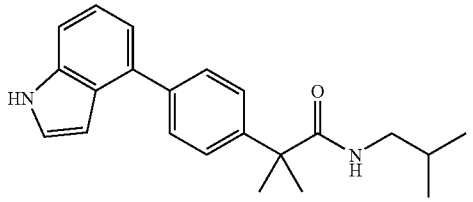<br>2-(4-(1H-indol-4-yl)phenyl)-N-isobutyl-2-methylpropanamide | 2.02 |

TABLE A-continued

| COMPOUND NO. | COMPOUND | SWEET EC$_{50}$ μM |
|---|---|---|
| A27 | 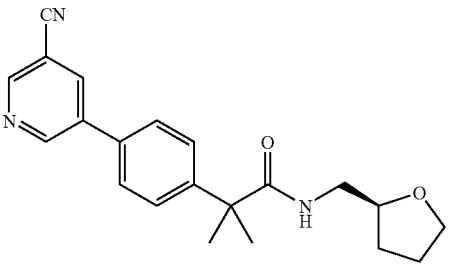<br>(S)-2-(4-(5-cyanopyridin-3-yl)phenyl)-2-methyl-N-((tetrahydrofuran-2-yl)methyl)propanamide | 2.06 |
| A28 | 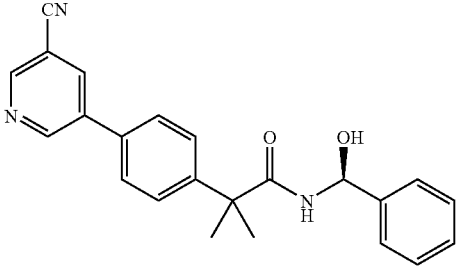<br>(S)-2-(4-(5-cyanopyridin-3-yl)phenyl)-N-(hydroxy(phenyl)methyl)-2-methylpropanamide | 2.06 |
| A29 | 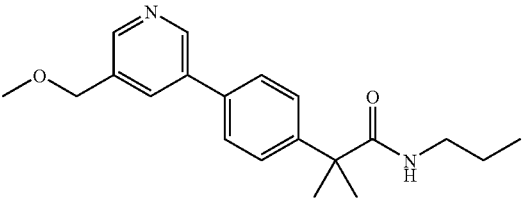<br>2-(4-(5-(methoxymethyl)pyridin-3-yl)phenyl)-2-methyl-N-propylpropanamide | 2.91 |
| A30 | 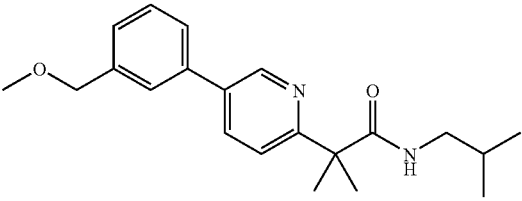<br>N-isobutyl-2-(5-(3-(methoxymethyl)phenyl)pyridin-2-yl)-2-methylpropanamide | 3.05 |
| A31 | 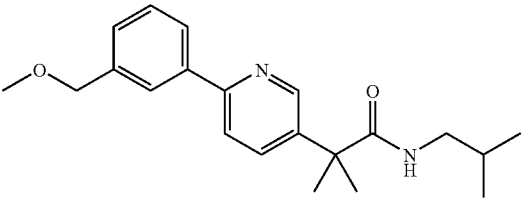<br>N-isobutyl-2-(6-(3-(methoxymethyl)phenyl)pyridin-3-yl)-2-methylpropanamide | 3.79 |

TABLE A-continued

| COMPOUND NO. | COMPOUND | SWEET EC$_{50}$ μM |
|---|---|---|
| A32 | 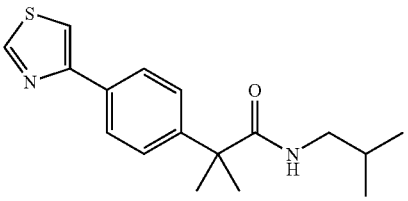<br>N-isobutyl-2-methyl-2-(4-(thiazol-4-yl)phenyl)propanamide | 5.40 |
| A33 | 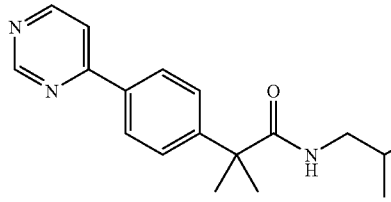<br>N-isobutyl-2-methyl-2-(4-(pyrimidin-4-yl)phenyl)propanamide | 5.40 |
| A34 | 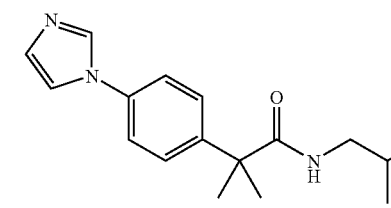<br>2-(4-(1H-imidazol-1-yl)phenyl)-N-isobutyl-2-methylpropanamide | 10.10 |
| A35 | 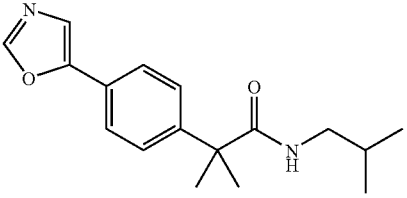<br>N-isobutyl-2-methyl-2-(4-(oxazol-5-yl)phenyl)propanamide | 11.49 |
| A36 | 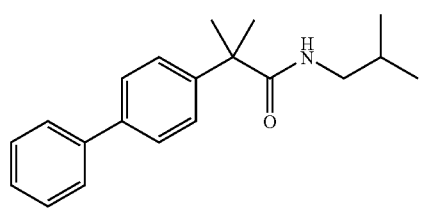<br>2-(biphenyl-4-yl)-N-isobutyl-2-methylpropanamide | 1.28 |
| A37 | 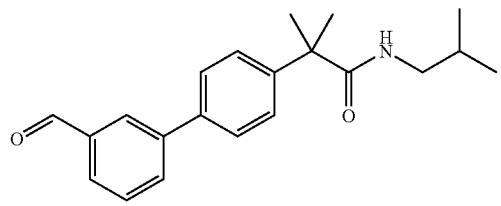<br>2-(3'-formylbiphenyl-4-yl)-N-isobutyl-2-methylpropanamide | 0.76 |

TABLE A-continued

| COMPOUND NO. | COMPOUND | SWEET EC$_{50}$ μM |
|---|---|---|
| A38 | N-isobutyl-2-methyl-2-(3'-(methylsulfonyl)biphenyl-4-yl)propanamide | 1.49 |
| A39 | 2-(biphenyl-4-yl)-N-isobutylacetamide | 1.54 |
| A40 | 2-(4-(6-cyanopyrazin-2-yl)phenyl)-2-methyl-N-(pentan-3-yl)propanamide | 0.03 |
| A41 | 2-(4-(6-cyanopyrazin-2-yl)phenyl)-2-methyl-N-(2-methylbutyl)propanamide | 0.05 |
| A42 | 2-(4-(6-cyanopyrazin-2-yl)phenyl)-N-(1-(furan-2-yl)ethyl)-2-methylpropanamide | 0.10 |

TABLE A-continued

| COMPOUND NO. | COMPOUND | SWEET EC$_{50}$ μM |
|---|---|---|
| A43 | 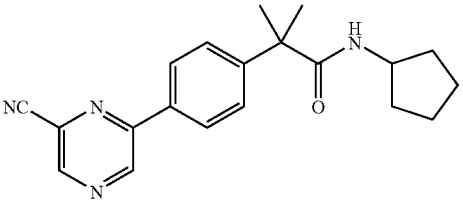<br>2-(4-(6-cyanopyrazin-2-yl)phenyl)-N-cyclopentyl-2-methylpropanamide | 0.13 |
| A44 | 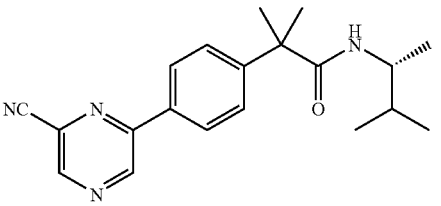<br>(R)-2-(4-(6-cyanopyrazin-2-yl)phenyl)-2-methyl-N-(3-methylbutan-2-yl)propanamide | 0.21 |
| A45 | 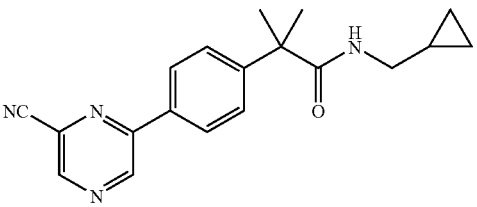<br>(2-(4-(6-cyanopyrazin-2-yl)phenyl)-N-(cyclopropylmethyl)-2-methylpropanamide | 0.27 |
| A46 | 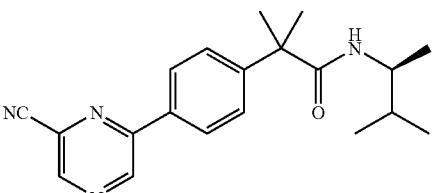<br>(S)-2-(4-(6-cyanopyrazin-2-yl)phenyl)-2-methyl-N-(3-methylbutan-2-yl)propanamide | 0.31 |
| A47 | 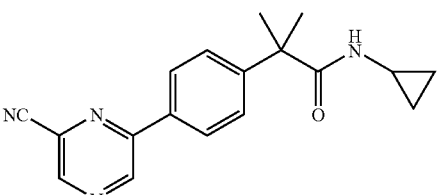<br>2-(4-(6-cyanopyrazin-2-yl)phenyl)-N-cyclopropyl-2-methylpropanamide | 0.32 |

TABLE A-continued
| COMPOUND NO. | COMPOUND | SWEET EC$_{50}$ μM |
|---|---|---|
| A48 | 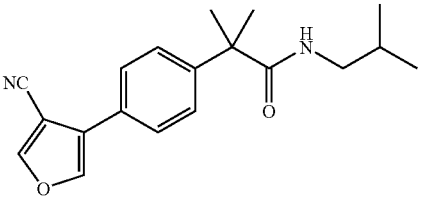<br>2-(4-(4-cyanofuran-3-yl)phenyl)-N-isobutyl-2-methylpropanamide | 0.32 |
| A49 | 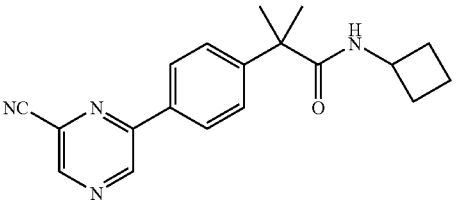<br>2-(4-(6-cyanopyrazin-2-yl)phenyl)-N-cyclobutyl-2-methylpropanamide | 0.37 |
| A50 | 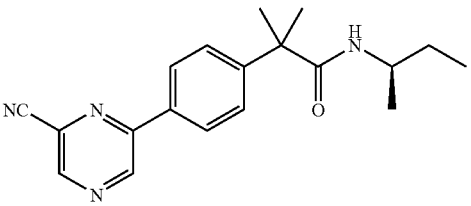<br>(R)-N-sec-butyl-2-(4-(6-cyanopyrazin-2-yl)phenyl)-2-methylpropanamide | 0.37 |
| A51 | 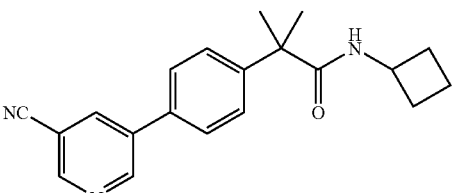<br>2-(4-(5-cyanopyridin-3-yl)phenyl)-N-cyclobutyl-2-methylpropanamide | 0.41 |
| A52 | 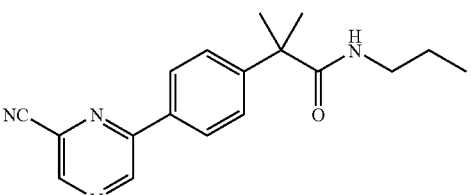<br>2-(4-(6-cyanopyrazin-2-yl)phenyl)-2-methyl-N-propylpropanamide | 0.47 |

TABLE A-continued

| COMPOUND NO. | COMPOUND | SWEET EC$_{50}$ μM |
|---|---|---|
| A53 | 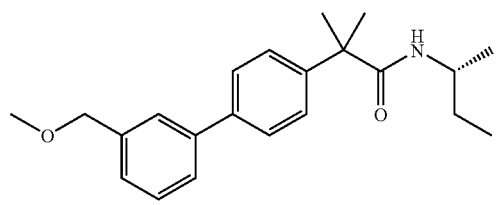<br>(R)-N-sec-butyl-2-(3'-(methoxymethyl)biphenyl-4-yl)-2-methylpropanamide | 0.55 |
| A54 | 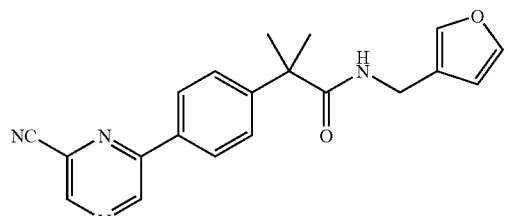<br>2-(4-(6-cyanopyrazin-2-yl)phenyl)-N-(furan-3-ylmethyl)-2-methylpropanamide | 0.59 |
| A55 | 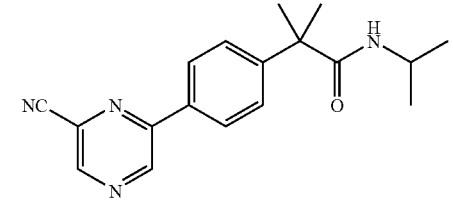<br>2-(4-(6-cyanopyrazin-2-yl)phenyl)-N-(furan-3-ylmethyl)-2-methylpropanamide | 0.65 |
| A56 | 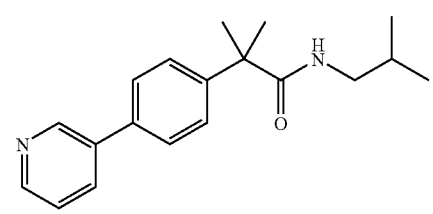<br>N-isobutyl-2-methyl-2-(4-(pyridin-3-yl)phenyl)propanamide | 0.77 |
| A57 | 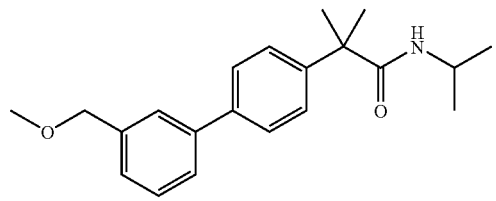<br>N-isopropyl-2-(3'-(methoxymethyl)biphenyl-4-yl)-2-methylpropanamide | 0.92 |

TABLE A-continued

| COMPOUND NO. | COMPOUND | SWEET EC$_{50}$ µM |
|---|---|---|
| A58 | 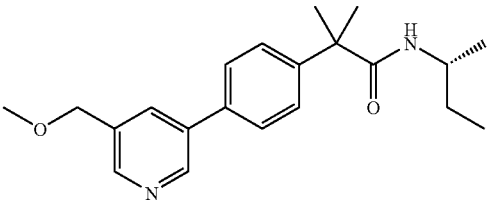<br>(R)-N-sec-butyl-2-(4-(5-(methoxymethyl)pyridin-3-yl)phenyl-2-methylpropanamide | 1.05 |
| A59 | 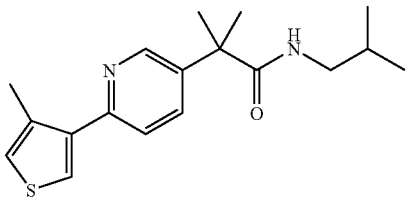<br>N-isobutyl-2-methyl-2-(6-(4-methylthiophen-3-yl)pyridin-3-yl)propanamide | 1.05 |
| A60 | 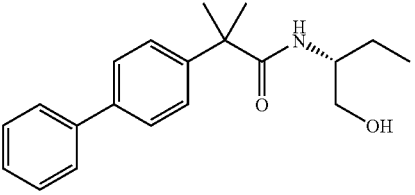<br>(R)-2-(biphenyl-4-yl)-N-(1-hydroxybutan-2-yl)-2-methylpropanamide | 1.10 |
| A61 | 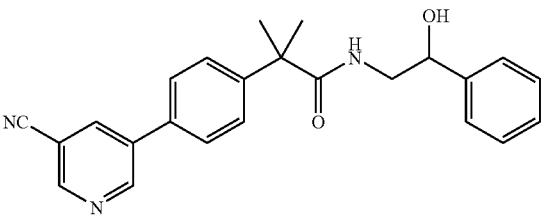<br>2-(4-(5-cyanopyridin-3-yl)phenyl)-N-(2-hydroxy-2-phenylethyl)-2-methylpropanamide | 1.17 |
| A62 | 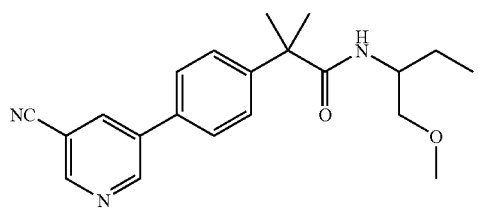<br>2-(4-(5-cyanopyridin-3-yl)phenyl)-N-(1-methoxybutan-2-yl)-2-methylpropanamide | 1.22 |

TABLE A-continued

| COMPOUND NO. | COMPOUND | SWEET EC$_{50}$ μM |
|---|---|---|
| A63 | 2-(4-(5-cyanofuran-2-yl)phenyl)-N-isobutyl-2-methylpropanamide | 1.29 |
| A64 | (S)-N-sec-butyl-2-(4-(5-(methoxymethyl)pyridin-3-yl)phenyl)-2-methylpropanamide | 1.29 |
| A65 | 2-(4-(6-cyanopyrazin-2-yl)phenyl)-N-(2-(furan-2-yl)-2-hydroxyethyl)-2-methylpropanamide | 1.31 |
| A66 | 4-(4-(1-(isobutylamino)-2-methyl-1-oxopropan-2-yl)phenyl)furan-2-carboxylic acid | 1.37 |
| A67 | 2-(2-hydroxybiphenyl-4-yl)-N-isobutyl-2-methylpropanamide | 1.42 |
| A68 | 2-(4-(5-ethoxypyridin-3-yl)phenyl)-N-isobutyl-2-methylpropanamide | 1.59 |

TABLE A-continued

| COMPOUND NO. | COMPOUND | SWEET EC$_{50}$ μM |
|---|---|---|
| A69 | 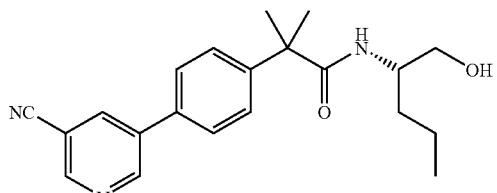<br>(S)-2-(4-(5-cyanopyridin-3-yl)phenyl)-N-(1-hydroxypentan-2-yl)-2-methylpropanamide | 1.66 |
| A70 | 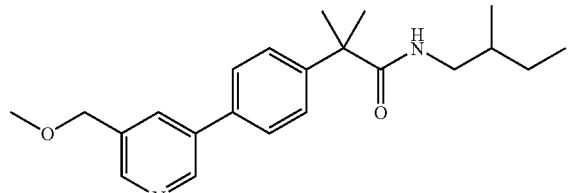<br>2-(4-(5-(methoxymethyl)pyridin-3-yl)phenyl)-2-methyl-N-(2-methylbutyl)propanamide | 0.51 |
| A71 | 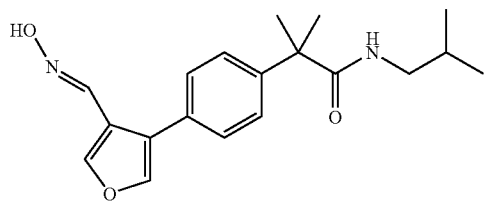<br>(E)-2-(4-(4-((hydroxyimino)methyl)furan-3-yl)phenyl)-N-isobutyl-2-methylpropanamide | 0.75 |
| A72 | 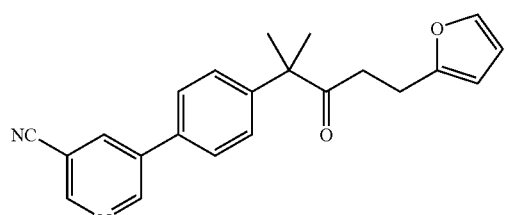<br>2-(4-(5-cyanopyridin-3-yl)phenyl)-N-(furan-2-ylmethyl)-2-methylpropanamide | 0.18 |
| A73 | 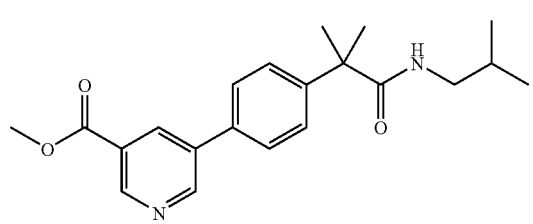<br>methyl 5-(4-(1-(isobutylamino)-2-methyl-1-oxopropan-2-yl)phenyl)nicotinate | 0.54 |

TABLE A-continued

| COMPOUND NO. | COMPOUND | SWEET EC$_{50}$ μM |
|---|---|---|
| A75 | (S)-2-(4-(5-cyanopyridin-3-yl)phenyl)-N-(1-hydroxybutan-2-yl)-2-methylpropanamide | 0.68 |
| A76 | N-isobutyl-2-(2-methoxybiphenyl-4-yl)-2-methylpropanamide | 0.96 |
| A77 | (S)-2-(4-(furan-3-yl)phenyl)-N-(1-hydroxybutan-2-yl)-2-methylpropanamide | 1.25 |
| A78 | 2-(3'-(methoxymethyl)biphenyl-4-yl)-2-methyl-N-propylpropanamide | 0.67 |
| A79 | 2-(4-(1,5-dihydrobenzo[e][1,3]dioxepin-6-yl)phenyl)-N-isobutyl-2-methylpropanamide | 0.67 |
| A80 | 2-(3'-cyano-2'-(hydroxymethyl)biphenyl-4-yl)-N-isobutyl-2-methylpropanamide | 0.67 |

TABLE A-continued

| COMPOUND NO. | COMPOUND | SWEET EC$_{50}$ μM |
|---|---|---|
| A81 | 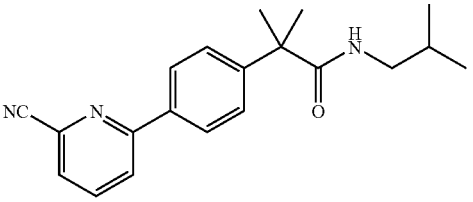<br>2-(4-(6-cyanopyridin-2-yl)phenyl)-N-isobutyl-2-methylpropanamide | 0.67 |
| A82 | 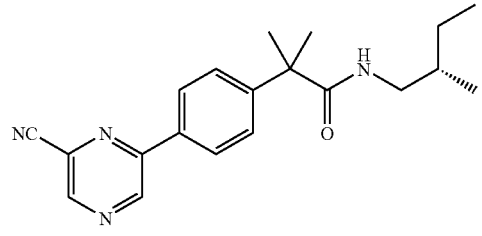<br>2-(4-(6-cyanopyridin-2-yl)phenyl)-N-isobutyl-2-methylpropanamide | 0.03 |
| A83 | 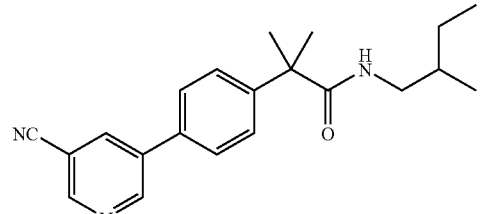<br>2-(4-(6-cyanopyridin-2-yl)phenyl)-N-isobutyl-2-methylpropanamide | 0.11 |
| A84 | 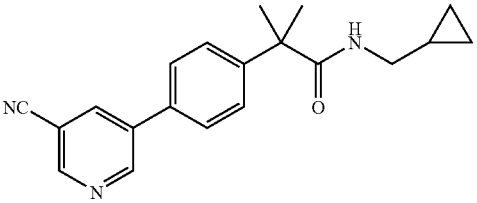<br>2-(4-(5-cyanopyridin-3-yl)phenyl)-N-(cyclopropylmethyl)-2-methylpropanamide | 0.11 |
| A85 | 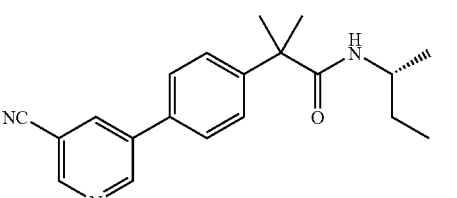<br>2-(4-(5-cyanopyridin-3-yl)phenyl)-N-(cyclopropylmethyl)-2-methylpropanamide | 0.15 |

TABLE A-continued

| COMPOUND NO. | COMPOUND | SWEET EC$_{50}$ μM |
|---|---|---|
| A86 | 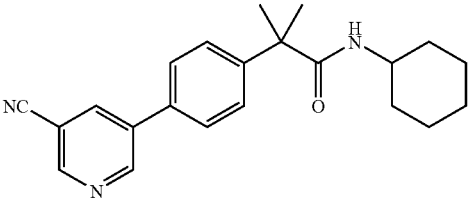<br>2-(4-(5-cyanopyridin-3-yl)phenyl)-N-cyclohexyl-2-methylpropanamide | 0.18 |
| A87 | 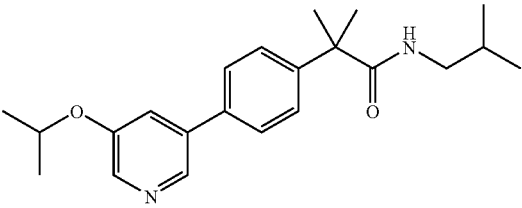<br>N-isobutyl-2-(4-(5-isopropoxypyridin-3-yl)phenyl)-2-methylpropanamide | 0.21 |
| A88 | 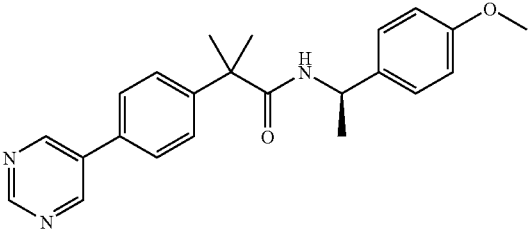<br>(R)-N-(1-(4-methoxyphenyl)ethyl)-2-methyl-2-(4-(pyrimidin-5-yl)phenyl)propanamide | 0.37 |
| A89 | 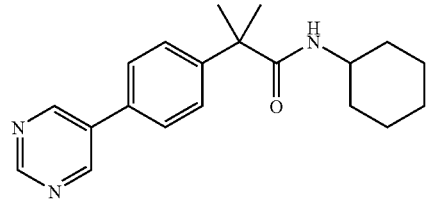<br>N-cyclohexyl-2-methyl-2-(4-(pyrimidin-5-yl)phenyl)propanamide | 0.41 |
| A90 | 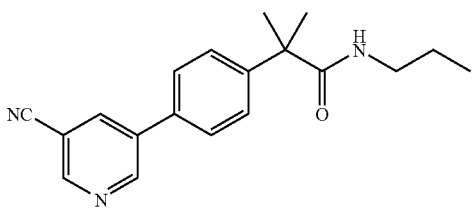<br>2-(4-(5-cyanopyridin-3-yl)phenyl)-2-methyl-N-propylpropanamide | 0.48 |

TABLE A-continued

| COMPOUND NO. | COMPOUND | SWEET EC$_{50}$ μM |
|---|---|---|
| A91 | 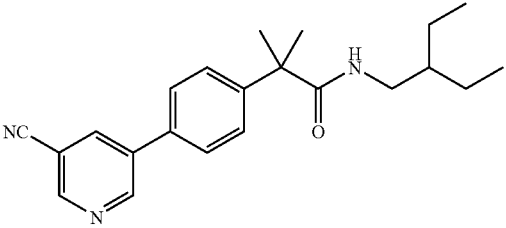<br>2-(4-(5-cyanopyridin-3-yl)phenyl)-N-(2-ethylbutyl)-2-methylpropanamide | 0.62 |
| A92 | 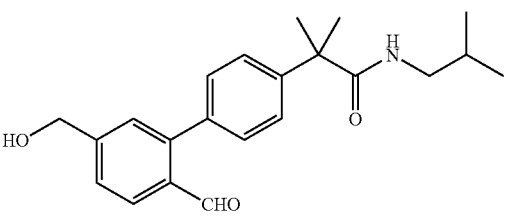<br>2-(2'-formyl-5'-(hydroxymethyl)biphenyl-4-yl)-N-isobutyl-2-methylpropanamide | 0.63 |
| A93 | 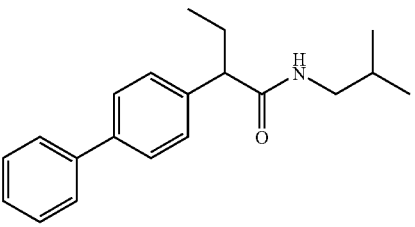<br>2-(biphenyl-4-yl)-N-isobutylbutanamide | 0.90 |

Example 53

Sweet Flavor and Sweet Flavor Enhancement Measurement Using Human Panelists: Difference from Reference Human Taste Test Procedures Purpose: To determine how the intensity of a test sample of an experimental compound differs from that of a reference sample in terms of sweetness. This type of study requires a larger number of evaluations in order to obtain statistically significant data, so the test may be repeated with the same or additional panelists.

Overview: A group of 10 or more panelists taste pairs of solutions where one sample is the "Reference" (which typically does not include an experimental compound and is an approved substance or Generally Recognized As Safe (GRAS) substance, i.e., a sweetener) and one sample is the "Test" (which may or may not include an experimental compound). Subjects rate the difference in intensity of the test sample compared to the reference sample for the key attribute on a scale of −5 (much less sweet than the reference) to +5 (much sweeter than the reference). A score of 0 indicates the test sample is equally as sweet as the reference.

Procedure: Ten or more Subjects are used for the Difference from Reference tests. Subjects have been previously familiarized with the key attribute taste and are trained to use the −5 to +5 scale. Subjects refrain from eating or drinking (except water) for at least 1 hour prior to the test. Subjects eat a cracker and rinse with water four times to clean the mouth.

Test solutions can include the experimental compound in water, the experimental compound plus a key tastant (e.g., 4% sucrose, 6% sucrose, 6% fructose, 6% fructose/glucose, or 7% fructose/glucose, at pH 7.1 or 2.8), and a range of key tastant only solutions as references.

Samples of the key tastant without the experimental compound are used to determine if the panel is rating accurately; i.e., the reference is tested against itself (blind) to determine how accurate the panel is rating on a given test day. The solutions are dispensed in 10 ml volumes into 1 oz. sample cups and served to the Subjects at room temperature.

Subjects first taste the reference sample then immediately taste the test sample and rate the difference in intensity of the key attribute on the Difference from Reference scale (−5 to +5). All samples are expectorated. Subjects may retaste the samples but can only use the volume of sample given. Subjects must rinse at least twice with water between pairs of samples. Eating a cracker between sample pairs may be required depending on the samples tasted.

The scores for each test are averaged across Subjects and standard error is calculated. Panel accuracy can be determined using the score from the blind reference test. ANOVA and multiple comparison tests (such as Tukey's Honestly Significant Difference test) can be used to determine differences among pairs, provided the reference sample is the same among all tests. If the identical test pair is tested in another session, a Student's t-test (paired, two-tailed; alpha=0.05) can be used to determine if there is any difference in the ratings between sessions.

A number of different reference sweeteners have been utilized for the measurement of sweet taste enhancement. A 6% fructose/glucose mixture was demonstrated to be approximately equal in sweet taste perception as 6% sucrose, which is within the range where panelists are sensitive to small changes in sweet taste perception. After initial studies in 6% fructose/glucose at pH 7.1, studies shift to evaluating the performance of the compound in a product prototype more similar to a cola beverage, i.e., higher concentrations of sweetener and lower pH.

The results of some human taste tests of the sweet compounds of the invention in aqueous compositions intended to model the composition of a carbonated beverage are shown below in Table B.

TABLE B

Sweet Taste Test Results

| Compound No. | Contents of Solution | pH | Perceived Equivalent Sweet Solution |
|---|---|---|---|
| 1 | 5 µM Compound 1 + 6% fructose/glucose | 7.1 | Greater than 6% but less than or equal to 8% fructose/glucose |
| 2 | 5 µM Compound 2 + 6% fructose/glucose | 7.1 | Greater than or equal to 9% fructose/glucose |

Example 53a

Sweet Flavor and Sweet Flavor Enhancement Measurement Using Human Panelists

Line Scale Sensory Testing for Human Taste Test Procedures

Purpose: To create a dose-response curve for perceived sweetness intensity of fructose-glucose concentrations. Test samples containing experimental compound are compared to this dose-response curve to determine equivalent sweetness intensity. This type of study requires a number of evaluations in order to obtain statistically significant data, so the test may be repeated with the same or additional panelists.

Overview: A group of eight or more panelists taste solutions including fructose-glucose at various concentrations, as well as the experimental compound, both with and without added fructose-glucose. Panelists rate sweetness intensity of all samples on an unstructured horizontal line scale, anchored from 0 to 10, where 0 equals no sweetness and 10 equals intense sweetness. Scores for sweetness intensity are averaged across panelists. Then using the average scores and/or equation of the line for the fructose-glucose dose-response curve, equivalent sweetness fructose-glucose concentrations are determined for the samples containing experimental compound.

Procedure: Eight or more subjects are used for the Line Scale tests. Subjects have been previously familiarized with the key attribute taste and are trained to use the 0 to 10 unstructured line scale. Subjects refrain from eating or drinking (except water) for at least 1 hour prior to the test. Subjects eat a cracker and rinse with water several times to clean the mouth.

Fructose-glucose solutions are provided at a wide range of concentrations, such as 0%, 2%, 4%, 6%, 8%, and 10% fructose-glucose, in order to create the dose-response curve. Samples containing experimental compound are prepared both alone and in a 6% fructose-glucose solution. All samples are made up in low sodium buffer pH 7.1. In order to aid dispersion, solutions can also be made up in 0.1% ethanol.

The solutions are dispensed in 20 ml volumes into 1 oz. sample cups and served to the subjects at room temperature. All samples are presented in randomized counterbalanced order to reduce response bias. Further, two sessions of testing may be used to check panel precision.

Subjects taste each sample individually and rate sweetness intensity on the line scale prior to tasting the next sample. All samples are expectorated. Subjects may retaste the samples but can only use the volume of sample given. Subjects must rinse with water between samples. Eating an unsalted cracker between sample pairs may be required depending on the samples tasted.

The scores for each sample are averaged across subjects and standard error is calculated. The dose-response curve is plotted graphically, and this may be used to ensure the panel is rating accurately; i.e. increasing the concentration of fructose-glucose should correspond to increased average scores for sweetness. A 2-way ANOVA (factors being samples and panelists) and multiple comparison tests (such as Tukey's Honestly Significant Difference test) can be used to determine differences among samples and/or panelists. A 3-way ANOVA, with sessions as the third factor, can be used to determine if there is any difference in the ratings between sessions.

The results of some human taste tests of the sweet compounds of the invention in aqueous compositions intended to model the composition of a carbonated beverage are shown below in Table C.

| Compound No. | Contents of Solution | Perceived Equivalent Sweet Solution |
|---|---|---|
| 20 | 10 µM Compound 20 + 6% fructose/glucose | Equal to 10% fructose/glucose |
| 20 | 10 µM Compound 20 | Equal to 6% fructose/glucose |
| 21 | 5 µM Compound 21 + 6% fructose/glucose | Greater than 10% but less than or equal to 12% fructose/glucose |
| 21 | 5 µM Compound 21 | Greater than 6% but less than or equal to 8% fructose/glucose |
| 22 | 5 µM Compound 22 + 6% fructose/glucose | Greater than 8% but less than or equal to 9% fructose/glucose |
| 23 | 5 µM Compound 23 + 6% fructose/glucose | Equal to 10% fructose/glucose |
| 23 | 2 µM Compound 23 | Greater than 2% but less than or equal to 4% fructose/glucose |
| 25 | 10 µM Compound 25 + 6% fructose/glucose | Equal to 10% fructose/glucose |
| 26 | 10 µM Compound 26 + 6% fructose/glucose | Greater than 8% but less than 10% fructose/glucose |
| 27 | 5 µM Compound 27 + 6% fructose/glucose | Equal to 8% fructose/glucose |
| 30 | 5 µM Compound 30 + 6% fructose/glucose | Equal to 10% fructose/glucose |
| 30 | 5 µM Compound 30 | Greater than 4% but less than 6% fructose/glucose |
| 32 | 10 µM Compound 32 + 6% fructose/glucose | Equal to 8% fructose/glucose |
| 39 | 15 µM Compound 39 + 6% fructose/glucose | Equal to 8% fructose/glucose |

-continued

| Compound No. | Contents of Solution | Perceived Equivalent Sweet Solution |
|---|---|---|
| 43 | 10 µM Compound 43 + 6% fructose/glucose | Equal to 8% fructose/glucose |
| 34 | 5 µM Compound 34 + 6% fructose/glucose | Equal to 8% fructose/glucose |

Example 54

Reduced Sugar Ice Cream

To illustrate the use of the disclosed amide compounds to reduce the sugar content of ice cream, comparable fully sugared and ⅔ sugared ice cream formulations containing the an amide compound of the invention (the compound of Example 23) were prepared with the composition shown in the following table, and taste tested by humans.

TABLE D

| Ingredients | Fully Sugared Ice Cream (% wt/wt) | ⅔ Sugared Ice Cream plus amide compound (% wt/wt) |
|---|---|---|
| Cream, Heavy, 36% butterfat | 39.37 | 39.37 |
| Milk, Whole, 3.25% butterfat | 38.62 | 44.58 |
| Sugar, granulated | 18.11 | 12.07 |
| Egg yolks, pasteurized | 3.00 | 3.00 |
| Natural Vanilla Flavor | 0.60 | 0.60 |
| Stabilizer* | 0.30 | 0.38 |
| Amide Compound, Example 23** | 0.00 | 6.6 ppm |

*IC Premium Stabilizer, commercially available from Danisco Inc., New Century, Kansas, USA, comprises Dextrose, Locust Bean Gum, Guar Gum and Carageenan.
**Added via liquid sweetener concentrate solution in ethanol, see below.

Preparation of Fully Sugared Ice Cream:

The fully sugared ice cream formualtion was formulated to weigh a total of 3000.00 g. Ingredients were weighed on a calibrated balance and all dairy ingredients were keep cold (40° F. (4° C.) or below) until processing.

The commercially available stabilizer composition was mixed into half of the granulated sugar using the whip attachment on a KITCHEN AIDE™ Mixer, at speed 2. This mixture was set aside.

The heavy cream and whole milk were placed into a 5000 mL stainless steel cylinder and mixed using a LIGHTNIN™ Mixer at from 500 to 650 rpms using a 2.5 inch (6.36 cm) impeller with three straight blades. A vortex was created by positioning the impeller blades at a 30 to 45° angle. The sugar/stabilizer mixture was slowly added to the vortex of the mixing milk/cream solution, and mixed for 10 minutes until the sugar dissolved and the stabilizer rehydrated. Care was taken to ensured that no lumps or undissolved stabilizer existed in the solution. The remaining sugar was added to the vortex and mixing continued for an additional 10 minutes. Egg yolks and vanilla flavor were added next to the mixture and mixing was continued for 5 more minutes.

The brix of the resulting ice cream base was determined to be from 32.0 to 34.0°. The density of the resulting ice cream base was determined to be from 110.0 to 111.0 g/100 mL.

The ice cream base liquid was placed in an electric steam jacketed kettle and pasteurized to a temperature of 180 to 185° F. (82 to 85° C.) and held for 1 minute. The product was poured into a sanitized container and placed into an ice bath where the temperature was brought down to 50 to 60° F. (10 to 16° C.) and placed in the refrigerator to bring the temperature down to 40° F. (4° C.).

The cold ice cream base (40° F. (4° C.) or below), which can be homogenized if desired, was added to a batch ice cream freezer and was frozen to an overrun (volume increase) of 34 to 38%. The final product was placed into quart ice cream containers and placed into the freezer to set to −5° F. (−21° C.).

Preparation of ⅔ Sugared Ice Cream Comprising Amide Compound 23:

The ice cream batch was 3000.00 g total formula weight. Ingredients were weighed on a calibrated balance and all dairy ingredients were kept cold (40° F. (4° C.) or below) until processing.

A water soluble liquid sweetener concentrate composition comprising 0.1% by weight of Example 23 in USP grade propylene glycol can be prepared by mixing the amide compound and propylene glycol by stirring the composition while warming to about 50° C., then milling the resulting liquid in a Silverson mill with a square basket cage at 300-600 rpms, to further ensure homogeneity of the liquid. An alternative method actually used was that the amide compound was dissolved in ethanol (1:1000 dilution), sonicated for 20 minutes, and 19.80 grams of the diluted sweet enhancer sample was added to the vanilla flavoring (which contains 20-30% ethyl alcohol) and sonicate that sample for an additional 20 minutes.

The stabilizer was mixed into half of the granulated sugar using the whip attachment on the KITCHEN AIDE™ Mixer at speed 2 and set aside.

Heavy cream and whole milk were placed into a 5000 mL stainless steel cylinder and mixed using a LIGHTNIN™ Mixer at 500 to 650 rpms using a 2.5 inch (6.35 cm) impeller with three straight blades. A vortex was created by positioning the impeller blades at a 30 to 45° angle. The sweet enhancer was added using the vanilla/ethanol mixture. Some milk/cream was added back to the weigh dish of the sweet enhancer to ensure all the amide compound was removed from the weigh dish. The sugar/stabilizer mixture was slowly added to the vortex of the mixing milk/cream solution. The resulting solution was mixed for 10 minutes until the sugar dissolved and the stabilizer rehydrated. Care was taken to ensured that no lumps or undissolved stabilizer existed in the solution. The remaining sugar was added to the vortex and mixing was continued for an additional 10 minutes. Egg yolks and vanilla flavor were next added and the mixing continued for 5 more minutes.

The brix of the resulting ice cream base was determined to be from 28.5 to 30.5°. The density of the resulting ice cream base was determined to be from 110.0 to 111.0 g/100 mL.

The ice cream base was placed in an electric steam jacketed kettle and pasteurized to a temperature of 180 to 185° F. (82 to 85° C.) and held for 1 minute. The product was poured into a sanitized container and placed into an ice bath, where the temperature was brought down to between 50 to 60° F. (10 to 16° C.) and placed in the refrigerator to bring the temperature down to 40° F. (4° C.). The cold ice cream base (40° F. (4° C.) or below), was added to a batch ice cream freezer and was frozen to an overrun of 34 to 38%. The final product was placed into quart ice cream containers and placed into the freezer to set to −5° F. (−21° C.).

Sensory Evaluation:

Ice cream samples were evaluated by tasters, using a rank rating design. Tasters used an anchored scale from 1 to 10 (1 being no sweetness, 10 being intense sweetness). Three digit coded samples were randomized and the following samples were given to tasters: full sugar version, ⅔ sugared version, ⅔ sugared+3.3 ppm or 6.6 ppm of compound 23. Tasters were instructed to hold the ice cream samples in their mouth for at least 5 seconds, expectorate the sample, and evaluate/rank the "peak" of sweetness intensity. See Table E:

TABLE E

Sensory Evaluation Results

| Product | Average Sweet Intensity Score |
|---|---|
| Fully Sugared Control | 7.857 |
| ⅔ Sugared Control | 3.643 |
| ⅔ Sugared + 3.3 ppm Compound 23 | 5.143 |
| ⅔ Sugared + 6.6 ppm Compound 23 | 7.357 |

Both levels of compound 23 (3.3 ppm and 6.6 ppm) scored higher in sweetness than the ⅔ sugared control sample. The ⅔ sugared+6.6 ppm compound 23 ice cream sample was nearly as sweet as the fully sugared ice cream. Qualitative feedback included comments about a "slight lingering" and "slight delay of sweetness" in the samples that contained compound 23.

Example 55

Reduced Sugar Frosted Breakfast Cereal

To illustrate the use of the amide compounds of the invention in reducing the sugar content of frosted breakfast cereals, fully sugared and ⅔ sugared cereal frosting containing compound 23 were prepared according to the formulations in the following table.

TABLE F

| Ingredients | Cereal Frosting Fully Sugared (% wt/wt) | Cereal Frosting ⅔ Sugared + Compound 23 (% wt/wt) |
|---|---|---|
| Sugar, granulated | 64.00 | 59.01 |
| HFCS 42, 71% solids* | 14.08 | 12.98 |
| Sugar, 20X powdered | 5.00 | 4.61 |
| Water | 15.61 | 21.59 |
| Tapioca Dextrin | 0.75 | 1.04 |
| Gum Arabic, pre-hydrated | 0.56 | 0.77 |
| Sweetener concencentrate compostion | 0.00 | As indicated below |

*HFCS: High Fructose Corn Syrup

The reduced sugar cereal had a less "white/sugary" appearance and more of a desirable natural cereal appearance.

Fully Sugared Cereal Processing 500.00 g of a fully sugared cereal frosting was formulated for coating frosted corn flake prototypes. Specifically, a KITCHEN AIDE™ Mixer with a wire whip attachment at speed 3 was used to mix the granulated sugar, powdered sugar, gum Arabic, and dextrin. Water and HFCS corn syrup were placed into a 1000 mL stainless steel cylinder and were mixed using a LIGHTNIN™ Mixer at 500 to 650 rpms using a 2.5 inch (6.35 cm) impeller with three straight blades until the HFCS was dissolved (5 minutes). A vortex was created by positioning the impeller blades at a 30 to 45° angle. The sugar/gum/dextrin dry mixture was added to the vortex very slowly and allowed to mix until the sugar dissolved and the gum rehydrated. Mixing was continued for 10 minutes after the last of the dry blend was added to form the frosting.

The resulting frosting was heated in a two quart stainless steel heating vessel to between 210 to 230° F. (99 to 110° C.), until the sugar was liquefied. The following proportions were used to coat the cereal.

|  | Fully Sugared Frosting | ⅔ Sugared Frosting |
|---|---|---|
| Fortified Corn Flakes | 644.30 g | 714.70 g |
| Frosting | 355.70 g | 285.30 g |

The warm frosting was drizzled onto the corn flakes while mixing with a spatula. An alternative method can be to drizzle small amounts of frosting in front of a curtain of compressed air (at least 30 to 40 psi) while mixing with a spatula.

The coated cereals were transferred to a stainless steel drum (20 quart (19 L)) and placed onto the rollers of a vacuum tumbler that was angled at 45°. The cereal was tumbled at low speed (10 to 20 rpm) as a heat gun with hot air at 170 to 220° F. (77 to 104° C.) was blown onto the flakes to evenly coat the flakes and to drive off some moisture.

The cereal was tumbled and hot air was applied to the tumbling cereal for 10 minutes. The temperature of the surface of the flakes was maintained at 200 to 220° F. (93-104° C.) as measured by a calibrated infrared thermometer.

The frosted corn flakes were transferred to a half sheet bake pan and baked in a 200° F. (93° C.) convection oven for 50 minutes to a moisture level below 4%. The baked frosted corn flakes were allowed to cool to 70° F. (21° C.) at ambient temperatures and was packaged and stored in double ZIPLOC™ plastic bags.

Processing Cereal with ⅔ Sugared Cereal Frosting Comprising Compound 23

A 100 gram sample of a solid sweetener concentrate composition was prepared from 1.000 g of compound 23 and 99.000 g of 10 D.E. maltodextrin. "DE" i.e. "Dextrin Equivalents" is a measure of the degree of depolymerization of the corn starches used to manufacture maltodextrins. Fifty grams of the maltodextrin was placed on the bottom of a clean and dried mortar and the 1.000 gr of compound 23 was added to the maltodextrin and slowly ground and mixed into the maltodextrin. The remaining 50 grams of maltodextrin was added to a planetary mixer with a wire whip attachment (KITCHEN AIDE™ Mixer), then the contents of the mortar were placed into the mixer and the mixer was turned on to a slow speed (setting 3), and allowed to mix for 10 minutes. A rubber spatula was used to scrap the walls and bottom of the bowl, then the mixture was blended on low for another 15 minutes. The 100× diluted solid sweetener concentrate composition was stored in an air tight amber glass container. The contents were mixed in the glass container before taking out aliquots of the dry diluted sweet enhancer.

Using the KITCHEN AIDE™ Mixer with the wire whip attachment, the granulated sugar, powdered sugar, gum arabic, dextrin, and the 1:100 diluted sweetener concentrate composition were mixed at speed 3. Water and the HFCS were placed into a 1000 mL stainless steel cylinder and mixed using a LIGHTNIN™ Mixer at 500 to 650 rpms using a 2.5 inch (6.35 cm) impeller with three straight blades until the HFCS was dissolved (5 minutes). A vortex was created by positioning the impeller blades at a 30 to 45° angle. The dry/sugar/gum dry blend was added to the vortex very slowly and allowed to mix until the sugar dissolved and the gum rehydrated. An additional 10 minute mixing time was allowed after the last of the dry blend was added, to form the frosting.

The resulting liquid frosting was added to a two quart (2 L) stainless steel heating vessel, and heated to 210 to 230° F. (99 to 110° C.) until liquefied. To coat the cereal, the following proportions were used.

| | Full Sugar | ⅔ Sugared + Compound 23 |
|---|---|---|
| Fortified Corn Flakes | 644.30 g | 714.0372 g |
| Frosting | 355.70 g | 285.30 g |
| Sweetener Concentrate | 0 | 0.6628 grams |

The warm frosting was drizzled onto the corn flakes while mixing with a spatula, and then transferred to a stainless steel drum (20 quart (19 L)), which was placed onto the rollers of the vacuum tumbler angled at 45°. The cereal was tumbled at low speed (10 to 20 rpm) as a heat gun with hot air at 170 to 220° F. (77 to 104° C.) was blown onto the flakes to evenly coat the flakes and to drive off some moisture. The cereal was tumbled and hot air was applied to the tumbling cereal for 10 minutes. The temperature of the surface of the flakes was maintained at 200 to 220° F. (93 to 104° C.).

The frosted corn flakes were transferred to a half sheet bake pan and baked in a 200° F. (93° C.) convection oven for 50 minutes to a moisture level of 4% or less. The baked frosted corn flakes were allowed to cool to 70° F. (21° C.) at ambient temperatures and was packaged and stored into double ZIPLOC™ plastic bags.

Sensory Evaluation:

Frosted corn flake cereal samples were evaluated using a rank rating design by tasters. Tasters use an anchored scale from 1 to 10 (1 being no sweetness, 10 being intense sweetness). Three digit coded samples were randomized and the following samples were given to tasters: fully sugared corn flakes, ⅔ sugared corn flakes, and corn flakes comprising ⅔ sugared frosting comprising 3.3 ppm or 6.6 ppm of compound 23. Tasters were instructed to hold the cereal samples in their mouth for at least 5 seconds, expectorate the sample, and evaluate/rank the "peak" of sweetness intensity. See Table E.

TABLE E

Sensory Evaluation Results

| Product | Avgage Sweet Intensity Score |
|---|---|
| ⅔ sugared flakes | 5 |
| Fully sugared flakes | 8 |
| ⅔ sugared + 6.6 ppm compound 23 | 7.5 |
| ⅔ sugared + 9.6 ppm compound 23 | 7.81 |

All the frosted corn flake samples comprising the amide compounds described herein scored higher sweetness intensity scores than the ⅔ sugared cornflake control. The cornflakes comprising frostin with 9.6 ppm of compound 23 had almost as much sweetness as the fully sugar frosted cornflake control.

Example 56

Reduced Sugar Dry Beverage Mixes

To exemplify the use of the disclosed amide compounds to reduce sugar content in dry beverage mixes or "bases," fully sugared and ⅔ sugared beverage bases simulating a powdered strawberry beverage mix containing compound 23, and appropriate control mixes were prepared according to the formulations in the following table.

TABLE F

| Ingredients | Beverage Base Fully Sugared (% wt/wt) | Beverage Base ⅔ Sugared + Compound 23 (% wt/wt) |
|---|---|---|
| Sugar, granulated | 7.17 | 4.90 |
| Citric Acid, granulated | 0.20 | 0.21 |
| Ascorbic Acid, granulated | 0.03 | 0.03 |
| Water | 92.39 | 94.65 |
| Red Dye #40, dry | 0.0025 | 0.0025 |
| Artificial Strawberry Flavor*** | 0.13 | 0.13 |
| Calcium Silicate** | 0.03 | 0.03 |
| Malic Acid, granulated* | 0.05 | 0.05 |
| Compound 23**** | 0.00 | 1.3 ppm |

*Flavoring acid. Others (such as tartaric, phosphoric, etc., and combinations) can used if other fruit or non-fruit flavors are used.
**Anti-caking agent. Others can be used (silicon dioxide, Tricalcium phosphate, etc.)
***Other fruit flavors (Natural or N&A) can used at levels of 0.15-1.00%.
****Added via a solid sweetener concentrate composition in maltodextrin, see below.

Fully Sugared Beverage Base Processing 1000.00 g of the finished beverage was formulated in the following manner. Granulated ingredients (sugar, acids) were mixed slowly in a KITCHEN AIDE™ mixer at speed 2 using the wire whip attachment for 3 minutes. Calcium silicate was added to the granulated ingredients and was allowed to mix for another 5 minutes until the silicate was evenly dispersed. The dry strawberry flavor and dry color were added last and allowed to mix for another 10 minutes. A plastic spatula was used to scrape the inside of the mixing bowl to ensure even mixing, and produce the dry beverage mix.

The water was placed in a stainless steel 3 L cylinder and a LIGHTNIN™ Mixer set at 500 to 650 rpms using a 2.5 inch (6.25 cm) impeller with three straight blades. This was used to create a vortex in the water. The impeller blades were positioned at a 30 to 45° angle. The dry beverage was slowly added to the vortex of the water and was mixed for an additional 5 minutes until all the sugar and acids had dissolved. This resulted in a liquid beverage with a pH of 2.96 and brix of 7.70°.

⅔ Sugared Beverage Base Comprising Compound 23

1000.00 g of the finished beverage was formulated. Compound 23 was diluted with maltodextrin (1:100) to form a sweetener concentrate composition prior to addition to the other dry beverage base ingredients. 50 g of the maltodextrin was placed on the bottom of a clean and dried mortar and 1.0000 g of compound 23 was added and slowly ground into the maltodextrin with the pestle. The remaining maltodextrin was added to a planetary mixer with a wire whip attachment (KITCHEN AIDE™ Mixer), and the contents of the mortar were placed into the mixer and the mixer was turned on to a slow speed (setting 3) and allowed to mix for an additional 10 minutes.

A rubber spatula was used to scrap the walls and bottom of the mortar. The mixture was blended on low for another 15 minutes. The 100× diluted sweetener concentrate composition was stored in an air tight amber glass container.

The contents of the glass container were re-mixed in the glass container before taking out aliquots of the dry diluted sweet enhancer. Using the KITCHEN AIDE™ Mixer with the wire whip attachment, the granulated ingredients of the beverage base (sugar, acid) were mixed slowly at speed 2 using the wire whip attachment for 3 minutes and 0.13 grams of the 1:100 diluted solid sweetener concentrate composition was added and mixed at speed 3 for 5 minutes. Calcium silicate was added and allowed to mix for another 5 minutes until the silicate was evenly dispersed. The dry flavor and dry color were added last and allowed to mix for another 10 minutes. A plastic spatula was used to scrape the inside of the mixing bowl to ensure complete recovery of the dry beverage base composition.

The water was placed in a stainless steel 3 L cylinder and a LIGHTNIN™ Mixer was set at 500 to 650 rpms using a 2.5 inch (6.35 cm) impeller with three straight blades. This was used to create a vortex in the water. The impeller blades were positioned at a 30 to 45° angle. The dry beverage base (53.525 grams) was slowly added to the vortex of the water and was mixed for an additional 5 minutes until all the sugar and acids had dissolved. This resulted in a beverage with a pH of 2.90 and brix of 7.70°.

Sensory Evaluation

Samples of control sugared strawberry beverages containing sugar at the full level indicated above (50, 66.67, 80, 90, and 100% of full sugar), and the strawberry beverage comprising ⅔ sugar+1.3 ppm compound 23 were given to tasters in randomized order. Tasters used an anchored scale from 1 to 10 (1 being no sweetness, 10 being intense sweetness). Tasters were instructed to hold the beverage in their mouth for at least 5 seconds, expectorate the sample, and evaluate/rank the "peak" of sweetness intensity of their various samples. They were allowed to re-taste and re-position their samples on the physical line scale. Once satisfied with their rankings, they wrote down their code and corresponding rank score.

TABLE G

Sensory Evaluation Results

| % Sugar | Sweet Score from Individual Tastors | | | | | | | | Average Scores |
|---|---|---|---|---|---|---|---|---|---|
| | #1 | #2 | #3 | #4 | #5 | #6 | #7 | #8 | |
| 50% | 2 | 2 | 1 | 1 | 1 | 1 | 1.5 | 1.5 | 1.375 |
| 66.67% | 3 | 3 | 3.5 | 3 | 2 | 2 | 3.5 | 3 | 2.875 |
| 80% | 4 | 6 | 4 | 6 | 3 | 5 | 6 | 4 | 4.75 |
| 90% | 6.5 | 9 | 7 | 8 | 7 | 7 | 8 | 7.5 | 7.5 |
| 100% | 6.5 | 9 | 8 | 6 | 7 | 7 | 9 | 9 | 7.688 |
| ⅔ Sugared + 1.3 ppm Cmpd 23 | 8 | 7 | 7 | 8 | 7.5 | 7 | 8 | 8 | 7.56 |

It was concluded that 1.3 ppm of compound 23 in a ⅔ sugared formulation had similar sweet intensity ratings to the 100% sugar formulation.

Example 57

Reduced Sugar Soda Syrup Concentrate

To demonstrate the use of the disclosed amide compounds to reduce the concentration of saccharide sugars in soda syrups, the concentrates used to dispense fountain soda drinks, a fully sugared strawberry soda syrup (such as those comprising high fructose corn syrups, HFCS) and ⅔ fully sugared HFCS soda syrups also containing the amide compound of Example 23 were prepared according to the formulations in the following table, and human taste tested.

TABLE H

| Ingredients | Soda Syrup Fully Sugared with HFCS (% wt/wt) | Soda Syrup ⅔ Sugared with HFCS + Compound 23 (% wt/wt) |
|---|---|---|
| Water | 25.0595 | 49.6665 |
| HFCS 55, 77 Brix | 74.00 | 49.33 |
| Sodium Benzoate | 0.05 | 0.05 |
| Phosphoric Acid, 75% | 0.32 | 0.37 |
| Citric Acid, granulated* | 0.02 | 0.02 |
| Red Dye #40, dry** | 0.0005 | 0.0005 |
| Natural Strawberry Flavor*** | 0.50 | 0.50 |
| Potassium Sorbate | 0.05 | 0.05 |
| Compound 23**** | 0.00 | 1.3 ppm (0.013 gr sweetener concentrate) |

*Other flavoring acids (such as tartaric acid, ascorbic acid, malic acid, etc.) and combinations can be used if other fruit or non-fruit flavors are used.
**Other colors (such as yellow #5, #6, caramel color, etc.) can be used.
***Other flavors (Natural or N&A) can be used such as cola, cherry, orange, lemon, citrus or non-fruit type flavors at levels of 0.15 to 1.00%
****Added in form of sweetner concentrate composition described below.

Fully Sugared HFCS Soda Syrup Processing

The soda syrup was formulated then mixed with carbonated water at a 5:1 throw ratio (volume to volume of carbonated water: soda syrup) and then tasted.

1000.00 g of the fully sugared syrup was formulated in the following manner. Water was placed into a 2000 mL stainless steel cylinder and equiped with a LIGHTNIN™ Mixer at 500 to 650 rpms using a 2.5 inch (6.35 cm) impeller with three straight blades. A vortex was created by positioning the impeller blades at a 30 to 45° angle. Sodium benzoate and potassium sorbate was added to the water vortex and mixed for 5 minutes until both were dissolved. The HFCS was added, followed by the Red Dye #40, and strawberry flavor. The acids were added last, phosphoric followed by the citric acid, and the syrup was allowed to mix for another 10 minutes until the colors and acids were well dispersed.

The resulting soda syrup was made into a carbonated strawberry soda by using a throw ratio of 5:1 (vol/vol) of carbonated water to soda syrup. The resulting strawberry soda had a brix of 10.0° (target was 9.5 to 10.5°) and a pH of 2.95 (target pH range was 2.80 to 3.10).

⅔ Sugared Soda Syrup Comprising HFCS+Compound 23

1000.00 g of the ⅔ sugared syrup comprising compound 23 was formulated in the following manner. Compound 23 was diluted with maltodextrin (1:100) to make a sweetener concentrate composition for addition to the soda syrup formulation. An alternative method is to make a solution of amide compound in propylene glycol that can be added directly into the liquid soda syrup formulation. A 100 g batch of dry sweetener concentrate composition was produced by weighing 1.000 g of the enhancer and 99.0000 g of 10 D.E. maltodextrin. 50 g of the maltodextrin was placed on the bottom of a clean and dried mortar and the 1.0000 g of amide compound was added and slowly mixed into the maltodextrin. In a planetary mixer with a wire whip attachment (KITCHEN AIDE™ Mixer), the rest of the maltodextrin was added to the mixing bowl, and the contents of the mortar was placed into the mixer and the mixer was turned on to a slow speed (setting 3). A rubber spatula was used to remove the contents of the mortar and the contents were allowed to mix for an additional 10 minutes. A rubber spatula was used to scrap the walls and bottom of the bowl. The mixture was blended on low for another 15 minutes. The 1000× sweetener concentrate composition was stored in an air tight amber glass container.

Using the KITCHEN AIDE™ Mixer with the wire whip attachment, the granulated ingredients (sugar, acids) were mixed slowly at speed 2 using the wire whip attachment for 3 minutes.

Water was placed into a 2000 mL stainless steel cylinder of a LIGHTNIN™ Mixer having a 2.5 inch (6.35 cm) impeller with three straight blades, and stirred at 500 to 650 rpm. A vortex was created by positioning the impeller blades at a 30 to 45° angle. Sodium benzoate and potassium sorbate was added to the water vortex and was mixed for 5 minutes until both were dissolved. The dry diluted sweet concentrate composition was slowly added and mixed for 5 minutes. The HFCS was added, followed by the Red#40 and strawberry flavor. The acids were added last, phosphoric followed by the citric and the syrup was allowed to mix for another 10 minutes until the colors and acids were well dispersed. The resulting soda syrup was made into a carbonated strawberry soda by using a throw ratio of 5:1 (vol/vol) of carbonated water to soda syrup. The resulting strawberry soda had a brix of 7.10° (target was 6.3 to 7.3°) and a pH of 2.98 (target pH range was 2.80 to 3.10).

Sensory Evaluation

The test strawberry beverage compositions were given to eight tasters in randomized order. Tasters used an anchored scale from 1 to 10 (1 being no sweetness, 10 being intense sweetness). Tasters were instructed to hold the strawberry soda in their mouth for at least 5 seconds, expectorate the sample, and evaluate/rank the "peak" of sweetness intensity of their various samples. They were allowed to re-taste and re-position their samples on the physical line scale. Once satisfied with their rankings, they wrote down their code and corresponding rank score.

TABLE I

Sensory Evaluation Results

| Product | Average Sweet Intensity Score |
| --- | --- |
| ⅔ Sugared with HFCS | 4.214 |
| Fully Sugared with HFCS | 7.357 |
| ⅔ Sugared with HFCS + 1.0 ppm compound 23 | 6.429 |
| ⅔ Sugared with HFCS + 1.3 ppm compound 23 | 7.214 |

Tasters could easily discriminate between the 100% HFCS soda and the ⅔ Sugared HFCS. Soda comprising ⅔ Fully Sugared HFCS+1.3 ppm of compound 23 had similar sweetness intensity to the 100% HFCS strawberry soda.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for increasing the sweet taste of a comestible or medicinal product comprising:
    (a) providing at least one comestible or medicinal product, or at least one precursor thereof, and
    (b) combining the at least one comestible or medicinal product or at least one precursor thereof with at least a sweet flavor modulating amount of at least one bi-aromatic amide compound, or one or more comestibly acceptable salts thereof, so as to form a modified comestible or medicinal product;
    wherein the bis-aromatic amide compound has the structure:

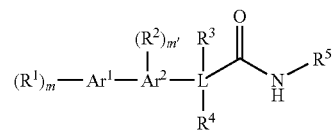

wherein
    $Ar^1$ and $Ar^2$ are independently selected from monocyclic aryl, fused bicyclic aryl, monocyclic heteroaryl, or fused bicyclic heteroaryl rings;
    (ii) m is selected from the integers 0, 1, 2, 3, 4, or 5;
    (iii) m' is selected from the integers 0, 1, 2, 3, or 4;
    (iv) each $R^1$ and $R^2$ is independently selected from the group consisting of an OH, $NH_2$, $NO_2$, SH, $SO_3H$, $PO_3H$, halogen, and a $C_1$-$C_6$ organic radical;
    (v) L is a carbon atom;
    (vi) $R^3$ is hydrogen, oxygen, hydroxy, halogen, or a $C_1$-$C_6$ organic radical;
    (vii) $R^4$ is hydrogen, oxygen, hydroxy, halogen, or a $C_1$-$C_6$ organic radical;
    (viii) $R^5$ is a $C_1$-$C_{14}$ organic radical comprising a normal or branched alkyl or cycloalkyl, wherein the normal or branched alkyl or cycloalkyl optionally comprises one to four substituents independently selected from OH, $NH_2$, $NO_2$, SH, $SO_3H$, $PO_3H$, halogen, and a $C_1$-$C_6$ organic radical;
    or a comestibly acceptable salt thereof.

2. The method of claim 1, wherein m and m' are independently selected from the integers 0, 1, or 2.

3. The method of claim 1, wherein m and m' are independently 0 or 1.

4. The method of claim 1, wherein the organic radicals are $C_1$-$C_4$ organic radicals.

5. The method of claim 1, wherein the $C_1$-$C_6$ organic radicals are independently selected from the group consisting of alkyl, alkoxy, alkoxy-alkyl, hydroxyalkyl, $NHR^6$, $NR^6R^{6'}$, CN, $CO_2H$, $CO_2R^6$, C(O)H, C(O)$R^6$, C(O)$NHR^6$, C(O)$NR^6R^{6'}$, OC(O)$R^6$, NHC(O)$R^6$, $SR^6$, S(O)$R^6$, S(O)$_2R^6$, S(O)$NHR^6$, alkenyl, cycloalkyl, cycloalkenyl, heterocycle, aryl, and heteroaryl, wherein $R^6$ is $C_1$-$C_4$ alkyl.

6. The method of claim 1, wherein $Ar^1$ and $Ar^2$ are independently selected from the group consisting of monocyclic aryl, and monocyclic heteroaryl rings.

7. The method of claim 1, wherein $Ar^1$ and $Ar^2$ are independently selected from the group consisting of phenyl, napthyl, indole, pyridyl, pyrimidyl, benzofuran, and benzothiofuran rings.

8. The method of claim 1, wherein $Ar^1$ is a phenyl ring.

9. The method of claim 8, wherein $Ar^1$ is a phenyl, pyridyl, pyrimidyl, or pyrazinyl ring.

10. The method of claim 1, wherein $Ar^1$ is a pyridyl ring.

11. The method of claim 1, wherein $R^3$ and $R^4$ are independently selected from hydrogen and a $C_1$-$C_4$ organic radical.

12. The method of claim 1, wherein $R^3$ and $R^4$ are independently selected from hydrogen, a $C_1$-$C_4$ alkyl, $C_1$-$C_4$ alkoxy, $C_1$-$C_4$ hydroxyalkyl, or $C_1$-$C_4$ alkoxyalkyl.

13. The method of claims 1, wherein $R^3$ and $R^4$ are independently selected from hydrogen and $C_1$-$C_4$ alkyls.

14. The method of claim 1, wherein at least one of $R^3$ and $R^4$ are methyl.

15. The method of claim 1, wherein one of $R^3$ and $R^4$ is a $C_1$-$C_4$ alkyl and the other of $R^3$ and $R^4$ is hydrogen.

16. The method of claim 1, wherein one of $R^3$ and $R^4$ is methyl and the other of $R^3$ and $R^4$ is hydrogen.

17. The method of claim 1, wherein $R^3$ and $R^4$ are methyl.

18. The method of claim 1, wherein $R^5$ is a $C_3$-$C_{10}$ branched alkyl.

19. The method of claim 1, wherein $R^5$ is a $C_1$-$C_{10}$ normal or branched alkyl or cycloalkyl, optionally substituted with 1, 2, or 3 aryl or hetereroaryl rings.

20. The method of claim 1, wherein $R^5$ is a $C_1$-$C_{10}$ normal or branched alkyl or cycloalkyl, substituted with 1, 2, or 3 substituents independently selected from the group consisting of hydroxy, fluoro, chloro, $NH_2$, $NO_2$, $NHCH_3$, $N(CH_3)_2$, $COOCH_3$, $SCH_3$, $SC_2H_5$, methyl, ethyl, propyl, isopropyl, vinyl, trifluoromethyl, methoxy, ethoxy, isopropoxy, and trifluoromethoxy groups.

21. The method of claim 1, wherein the modified comestible or medicinal product further comprises at least a sweet flavoring agent amount of one or more of sucrose, fructose, glucose, erythritol, isomalt, lactitol, mannitol, sorbitol, xylitol, aspartame, neotame, saccharin, acesulfame-K, cyclamate, Sucralose, and alitame, or a mixture thereof.

22. The method of claim 1, wherein the modified comestible or medicinal product further comprises a sweet flavoring agent amount of fructose.

23. The method of any claim 1, wherein the modified comestible or medicinal product modified comestible or medicinal product has a sweeter taste than a control comestible or medicinal product that does not comprise the bis-aromatic amide compound, as judged by the majority of a panel of at least eight human taste testers.

24. The method of claim 1, wherein the modified comestible or medicinal product is selected from the group consisting of confectioneries, bakery products, ice creams, dairy products, sweet and savory snacks, and snack bars.

25. The method of claim 1, wherein the modified comestible or medicinal product is selected from the group consisting of meal replacement products, ready meals, soups, pastas, noodles, canned foods, frozen foods, dried foods, chilled foods, oils and fats, baby foods, and spreads.

26. The method of claim 1, wherein the modified comestible or medicinal product is a frozen food, an uncooked food, or a fully or partially cooked food.

27. The method of claim 1, wherein the modified comestible or medicinal product is a snack food.

28. The method of claim 1, wherein the modified comestible or medicinal product is a cake, cookie, pie, candy, chewing gum, gelatin, ice cream, sorbet, pudding, jam, jelly, salad dressing, condiment, cereal, canned fruit, or fruit sauce.

29. The method of claim 1, wherein the modified comestible or medicinal product is a beverage, a beverage mix, or a beverage concentrate.

30. The method of claim 1, wherein the modified comestible or medicinal product is a solid beverage mix also comprising a saccharide sweetener.

31. The method of claim 1, wherein the modified comestible or medicinal product is a liquid beverage concentrate composition also comprising a saccharide sweetener.

32. The method of claim 1, wherein the modified comestible or medicinal product is a soda.

33. The method of claim 1, wherein the modified comestible or medicinal product is a fruit or vegetable juice.

34. The method of claim 1, wherein the modified comestible or medicinal product is ice cream.

35. The method of claim 1, wherein the modified comestible or medicinal product is a cereal.

36. The method of claim 1, wherein the modified comestible or medicinal product comprises a sweet coating, frosting, or glaze comprising a mixture of the at least one bis-aromatic amide compound and one or more other sweeteners independently selected from sucrose, fructose, glucose, erythritol, isomalt, lactitol, mannitol, sorbitol, xylitol, aspartame, neotame, saccharin, acesulfame-K, cyclamate, Sucralose, and alitame, or a mixture thereof.

37. The method of claim 1, wherein the modified comestible or medicinal product has a sweeter taste than a control comestible or medicinal product that does not comprise the bis-aromatic amide compound, as judged by the majority of a panel of at least eight human taste testers.

38. The method of claim 1, wherein the bis-aromatic amide compound has an $EC_{50}$ for binding an hT1R2/hT1R3 receptor expressed in an HEK293-Gα15 cell line of less than about 2 μM.

39. The method of claim 1, wherein the one or more bis-aromatic amide compounds contacted or mixed with one or more precursors of the comestible or medicinal product to form a sweetener concentrate composition comprising from about 10 to about 100,000 ppm of the one or more bis-aromatic amide compounds, then the sweetener concentrate composition is used to prepare the comestible or medicinal product.

40. The method of claim 39 wherein from about 100 to about 1000 ppm of the one or more bis-aromatic amide compounds are present in the sweetener concentrate composition.

41. The method of claim 39 wherein the sweetener concentrates composition is a liquid solution, dispersion, or emulsion of the bis-aromatic amide compound in one or more precursors of the comestible or medicinal product.

42. The method of claim 39 wherein the sweetener concentrates composition is a solid.

43. A method for increasing the sweet taste of a comestible or medicinal product comprising:
(a) providing at least one comestible or medicinal product, or at least one precursor thereof, and
(b) combining the at least one comestible or medicinal product or at least one precursor thereof with from about 0.01 to about 100 ppm of at least one bis-aromatic amide compound, or a comestibly acceptable salt thereof, and a sweet flavoring agent amount of sucrose, fructose, glucose, or a mixture thereof, so as to form a modified comestible or medicinal product;
wherein the bis-aromatic amide compound has the structure:

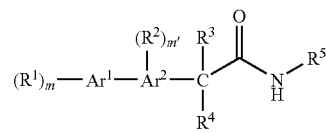

wherein
(i) $Ar^1$ and $Ar^2$ are independently selected from phenyl, napthyl, indolyl, pyridyl, pyrimidyl, pyrrolyl, furanyl, thiofuranyl, quinolinyl, benzofuranyl, triazolyl, and benzothiofuranyl rings;
(ii) m is selected from the integers 0, 1, 2, or 3;
(iii) m' is selected from the integers 0, 1, or 2;
(iv) each $R^1$ and $R^2$ is independently selected from the group consisting of a hydroxy, fluoro, chloro, $NH_2$, $NO_2$, $NHCH_3$, $N(CH_3)_2$, $COOCH_3$, $SCH_3$, $SC_2H_5$, methyl, ethyl, propyl, isopropyl, vinyl, allyl, $S(O)CH_3$, $S(O)_2CH_3$, CN, $CH_2OH$, C(O)H, $C(O)CH_3$, trifluoromethyl, methoxy, ethoxy, isopropoxy, and trifluoromethoxy radical;
(v) $R^3$ is a $C_1$-$C_4$ alkyl;
(vi) $R^4$ is hydrogen, or a $C_1$-$C_4$ alkyl;
(vii) $R^5$ is a $C_1$-$C_{10}$ normal or branched alkyl or cycloalkyl, wherein the normal or branched alkyl or cycloalkyl optionally comprises one to or two substituents independently selected from hydroxy, fluoro, chloro, $NH_2$, $NO_2$, $NHCH_3$, $N(CH_3)_2$, $COOCH_3$, $SCH_3$, $SC_2H_5$, methyl, ethyl, propyl, isopropyl, vinyl, allyl, $S(O)CH_3$, $S(O)_2CH_3$, CN, $CH_2OH$, C(O)H, $C(O)CH_3$, trifluoromethyl, methoxy, ethoxy, isopropoxy, and trifluoromethoxy radical;
or a comestibly acceptable salt thereof.

44. The method of claim 43, wherein $R^3$ and $R^4$ are methyl, and $R^5$ is a $C_3$-$C_{10}$ branched alkyl.

45. A comestible or medicinal product produced by the process of claims 43 or 44.

46. A sweet comestible or medicinal product comprising from about 0.01 to about 100 ppm of at least one bis-aromatic amide compound, or a comestibly acceptable salt thereof, and at least a sweet flavoring agent amount of one or more natural, semi-synthetic, or synthetic sweet flavoring agents, or a mixture thereof;
wherein the bis-aromatic amide compound has the structure:

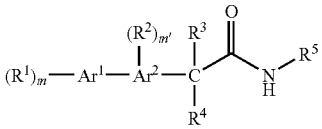

Wherein
(i) $Ar^1$ and $Ar^2$ are independently selected from a phenyl, pyridyl, pyrimidyl, pyrazinyl, pyrrolyl, pyrazolyl, furanyl, thiofuranyl, triazolyl, isoxazolyl, oxadiazolyl, or indolyl ring;
(ii) m and m' are independently selected from the integers 0, 1, or 2;
(iii) each $R^1$ and $R^2$ is independently selected from the group consisting of OH, $NH_2$, $NO_2$, SH, $SO_3H$, $PO_3H$, halogen, and a $C_1$-$C_4$ organic radical;
(iv) $R^3$ and $R^4$ are independently selected from hydrogen and methyl,
(v) $R^5$ is a $C_3$-$C_{10}$ branched alkyl optionally comprising one, two, or three substituents independently selected from OH, $NH_2$, a halogen, and a $C_1$-$C_6$ organic radical;
or a comestibly acceptable salt thereof.

47. The sweet comestible or medicinal product of claim 46 wherein $Ar^1$ a phenyl, pyridyl, pyrimidyl, pyrazinyl, pyrrolyl, pyrazolyl, furanyl, thiofuranyl, or indolyl ring.

48. The sweet comestible or medicinal product of claim 46 wherein $Ar^2$ is a phenyl, pyridyl, pyrimidyl, pyrazinyl, pyrazolyl, furanyl, thiofuranyl, isoxazolyl, oxadiazolyl, or triazolyl ring.

49. The sweet comestible or medicinal product of claim 46, wherein the one or more natural, semi-synthetic, or synthetic sweet flavoring agents comprising sucrose, fructose, glucose, erythritol, isomalt, lactitol, mannitol, sorbitol, xylitol, aspartame, neotame, saccharin, acesulfame-K, cyclamate, Sucralose, or alitame, or a mixture thereof.

50. A sweet comestible or medicinal product of claim 46 that is a confectionery, bakery product, ice cream, dairy product, sweet snack, cereal, beverage, beverage mix, or beverage concentrate.

51. A bis-aromatic amide compound having the structure:

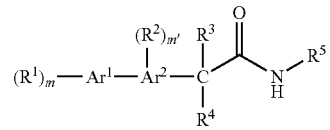

wherein
(i) $Ar^1$ and $Ar^2$ are independently selected from a phenyl or monocyclic heteroaryl rings;
(ii) m and m' are independently selected from the integers 0, 1, or 2;
(iii) each $R^1$ and $R^2$ is independently selected from the group consisting of OH, $NH_2$, $NO_2$, SH, $SO_3H$, $PO_3H$, halogen, and a $C_1$-$C_4$ organic radical;
(iv) $R^3$ and $R^4$ are independently selected from hydrogen and a $C_1$-$C_4$ alkyl,
(v) $R^5$ is a $C_3$-$C_{10}$ branched alkyl optionally comprising one, two, or three substituents independently selected from OH, $NH_2$, a halogen, and a $C_1$-$C_6$ organic radical;
or a comestibly acceptable salt thereof.

52. The bi-aromatic amide compound of claim 51 or a comestibly acceptable salt thereof, wherein $Ar^2$ is phenyl.

53. The bis-aromatic amide compound of claim 51 or a comestibly acceptable salt thereof, wherein $Ar^1$ is a pyridyl, pyrimidyl or pyrazinyl ring.

54. The bis-aromatic amide compound of claim 51 or a comestibly acceptable salt thereof, wherein $R^3$ and $R^4$ are methyl.

55. The bis-aromatic amide compound of claim 51 or a comestibly acceptable salt thereof, wherein $R^5$ is a $C_3$-$C_{10}$ branched alkyl.

56. A comestible composition comprising from about 0.001 to about 10 ppm of one or more of the bis-aromatic amide compounds of claim 51.

57. A sweetener concentrate composition comprising from about 10 to about 100,000 ppm of one or more of the bis-aromatic amide compounds of claim 51, and one or more comestibly acceptable carriers.

58. The sweetener concentrates composition of claim 57 comprising a solution, dispersion, or emulsion of the bis-aromatic amide compound in the one or more comestibly acceptable liquids.

59. The sweetener concentrate composition of claim 58 wherein the comestibly acceptable liquids are selected from a water, a comestibly acceptable organic solvent, or comestibly acceptable oils or melted fats, or a mixture thereof.

60. The sweetener concentrates composition of claim 59 wherein the comestibly acceptable organic solvents are selected from ethanol, propylene glycol, dipropylene glycol and methyl, ethyl, and acetate esters thereof, glycerol, and corn syrup.

61. The sweetener concentrates composition of claim 59 wherein the comestibly acceptable oils or melted fats comprise triacetylesters of glycerol.

62. The sweetener concentrates composition of claim 57 wherein the one or more comestibly acceptable carriers is a comestibly acceptable solid.

63. The sweetener concentrates composition of claim 62 wherein the comestibly acceptable solid comprises a saccharide or polysaccharide.

64. The sweetener concentrates composition of claim 62 wherein the comestibly acceptable solid comprises sucrose, fructose, or glucose.

65. The sweetener concentrates composition of claim 62 wherein the comestibly acceptable solid comprises starch, modified starches, dextrins, maltodextrins, celluloses, modified celluloses, pectins, alginates, chitosan, chitosan derivatives, gum arabic, carrageenans, locust bean gum, and guar gum.

66. A compound having the formula:
2-(4-(6-cyanopyrazin-2-yl)phenyl)-N-isobutyl-2-methylpropanamide;
2-(4-(5-cyanopyridin-3-yl)phenyl)-2-methyl-N-(pentan-3-yl)propanamide;
(R)-N-sec-butyl-2-(4-(5-cyanopyridin-3-yl)phenyl)-2-methylpropanamide;
2-(4-(5-cyanopyridin-3-yl)phenyl)-N-isobutyl-2-methylpropanamide;
2-methyl-N-(2-methylbutyl)-2-(4-(pyrimidin-5-yl)phenyl)propanamide;
2-(4-(5-(ethoxymethyl)pyridin-3-yl)phenyl)-N-isobutyl-2-methylpropanamide;
N-isobutyl-2-(2-methoxy-3'-(methoxymethyl)biphenyl-4-yl)-2-methylpropanamide;
N-isobutyl-2-(4-(6-(methoxymethyl)pyrazin-2-yl)phenyl)-2-methylpropanamide;
N-isobutyl-2-(3'-(methoxymethyl)biphenyl-4-yl)-2-methylpropanamide;
N-isobutyl-2-(4-(5-(methoxymethyl)pyridin-3-yl)phenyl)-2-methylpropanamide;
N-isobutyl-2-methyl-2-(4-(1-methyl-1H-pyrrol-2-yl)phenyl)propanamide;
2-(2'-(hydroxymethyl)biphenyl-4-yl)-N-isobutyl-2-methylpropanamide;
(S)-N-(1-hydroxybutan-2-yl)-2-(3'-(methoxymethyl)biphenyl-4-yl)-2-methylpropanamide;
N-isobutyl-2-methyl-2-(4-(pyrimidin-5-yl)phenyl)propanamide;
2-(4-(6-cyanopyrazin-2-yl)phenyl)-N-(2-methoxypropyl)-2-methylpropanamide;
(R)-N-sec-butyl-2-(4-(6-cyanopyrazin-2-yl)phenyl)-2-methylpropanamide;
or a comestibly acceptable salt thereof.

67. A comestible composition comprising at least a sweet flavor modulating amount of at least one of the compounds of claim 66.

68. A method for increasing the sweet taste of a comestible or medicinal product comprising:
(a) providing at least one comestible or medicinal product, or at least one precursor thereof, and
(b) combining the at least one comestible or medicinal product or at least one precursor thereof with at least a sweet flavor modulating amount of at least one bis-aromatic amide compound, or one or more comestibly acceptable salts thereof, so as to form a modified comestible or medicinal product;
wherein the bis-aromatic amide compound has the structure:

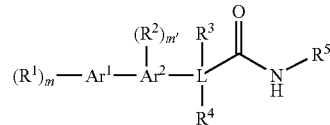

wherein
(i) Ar¹ and Ar² are independently selected from monocyclic aryl, fused bicyclic aryl, monocyclic heteroaryl, or fused bicyclic heteroaryl rings;
(ii) m is selected from the integers 0, 1, 2, 3, 4, or 5;
(iii) m' is selected from the integers 0, 1, 2, 3, or 4;
(iv) each $R^1$ and $R^2$ is independently selected from the group consisting of an OH, $NH_2$, $NO_2$, SH, $SO_3H$, $PO_3H$, halogen, and a $C_1$-$C_6$ organic radical;
(v) L is a carbon or nitrogen atom;
(vi) $R^3$ is hydrogen, oxygen, hydroxy, halogen, or a $C_1$-$C_6$ organic radical;
(vii) $R^4$ is absent, or hydrogen, oxygen, hydroxy, halogen, or a $C_1$-$C_6$ organic radical;
(viii) $R^5$ is a $C_1$-$C_{14}$ organic radical comprising a normal or branched alkyl or cycloalkyl, wherein the normal or branched alkyl or cycloalkyl optionally comprises one to four substituents independently selected from OH, $NH_2$, $NO_2$, SH, $SO_3H$, $PO_3H$, halogen, and a $C_1$-$C_6$ organic radical;
or a comestibly acceptable salt thereof.

* * * * *